US010704045B2

(12) United States Patent
Killmer et al.

(10) Patent No.: US 10,704,045 B2
(45) Date of Patent: Jul. 7, 2020

(54) METHODS AND COMPOSITIONS FOR INCREASED DOUBLE STRANDED RNA PRODUCTION

(71) Applicant: APSE, INC., St. Louis, MO (US)

(72) Inventors: John L. Killmer, St. Louis, MO (US); Patrick D. McLaughlin, St. Louis, MO (US); Juan Pedro Humberto Arhancet, St. Louis, MO (US)

(73) Assignee: APSE, INC., St. Louis, MO (US)

( * ) Notice: Subject to any disclaimer, the term of this patent is extended or adjusted under 35 U.S.C. 154(b) by 0 days.

(21) Appl. No.: 16/084,545

(22) PCT Filed: Mar. 9, 2017

(86) PCT No.: PCT/US2017/021661
§ 371 (c)(1),
(2) Date: Sep. 12, 2018

(87) PCT Pub. No.: WO2017/160600
PCT Pub. Date: Sep. 21, 2017

(65) Prior Publication Data

US 2019/0093108 A1 Mar. 28, 2019

Related U.S. Application Data

(60) Provisional application No. 62/308,381, filed on Mar. 15, 2016.

(51) Int. Cl.

| | |
|---|---|
| ***C12N 15/113*** | (2010.01) |
| ***C12N 15/11*** | (2006.01) |
| ***C07K 14/005*** | (2006.01) |

(52) U.S. Cl.
CPC .......... *C12N 15/113* (2013.01); *C07K 14/005* (2013.01); *C12N 15/111* (2013.01); *C12N 2310/14* (2013.01); *C12N 2330/50* (2013.01); *C12N 2795/18122* (2013.01)

(58) Field of Classification Search
None
See application file for complete search history.

(56) References Cited

U.S. PATENT DOCUMENTS

| | | | | |
|---|---|---|---|---|
| 2004/0214318 | A1 | 10/2004 | Chapman et al. | |
| 2014/0271559 | A1 | 9/2014 | Baum et al. | |
| 2014/0302593 | A1 | 10/2014 | Arhancet et al. | |
| 2016/0194613 | A1* | 7/2016 | Williams ................ | C12N 7/00 514/44 A |

FOREIGN PATENT DOCUMENTS

| | | | |
|---|---|---|---|
| WO | 2013117910 | A1 | 8/2013 |
| WO | 2014204667 | A1 | 12/2014 |
| WO | 2015042556 | A1 | 3/2015 |
| WO | 2016183022 | A1 | 11/2016 |

OTHER PUBLICATIONS

Dykeman, et al., "Packaging Signals in Two Single-Stranded RNA Viruses Imply a Conserved Assembly Mechanism and Geometry of the Packaged Genome," Journal of Molecular Biology, vol. 425, Issue 17, pp. 3235-3249 (Sep. 9, 2013).
International Search Report of PCT/US2017/021661 dated May 24, 2017.
Written Opinion of PCT/US2017/021661 dated May 24, 2017.

* cited by examiner

*Primary Examiner* — J. E Angell
(74) *Attorney, Agent, or Firm* — Polsinelli PC; Christopher M. Cabral

(57) ABSTRACT

Methods and materials for improved in vivo production of dsRNA are presented. Yields of dsRNA are significantly increased in the presence of capsid protein. The improved yield of dsRNA is not dependent on the presence of specific cognate binding sites for capsid protein associated with the dsRNA, but is dependent on capsid protein.

33 Claims, 6 Drawing Sheets

Specification includes a Sequence Listing.

METHODS AND COMPOSITIONS FOR INCREASED DOUBLE STRANDED RNA PRODUCTION

CROSS REFERENCE TO RELATED APPLICATIONS

This application is the 35 U.S.C. 371 National Stage of International Application Number PCT/US2017/021661, filed Mar. 9, 2017, which claims the benefit of U.S. Provisional Application No. 62/308,381 filed Mar. 15, 2016, the entire disclosure of which is hereby incorporated by reference.

INCORPORATION OF SEQUENCE LISTING

A Sequence Listing is provided herewith as a text file entitled "103827-5009_sequences_ST25.txt" created on Sep. 10, 2018 and having a size of 409 KB. The contents of the text file are incorporated by reference herein in their entirety.

FIELD OF THE INVENTION

The present invention relates to methods and compositions for increasing in vivo production of double-stranded RNA.

BACKGROUND OF THE INVENTION

The ability to suppress gene expression with RNA homologous to targeted gene sequences has greatly increased demand for large scale production of such RNA. However, the chemical fragility of RNA limits commercial development of many of these techniques. Large scale production of purified RNA is constrained by the high costs associated with in vitro synthesis methods and by the low yields and complex processing requirements associated with in vivo methods.

The susceptibility of RNA to enzymatic and environmental degradation varies widely depending on the nature of the RNA molecule. Single-stranded RNA (ssRNA) is extremely sensitive to degradation and in vivo production of such molecules requires use of production strains lacking endogenous RNAses and benefits by coupling production of the RNA to encapsidation within viral capsid shells to produce Virus-Like Particles (VLPs). Encapsidation reduces degradation of RNA during production and allows more aggressive treatment during purification. VLPs effectively preserve such fragile RNA from degradation by sequestering the RNA within a relatively inert protein shell. Double stranded RNA (dsRNA) are somewhat less susceptible to degradation by cellular and environmental RNAses, although the highest in vivo yields of dsRNA also involve production strains lacking RNAses and many dsRNA also benefit from encapsidation. Unfortunately, the semi-rigid nature of the double-stranded stem region of dsRNA limits the range of dsRNA that can be encapsidated since the length of the double-stranded stem structure cannot exceed the interior diameter of the capsid.

In the course of exploring techniques for increasing the range of dsRNA stems that can be encapsidated, the inventors discovered that under certain conditions a large amount of unencapsidated dsRNA can be recovered directly from cell lysates, but only when the host cells co-express capsid protein or specific portions thereof. The presence of high quantities of intact unencapsidated dsRNA in crude cell lysates represents a significant advance in the ability to generate commercial quantities of such RNA for gene suppression and other activities.

Dimers of bacteriophage capsid proteins such as those of the leviviruses MS2 or Qβ recognize and bind with affinity to cognate pac sequences. Such pac sequences comprise approximately 19-21 nucleotides comprising an 8 base pair bulged stem and 4 base loop capable of forming a discrete hairpin structure. Such sequences may be referred to herein as pac-sites, pac sequences, pac-site sequences, pac-site hairpins, or pac-site hairpin sequences. The interaction of capsid dimers with their cognate pac site hairpin is well-characterized and is known to play at least two key roles in the bacteriophage life cycle. Binding of capsid dimers to the cognate pac sites is required for programmed translational repression of the phage encoded replicase, which is only expressed early in infection. In addition, capsid protein binding to both to pac-site sequences and multiple dispersed and degenerate RNA sites with cognate coat protein affinity (the packaging signals described by Dykeman et al., *Packaging Signals in Two Single-Stranded RNA Viruses Imply a Conserved Assembly Mechanism and Geometery of the Packaged Genome* J. Mol. Biol. 425:3235-3249 (2013)) are required for proper assembly into progeny bacteriophage.

The interaction of capsid dimers with cognate pac sites is the subject of a number of different published in vitro and in vivo methods designed to allow encapsidation of heterologous RNAs of various kinds by associating the desired cargo molecule with pac site sequences, either by direct covalent linkage or by various affinity methods. The present invention differs markedly from such approaches in that it comprises co-expression of capsid proteins to produce unencapsidated dsRNA rather than encapsidated RNA. Further, the present invention allows in vivo production of dsRNA entirely lacking pac or any recognized dispersed and degenerate RNA sites with cognate protein affinity. In vivo production of such dsRNA molecules is highly desirable since reducing extraneous sequence reduces the chance of off-target RNAi interactions.

SUMMARY OF THE INVENTION

The invention described in the following embodiments provides methods and compositions for producing large quantities of unencapsidated dsRNA in vivo. The disclosed methods and compositions represent a significant improvement over current in vivo methods of producing dsRNA.

In an embodiment the invention comprises a microbial cell containing a gene encoding a self-complementary stretch of sequence separated by non-complementary sequence such that upon hybridization of the complementary sequences a stem-loop structure is formed, wherein the stem portion of the molecule functions as an RNAi precursor when introduced into the target organism. The microbial cell also contains a bacteriophage coat protein gene encoding a capsid protein. Expression of the dsRNA gene and the coat protein gene results in increased accumulation of un-degraded dsRNA and capsid protein. The amount of dsRNA produced in this way greatly exceeds the amount of dsRNA produced in the absence of capsid protein.

In one embodiment the bacteriophage capsid protein is encoded by the coat protein gene of a species of leviviridae. In a preferred embodiment the coat protein gene encodes the capsid protein of bacteriophage MS2. In another preferred embodiment the coat protein gene encodes the capsid protein of bacteriophage Qbeta.

In an embodiment the capsid protein comprises the N-terminus of the MS2 capsid protein. In another embodiment the capsid protein comprises the N-terminal 41, 35, 25, 21 or 12 amino acids of the MS2 capsid protein. In an embodiment the capsid protein comprises the N-terminus of the Qbeta capsid protein. In another embodiment the capsid protein comprises the N-terminal 41, 35, 25, 21 or 12 amino acids of the Qbeta capsid protein.

In an embodiment the gene encoding the dsRNA may be associated with and expressed from an inducible transcriptional promoter. The coat protein gene may be associated with and expressed from a constitutive or inducible transcriptional promoter. The inducible transcriptional promoter associated with expression of the dsRNA may be the same inducible transcriptional promoter or a different transcriptional promoter from a transcriptional promoter associated with expression of the coat protein gene. In one embodiment the inducible transcriptional promoter associated with expression of the coat protein gene is induced before induction of the inducible transcriptional promoter associated with expression of the dsRNA to allow accumulation of capsid protein prior to production of dsRNA. In another embodiment the transcriptional promoter associated with expression of the coat protein gene is a constitutive transcriptional promoter.

In an embodiment the gene encoding the dsRNA and the coat protein gene encoding the capsid protein are present on a plasmid or extrachromosomal element. The gene encoding the dsRNA and the coat protein gene may be present on the same plasmid or extrachromosomal element or may be present on separate plasmids or extrachromosomal elements. In another embodiment one or both of the genes encoding the dsRNA and the coat protein may be present on the microbial host cell chromosome or chromosomes.

In related embodiments, the dsRNA may be purified from the microbial host cell by lysing the cells to produce a lysate and purifying the dsRNA from the cellular constituents within the lysate prior to processing the purified dsRNA for application. Such processing may include, but is not limited to mixing with excipients, binders or fillers to improve physical handling characteristics, stabilizers to reduce degradation, or other active agents such as chemical pesticides, fungicides, defoliants or other RNAi molecules to broaden the spectrum of application targets, and may include pelletizing, spray drying or dissolving the materials into liquid carriers. In another embodiment the dsRNA is not further purified from the lysate but is processed directly for application. In still another embodiment the microbial host cell is not lysed but is processed directly for application and the dsRNA remains unpurified within the processed cells.

DETAILED DESCRIPTION OF THE INVENTION

The present invention comprises compositions and methods for producing large quantities of dsRNA in vivo and in some embodiments, recovering such dsRNA directly from cell lysates. In its most basic form, the invention involves co-expressing a bacteriophage capsid protein, or a portion thereof, in conjunction with the desired dsRNA for a period of time sufficient to allow accumulation of the dsRNA in a host cell, lysing the host cell, and optionally recovering intact unencapsidated dsRNA directly from the cell lysate. In the absence of bacteriophage capsid protein intact dsRNA is present in cell lysates in only very small quantities, if at all. In contrast, in the presence of bacteriophage capsid protein a relatively large quantity of unencapsidated dsRNA can be recovered from cell lysates.

A number of permutations of RNA structure and coat protein were explored to determine the essential elements of the invention and to optimize the yield of dsRNA produced by the invention. This work is summarized in Table 1 which outlines the various elements of the invention described in detail and in the examples below. The leftmost column of Table 1 refer to individual figures representing cartoon depiction of the predicted RNA structure produced from each of the listed plasmid constructs. In each figure "S" represents the sense strand, "AS" represents antisense strand, and the small hairpin structures represent pac site sequences). The table also lists the coat protein (if any) and the yields of dsRNA (or ssRNA, as indicated) associated with each of the listed plasmid constructs.

TABLE 1

Production of RNA by *E. coli* HT115(DE3) as a function of variation in RNA structure and the presence or absence of coat protein and coat protein variants (n.a. = not applicable; n.d. = not determined).

Figure 1:
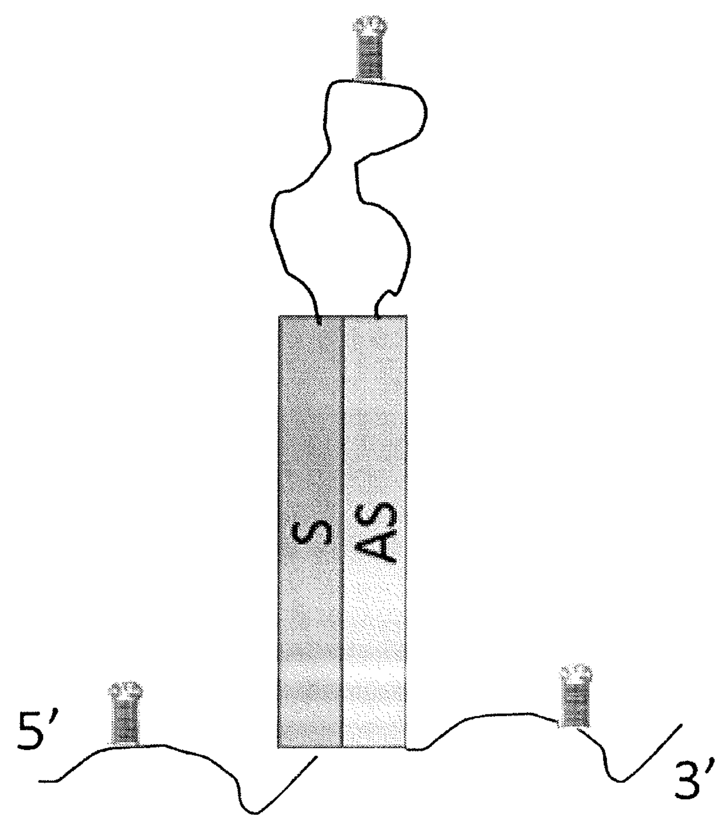
FIG. 1 depicts an RNA stem-loop structure with three pac-site hairpin sequences, one located 5' of the stem-loop structure, one within the loop of the stem-loop structure, and the other 3' of the stem-loop structure.
Figure 2:
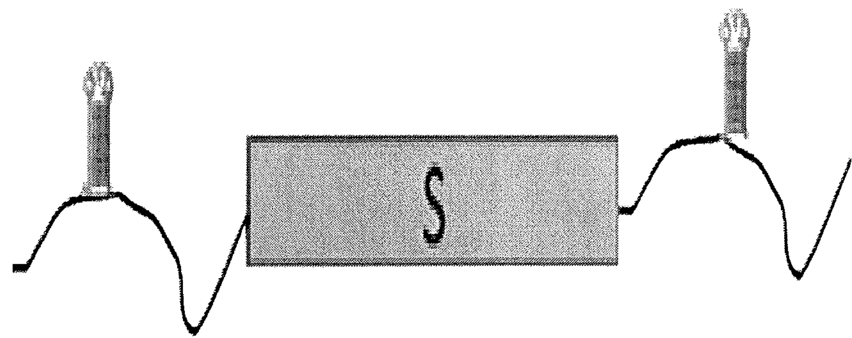
FIG. 2 depicts a single strand (sense) sequence flanked on each side by a pac-site hairpin sequence.
Figure 3:
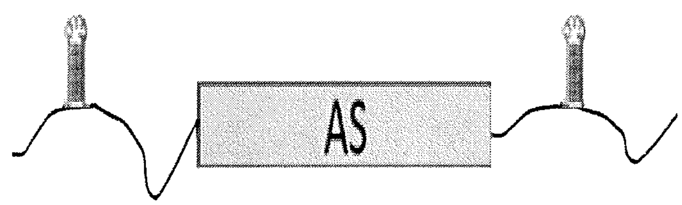
FIG. 3 depicts a single strand (antisense) sequence flanked on each side by a pac-site hairpin sequence.

| RNA Structure as depicted in | Plasmid | Loop size (bases) | Stem size (bp) | Stem sequence | Coat protein | RNA en capsid (mg/L) | RNA ex capsid (mg/L) |
|---|---|---|---|---|---|---|---|
| FIG. 1 | pAPSE10180 | 139 | 180 | ErkA | MS2 | <2 | 75-90 |
| FIG. 1 | pAPSE10181 | 139 | 180 | ErkA | none | n.a | <2. |
| FIG. 2 | pAPSE10189 | n.a. | n.a. | beta actin | MS2 | 20 | <2 |
| FIG. 3 | pAPSE10190 | n.a. | n.a. | beta actin | MS2 | 20 | <2 |
| FIG. 2 | pAPSE10274 | n.a. | n.a. | beta actin | none | n.a. | <2 |
| FIG. 3 | pAPSE10275 | n.a. | n.a. | beta actin | none | n.a. | <2 |

TABLE 1-continued

Production of RNA by *E. coli* HT115(DE3) as a function of variation in RNA structure and the presence or absence of coat protein and coat protein variants (n.a. = not applicable; n.d. = not determined).

Figure 4:
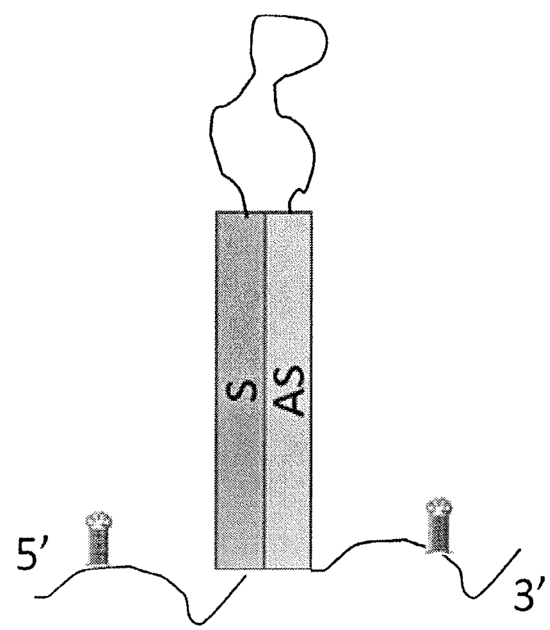
FIG. 4 depicts an RNA stem-loop structure with two pac-site hairpin sequences, one located 5' of the stem-loop structure and the other 3' of the stem-loop structure.
Figure 5:
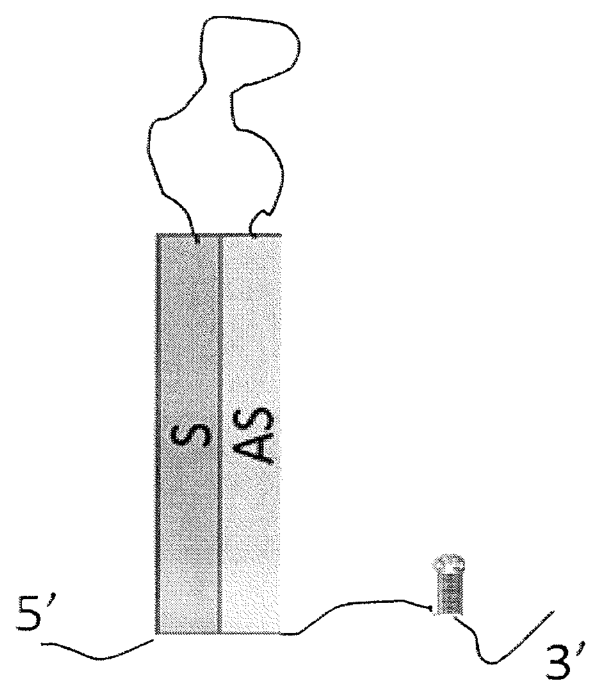
FIG. 5 depicts an RNA stem-loop structure with a single pac-site hairpin sequence located 3' of the stem-loop structure.
Figure 6:
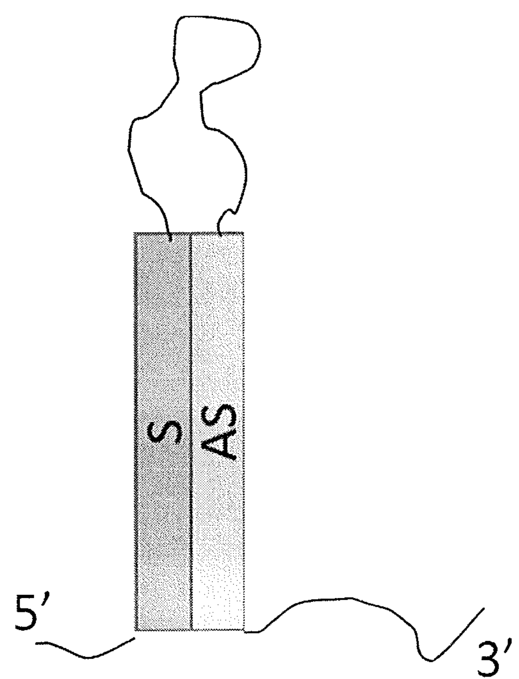
FIG. 6 depicts an RNA stem loop structure lacking any pac site hairpin sequences.

| RNA Structure as depicted in | Plasmid | Loop size (bases) | Stem size (bp) | Stem sequence | Coat protein | RNA en capsid (mg/L) | RNA ex capsid (mg/L) |
|---|---|---|---|---|---|---|---|
| FIG. 1 | pAPSE10269 | 166 | 294 | beta actin | MS2 | 2-10 | 200 |
| FIG. 1 | pAPSE10306 | 166 | 294 | beta actin | none | n.a. | 3 |
| FIG. 4 | pAPSE10216 | 166 | 294 | beta actin | MS2 | 5-20 | 50-250 |
| FIG. 4 | pAPSE10305 | 166 | 294 | beta actin | none | n.a. | 4 |
| FIG. 5 | pAPSE10219 | 166 | 294 | beta actin | MS2 | 5-20 | 30-60 |
| FIG. 5 | pAPSE10304 | 166 | 294 | beta actin | none | n.a. | 3 |
| FIG. 6 | pAPSE10279 | 166 | 294 | beta actin | MS2 | 4 | 65 |
| FIG. 6 | pAPSE10303 | 166 | 294 | beta actin | none | n.a. | 4 |
| FIG. 4 | pAPSE10270 | 116 | 294 | beta actin | MS2 | 2-10 | 200 |
| FIG. 4 | pAPSE10271 | 136 | 294 | beta actin | MS2 | 2-10 | 200 |
| FIG. 4 | pAPSE10272 | 156 | 294 | beta actin | MS2 | 2-10 | 200 |
| FIG. 4 | pAPSE10292 | 131 | 294 | beta actin | MS2 | 2-10 | 150 |
| FIG. 4 | pAPSE10291 | 142 | 294 | beta actin | MS2 | 2-10 | 160 |
| FIG. 4 | pAPSE10276 | 166 | 50 | beta actin | MS2 | 5-10 | 80-120 |
| FIG. 4 | pAPSE10277 | 166 | 75 | beta actin | MS2 | 20-30 | 200-250 |
| FIG. 4 | pAPSE10366 | 166 | 294 | beta actin | none (eGFP) | n.a. | <2 |
| FIG. 4 | pAPSE10181 and pAPSE10149 | 139 | 180 | ErkA | MS2 in trans | n.d. | 200 |
| FIG. 1 | pAPSE10359 | 166 | 294 | beta actin | Qbeta | n.d. | n.d. |
| FIG. 4 | pAPSE10357 | 166 | 294 | beta actin | none (U1A) | n.d. | n.a. |
| FIG. 1 | pAPSE10372 | 139 | 180 | ErkA | none (MS2 N-term fragment) | n.a. | 75 |

A. Definitions

As used herein, the term "capsid protein" or "capsid" refers to the coat protein of bacteriophage MS2 or Qβ, capable of binding the bacteriophage RNA pac site with high affinity and assembling into a complex hollow tertiary structure in which the bacteriophage RNA is entirely encapsidated within the hollow tertiary structure. In a VLP, the capsid protein forms a hollow tertiary structure in which the heterologous RNA is entirely encapsidated. The term "capsid" also refers to the hollow tertiary structure formed by assembly of individual capsid proteins.

As used herein "ssRNA" and "dsRNA" refer to "single-stranded RNA and double stranded RNA, respectively. An ssRNA is comprised of an RNA sequence of any length that lacks sufficient internal homology to form any significant secondary structures such as hairpins or other structures dependent on hybridization of internal complementary sequences with one another via Watson-Crick base pairing of nucleotide bases between the complementary sequences. In contrast, a dsRNA comprises RNA sequences with sufficient internal homology to form significant secondary structures such as hairpins due to hybridization of internal complementary sequences with one another via Watson-Crick base pairing of nucleotide bases within the complementary sequences. Significant secondary structures generally involve stretches of homology greater than approximately nine bases, but the exact length depends to some extent on context and on whether such secondary structures impart any biological function to the molecule.

As used herein "plasmid" or "extrachromosomal element" refers to any extrachromosomal episome capable of replication or stable maintenance within the host cell. Specifically embraced by this definition are plasmids such as pBR322, pCG1, and pACYC184 which represent the backbones of the described plasmids. Those of ordinary skill in the art will recognize that other plasmids or stably maintained viral episomes can provide the same required functions of maintenance, expression and selection and that alternatives to the basic plasmids described herein may be generated from such other plasmids or stably maintained viral episomes without undue experimentation. A key feature of the present invention is the ability to express the genes encoding a dsRNA and a capsid protein, not specific modes of replication, expression or the selective markers found on episomes containing the genes encoding the dsRNA and capsid protein.

"Substantially similar sequence" refers to sequence variants of the claimed capsid proteins that retain the ability to facilitate accumulation of dsRNA in a microbial host cell as described herein. Such substantially similar sequences include sequences with at least 26% identity and 47% similarity as shown by the differences between MS2 and Qbeta capsid protein sequences (as determined by blastp). Consequentially, substantially similar sequences encompass conserved and homologous substitutions allowing sequence variants with as little as 95%, 90%, 80%, 70%, 60%, 50%, 40%, 30% or 25% identity to, and 95%, 90%, 80%, 70%, 60%, 50% or 40% similarity to, MS2 or Qbeta capsid protein sequences to facilitate accumulation of dsRNA in a microbial host.

B. Common Materials, and Methods

Routine microbial and molecular cloning methods and tools, including those for generating and purifying DNA, RNA, and proteins, and for transforming host organisms and expressing recombinant proteins and nucleic acids as described herein, are fully within the capabilities of a person of ordinary skill in the art and are well described in the literature. See, e.g., Sambrook, et al., Molecular Cloning: A Laboratory Manual, 2nd ed., Cold Spring Harbor Laboratory Press, Cold Spring Harbor, N.Y. (1989); Davis, et al., Basic Methods in Molecular Biology, Elsevier Science Publishing Co., Inc., N.Y. (1986); and Ausubel, et al, Current Protocols in Molecular Biology, Greene Publ. Assoc., Wiley-Interscience, NY (1995). The disclosures in each of which are herein incorporated by reference.

Each of the recombinant DNA constructs described in further detail below are based on a common plasmid vector series derived from plasmid pBR322. The first of this plasmid vector series contains a custom synthetic DNA fragment (produced by PCR GenScript, Piscataway, N.J.) comprising a T7 promoter sequence capable of driving transcription of a single copy of the bacteriophage MS2 capsid gene followed by a T7 terminator. This synthetic sequence was inserted as a BamHI-SphI restriction fragment into the corresponding sites of pBR322 to form plasmid pAPSE10118. A second synthetic sequence comprising a T7 promoter sequence followed by an MS2 pac site sequence, a multi-cloning site containing, in order (5' to 3') AsiSI-PmeI-AscI-RsrII-NotI-PacI restriction sites, a second high affinity variant MS2 pac type sequence (C-pac), a T7 terminator and an SphI restriction site was synthesized (PCR Genscript, Piscataway, N.J.) and inserted into the EcoRV site of pAPSE10118 to form pAPSE10136. The two are oriented such that the T7 promoters direct transcription of the same strand of pAPSE10136 (clockwise on the standard pBR322 map) but are separated from one another by a single T7 terminator.

A 180 nucleotide fragment of the ErkA gene of *Drosophila melanogaster* (corresponding to the sequence of GenBank Accession NM_001300706 between nucleotides 156-335) was amplified by PCR incorporating AsiSI and PmeI restriction sites on the 5' and 3' sides, respectively. Insertion of this ErkA gene fragment into the corresponding sites of pAPSE10136 produced pAPSE10169. A second, complimentary copy of the ErkA gene fragment sequence was generated by PCR amplification incorporating a PmeI restriction site on the 5' end, followed by a synthetic loop sequence containing an additional MS2 pac sequence, followed by a NotI restriction site, followed by the complementary (anti-sense) ErkA gene fragment sequence and a Pad restriction site on the 3' end of the PCR fragment. The synthetic loop sequence comprises random sequence incapable of hybridizing with the ErkA gene fragment sequences. This complementary (anti-sense) copy of the ErkA gene fragment is inserted into the PmeI and PacI restriction sites of pAPSE10136 to form pAPSE10180 (SEQ ID NO: 1). A second series of plasmid vectors, lacking the MS2 capsid protein is derived from pAPSE10180 by deleting the MS2 capsid expression sequences by SphI restriction digestion and re-ligation to produce pAPSE 10181 (SEQ ID NO: 2).

Plasmids pAPSE10180 and pAPSE10181 represent the basic platform for expression of the RNA constructs discussed herein. Transcription of the ErkA cassette in these plasmids is predicted to produce an RNA transcript capable of forming a large stem-loop structure comprising a 180 base pair stem and a 139 base loop with 3 individual MS2 pac sequences located 5' and 3' of the stem and within the loop itself. One of ordinary skill in the art will understand that substitution of the ErkA gene fragment sequences by other sequences can be easily accomplished by standard cloning and sub-cloning methods.

Transformation of plasmids pAPSE10180 or pAPSE10181, or any of their derivatives, into host cells capable of inducible expression of T7 polymerase produces cell lines capable of expressing RNA transcripts. All such strains inducibly producing RNA transcripts are referred to generally herein as "expression strains". Unless otherwise indicated, each of the plasmids described herein was electroporated into *E. coli* strain HT115(DE3) with genotype $F^{31}$, mcrA, mcrB, IN (rrnD-rrnE)1, rnc14::Tn10 (Lambda DE3 lysogen: lacUV5 promoter-T7 polymerase)) and the resulting recombinant transformants were selected on LB agar plates containing 12 μg/ml tetracycline and/or 100 μg/ml ampicillin. Single colonies were isolated, the presence of intact plasmid confirmed by restriction enzyme analysis and the confirmed transformed cells archived for future use.

Standard expression studies comprised inoculating transformed cells into 100 ml of Super Broth containing 0.1% glucose, 0.4% lactose, 100 μg/ml ampicillin and/or 12.5 μg/ml tetracycline and incubating the cultures with vigorous shaking at 37° C. Expression of the T7 polymerase was achieved by auto-induction by depletion of the available glucose and the presence of the lactose inducer. This ensures that all cultures are induced at the same growth stage. Cells were harvested twelve to eighteen hours post-induction (late stationary phase) by centrifugation at 3,000 g at 4° C. for 30 minutes and stored on ice until lysis.

RNA was isolated from harvested cells by resuspending a 5 ml equivalent of cell culture of harvested cells in sonication buffer comprising Tris-HCl pH 7, 10 mM NaCl and sonicating the suspended cells on ice for 3 minutes. Cell debris was removed by centrifugation at 16,000 g the supernatant (cleared lysate) was immediately processed to recover RNA and VLPs as described. RNA was recovered from half of the cleared lysate using the commercial Purelink RNA Mini Kit method (Ambion Cat. No. 12183018A, Thermo Fisher Scientific Inc., Waltham, Mass.) according to the manufacturer's instructions.

VLPs were purified from the remaining half of the cleared lysate which were diluted to a total volume of 1 ml and treated with 100 units of Benzonase® Nuclease (Sigma Aldrich, St. Louis, Mo.) at 37° C. for two hours. Subsequently, 0.15 mg of Proteinase K was added and the enzymatically treated cleared lysate incubated at 37° C. for an additional three hours. The VLPS were recovered from the enzymatically treated cleared lysate by fractional precipitation. A saturated ammonium sulfate solution was prepared by adding ammonium sulfate to water until it reached saturation (approximately 4.1 M). Fifty microliters of the saturated ammonium sulfate solution was added to the enzymatically treated cleared lysate and the mixture placed on ice and incubated for two hours. Unwanted precipitate was removed from the mixture by centrifugation at 16,000 g and the aqueous solution transferred to a clean Eppendorf tube. The aqueous solution was then subjected to a second precipitation by the addition of 0.171 g of dry ammonium sulfate directly to the aqueous solution. The aqueous solution was vortexed and incubated on ice for two hours. The precipitate was spun down at 16,000 g the aqueous phase discarded and the solid precipitate representing purified VLPs resuspended in 100 microliters of sonication buffer.

RNA was recovered from the resuspended purified VLPs by adding 3 volumes of Trizol LS Reagent (Ambion Cat. No. 10296028, Thermo Fisher Scientific Inc.), vigorously vortexing the mixture, adding 1 ml of chloroform, further vortexing the mixture before pulse centrifugation to separate the aqueous and organic phases of the mixture. The aqueous phase was placed in a clean Eppendorf tube and the RNA purified with a commercial RNA Clean & Concentrator™ kit (Cat. No. R1018, Zymo Research, Irvine, Calif.) according to the manufacturer's instructions.

RNA from bacterial and VLP samples were dissolved in 50 μl of nuclease-free water. To determine the concentration of dsRNA in a sample, the samples were treated with RNAse A (Invitrogen Cat. No. AM2274, Thermo Fisher Scientific Inc.) to degrade single stranded RNA under the manufacturers recommended conditions, the concentration of dsRNA was determined spectrophotmetrically by measuring $OD_{260}$ and 1 μg loaded onto Novex 6% TBE-urea gels (Invitrogen, Thermo Fisher Scientific Inc.). One lane of each gel was loaded with dsDNA size markers of known concentration and the samples were electrophoresed, the gel was stained with ethidium bromide and each band quantitated by densitometry using the dsDNA markers as a standard curve.

RNA yields from constructs producing ssRNA were determined by annealing the sense or anti-sense strand recovered from the induced cells or VLPs with an excess of the cognate strand. The annealed mixture was then treated with RNAse A and the amount of dsRNA incorporating the ssRNA of interest measured as described above.

Little or no differences in final cell densities were observed between any of the cultures from which the samples were harvested and in all cases the cultures appear to have reached stationary phase prior to harvest. To allow direct sample to sample comparison of RNA yields, all dsRNA and ssRNA concentrations are reported as the amount of such RNA present in a 1 L equivalent of culture.

Northern blot analysis was used to verify the identity of bands containing the dsRNA transcripts using a DNA oligonucleotide probe against the random sequence comprising the loop of each dsRNA construct (5'-GGCCGGCGTCTATTAGTAGATGCC-3', SEQ ID NO 3). RNA from the 6% polyacrylamide denaturing Urea-TBE gel was transferred to a positively-charged BrightStar—Plus nylon membrane (Ambion Cat. No. 10102, Thermo Fisher Scientific Inc.) using the semi-dry Trans-Blot SD transfer apparatus (Bio-Rad, Hercules, Calif.) for 1 hour at constant current of 0.3 A. RNA was fixed on the membrane by the SpectroLinker XL-1500 UV crosslinking apparatus (Spectronics Corporation, Westbury, N.Y.) using the "optimal crosslink" setting. The membrane was briefly rinsed with water and prehybridized in 50 ml of 5×SSC, 0.1% SDS buffer at 45° C. with gentle shaking. Probe hybridization was carried out overnight at 45° C. in 3 ml of prehybridization buffer with gentle shaking. The oligonucleotide probe targeting the hairpin RNA loop was conjugated with TAMRA. Three washes (for 2 minutes each) with 100 ml of water were completed at room temperature and the blot with a ChemiDoc MP imaging system (BioRad, Hercules, Calif.), using the rhodamine channel.

C. Preferred Embodiments

The following are among the preferred embodiments of the invention.

One embodiment of the present invention comprises a bacterial host cell containing a plasmid encoding both a gene for the desired dsRNA and a bacteriophage capsid protein gene, such that the dsRNA and the capsid protein genes are transcribed so that the desired dsRNA is produced and the capsid protein gene translated to produce capsid protein and wherein, after a suitable period of time, unencapsidated dsRNA accumulates within the cell to a much higher degree than in the absence of capsid protein. In other embodiments the dsRNA gene and the capsid protein gene may be present on separate compatible plasmids, autonomously maintained phage or other epigenetic elements, or one or both genes may be present within the chromosome of the bacterial host cell.

In an embodiment the dsRNA gene and the capsid protein gene are each transcribed from a transcriptional promoter. The transcriptional promoter may be inducible. In one embodiment the transcriptional promoters are identical; in other embodiments the promoters are different. In still other embodiments the transcriptional promoters may be differentially induced. In such differentially inducible embodiments it may be preferable to induce expression of the capsid protein prior to inducing expression of the dsRNA.

In another embodiment the capsid protein and the dsRNA may be transcribed as a single transcript from a single promoter. The promoter may be inducible. In such embodiments the dsRNA is cleaved from the initial RNA transcript containing the capsid protein coding sequence by post transcriptional processing, such post transcriptional processing may depend on bacterial host cell processes or may be directed by other RNA processing systems such as ribozymes or specific ribonucleases.

In one embodiment one or both of the dsRNA and the capsid protein genes are inducibly transcribed from a transcriptional promoter and transcription is terminated by a transcriptional terminator. In an embodiment the inducible transcriptional promoter is the bacteriophage T7 gene 1 promoter. In other embodiments the inducible transcriptional promoter may be the bacteriophage Lambda $P_L$ or $P_R$ promoters, the lac operon, trp operon, or synthetic tac promoter, or bacteriophage T5 promoter. Other transcription promoters, both constitutive and inducible, known to those of ordinary skill in the art, may also be used in some embodiments. In an embodiment the transcriptional terminator is the bacteriophage T7 late terminator. Other transcription terminators, both rho-dependent and rho-independent, known to those of ordinary skill in the art may also be used in some embodiments.

In an embodiment the coat protein gene encodes a leviviral capsid protein. The coat protein gene may be the MS2 coat protein gene encoding the MS2 capsid protein or substantially similar sequences retaining the ability to allow accumulation of dsRNA in a microbial host cell. The coat protein gene may encode the Qbeta coat protein gene encoding the Qbeta capsid protein or substantially similar sequences retaining the ability to allow accumulation of dsRNA in a microbial host cell.

In an embodiment the dsRNA is recovered from the bacterial host cells co-expressing bacteriophage capsid protein by chemical or mechanical methods to produce a host cell lysate. In an embodiment the dsRNA is further purified from the host cell lysate to remove host cell derived proteins, nucleic acids and membranes including capsid protein. In another embodiment the host cell lysate is directly processed without further purification. In another embodiment bacterial host cells are killed, by chemical or heat or other means without lysis and the intact killed cells processed without further purification.

EXAMPLES

Example 1

Unencapsidated dsRNAs are Produced at Higher Levels in the Presence of Capsid Protein than in the Absence of Capsid Protein.

Expression strains containing pAPSE10180 and pAPSE10181 were constructed and dsRNA production induced by the standard expression procedure described above. The amount of encapsidated and unencapsidated dsRNA each strain produced was measured as described. The initial impetus for this experiment was to determine whether an RNA molecule with a 180 base pair double-stranded stem structure could be packed within a VLP. A 180 bp dsRNA stem is approximately 60 nm in length, whereas the interior diameter of an MS2 capsid is approximately 20 nm. Based on this geometric limitation, little or no encapsidation was expected and, due to host nuclease activity, little or no unencapsidated dsRNA was expected to be recoverable from the cell lysates. As expected only small amounts of encapsidated dsRNA (en capsid) were recovered (<2 mg/L) from the pAPSE10180 expression cells. In contrast, surprisingly large amounts of unencapsidated dsRNA (ex capsid) were recovered (75-90 mg/L) from the pAPSE10180 expression cells. Even more surprisingly, virtually no unencapsidated dsRNA was recovered from the pAPSE10181 expression cells.

To determine whether accumulation of RNA is a specific property of the ErkA sequence, or is a more general property of expressing dsRNA in the presence of capsid protein, a series of expression constructs expressing a 294 base sequence from the beta actin gene of the Colorado potato beetle (*Leptinotarsa decemlineata* strain Freeville, GenBank Accession NM_001300706 between nucleotides 156-335) were produced and tested.

Initially, plasmids expressing the 294 base beta actin sequence from Colorado potato beetle in the sense and the anti-sense orientation were constructed from pAPSE10180 by replacing the ErkA sequences, to produce pAPSE10189 (SEQ ID NO: 4 and pAPSE10190 (SEQ ID NO: 5) respectively. The beta actin sense and antisense strand sequences were amplified by PCR (Accuprime Pfx, Invitrogen Cat. No. 12344040, Thermo Fisher Scientific Inc.) from a gBlock template using primers that introduce the AsiSI and PmeI restriction sites at the 5' and 3' ends respectively (gBlock template DNA and PCR primers were synthesized by Integrated DNA Technologies, Coralville Iowa; all restriction endonucleases were from New England BioLabs, Beverly, Mass.). Restriction digest of pAPSE 10180 and the beta actin sense and antisense PCR fragment with AsiSI and PmeI resulted in DNA fragments that could be ligated together in the desired manner. The pAPSE10180 plasmid backbone lacking the ErkA sequence was gel purified and the sense and antisense beta actin sequences were ligated into the gel purified vector to produce pAPSE 10189 and pAPSE 10190, respectively. When transformed into a suitable expression host, such as HT115(DE3) the cells containing pAPSE10189 produces a ssRNA transcript comprising 294 bases of the sense strand of the beta actin gene flanked by pac sequences as well as co-express MS2 capsid protein, when cultured and induced as described above. Likewise, cells containing pAPSE10190 produces a ssRNA transcript comprising 294 bases of the anti-sense strand of the same region of the beta actin gene flanked by pac sequences as well as co-express MS2 capsid protein when transformed into a suitable expression host, cultured and induced as described. A second set of plasmids, lacking the ability to express MS2 capsid protein were also produced by replacing the ErkA sequences of pAPSE 10181 with the sense and anti-sense 294 base fragments of the beta actin gene as described above. These plasmids, pASPE10274 (SEQ ID NO: 6) and pAPSE10275 (SEQ ID NO: 7) respectively, were transformed into HT115(DE3) and cultured and induced as described.

Analysis of un-encapsidated RNA recovered from the cells whether co-expressed with capsid protein (as with pAPSE10189 and pAPSE10190) or not (pAPSE10274 and pAPSE10275) showed that virtually no ssRNA can be recovered. However, VLPs recovered from pAPSE10189 and pAPSE10190 yield at least 20 mg/L of ssRNA of sense or anti-sense sequence respectively. This confirms that the plasmid expression systems are capable of producing ssRNA and capsid protein as expected.

A dsRNA expression cassette comprising the 294 base Colorado potato beetle beta actin genes was constructed by a process similar to that described for the dsRNA ErkA expression cassette. In this case, the random DNA sequence comprising the loop between the sense and anti-sense strands of the beta actin sequences comprised 166 bases, including the same internal pac site sequence as found in pAPSE10180 and 10181. This beta actin expression cassette was cloned into pAPSE10180 replacing the ErkA related stem loop sequence to form plasmid pAPSE10269 (SEQ ID NO: 8), and into pAPSE10181 to form plasmid pAPSE10306 (SEQ ID NO: 9). The plasmids were transformed into HT115(DE3), cultured, and induced as described. Analysis of the encapsidated dsRNA produced by the cells containing pAPSE10269 strain showed that 2-10 mg/L dsRNA could be recovered from VLPs. However, much higher levels of the beta actin dsRNA could be recovered from the cells containing pAPSE10269 in unencapsidated form (200 mg/L). Strikingly, analysis of the RNA produced by the pAPSE10306 strain showed that in the absence of co-expressed capsid protein only about 3 mg/L of dsRNA could be recovered.

Thus, the high levels of unencapsidated dsRNA are consistent with a model in which such dsRNA are not packaged efficiently, but for some reason appear to be present within cells co-expressing capsid protein with the dsRNA at much higher levels than in cells which lack capsid protein. One model to account for this observation is that binding of capsid protein to the pac sites inhibits degradation by host cell nucleases.

Example 2

Specific Pac Site-Capsid Protein Interaction is not Required for High Level Production of dsRNA.

To test whether capsid protein bound to pac sites in the dsRNA results in the observed increase in dsRNA production in cells co-expressing capsid protein, perhaps inhibiting endogenous host nuclease degradation of the bound dsRNA, a series of constructs comprising the basic beta actin dsRNA described above were produced with varying numbers and locations of pac sites. Plasmids pAPSE10216 (SEQ ID NO: 10) and pAPSE10305 (SEQ ID NO: 11), are identical to pAPSE10269 and pAPSE10306 respectively, except they lack the internal loop pac site. Plasmids pAPSE10219 (SEQ ID NO: 12) and pAPSE10304 (SEQ ID NO: 13) are identical to pAPSE10217 and pAPSE10306 respectively, except they have only a single pac site located on the 3' end of the stem of the dsRNA. Plasmids pAPSE10279 (SEQ ID NO: 14) and pAPSE10303 (SEQ ID NO: 15) are identical to pAPSE10216 and pAPSE10306 except they lack all pac site sequences entirely. Each of these plasmids was transformed into *E. coli* HT 115(DE3), cultured and induced as described. Analysis of the encapsidated RNA recovered from VLPs of each of pAPSE10216 and pAPSE10219 show that 5-20 mg/L of dsRNA is encapsidated. Strikingly, even the strain containing pAPSE10279 entirely lacking pac sites produced 4 mg/L of encapsidated dsRNA, indicating that this level of encapsidation may represent non-specific entrainment of dsRNA present in the cells at the time the capsids were formed. Furthermore, the strain containing pAPSE10216 produced as much as 250 mg/L of unencapsidated dsRNA in the presence of capsid protein. The strains containing pAPSE10219 and pAPSE10279 produced 30-60 mg/L and 65 mg/L of unencapsidated dsRNA, respectively in the presence of capsid protein. All of the strains containing plasmids comprising the expression cassettes without co-expression of capsid protein produced <4 mg/L of dsRNA.

Together, these results indicate that the ability of capsid protein to increase the amount of unencapsidated dsRNA that can be recovered from cell lysates is not dependent on the specific binding of capsid protein to its cognate pac site sequence. Although the highest levels of unencapsidated dsRNA are recovered from constructs containing at least 5' and 3' flanking pac sites (approximately 200 mg/L), significant amounts of unencapsidated dsRNA are produced by constructs having only a single 3' flanking pac site, or lacking pac sites entirely. Cells containing plasmids producing dsRNA lacking pac sites altogether produce significantly higher amounts of dsRNA (65 mg/L) when capsid protein is co-expressed with the dsRNA relative to the cell lines lacking capsid protein altogether (3-4 mg/L). The approximately 16× increase in recoverable dsRNA between cells co-expressing capsid protein and those lacking capsid protein (65 mg/L versus 3-4 mg/L) is much more than the approximately 3×-4× increase due to the presence of pac sites (65 mg/L versus 200-250 mg/L). The effect of capsid protein co-expression appears to involve something other than mere binding to cognate pac site sequences that may (or may not) be present on the dsRNA.

Example 3

Loop Size and Structure are Irrelevant to High Level Production of dsRNA.

To test what effect, if any, differences in loop sequence might exert on the production of dsRNA in the presence and absence of co-expressed capsid protein, a series of constructs with different lengths of internal non-homologous loop sequences were inserted between each of the 294 base sense and anti-sense beta actin sequences of pAPSE 10269.

Plasmids pAPSE10270 (SEQ ID NO: 16), pAPSE10271 (SEQ ID NO: 17), pAPSE10272 (SEQ ID NO: 18) and pAPSE10292 (SEQ ID NO: 19) have non-homologous loop sizes of 116 bases, 136 bases, 156 bases and 166 bases respectively. Each of these loop sequences has very little propensity for any secondary structure as determined by the m-fold structure prediction program (Zucker and Stiegler (1981) *Optimal computer folding of large RNA sequences using thermodynamics and auxiliary information* Nucl. Acids. Res. 9(1):133-48). In addition, the 139 base loop sequence found associated with the ErkA stem sequences in pAPSE10180 and having a slightly higher propensity for structural interactions within the loop was also placed between the sense and anti-sense beta actin sequences of pAPSE 10269, to form pAPSE10292. Additionally, pAPSE10291 (SEQ ID NO: 20) comprising a 142 base loop sequence with a high degree of propensity for forming secondary structure based on internal homology was synthesized and constructed as described.

Each of the plasmids described in this Example were transformed into *E. coli* expression strain HT115(DE3), cultured and induced and the amount of encapsidated and unencapsidated dsRNA determined as described. In each case 2-10 mg/L of dsRNA was recovered from the VLPs produced by inducing expression of the plasmid, indicating that loop size or structure had little or no effect on the ability of VLPs to encapsidate the dsRNA. Likewise, expression from each of the plasmids produced between 100 and 200 mg/L unencapsidated dsRNA, indicating that loop size or structure had little or no effect on overall production of unencapsidated dsRNA in the presence of capsid protein.

Example 4

Stem Size is Irrelevant to High Level Production of dsRNA.

Differences in stem sequence derived from the *Drosophila melanogaster* ErkA gene sequences expressed from pAPSE10180 and the Colorado potato beetle beta actin gene sequences expressed from pAPSE10269 do not make a significant difference in the ability in expression strains to produce large quantities of unencapsidated dsRNA (75-90 mg/L from pAPSE10180 versus 200 mg/L from pAPSE10269). Nor does the length of the dsRNA stem (180 base pairs in the dsRNA produced from pAPSE10180 and 294 base pairs in dsRNA from pAPSE10269). To more systematically test what affect, if any, differences stem sequence length might exert on the production of dsRNA in the presence and absence of co-expressed capsid protein, a series of expression constructs with different lengths of stem sequences were substituted for each of the 294 base stem forming sense and anti-sense beta actin sequences of pAPSE10269.

Plasmids pAPSE10276 (SEQ ID NO: 21) and pAPSE10277 (SEQ ID NO: 22) encode dsRNA with potential double-stranded stems of 50 and 75 base pairs respectively. The dsRNA expressed by both plasmids comprise 166 bases of non-homologous loop sequence. Although these dsRNA structures are significantly shorter than those in dsRNA from the corresponding ErkA and beta actin constructs, they still exceed the interior diameter of the MS2 VLP.

When transformed into the *E. coli* expression strain HT 115(DE3), cultured and induced as described, pAPSE 10276 produces 5-10 mg/L of encapsidated dsRNA and 80-120 mg/L of unencapsidated dsRNA. Plasmid pAPSE 10277 produces 20-30 mg/L encapsidated dsRNA and 200-250 mg/L unencapsidated dsRNA. These values are similar to those observed for pAPSE10180 and pAPSE10269 described earlier in this Example, indicating that differences in stem length and sequence do not play a major role in producing dsRNA in cells co-expressing capsid protein.

Example 5

Capsid Protein is Required for High Level Production of dsRNA.

To confirm the requirement for capsid protein, plasmid pAPSE10216, which produces a dsRNA product at high levels in the presence of capsid protein, was altered to replace the MS2 coat protein gene with eGFP. A gBlock template comprising the T7 promoter to T7 terminator sequences of pAPSE10216 (spanning the sequences between the unique BamHI and SalI sites of the plasmid) in which the coding sequence of MS2 coat protein was replaced with the coding sequence of eGFP was designed, produced and amplified with primers encompassing the BamHI site on the 5' side and the SalI site on the 3' side. The resulting 1 kb fragment was digested with BamHI and SalI and then ligated into BamHI-SalI digested pAPSE10216 to form pAPSE10366 (SEQ ID NO: 24). Plasmid pAPSE10366 was confirmed by restriction digest and transformed into the *E. coli* expression strain HT 115(DE3), cultured and induced as described, pAPSE10366 produces <2 mg/L of unencapsidated dsRNA, in contrast to the 200 mg/L produced by pAPSE10216. In addition, the cells expressed high amounts of eGFP as evidenced by the intense fluorescence produced on induction (data not shown) confirming that the basic dual expression plasmid used throughout these studies performs as expected. This result further demonstrates that capsid protein is necessary for accumulation of unencapsidated dsRNA in cells expressing the target RNA gene that otherwise accumulate unencapsidated dsRNA in the presence of capsid protein.

To further confirm that the presence of capsid protein is essential to the high levels of unencapsidated dsRNA production a plasmid compatible with pAPSE10181 and capable of inducible expression of the MS2 capsid protein is constructed. pAPSE10149 (SEQ ID NO: 23) is based on pACYC184. This plasmid comprises a P15A origin of replication that is not excluded by the colE1 based origin of replication of pAPSE10181 and a chloramphenicol acetyl transferase antibiotic marker to allow selection of co-transformants containing both pAPSE 10181 (encoding ampicillin resistance) and pAPSE10149 (encoding chloramphenicol resistance). Plasmid pAPSE10149 also comprises the same T7 promoter sequence capable of driving transcription of a single copy of the bacteriophage MS2 capsid gene followed by a T7 terminator as found in pAPSE10118 cloned into the BamHI and SphI sites of pACYC184. Plasmid pAPSE10149 is transformed into expression strains already containing pAPSE10181 to produce ampicillin and chloramphenicol resistant double transformants. Expression studies of such double transformants show that co-expression of the capsid protein from pAPSE10149 in conjunction with pAPSE10181 produces 200 mg/L of unencapsidated dsRNA whereas cells containing pAPSE10181 alone produce <2 mg/L of unencapsidated dsRNA (see Example 1). This demonstrates that providing capsid protein in trans is sufficient to facilitate production of high levels of unencapsidated dsRNA to host cells containing a plasmid expressing the dsRNA target that otherwise fail to accumulate unencapsidated dsRNA in the absence of capsid protein.

Example 6

Other Capsid Proteins can Induce High Level Production of dsRNA.

To test whether the accumulation of unencapsidated dsRNA is a unique property of bacteriophage MS2 capsid protein, or whether other capsid proteins share this property, a plasmid expression system analogous to pAPSE10216 was constructed. This plasmid, pAPSE10359 (SEQ ID NO: 25) comprises a Qbeta capsid protein and Qbeta pac sites at the 5' and 3' ends of the beta actin dsRNA expression cassette, but is in all other aspects similar to pAPSE10216.

Briefly, the Qbeta coat protein gene sequence (Genebank Accession NC_001890 between nucleotides 1343 and 1744) was synthesized as a gBlock fragment by Integrated DNA Technologies, Coralville, Iowa The synthetic fragment was amplified with PCR with primers that introduced a BamHI restriction site followed by a T7 promoter sequence upstream of the Qbeta coat protein gene followed by a T7 terminator and a SphI restriction site. The amplified synthetic fragment and plasmid pBR322 were digested with BamHI and SphI and ligated together to form intermediate plasmid pAPSE10358. The beta actin dsRNA sequence of pAPSE10269 was amplified by PCR with primers that introduced an EcoRI restriction site followed by a Qbeta pac sequence followed by the beta actin dsRNA sequence followed by a second copy of the Qbeta pac sequence followed by a BamHI restriction site. This amplified beta actin containing sequence and plasmid pAPSE10358 were digested with EcoRI and BamHI and ligated together to form pAPSE10374. Plasmids pAPSE10374 and pAPSE10216 were digested with AsiSI and NotI. This cleaves pAPSE 10374 into two fragments of 4,713 and 113 base pairs and pAPSE10216 into two fragments of 5,204 and 786 base pairs. The 4,713 and 786 base pair fragments were isolated and ligated together to produce pAPSE10359.

When transformed into the *E. coli* expression strain HT 115(DE3), cultured and induced as described, pAPSE10359 will produce a large amount of unencapsidated dsRNA relative to the amount of dsRNA produced from a similar construct lacking capsid protein (pAPSE10305). This pattern, similar to that observed for pAPSE10216 and pAPSE10305 described in Example 1, will confirm that expression of the Qbeta capsid protein, like the MS2 capsid protein, is sufficient to increase the amount of dsRNA produced in vivo.

Example 7

RNA Binding Proteins Other than Capsid Proteins are not Sufficient for High Level Production of dsRNA.

To test whether the accumulation of unencapsidated dsRNA is a function of general RNA binding or is specific to bacteriophage capsid proteins, a plasmid expression system, pAPSE10357 (SEQ ID NO: 26) was constructed comprising the RNA binding domain of the human U1A protein and its hairpin cognate binding site from human U1 snRNA 5' and 3' of the sense and antisense stem loop structure of the beta actin dsRNA. Plasmid pAPSE10357 is similar to pAPSE10216 with the capsid protein replaced by the human U1A RNA binding protein and U1A binding site sequences at the 5' and 3' ends of the beta actin dsRNA expression cassette, but is in all other aspects similar to pAPSE10216.

The DNA sequence encoding the N-terminal 102 amino acids comprising the RNA binding domain of the human U1A protein was amplified from a cloned copy of the U 1A protein (Plasmid pAV105, Professor Kathleen Hall, Washington University, St. Louis, Mo.) using PCR primers that introduced a BamHI restriction site followed by a T7 promoter sequence upstream of the U1A gene fragment followed by a T7 terminator and a SphI restriction site. The amplified synthetic fragment and plasmid pBR322 were digested with BamHI and SphI and ligated together to form intermediate plasmid pAPSE10356. The beta actin dsRNA sequence of pAPSE10269 was amplified by PCR with primers that introduced an EcoRI restriction site followed by the hairpin binding site sequence from human U1 snRNA sequence followed by the beta actin dsRNA sequence followed by a second copy of the hairpin binding site sequence from human U1 snRNA sequence followed by a BamHI restriction site. This amplified beta actin containing sequence and plasmid pAPSE10356 were digested with EcoRI and BamHI and ligated together to form pAPSE10373. Plasmids pAPSE10373 and pAPSE10216 were digested with AsiSI and NotI. This cleaves pAPSE10373 into two fragments of 4,627 and 113 base pairs and pAPSE10216 into two fragments of 5,204 and 786 base pairs. The 4,713 and 786 base pair fragments were isolated and ligated together to produce pAPSE10357.

When transformed into the *E. coli* expression strain HT115(DE3), cultured and induced as described, pAPSE10357 will not produce a significant amount of unencapsidated dsRNA relative to the amount of dsRNA produced from a similar construct lacking capsid protein (pAPSE10305). This will confirm that the mere presence of an RNA binding site and binding protein in conjunction with the dsRNA is not sufficient to increase the amount of dsRNA produced in vivo. Alternatively, production of significant amounts of unencapsidated dsRNA will indicate that the presence of RNA binding sites at the 5' and 3' end and the cognate RNA binding protein is sufficient for increasing in vivo production of dsRNA.

Example 8

The N-Terminus of Capsid Protein is Sufficient for High Level Production of dsRNA To examine whether the increased production of dsRNA from plasmids containing both the dsRNA gene and the coat protein gene requires the intact capsid protein or whether only a portion of the protein is required, a frame-shift mutation was introduced into the coat protein gene sequence of pAPSE10180. Double digestion of pAPSE10180 with the restriction enzymes StuI and PmlI produces two restriction fragments, a large fragment of 5,485 base pairs and a small thirteen base pair fragment comprising about 4 codons of the capsid protein CDS about 40 codons from the coat protein start codon of pAPSE10180. The restriction enzymes produce blunt-ended termini and the larger fragment was religated to produce plasmid pAPSE10372 (SEQ ID NO: 27), which, in addition to producing an intact inducible dsRNA ErkA-specific sequence, also comprises an inducible frame-shifted protein that includes the N-term 41 codons of the MS2 coat protein followed by 27 codons of frame-shifted sequence before terminating at a stop codon (SEQ ID NO: 28). When pAPSE10372 was transformed into *E. coli* expression strain HTE115(DE3) and cultured and induced as described, 75 mg/L of dsRNA was produced. This indicates that the N terminus of the capsid protein alone is sufficient to increase production of dsRNA as well as the intact capsid protein (compare yields from pAPSE10180 and pAPSE10372 in Table 1).

The N-terminus of the MS2 capsid protein forms a distinctive three-dimensional structure comprised of four separate beta sheets (D. Peabody, *The RNA binding site of bacteriophage MS2 coat protein*, The EMBO Journal 12(2) 595-600 (1993)). Each of these sheets, βD from amino acids 31-35, βC from amino acids 22-25, βB from amino acids 19-21 and βA amino acids 8-11 may play a role in the ability of the N-terminus capsid protein fragment to improve dsRNA production. Note that the nomenclature is that of Peabody and the numbering includes the N-terminal methionine omitted by Peabody. Progressive deletion of each of these structural motifs can determine the minimum sequence requirement for improving dsRNA production.

Example 9

Fed Batch Fermentation Produces Very High Level Production of dsRNA

To determine whether quantities of dsRNA could be increased by improving the microbial growth conditions, glucose fed batch fermentations were conducted. Briefly, fed-batch fermentations were carried out in an Eppendorf BioFlo 115 fermenter at 37° C. The pH was controlled by automatic addition of 30% ammonium hydroxide. The dissolved oxygen probe was calibrated to 0% by unplugging the DO probe and to 100% with air saturation. The vessel was aerated at 2 vvm and dissolved oxygen maintained at 30% by cascade control of agitation. An overnight culture of HT 115 (DE3) containing pAPSE10379 was grown in LB containing 100 ug/ul of ampicillin and 12.5 ug/ul of tetracycline at 37° C. to inoculate the seed medium. The seed media is a defined media consisting of 5.68 g/L $Na_2HPO_4$, 1.34 g/L $KH_2PO_4$, 6.6 g/L $(NH_4)_2SO_4$, 10 g/L glucose, 1× trace metal and 1× vitamin solutions maintained at a pH of 7.0. To ensure plasmid stability antibiotics are added at 100 ug/ul ampicillin and 12.5 ug/ul tetracycline. At saturation ($OD_{600}$ 3-5) the seed cultures are used to provide 10% inoculum for the fermenter.

During fed batch-cultures a 50% (w/v) solution of glucose was added according to a carbon limiting DO stat feeding strategy. The basal medium consists of 6 g/L $K_2HPO_4$, 3 g/L $NaHPO_4$, 10 g/L $(NH_4)_2SO_4$, 1 g/L $MgSO_4$, 1× trace metal solution with antibiotics added at 100 ug/ul of ampicillin and 12.5 ug/ul of tetracycline. Upon exhaustion of the initial carbon source provided by the glucose the feed solution is added automatically in a manner that maintains the DO level at 30% of saturation.

Once the cell culture has reached an $OD_{600}$ of 60 the cells are induced with 1 mM IPTG or a feed of 20 g/L of lactose by switching the glucose feed to a lactose feed. After induction 1 mL samples are taken at different times post induction. The samples are lysed by sonication of the cell pellet into 20 mM Tris-HCl at pH 7. Total RNA from the cell pellet is purified using well-known Trizol extraction procedures. Briefly 1 volume of cell lysate is added to 1 volumes of Trizol RNA extraction reagent. Addition of 1 volume of chloroform results in the RNA partitioning to the aqueous layer leaving the protein and DNA contaminants behind.

To analyze the yield of dsRNA the total RNA sample is diluted to 1 ug/ul and subjected to RNAseA treatment. The reaction is carried out in 20 mM Tris at pH 7.0 and 37° C. for 40 minutes. Once this is done proteinase K is added to the reaction to remove the nuclease and is allowed to react at 37° C. for 40 minutes. Upon completion of this step the dsRNA remaining is diluted in half, quarters and eighths in order to determine the concentration of the dsRNA using gel densitometry.

Quantification of dsRNA yield by gel densitometry was performed by comparing the intensity of dsRNA bands versus dsDNA bands of known mass and weight on a 1.5% agarose gel containing ethidium bromide. The lambda 100 bp quantifiable DNA marker was used and a standard curve was generated to determine the range in which the dsRNA from the fermentation can be reliably quantified. The computer program calculates the amount of dsRNA in the amount of sample loaded on the gel and a back calculation that considers the dilution steps is performed. Yields of dsRNA at levels as high as 3 g/L have been calculated with both IPTG and lactose as inducers under these conditions. These results indicate that further increases in dsRNA production are possible by improving fermentation conditions.

Example 10

Compositions and Methods for dsRNA Production in Gram Positive Bacteria

The ability of gram-positive bacteria to produce increased levels of dsRNA by co-expression of capsid proteins can be examined in the following manner. *Corynebacterium glutamicum* MB001(DE3) strain DSM 102071, containing an inducible T7 RNA polymerase gene (described in Kortmann, et al., *A chromosomally encoded T7 RNA polymerase-dependent gene expression system for Corynebacterium glutamicum; construction and comparative evaluation at the single cell level*. Microb Technol. 8(2):253-65. March 2015) is modified to knockout the rnc gene homolog encoding RNAse III. Briefly, PCR primers capable of amplifying a 1.2 kb sequence homologous to the sequence present in *C. glutamicum* strain MB001(DE3) immediately upstream of the rnc gene and PCR primers capable of amplifying a 1.5 kb sequence homologous to the sequence immediately downstream of the rnc gene are synthesized. A PCR amplification reaction using *C. glutamicum* strain MB001(DE3) genomic DNA and said primers results in a single DNA fragment comprising the 1.2 kb and 1.5 kb target sequences joined together (by standard overlap PCR methods) to produce an approximately 2.7 kb SalI-BamHI synthetic DNA fragment. This SalI-BamHI DNA fragment and plasmid pK18mobsacB (ATCC 87097, described by Schafer, et al., *Small mobilizable multi-purpose cloning vectors derived from the Escherichia coli plasmids pK*18 *and pK*19*: selection of defined deletions in the chromosome of Corynebacterium glutamicum*. Gene 145:69-73) are digested with SalI and BamHI and the products ligated together to produce plasmid pAPSE10429 (SEQ ID NO: 29). Plasmid pAPSE10429 is transformed into *C. glutamicum* strain MB001 and transformants selected on kanamycin containing solid LB medium to identify chromosomal integrants. Kanamycin resistant clones are transferred to a solid LB medium containing 20% sucrose. Conversion of sucrose by the sacB gene product is toxic to *C. glutamicum* strain MB001 so only those chromosomal integrants that subsequently delete the sacB gene from the chromosome can survive on such media. Surviving colonies are grown up and screened by PCR to confirm concomitant loss of the rnc locus from the chromosome. The desired strain is designated *C. glutamicum* MB001(DE3) rnc. This strain possesses an inducible T7 RNA polymerase and lacks the rnc gene and is suitable for testing the efficacy of dsRNA production in the presence and absence of capsid protein.

A shuttle vector capable of expression of capsid coat protein and dsRNA in both *E. coli* and *C. glutamicum* is constructed by synthesizing a DNA comprising the origin of replication of the gram-positive plasmid pCG1 (GeneBank Accession No. AB027714; described by Trautwetter and Blanco, *Structural organization of the Corynebacterium glutamicum plasmid pCG*100. J. Gen. Microbiol. 137:2093-101 1991) and the kanamycin resistance gene of pK18mobsacB. This synthetic DNA (SEQ ID NO: 30) is ligated into the previously described dsRNA containing plasmids at the unique NruI restriction site to allow testing whether the presence of capsid protein in gram-positive *C. glutamicum* MB001(DE3) rnc strain produces dsRNA at high levels as described below.

Insertion of the synthetic DNA comprising the pCG1 origin of replication and the kanamycin resistance gene is accomplished by digesting pAPSE10279 with NruI and ligating the phosphorylated synthetic DNA into the plasmid to produce plasmid pAPSE10430 (SEQ ID NO: 31). Plasmid pAPSE10430 contains the kanamycin resistance gene, the bacteriophage MS2 coat protein, and the dsRNA construct based on the previously described 294 base sense and antisense sequences homologous to the Colorado potato beetle beta actin gene separated by a 166 base non-homologous loop and entirely lacking any pac sequences. In similar fashion, the synthetic DNA comprising the pCG1 origin of replication and the kanamycin resistance gene is also ligated into NruI digested pAPSE10303 to produce pAPSE10431 (SEQ ID NO: 32). Plasmid pAPSE10431 contains resistance genes to ampicillin and kanamycin, as well as the same inducible dsRNA construct as pAPSE10430. However, pAPSE10431 lacks the inducible MS2 coat protein gene of pAPSE10430. The relevant features of pAPSE10430 and pAPSE10431 are presented in Table 2 and the relationship between these two plasmids and their parental plasmids, pAPSE10279 and pAPSE10303, respectively, can be determined by comparing Table 2 and Table 1.

Additional plasmids containing one, two, and three pac sites, with and without MS2 coat protein, are constructed using the same procedure. Plasmid pAPSE10432 (SEQ ID NO: 33) containing a single pac site 3' of the beta actin stem loop structure and encoding the MS2 coat protein gene is produced by ligating the synthetic DNA fragment into the NruI site of pAPSE10219. Plasmid pAPSE10433 (SEQ ID NO: 34) is produced by ligating the synthetic DNA fragment into the NruI site of pAPSE10304. Plasmid pAPSE10433 is identical to pAPSE10432 except it lacks an inducible MS2 coat protein gene. Plasmid pAPSE10434 (SEQ ID NO: 35) containing two pac site sequences located one on either side of the beta actin stem loop and encoding the MS2 coat protein is produced by ligating the synthetic DNA fragment into the NruI site of pAPSE10216. Plasmid pAPSE10435 (SEQ ID NO: 36) is produced by ligating the synthetic DNA fragment into the NruI site of pAPSE10305. Plasmid pAPSE10435 is identical to pAPSE10434 except it lacks an inducible MS2 coat protein gene. Plasmid pAPSE10436 (SEQ ID NO: 37) containing three pac site sequences with one each 5' and 3' of the beta actin stem loop and one within the loop sequence itself (as depicted in FIG. 1) and encoding the MS2 coat protein is produced by ligating the synthetic DNA fragment into the NruI site of pAPSE10269. Plasmid pAPSE10437 (SEQ ID NO: 38) is produced by ligating the synthetic DNA fragment into the NruI site of pAPSE10306. Plasmid pAPSE10437 is identical to pAPSE 104360 except it lacks an inducible MS2 coat protein gene.

In each case, following ligation of the synthetic DNA fragment into the NruI site of the target plasmid, transformants the ligation reactions are desalted and transformed in to *C. glutamicum* MB001(DE3) rnc and selected for resistance to kanamycin. The selected clones are subsequently grown at 32° C. in 100 ml of LB media containing kanamycin until the culture reaches OD600 0.8, at which time isopropyl β-D-thiogalactopyranoside is added to a final concentration of 1 mM to induce T7 polymerase directed transcription of the MS2 coat protein and the dsRNA, or just the dsRNA precursor in the plasmids lacking coat protein. The induced cultures are allowed to grow for at least 4 hours post-induction to allow sufficient time for accumulation of the MS2 coat protein and dsRNA target. Cells are collected by centrifugation at 3,000 g at 4 C. Each pellet is stored at 4° C. until processing.

The dsRNA is purified by re-suspending each pellet in approximately 0.1 volume of 20 mM Tris-HCl, pH 7.0, containing 10 mM NaCl and sonicated to lyse the cells. Cell debris is removed by centrifugation at 16,000 g. The resulting lysate is mixed with 3 volumes of Trizol (Ambion Life Technologies) and the RNA is extracted by adding 1 volume of chloroform. Addition of NaCl to a final concentration of 500 mM to the aqueous layer and subsequent ethanol precipitation results in a pellet containing the 294 bp siRNA precursor and RNA from the *C. glutamicum* host.

To determine the amount of dsRNA produced by the *C. glutamicum* transformed with plasmids containing various pac site configurations, with and without MS2 coat protein, the ethanol pellets are resuspended and treated with RNAseA for 1 hour at 37° C. followed by Proteinase K digestion for 1 hour at 37° C. Quantification of the dsRNA is accomplished by gel densitometry using a BioRad ChemiDoc MP Imaging System. Several dilutions of the treated dsRNA are run on a 1.5% agarose gel containing 0.001% ethidium bromide. A 100 bp quantifiable dsDNA ladder (QuantiBP DNA ladder Lambda) is used as the standard curve and the dsRNA is quantified at the concentration that falls within the linear range of the standard curve. Software such as Image Lab 4.1 determines the concentration of the dsRNA loaded on the gel and a final yield of dsRNA is determined by accounting for the dilutions associated with the dsRNA samples present on the gel.

Table 2 summarizes the predicted results of the dsRNA yield determination of the Colorado potato beetle beta actin dsRNA produced by *C. glutamicum* MB001(DE3) rnc and the various plasmids described above. Such results confirm that gram positive hosts such as *C. glutamicum* produce large quantities of dsRNA by co-expression of the MS2 coat gene and a dsRNA target of interest.

TABLE 2

Predicted production of dsRNA by *C. glutamicum* MB001(DE3) rnc as a function of variation in dsRNA structure and the presence or absence of coat protein.

| RNA Structure as depicted in | Plasmid | Loop size (bases) | Stem size (bp) | Stem sequence | Coat protein | dsRNA (mg/L) |
|---|---|---|---|---|---|---|
| FIG. 6 | pAPSE10430 | 166 | 294 | beta actin | MS2 | ~60 |
| FIG. 6 | pAPSE10431 | 166 | 294 | beta actin | none | ~4 |
| FIG. 5 | pAPSE10432 | 166 | 294 | beta actin | MS2 | ~120 |
| FIG. 5 | pAPSE10433 | 166 | 294 | beta actin | none | ~4 |
| FIG. 4 | pAPSE10434 | 166 | 294 | beta actin | MS2 | ~250 |
| FIG. 4 | pAPSE10435 | 166 | 294 | beta actin | none | ~4 |
| FIG. 1 | pAPSE10436 | 166 | 294 | beta actin | MS2 | ~250 |
| FIG. 1 | pAPSE10437 | 166 | 294 | beta actin | none | 4 |

Example 11

Compositions and Methods for dsRNA Production in Yeast

To create a *Saccharomyces cerevisiae* production host suitable for dsRNA accumulation utilizing the MS2 bacteriophage coat protein, the Rntl gene of *S cerevisiae* YPH 500 (ATCC 76626) is knocked out according to the procedure of Gardenr and Jasperson (Gardner, J M and Jaspersen, S L, *Manipulating the yeast genome: deletion, mutation and tagging by PCR*. Methods Mol Biol. 1205:45-78, 2014). The KanMx4 gene is amplified from pML104-KanMx4 plasmid (Laughery, et al., *New vectors for simple and streamlined CRISPR-Cas9 genome editing in Saccharomyces cerevisiae*. Yeast 32(12):711-20 Sep. 21, 2015) with PCR primers including 60 base pair (bp) upstream (forward primer) and 60 bp downstream (reverse primer) regions of the *S. cerevisiae* Rntl gene. The resulting PCR product is introduced into chemically competent *S. cerevisiae* cells following the established *S. cerevisiae* transformation protocol. The transformed cells are incubated overnight without selection marker to allow for homologous recombination to occur, where in the kanMx4 gene carrying 60 bp upstream and downstream regions of Rntl replaced the Rntl gene. Following overnight incubation, the transformed cells are plated on YPD plates carrying G418 as selection marker. G418 resistant colonies are screened by PCR to confirm presence of kanMx4 gene and deletion of Rntl gene in the YPH 500 genome.

*S. cerevisiae* expression vectors pESC-His, pESC-Leu, pESC-Ura and pESC-Trp are widely used for recombinant protein expression in *S. cerevisiae*. Each of the pESC vectors (Agilent Technologies, Santa Clara Calif.) contains one of four different yeast-selectable markers (HIS3, TRP1, LEU2, or URA3) in the same vector backbone, which allows expression of two different genes in a single yeast cell. The pESC series vectors are used with *S. cerevisiae* strain YPH 500 (MATα ura3-52 lys2-801_amber ade2-101_ochre trp1-Δ63 his3-Δ200 leu2-Δ1). In this example, the pESC-Trp vector is selected for expression of MS2 coat protein and target dsRNA sequence inside *S. cerevisiae*, although any of the other pESC vectors could be employed using similar methods since these vectors can replicate in *S. cerevisiae* as well as *E. coli*, which facilitates molecular manipulations necessary to produce dsRNA.

The pESC-Trp vector is modified by cloning a 50-base pair multi-cloning site linker containing BamHI, SwaI, AsiSI, NotI, SacII and NheI sites, downstream of the GAL1 promoter into the existing BamHI and NheI sites. Following this, the beta actin stem loop sequence (dsRNA) of pAPSE10279 is excised as an AsiSI/NotI fragment and ligated into the AsiS1/Not1 sites of the modified pESC-Trp vector. Expression of the dsRNA in this plasmid is under the control of galactose inducible promoter GAL1. The new vector is named pAPSE10439 (SEQ ID NO: 39). Another plasmid, pAPSE10440 (SEQ ID NO: 40), which is identical to pAPSE10439, but also includes the MS2 coat protein. Plasmid pAPSE10440 is constructed by PCR amplifying the MS2 coat protein expression sequences of pAPSE10279 with a forward primer carrying an EcoRI restriction site on the 5' end and the reverse primer carrying SacI site on the 3' end. The PCR product is digested with EcoRI and SacI and cloned into the cognate sites of pAPSE10439. Thus, pAPSE10439 inducibly expresses the dsRNA from the GAL1 promoter, whereas pAPSE10440 inducibly expresses the dsRNA sequence from the GAL1 promoter and the MS2 coat protein from the GAL10 promoter, Similar plasmid pairs are constructed using this technique. Plasmids pAPSE10441 (SEQ ID NO: 41) and pAPSE10442 (SEQ ID NO: 42) are produced by digesting pAPSE10439 and pAPSE10440 with AsiSI and NotI and isolating the vector fragment. Plasmid pAPSE10219 is also digested with AsiSI and NotI and the dsRNA sequence is isolated. The isolated dsRNA sequence is ligated into the pAPSE10439 vector to form pAPSE10441 and the isolated dsRNA sequence is ligated into the pAPSE10440 vector to form pAPSE10442. Plasmids pAPSE10443 (SEQ ID NO: 43) and pAPSE10444 (SEQ ID NO: 44) are produced by digesting pAPSE10439 and pAPSE10440 with AsiSI and NotI and isolating the vector fragment. Plasmid pAPSE10216 is also digested with AsiSI and NotI and the dsRNA sequence is isolated. The isolated dsRNA sequence is ligated into the pAPSE10439 vector to form pAPSE10443 and the isolated dsRNA sequence is ligated into the pAPSE10440 vector to form pAPSE10444. Plasmids pAPSE10445 (SEQ ID NO: 45) and pAPSE10446 (SEQ ID NO: 46) are produced by digesting pAPSE10439 and pAPSE10440 with AsiSI and NotI and isolating the vector fragment. Plasmid pAPSE10269 is also digested with AsiSI and NotI and the dsRNA sequence is isolated. The isolated dsRNA sequence is ligated into the pAPSE10439 vector to form pAPSE10445 and the isolated dsRNA sequence is ligated into the pAPSE10440 vector to form pAPSE10446.

Chemically competent YPH 500 DRnt1 cells are transformed with each of the above mentioned plasmids (pAPSE10439-46) separately and individual clones selected on synthetic dextrose minimal (SD) tryptophan (trp) drop out plates. After inoculating the 100 ml SD-Trp drop out broth the cultures are grown for 12 to 16 hours. The cells from the culture are then harvested by centrifugation at 3000 g for 5 minutes, the cell pellet is washed once with sterile water and the cells re-suspended in synthetic galactose minimal broth (SG) lacking tryptophan. The cells are grown in the SG-trp drop out broth overnight to induce production and accumulation of dsRNA and MS2 coat protein (where appropriate). Cells are harvested by centrifugation at 3,000 g at 4 C. Each pellet is stored at −20° C. until processing.

The dsRNA is purified by re-suspending each pellet (10 ml culture) in approximately 1.0 ml of yeast cell lysis buffer (Sigma C4482). The resulting lysate is mixed with 3 volumes of Trizol (Ambion Life Technologies) and the RNA extracted by adding 1 volume of chloroform. Addition of NaCl to a final concentration of 500 mM to the aqueous layer and subsequent ethanol precipitation results in a pellet containing the dsRNA and RNA from the *S. cerevisiae* host. The resulting RNA pellet is dissolved in 20 mM Tris HCl pH 7.0 and RNA concentration of the sample determined. To determine the amount of dsRNA produced by the *S. cerevisiae* strains, a known amount of RNA (10 ug) from each RNA sample from pAPSE10439-pAPSE10446) are digested with RNAseA for 1 hour at 37° C. followed by Proteinase K digestion for 1 hour at 37° C. The resulting samples contain only the dsRNA target. Quantification of the dsRNA is done by gel densitometry using a BioRad ChemiDoc MP Imaging System. Several dilutions of the RNAse A reaction are run on a gel that contains 1.5% agarose and 0.001% ethidium bromide. A 100 bp quantifiable dsDNA ladder (QuantiBP DNA ladder Lambda) is used as the standard curve and the dsRNA is quantified at the concentration that falls within the linear range of the standard curve. Using Image Lab 4.1 software, the concentration of the dsRNA loaded on the gel is determine and a final yield of dsRNA calculated by accounting for the dilutions of the dsRNA loaded on the gel.

Table 3 summarizes the predicted results of the dsRNA yield determination of the Colorado potato beetle beta actin dsRNA produced by *S. cerevisiae* YPH-500 and the various plasmids described above. Such results confirm that yeasts such as *S. cerevisiae* produce large quantities of dsRNA by co-expression of the MS2 coat gene and a dsRNA target of interest.

TABLE 3

Predicted production of dsRNA by *S. cerevisiae* YPH 500 as a function of variation in dsRNA structure and the presence or absence of coat protein.

| RNA Structure as depicted in | Plasmid | Loop size (bases) | Stem size (bp) | Stem sequence | Coat protein | dsRNA (mg/L) |
|---|---|---|---|---|---|---|
| FIG. 6 | pAPSE10440 | 166 | 294 | beta actin | MS2 | ~60 |
| FIG. 6 | pAPSE10439 | 166 | 294 | beta actin | none | ~4 |
| FIG. 5 | pAPSE10442 | 166 | 294 | beta actin | MS2 | ~120 |
| FIG. 5 | pAPSE10441 | 166 | 294 | beta actin | none | ~4 |
| FIG. 4 | pAPSE10444 | 166 | 294 | beta actin | MS2 | ~250 |
| FIG. 4 | pAPSE10443 | 166 | 294 | beta actin | none | ~4 |
| FIG. 1 | pAPSE10446 | 166 | 294 | beta actin | MS2 | ~250 |
| FIG. 1 | pAPSE10445 | 166 | 294 | beta actin | none | 4 |

What is claimed is:

1. A method for producing recoverable unencapsidated dsRNA in a microbial cell, the microbial cell comprising (i) a leviviridae coat protein gene encoding a capsid protein selected from MS2, Qβ and an amino-terminal fragment of MS2 or Qβ and (ii) an expression cassette comprising a promoter operably linked to a DNA sequence encoding a heterologous dsRNA molecule, said dsRNA molecule comprising a self-complementary stretch of sequence separated by non-complementary sequence such that upon hybridization of the complementary sequences a stem-loop structure is formed, the stem structure having a length exceeding the interior diameter of an MS2 capsid, the method comprising the step of culturing the microbial cell under conditions such that the dsRNA and the coat protein gene are co-expressed in the microbial cell, wherein the amount of unencapsidated dsRNA produced in the microbial cell is significantly increased compared to the amount of unencapsidated dsRNA produced in the microbial cell when the coat protein gene is not co-expressed.

2. The method of claim 1, wherein the capsid protein is encoded by the coat protein gene of bacteriophage MS2.

3. The method of claim 1, wherein the capsid protein is encoded by the coat protein gene of bacteriophage Qβ.

4. The method of claim 1, wherein the gene encoding the dsRNA and the coat protein gene encoding the capsid protein are expressed from an inducible promoter.

5. The method of claim 4, wherein the coat protein gene encoding the capsid protein is expressed from a constitutive promoter and the gene encoding the dsRNA is expressed from an inducible promoter.

6. The method of claim 1, wherein the coat protein gene encoding the capsid protein is expressed prior to or concomitant with the gene encoding the dsRNA.

7. The method of claim 1, wherein the gene encoding the dsRNA and the coat protein gene encoding the capsid protein are present on one plasmid or extrachromosomal element within the microbial cell.

8. The method of claim 1, wherein the gene encoding the dsRNA and the coat protein gene encoding the capsid protein are present on separate plasmids or extrachromosomal elements within the microbial cell.

9. The method of claim 1, wherein one of the genes encoding the dsRNA and the capsid protein are present on a plasmid or extrachromosomal element and the other of the genes encoding the dsRNA and the capsid protein are present on the chromosome of the microbial cell.

10. The method of claim 1, wherein the gene encoding the dsRNA and the coat protein gene encoding the capsid protein are present on the chromosome of the microbial cell.

11. The method of claim 1, wherein the dsRNA is an RNAi precursor.

12. The method of claim 1, wherein after producing the dsRNA the microbial cell is subsequently lysed and the dsRNA purified from the lysate prior to processing for application.

13. The method of claim 1, wherein after producing the dsRNA the microbial cell is lysed and processed for application without further purification of the dsRNA.

14. The method of claim 1, wherein after producing the dsRNA the microbial cells are processed for application without lysis or further purification of the dsRNA.

15. The method of claim 1, wherein the capsid protein is an amino-terminal fragment of MS2 or Qβ comprising at least the first 11 amino acids and not more than the first 41 amino acids of the capsid protein.

16. The method of claim 15, wherein the amino-terminal fragment comprises the first 41 amino acids of the capsid protein.

17. The method of claim 15, wherein the amino-terminal fragment comprises the first 35 amino acids of the capsid protein.

18. The method of claim 15, wherein the amino-terminal fragment comprises the first 25 amino acids of the capsid protein.

19. The method of claim 15, wherein the amino-terminal fragment comprises the first 21 amino acids of the capsid protein.

20. The method of claim 15, wherein the amino-terminal fragment comprises the first 11 amino acids of the capsid protein.

21. The method of claim 1, wherein the microbial cell is a bacterium.

22. The method of claim 1, wherein the microbial cell is a gram-negative bacterium.

23. The method of claim 1, wherein the microbial cell is a strain of *Escherichia coli*.

24. The method of claim 1, wherein the microbial cell is a gram-positive bacterium.

25. The method of claim 1, wherein the microbial cell is a strain of *Corynebacterium glutamicum*.

26. The method of claim 1, wherein the microbial cell is a yeast.

27. The method of claim 1, wherein the microbial cell is a strain of *Saccharomyces cerevisiae*.

28. The method of claim 1, wherein the expression cassette does not comprise a DNA sequence encoding a cognate packaging sequence that is recognized by the capsid protein.

29. The method of claim 1, wherein the microbial cell is cultured under shake flask fermentation conditions whereby at least 65 mg/L of recoverable unencapsidated dsRNA accumulates in the microbial cell.

30. The method of claim 1, wherein the microbial cell is cultured under fed batch fermentation conditions whereby at least 3 g/L of recoverable unencapsidated dsRNA accumulates in the microbial cell.

31. The method of claim 1, wherein stem structure of the dsRNA is at least 75 base pairs in length.

32. The method of claim 1, further comprising a step of recovering the unencapsidated dsRNA from a lysate of the microbial cell.

33. The method of claim 1, wherein the stem structure of the dsRNA is at least 20 nm in length.

* * * * *

SEQUENCE LISTING

```
<160> NUMBER OF SEQ ID NOS: 46

<210> SEQ ID NO 1
<211> LENGTH: 5498
<212> TYPE: DNA
<213> ORGANISM: Artificial Sequence
<220> FEATURE:
<223> OTHER INFORMATION: Recombinant plasmid pAPSE10180; ErkA stem
      loop + capsid protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (127)..(145)
<223> OTHER INFORMATION: bacteriophage MS2 pac sequence
<220> FEATURE:
<221> NAME/KEY: misc_feature
<222> LOCATION: (175)..(182)
<223> OTHER INFORMATION: restriction endonuclease AsiSI recognition site
<220> FEATURE:
<221> NAME/KEY: misc_feature
<222> LOCATION: (179)..(384)
<223> OTHER INFORMATION: ErkA sense strand gene fragment
<220> FEATURE:
<221> NAME/KEY: misc_feature
<222> LOCATION: (436)..(454)
<223> OTHER INFORMATION: bacteriophage MS2 pac sequence
<220> FEATURE:
```

```
<221> NAME/KEY: misc_feature
<222> LOCATION: (504)..(511)
<223> OTHER INFORMATION: restriction endonuclease NotI recognition site
<220> FEATURE:
<221> NAME/KEY: misc_feature
<222> LOCATION: (505)..(696)
<223> OTHER INFORMATION: ErkA antisense strand gene fragment
<220> FEATURE:
<221> NAME/KEY: misc_feature
<222> LOCATION: (692)..(699)
<223> OTHER INFORMATION: restriction endonuclease PacI recognition site
<220> FEATURE:
<221> NAME/KEY: misc_feature
<222> LOCATION: (709)..(727)
<223> OTHER INFORMATION: bacteriophage MS2 pac sequence
<220> FEATURE:
<221> NAME/KEY: terminator
<222> LOCATION: (743)..(790)
<223> OTHER INFORMATION: bacteriophage T7 transcription terminator
<220> FEATURE:
<221> NAME/KEY: promoter
<222> LOCATION: (1116)..(1134)
<223> OTHER INFORMATION: bacteriophage T7 gene 1 promoter
<220> FEATURE:
<221> NAME/KEY: gene
<222> LOCATION: (1207)..(1596)
<223> OTHER INFORMATION: bacteriophage MS2 coat protein gene
<220> FEATURE:
<221> NAME/KEY: terminator
<222> LOCATION: (1448)..(1495)
<223> OTHER INFORMATION: bacteriophage T7 transcription terminator

<400> SEQUENCE: 1

ttcagatctc gatcccgcga aattaatacg actcactata gggagaccac aacggtttcc     60

ctctagatca caagtttgta caaaaaagca ggctaagaag gagatataca tacgccggcc    120

attcaaacat gaggattacc catgtaacct aaggccggtg tccaggcgcg ctccgcgatc    180

gcacgcggac aaagttcctc aatctaatgc tgaagttata aggggacaaa tatttgaagt    240

tggtcctagg tatattaaac tcgcctatat aggtgaagga gcttatggca tggttgtgtc    300

tgcggatgac acgctaacaa accaaagagt tgcaataaaa aaaatatcgc cctttgaaca    360

ccaaacttat tgctactaca gtttaaacgc aatcgcagca aactccggca tctactaata    420

gacgccggcc attcaacatg aggattaccc atgtaaccta agaagacaac aaagaagttc    480

aactctttat gtattgatct tccgcggccg ccaataagtt tggtgttcaa agggcgatat    540

tttttttatt gcaactcttt ggtttgttag cgtgtcatcc gcagacacaa ccatgccata    600

agctccttca cctatatagg cgagtttaat atacctagga ccaacttcaa atatttgtcc    660

ccttataact tcagcattag attgaggaac tttaattaag gagttcaaac atgaggatca    720

cccatgtcga agctcccaca ccctagcata accccttggg gcctctaaac gggtcttgag    780

gggttttttg ctgaaaggag gaactatatc cggatatcca caggacgggt gtggtcgcca    840

tgatcgcgta gtcgatagtg gctccaagta gcgaagcgag caggactggg cggcgggcat    900

gcatcgtcca ttccgacagc atcgccagtc actatggcgt gctgctagcg ctatatgcgt    960

tgatgcaatt tctatgcgca cccgttctcg gagcactgtc cgaccgcttt ggccgccgcc   1020

cagtcctgct cgcttcgcta cttggagcca ctatcgacta cgcgatcatg gcgaccacac   1080

ccgtcctgtg gatccagatc tcgatcccgc gaaattaata cgactcacta tagggagacc   1140

acaacggttt ccctctagat cacaagtttg tacaaaaaag caggctaaga aggagatata   1200

catatggcgt ctaactttac ccaattcgtt ctggttgata acggcggtac gggtgacgtt   1260

accgtagctc cgtccaactt cgccaacggt gttgcggaat ggattagctc taacagccgc   1320

tctcaggcct acaaagtcac gtgctccgtt cgtcagtcta gcgcgcagaa tcgcaaatac   1380
```

```
accatcaaag ttgaagtacc gaaagtcgca acgcagaccg taggcggcgt agaactccca   1440
gttgcggcct ggcgctctta cctcaacatg gaactgacta ttccgatttt tgcgacgaac   1500
tccgactgcg aactgattgt taaggcaatg cagggcctgc tgaaagacgg taatccgatc   1560
ccatctgcaa tcgctgctaa ctctggcatt tactaataag cggacgcgct gccaccgctg   1620
agcaataact agcataaccc cttggggcct ctaaacgggt cttgaggggt tttttgctga   1680
aaggaggaac tatatccggc atgcaccatt ccttgcggcg gcggtgctca acggcctcaa   1740
cctactactg ggctgcttcc taatgcagga gtcgcataag ggagagcgtc gaccgatgcc   1800
cttgagagcc ttcaacccag tcagctcctt ccggtgggcg cggggcatga ctatcgtcgc   1860
cgcacttatg actgtcttct ttatcatgca actcgtagga caggtgccgg cagcgctctg   1920
ggtcattttc ggcgaggacc gctttcgctg gagcgcgacg atgatcggcc tgtcgcttgc   1980
ggtattcgga atcttgcacg ccctcgctca agccttcgtc actggtcccg ccaccaaacg   2040
tttcggcgag aagcaggcca ttatcgccgg catggcggcc gacgcgctgg gctacgtctt   2100
gctggcgttc gcgacgcgag gctggatggc cttccccatt atgattcttc tcgcttccgg   2160
cggcatcggg atgcccgcgt tgcaggccat gctgtccagg caggtagatg acgaccatca   2220
gggacagctt caaggatcgc tcgcggctct taccagccta acttcgatca ttggaccgct   2280
gatcgtcacg gcgatttatg ccgcctcggc gagcacatgg aacgggttgg catggattgt   2340
aggcgccgcc ctataccttg tctgcctccc cgcgttgcgt cgcggtgcat ggagccgggc   2400
cacctcgacc tgaatggaag ccggcggcac ctcgctaacg gattcaccac tccaagaatt   2460
ggagccaatc aattcttgcg gagaactgtg aatgcgcaaa ccaacccttg gcagaacata   2520
tccatcgcgt ccgccatctc cagcagccgc acgcggcgca tctcgggcag cgttgggtcc   2580
tggccacggg tgcgcatgat cgtgctcctg tcgttgagga cccggctagg ctggcggggt   2640
tgccttactg gttagcagaa tgaatcaccg atacgcgagc gaacgtgaag cgactgctgc   2700
tgcaaaacgt ctgcgacctg agcaacaaca tgaatggtct tcggtttccg tgtttcgtaa   2760
agtctggaaa cgcggaagtc agcgccctgc accattatgt tccggatctg catcgcagga   2820
tgctgctggc taccctgtgg aacacctaca tctgtattaa cgaagcgctg gcattgaccc   2880
tgagtgattt ttctctggtc ccgccgcatc cataccgcca gttgtttacc ctcacaacgt   2940
tccagtaacc gggcatgttc atcatcagta acccgtatcg tgagcatcct ctctcgtttc   3000
atcggtatca ttacccccat gaacagaaat cccccttaca cggaggcatc agtgaccaaa   3060
caggaaaaaa ccgcccttaa catggcccgc tttatcagaa gccagacatt aacgcttctg   3120
gagaaactca acgagctgga cgcggatgaa caggcagaca tctgtgaatc gcttcacgac   3180
cacgctgatg agctttaccg cagctgcctc gcgcgtttcg gtgatgacgg tgaaaacctc   3240
tgacacatgc agctcccgga gacggtcaca gcttgtctgt aagcggatgc cgggagcaga   3300
caagcccgtc agggcgcgtc agcgggtgtt ggcgggtgtc ggggcgcagc catgacccag   3360
tcacgtagcg atagcggagt gtatactggc ttaactatgc ggcatcagag cagattgtac   3420
tgagagtgca ccatatgcgg tgtgaaatac cgcacagatg cgtaaggaga aaataccgca   3480
tcaggcgctc ttccgcttcc tcgctcactg actcgctgcg ctcggtcgtt cggctgcggc   3540
gagcggtatc agctcactca aaggcggtaa tacggttatc cacagaatca ggggataacg   3600
caggaaagaa catgtgagca aaaggccagc aaaaggccag gaaccgtaaa aaggccgcgt   3660
tgctggcgtt tttccatagg ctccgccccc ctgacgagca tcacaaaaat cgacgctcaa   3720
```

-continued

```
gtcagaggtg gcgaaacccg acaggactat aaagatacca ggcgtttccc cctggaagct   3780

ccctcgtgcg ctctcctgtt ccgaccctgc cgcttaccgg atacctgtcc gcctttctcc   3840

cttcgggaag cgtggcgctt tctcatagct cacgctgtag gtatctcagt tcggtgtagg   3900

tcgttcgctc caagctgggc tgtgtgcacg aaccccccgt tcagcccgac cgctgcgcct   3960

tatccggtaa ctatcgtctt gagtccaacc cggtaagaca cgacttatcg ccactggcag   4020

cagccactgg taacaggatt agcagagcga ggtatgtagg cggtgctaca gagttcttga   4080

agtggtggcc taactacggc tacactagaa ggacagtatt tggtatctgc gctctgctga   4140

agccagttac cttcggaaaa agagttggta gctcttgatc cggcaaacaa accaccgctg   4200

gtagcggtgg tttttttgtt tgcaagcagc agattacgcg cagaaaaaaa ggatctcaag   4260

aagatccttt gatcttttct acggggtctg acgctcagtg gaacgaaaac tcacgttaag   4320

ggattttggt catgagatta tcaaaaagga tcttcaccta gatcctttta aattaaaaat   4380

gaagttttaa atcaatctaa agtatatatg agtaaacttg gtctgacagt taccaatgct   4440

taatcagtga ggcacctatc tcagcgatct gtctatttcg ttcatccata gttgcctgac   4500

tccccgtcgt gtagataact acgatacggg agggcttacc atctggcccc agtgctgcaa   4560

tgataccgcg agacccacgc tcaccggctc cagatttatc agcaataaac cagccagccg   4620

gaagggccga gcgcagaagt ggtcctgcaa ctttatccgc ctccatccag tctattaatt   4680

gttgccggga agctagagta agtagttcgc cagttaatag tttgcgcaac gttgttgcca   4740

ttgctgcagg catcgtggtg tcacgctcgt cgtttggtat ggcttcattc agctccggtt   4800

cccaacgatc aaggcgagtt acatgatccc ccatgttgtg caaaaaagcg gttagctcct   4860

tcggtcctcc gatcgttgtc agaagtaagt tggccgcagt gttatcactc atggttatgg   4920

cagcactgca taattctctt actgtcatgc catccgtaag atgcttttct gtgactggtg   4980

agtactcaac caagtcattc tgagaatagt gtatgcggcg accgagttgc tcttgcccgg   5040

cgtcaacacg ggataatacc gcgccacata gcagaacttt aaaagtgctc atcattggaa   5100

aacgttcttc ggggcgaaaa ctctcaagga tcttaccgct gttgagatcc agttcgatgt   5160

aacccactcg tgcacccaac tgatcttcag catcttttac tttcaccagc gtttctgggt   5220

gagcaaaaac aggaaggcaa aatgccgcaa aaaagggaat aagggcgaca cggaaatgtt   5280

gaatactcat actcttcctt tttcaatatt attgaagcat ttatcagggt tattgtctca   5340

tgagcggata catatttgaa tgtatttaga aaaataaaca aataggggtt ccgcgcacat   5400

ttccccgaaa agtgccacct gacgtctaag aaaccattat tatcatgaca ttaacctata   5460

aaaataggcg tatcacgagg ccctttcgtc ttcaagaa                           5498
```

```
<210> SEQ ID NO 2
<211> LENGTH: 4696
<212> TYPE: DNA
<213> ORGANISM: Artificial Sequence
<220> FEATURE:
<223> OTHER INFORMATION: Recombinant plasmid pAPSE10181; ErkA stem
      loop - coat protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (127)..(145)
<223> OTHER INFORMATION: bacteriophage MS2 pac sequence
<220> FEATURE:
<221> NAME/KEY: misc_feature
<222> LOCATION: (175)..(182)
```

```
<223> OTHER INFORMATION: restriction endonuclease AsiSI recognition site
<220> FEATURE:
<221> NAME/KEY: misc_feature
<222> LOCATION: (179)..(384)
<223> OTHER INFORMATION: ErkA sense strand gene fragment
<220> FEATURE:
<221> NAME/KEY: misc_feature
<222> LOCATION: (436)..(454)
<223> OTHER INFORMATION: bacteriophage MS2 pac sequence
<220> FEATURE:
<221> NAME/KEY: misc_feature
<222> LOCATION: (504)..(511)
<223> OTHER INFORMATION: restriction endonuclease NotI recognition site
<220> FEATURE:
<221> NAME/KEY: misc_feature
<222> LOCATION: (505)..(696)
<223> OTHER INFORMATION: ErkA antisense strand gene fragment
<220> FEATURE:
<221> NAME/KEY: misc_feature
<222> LOCATION: (692)..(699)
<223> OTHER INFORMATION: restriction endonuclease PacI recognition site
<220> FEATURE:
<221> NAME/KEY: misc_feature
<222> LOCATION: (709)..(727)
<223> OTHER INFORMATION: bacteriophage MS2 pac sequence
<220> FEATURE:
<221> NAME/KEY: terminator
<222> LOCATION: (743)..(790)
<223> OTHER INFORMATION: bacteriophage T7 transcription terminator
<220> FEATURE:
<221> NAME/KEY: misc_feature
<222> LOCATION: (897)..(902)
<223> OTHER INFORMATION: restriction endonuclease SphI recognition site

<400> SEQUENCE: 2

ttcagatctc gatcccgcga aattaatacg actcactata gggagaccac aacggtttcc     60

ctctagatca caagtttgta caaaaaagca ggctaagaag gagatataca tacgccggcc    120

attcaaacat gaggattacc catgtaacct aaggccggtg tccaggcgcg ctccgcgatc    180

gcacgcggac aaagttcctc aatctaatgc tgaagttata aggggacaaa tatttgaagt    240

tggtcctagg tatattaaac tcgcctatat aggtgaagga gcttatggca tggttgtgtc    300

tgcggatgac acgctaacaa accaaagagt tgcaataaaa aaaatatcgc cctttgaaca    360

ccaaacttat tgctactaca gtttaaacgc aatcgcagca aactccggca tctactaata    420

gacgccggcc attcaacatg aggattaccc atgtaaccta agaagacaac aaagaagttc    480

aactctttat gtattgatct tccgcggccg ccaataagtt tggtgttcaa agggcgatat    540

ttttttttatt gcaactcttt ggtttgttag cgtgtcatcc gcagacacaa ccatgccata    600

agctccttca cctatatagg cgagtttaat atacctagga ccaacttcaa atatttgtcc    660

ccttataact tcagcattag attgaggaac tttaattaag gagttcaaac atgaggatca    720

cccatgtcga agctcccaca ccctagcata accccttggg gcctctaaac gggtcttgag    780

gggttttttg ctgaaaggag gaactatatc cggatatcca caggacgggt gtggtcgcca    840

tgatcgcgta gtcgatagtg gctccaagta gcgaagcgag caggactggg cggcgggcat    900

gcaccattcc ttgcggcggc ggtgctcaac ggcctcaacc tactactggg ctgcttccta    960

atgcaggagt cgcataaggg agagcgtcga ccgatgccct tgagagcctt caacccagtc   1020

agctccttcc ggtgggcgcg gggcatgact atcgtcgccg cacttatgac tgtcttcttt   1080

atcatgcaac tcgtaggaca ggtgccggca gcgctctggg tcattttcgg cgaggaccgc   1140

tttcgctgga gcgcgacgat gatcggcctg tcgcttgcgg tattcggaat cttgcacgcc   1200

ctcgctcaag ccttcgtcac tggtcccgcc accaaacgtt tcggcgagaa gcaggccatt   1260

atcgccggca tggcggccga cgcgctgggc tacgtcttgc tggcgttcgc gacgcgaggc   1320
```

```
tggatggcct tccccattat gattcttctc gcttccggcg gcatcgggat gcccgcgttg   1380
caggccatgc tgtccaggca ggtagatgac gaccatcagg gacagcttca aggatcgctc   1440
gcggctctta ccagcctaac ttcgatcatt ggaccgctga tcgtcacggc gatttatgcc   1500
gcctcggcga gcacatggaa cgggttggca tggattgtag gcgccgccct ataccttgtc   1560
tgcctccccg cgttgcgtcg cggtgcatgg agccgggcca cctcgacctg aatggaagcc   1620
ggcggcacct cgctaacgga ttcaccactc caagaattgg agccaatcaa ttcttgcgga   1680
gaactgtgaa tgcgcaaacc aacccttggc agaacatatc catcgcgtcc gccatctcca   1740
gcagccgcac gcggcgcatc tcgggcagcg ttgggtcctg gccacgggtg cgcatgatcg   1800
tgctcctgtc gttgaggacc cggctaggct ggcggggttg ccttactggt tagcagaatg   1860
aatcaccgat acgcgagcga acgtgaagcg actgctgctg caaaacgtct gcgacctgag   1920
caacaacatg aatggtcttc ggtttccgtg tttcgtaaag tctggaaacg cggaagtcag   1980
cgccctgcac cattatgttc cggatctgca tcgcaggatg ctgctggcta ccctgtggaa   2040
cacctacatc tgtattaacg aagcgctggc attgaccctg agtgattttt ctctggtccc   2100
gccgcatcca taccgccagt tgtttaccct cacaacgttc cagtaaccgg gcatgttcat   2160
catcagtaac ccgtatcgtg agcatcctct ctcgtttcat cggtatcatt acccccatga   2220
acagaaatcc cccttacacg gaggcatcag tgaccaaaca ggaaaaaacc gcccttaaca   2280
tggcccgctt tatcagaagc cagacattaa cgcttctgga gaaactcaac gagctggacg   2340
cggatgaaca ggcagacatc tgtgaatcgc ttcacgacca cgctgatgag ctttaccgca   2400
gctgcctcgc gcgtttcggt gatgacggtg aaaacctctg acacatgcag ctcccggaga   2460
cggtcacagc ttgtctgtaa gcggatgccg ggagcagaca agcccgtcag ggcgcgtcag   2520
cgggtgttgg cgggtgtcgg ggcgcagcca tgacccagtc acgtagcgat agcggagtgt   2580
atactggctt aactatgcgg catcagagca gattgtactg agagtgcacc atatgcggtg   2640
tgaaataccg cacagatgcg taaggagaaa ataccgcatc aggcgctctt ccgcttcctc   2700
gctcactgac tcgctgcgct cggtcgttcg gctgcggcga gcggtatcag ctcactcaaa   2760
ggcggtaata cggttatcca cagaatcagg ggataacgca ggaaagaaca tgtgagcaaa   2820
aggccagcaa aaggccagga accgtaaaaa ggccgcgttg ctggcgtttt tccataggct   2880
ccgcccccct gacgagcatc acaaaaatcg acgctcaagt cagaggtggc gaaacccgac   2940
aggactataa agataccagg cgtttccccc tggaagctcc ctcgtgcgct ctcctgttcc   3000
gaccctgccg cttaccggat acctgtccgc ctttctccct tcgggaagcg tggcgctttc   3060
tcatagctca cgctgtaggt atctcagttc ggtgtaggtc gttcgctcca agctgggctg   3120
tgtgcacgaa ccccccgttc agcccgaccg ctgcgcctta tccggtaact atcgtcttga   3180
gtccaacccg gtaagacacg acttatcgcc actggcagca gccactggta acaggattag   3240
cagagcgagg tatgtaggcg gtgctacaga gttcttgaag tggtggccta actacggcta   3300
cactagaagg acagtatttg gtatctgcgc tctgctgaag ccagttacct tcggaaaaag   3360
agttggtagc tcttgatccg gcaaacaaac caccgctggt agcggtggtt tttttgtttg   3420
caagcagcag attacgcgca gaaaaaaagg atctcaagaa gatcctttga tcttttctac   3480
ggggtctgac gctcagtgga acgaaaactc acgttaaggg attttggtca tgagattatc   3540
aaaaaggatc ttcacctaga tccttttaaa ttaaaaatga agttttaaat caatctaaag   3600
tatatatgag taaacttggt ctgacagtta ccaatgctta atcagtgagg cacctatctc   3660
```

```
agcgatctgt ctatttcgtt catccatagt tgcctgactc cccgtcgtgt agataactac   3720

gatacgggag ggcttaccat ctggccccag tgctgcaatg ataccgcgag acccacgctc   3780

accggctcca gatttatcag caataaacca gccagccgga agggccgagc gcagaagtgg   3840

tcctgcaact ttatccgcct ccatccagtc tattaattgt tgccgggaag ctagagtaag   3900

tagttcgcca gttaatagtt tgcgcaacgt tgttgccatt gctgcaggca tcgtggtgtc   3960

acgctcgtcg tttggtatgg cttcattcag ctccggttcc caacgatcaa ggcgagttac   4020

atgatccccc atgttgtgca aaaaagcggt tagctccttc ggtcctccga tcgttgtcag   4080

aagtaagttg gccgcagtgt tatcactcat ggttatggca gcactgcata attctcttac   4140

tgtcatgcca tccgtaagat gcttttctgt gactggtgag tactcaacca agtcattctg   4200

agaatagtgt atgcggcgac cgagttgctc ttgcccggcg tcaacacggg ataataccgc   4260

gccacatagc agaactttaa aagtgctcat cattggaaaa cgttcttcgg ggcgaaaact   4320

ctcaaggatc ttaccgctgt tgagatccag ttcgatgtaa cccactcgtg cacccaactg   4380

atcttcagca tcttttactt tcaccagcgt ttctgggtga gcaaaaacag gaaggcaaaa   4440

tgccgcaaaa aagggaataa gggcgacacg gaaatgttga atactcatac tcttcctttt   4500

tcaatattat tgaagcattt atcagggtta ttgtctcatg agcggataca tatttgaatg   4560

tatttagaaa aataaacaaa taggggttcc gcgcacattt ccccgaaaag tgccacctga   4620

cgtctaagaa accattatta tcatgacatt aacctataaa aataggcgta tcacgaggcc   4680

ctttcgtctt caagaa                                                   4696
```

<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide probe

<400> SEQUENCE: 3

```
ggccggcgtc tattagtaga tgcc                                            24
```

<210> SEQ ID NO 4
<211> LENGTH: 5591
<212> TYPE: DNA
<213> ORGANISM: Artificial Sequence
<220> FEATURE:
<223> OTHER INFORMATION: Recombinant plasmid pAPSE10189; beta actin sense strand + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)

<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: promoter
<222> LOCATION: (1209)..(1227)
<223> OTHER INFORMATION: bacteriophage T7 gene 1 promoter
<220> FEATURE:
<221> NAME/KEY: gene
<222> LOCATION: (1300)..(1689)
<223> OTHER INFORMATION: bacteriophage MS2 cot protein gene
<220> FEATURE:
<221> NAME/KEY: gene
<222> LOCATION: (1300)..(1689)
<223> OTHER INFORMATION: bacteriophage MS2 coat protein gene
<220> FEATURE:
<221> NAME/KEY: terminator
<222> LOCATION: (1722)..(1769)
<223> OTHER INFORMATION: bacteriophage T7 transcription terminator

<400> SEQUENCE: 4

```
ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

catgtgtgac gacgatgtag cggctcttgt cgtagacaat ggatccggta tgtgcaaagc    480

cggtttcgca ggagatgacg caccccgtgc cgtcttcccc tcgatcgtcg gtcgcccaag    540

gcatcaagga gtcatggtcg gtatgggaca aaaggactca tacgtaggag atgaagccca    600

aagcaaaaga ggtatcctca ccctgaaata ccccatcgaa cacggtatca tcaccaactg    660

ggatgagttt aaacctttcg gattataaca tcacatctag gcgcgcctga cgatcaacca    720

taccagacgg accgaatacc cggtctgaac gagggcggcc gcggtaccca agaagtactt    780

agagttaatt aaggagttca aacatgagga tcacccatgt cgaagctccc acaccctagc    840

ataacccctt ggggcctcta aacgggtctt gaggggtttt ttgctgaaag gaggaactat    900

atccggatat ccacaggacg ggtgtggtcg ccatgatcgc gtagtcgata gtggctccaa    960

gtagcgaagc gagcaggact gggcggcggg catgcatcgt ccattccgac agcatcgcca   1020

gtcactatgg cgtgctgcta gcgctatatg cgttgatgca atttctatgc gcacccgttc   1080

tcggagcact gtccgaccgc tttggccgcc gcccagtcct gctcgcttcg ctacttggag   1140

ccactatcga ctacgcgatc atggcgacca cacccgtcct gtggatccag atctcgatcc   1200

cgcgaaatta atacgactca ctatagggag accacaacgg tttccctcta gatcacaagt   1260

ttgtacaaaa aagcaggcta agaaggagat atacatatgg cgtctaactt tacccaattc   1320

gttctggttg ataacggcgg tacgggtgac gttaccgtag ctccgtccaa cttcgccaac   1380

ggtgttgcgg aatggattag ctctaacagc cgctctcagg cctacaaagt cacgtgctcc   1440

gttcgtcagt ctagcgcgca gaatcgcaaa tacaccatca aagttgaagt accgaaagtc   1500

gcaacgcaga ccgtaggcgg cgtagaactc ccagttgcgg cctggcgctc ttacctcaac   1560

atggaactga ctattccgat tttgcgacg aactccgact gcgaactgat tgttaaggca   1620

atgcagggcc tgctgaaaga cggtaatccg atcccatctg caatcgctgc taactctggc   1680
```

```
atttactaat aagcggacgc gctgccaccg ctgagcaata actagcataa ccccttgggg   1740
cctctaaacg ggtcttgagg ggttttttgc tgaaaggagg aactatatcc ggcatgcacc   1800
attccttgcg gcggcggtgc tcaacggcct caacctacta ctgggctgct tcctaatgca   1860
ggagtcgcat aagggagagc gtcgaccgat gcccttgaga gccttcaacc cagtcagctc   1920
cttccggtgg gcgcggggca tgactatcgt cgccgcactt atgactgtct tctttatcat   1980
gcaactcgta ggacaggtgc cggcagcgct ctgggtcatt ttcggcgagg accgctttcg   2040
ctggagcgcg acgatgatcg gcctgtcgct tgcggtattc ggaatcttgc acgccctcgc   2100
tcaagccttc gtcactggtc ccgccaccaa acgtttcggc gagaagcagg ccattatcgc   2160
cggcatggcg gccgacgcgc tgggctacgt cttgctggcg ttcgcgacgc gaggctggat   2220
ggccttcccc attatgattc ttctcgcttc cggcggcatc gggatgcccg cgttgcaggc   2280
catgctgtcc aggcaggtag atgacgacca tcagggacag cttcaaggat cgctcgcggc   2340
tcttaccagc ctaacttcga tcattggacc gctgatcgtc acggcgattt atgccgcctc   2400
ggcgagcaca tggaacgggt tggcatggat tgtaggcgcc gccctatacc ttgtctgcct   2460
ccccgcgttg cgtcgcggtg catggagccg ggccacctcg acctgaatgg aagccggcgg   2520
cacctcgcta acggattcac cactccaaga attggagcca atcaattctt gcggagaact   2580
gtgaatgcgc aaaccaaccc ttggcagaac atatccatcg cgtccgccat ctccagcagc   2640
cgcacgcggc gcatctcggg cagcgttggg tcctggccac gggtgcgcat gatcgtgctc   2700
ctgtcgttga ggacccggct aggctggcgg ggttgcctta ctggttagca gaatgaatca   2760
ccgatacgcg agcgaacgtg aagcgactgc tgctgcaaaa cgtctgcgac ctgagcaaca   2820
acatgaatgg tcttcggttt ccgtgtttcg taaagtctgg aaacgcggaa gtcagcgccc   2880
tgcaccatta tgttccggat ctgcatcgca ggatgctgct ggctaccctg tggaacacct   2940
acatctgtat taacgaagcg ctggcattga ccctgagtga tttttctctg gtcccgccgc   3000
atccataccg ccagttgttt accctcacaa cgttccagta accgggcatg ttcatcatca   3060
gtaacccgta tcgtgagcat cctctctcgt ttcatcggta tcattacccc catgaacaga   3120
aatccccctt acacggaggc atcagtgacc aaacaggaaa aaaccgccct taacatggcc   3180
cgctttatca gaagccagac attaacgctt ctggagaaac tcaacgagct ggacgcggat   3240
gaacaggcag acatctgtga atcgcttcac gaccacgctg atgagcttta ccgcagctgc   3300
ctcgcgcgtt tcggtgatga cggtgaaaac ctctgacaca tgcagctccc ggagacggtc   3360
acagcttgtc tgtaagcgga tgccgggagc agacaagccc gtcagggcgc gtcagcgggt   3420
gttggcgggt gtcggggcgc agccatgacc cagtcacgta gcgatagcgg agtgtatact   3480
ggcttaacta tgcggcatca gagcagattg tactgagagt gcaccatatg cggtgtgaaa   3540
taccgcacag atgcgtaagg agaaaatacc gcatcaggcg ctcttccgct tcctcgctca   3600
ctgactcgct gcgctcggtc gttcggctgc ggcgagcggt atcagctcac tcaaaggcgg   3660
taatacggtt atccacagaa tcaggggata acgcaggaaa gaacatgtga gcaaaaggcc   3720
agcaaaaggc caggaaccgt aaaaaggccg cgttgctggc gtttttccat aggctccgcc   3780
cccctgacga gcatcacaaa aatcgacgct caagtcagag gtggcgaaac ccgacaggac   3840
tataaagata ccaggcgttt ccccctggaa gctccctcgt gcgctctcct gttccgaccc   3900
tgccgcttac cggatacctg tccgcctttc tcccttcggg aagcgtggcg ctttctcata   3960
gctcacgctg taggtatctc agttcggtgt aggtcgttcg ctccaagctg ggctgtgtgc   4020
```

```
acgaaccccc cgttcagccc gaccgctgcg ccttatccgg taactatcgt cttgagtcca   4080

acccggtaag acacgactta tcgccactgg cagcagccac tggtaacagg attagcagag   4140

cgaggtatgt aggcggtgct acagagttct tgaagtggtg gcctaactac ggctacacta   4200

gaaggacagt atttggtatc tgcgctctgc tgaagccagt taccttcgga aaaagagttg   4260

gtagctcttg atccggcaaa caaaccaccg ctggtagcgg tggttttttt gtttgcaagc   4320

agcagattac gcgcagaaaa aaaggatctc aagaagatcc tttgatcttt tctacggggt   4380

ctgacgctca gtggaacgaa aactcacgtt aagggatttt ggtcatgaga ttatcaaaaa   4440

ggatcttcac ctagatcctt ttaaattaaa aatgaagttt taaatcaatc taaagtatat   4500

atgagtaaac ttggtctgac agttaccaat gcttaatcag tgaggcacct atctcagcga   4560

tctgtctatt tcgttcatcc atagttgcct gactccccgt cgtgtagata actacgatac   4620

gggagggctt accatctggc cccagtgctg caatgatacc gcgagaccca cgctcaccgg   4680

ctccagattt atcagcaata aaccagccag ccggaagggc cgagcgcaga agtggtcctg   4740

caactttatc cgcctccatc cagtctatta attgttgccg ggaagctaga gtaagtagtt   4800

cgccagttaa tagtttgcgc aacgttgttg ccattgctgc aggcatcgtg gtgtcacgct   4860

cgtcgtttgg tatggcttca ttcagctccg gttcccaacg atcaaggcga gttacatgat   4920

cccccatgtt gtgcaaaaaa gcggttagct ccttcggtcc tccgatcgtt gtcagaagta   4980

agttggccgc agtgttatca ctcatggtta tggcagcact gcataattct cttactgtca   5040

tgccatccgt aagatgcttt tctgtgactg gtgagtactc aaccaagtca ttctgagaat   5100

agtgtatgcg gcgaccgagt tgctcttgcc cggcgtcaac acgggataat accgcgccac   5160

atagcagaac tttaaaagtg ctcatcattg gaaaacgttc ttcggggcga aaactctcaa   5220

ggatcttacc gctgttgaga tccagttcga tgtaacccac tcgtgcaccc aactgatctt   5280

cagcatcttt tactttcacc agcgtttctg ggtgagcaaa aacaggaagg caaaatgccg   5340

caaaaaaggg aataagggcg acacggaaat gttgaatact catactcttc ctttttcaat   5400

attattgaag catttatcag ggttattgtc tcatgagcgg atacatattt gaatgtattt   5460

agaaaaataa acaaataggg gttccgcgca catttccccg aaaagtgcca cctgacgtct   5520

aagaaaccat tattatcatg acattaacct ataaaaatag gcgtatcacg aggccctttc   5580

gtcttcaaga a                                                        5591
```

<210> SEQ ID NO 5
<211> LENGTH: 5591
<212> TYPE: DNA
<213> ORGANISM: Artificial Sequence
<220> FEATURE:
<223> OTHER INFORMATION: Recombinant plasmid pAPSE10190; beta actin antisense strand + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin antisense strand gene fragment
<220> FEATURE:

<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: promoter
<222> LOCATION: (1209)..(1227)
<223> OTHER INFORMATION: bacteriophage T7 gene 1 promoter
<220> FEATURE:
<221> NAME/KEY: gene
<222> LOCATION: (1300)..(1689)
<223> OTHER INFORMATION: bacteriophage MS2 coat protein gene
<220> FEATURE:
<221> NAME/KEY: terminator
<222> LOCATION: (1722)..(1769)
<223> OTHER INFORMATION: bacteriophage T7 transcription terminator

<400> SEQUENCE: 5

```
ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gctcatccca gttggtgatg ataccgtgtt cgatggggta tttcagggtg    420

aggatacctc ttttgctttg ggcttcatct cctacgtatg agtccttttg tcccataccg    480

accatgactc cttgatgcct tgggcgaccg acgatcgagg ggaagacggc acggggtgcg    540

tcatctcctg cgaaaccggc tttgcacata ccggatccat tgtctacgac aagagccgct    600

acatcgtcgt cacacatgtt gtcttttgag gttggacact gctcactaga cagaaaaacc    660

tcgtgcgttt aaacctttcg gattataaca tcacatctag gcgcgcctga cgatcaacca    720

taccagacgg accgaatacc cggtctgaac gagggcggcc gcggtaccca agaagtactt    780

agagttaatt aaggagttca aacatgagga tcacccatgt cgaagctccc acaccctagc    840

ataacccctt ggggcctcta aacgggtctt gaggggtttt ttgctgaaag gaggaactat    900

atccggatat ccacaggacg ggtgtggtcg ccatgatcgc gtagtcgata gtggctccaa    960

gtagcgaagc gagcaggact gggcggcggg catgcatcgt ccattccgac agcatcgcca   1020

gtcactatgg cgtgctgcta gcgctatatg cgttgatgca atttctatgc gcacccgttc   1080

tcggagcact gtccgaccgc tttggccgcc gcccagtcct gctcgcttcg ctacttggag   1140

ccactatcga ctacgcgatc atggcgacca cacccgtcct gtggatccag atctcgatcc   1200

cgcgaaatta atacgactca ctatagggag accacaacgg tttccctcta gatcacaagt   1260

ttgtacaaaa aagcaggcta agaaggagat atacatatgg cgtctaactt tacccaattc   1320

gttctggttg ataacggcgg tacgggtgac gttaccgtag ctccgtccaa cttcgccaac   1380

ggtgttgcgg aatggattag ctctaacagc cgctctcagg cctacaaagt cacgtgctcc   1440

gttcgtcagt ctagcgcgca gaatcgcaaa tacaccatca aagttgaagt accgaaagtc   1500

gcaacgcaga ccgtaggcgg cgtagaactc ccagttgcgg cctggcgctc ttacctcaac   1560

atggaactga ctattccgat tttgcgacg aactccgact gcgaactgat tgttaaggca    1620
```

```
atgcagggcc tgctgaaaga cggtaatccg atcccatctg caatcgctgc taactctggc   1680

atttactaat aagcggacgc gctgccaccg ctgagcaata actagcataa ccccttgggg   1740

cctctaaacg ggtcttgagg ggttttttgc tgaaaggagg aactatatcc ggcatgcacc   1800

attccttgcg gcggcggtgc tcaacggcct caacctacta ctgggctgct tcctaatgca   1860

ggagtcgcat aagggagagc gtcgaccgat gcccttgaga gccttcaacc cagtcagctc   1920

cttccggtgg gcgcggggca tgactatcgt cgccgcactt atgactgtct tctttatcat   1980

gcaactcgta ggacaggtgc cggcagcgct ctgggtcatt ttcggcgagg accgctttcg   2040

ctggagcgcg acgatgatcg gcctgtcgct tgcggtattc ggaatcttgc acgccctcgc   2100

tcaagccttc gtcactggtc ccgccaccaa acgtttcggc gagaagcagg ccattatcgc   2160

cggcatggcg gccgacgcgc tgggctacgt cttgctggcg ttcgcgacgc gaggctggat   2220

ggccttcccc attatgattc ttctcgcttc cggcggcatc gggatgcccg cgttgcaggc   2280

catgctgtcc aggcaggtag atgacgacca tcagggacag cttcaaggat cgctcgcggc   2340

tcttaccagc ctaacttcga tcattggacc gctgatcgtc acggcgattt atgccgcctc   2400

ggcgagcaca tggaacgggt tggcatggat tgtaggcgcc gccctatacc ttgtctgcct   2460

ccccgcgttg cgtcgcggtg catggagccg ggccacctcg acctgaatgg aagccggcgg   2520

cacctcgcta acggattcac cactccaaga attggagcca atcaattctt gcggagaact   2580

gtgaatgcgc aaaccaaccc ttggcagaac atatccatcg cgtccgccat ctccagcagc   2640

cgcacgcggc gcatctcggg cagcgttggg tcctggccac gggtgcgcat gatcgtgctc   2700

ctgtcgttga ggacccggct aggctggcgg ggttgcctta ctggttagca gaatgaatca   2760

ccgatacgcg agcgaacgtg aagcgactgc tgctgcaaaa cgtctgcgac ctgagcaaca   2820

acatgaatgg tcttcggttt ccgtgtttcg taaagtctgg aaacgcggaa gtcagcgccc   2880

tgcaccatta tgttccggat ctgcatcgca ggatgctgct ggctaccctg tggaacacct   2940

acatctgtat taacgaagcg ctggcattga ccctgagtga tttttctctg gtcccgccgc   3000

atccataccg ccagttgttt accctcacaa cgttccagta accgggcatg ttcatcatca   3060

gtaacccgta tcgtgagcat cctctctcgt ttcatcggta tcattacccc catgaacaga   3120

aatccccctt acacggaggc atcagtgacc aaacaggaaa aaaccgccct taacatggcc   3180

cgctttatca gaagccagac attaacgctt ctggagaaac tcaacgagct ggacgcggat   3240

gaacaggcag acatctgtga atcgcttcac gaccacgctg atgagcttta ccgcagctgc   3300

ctcgcgcgtt tcggtgatga cggtgaaaac ctctgacaca tgcagctccc ggagacggtc   3360

acagcttgtc tgtaagcgga tgccgggagc agacaagccc gtcagggcgc gtcagcgggt   3420

gttggcgggt gtcggggcgc agccatgacc cagtcacgta gcgatagcgg agtgtatact   3480

ggcttaacta tgcggcatca gagcagattg tactgagagt gcaccatatg cggtgtgaaa   3540

taccgcacag atgcgtaagg agaaaatacc gcatcaggcg ctcttccgct tcctcgctca   3600

ctgactcgct gcgctcggtc gttcggctgc ggcgagcggt atcagctcac tcaaaggcgg   3660

taatacggtt atccacagaa tcaggggata acgcaggaaa gaacatgtga gcaaaaggcc   3720

agcaaaaggc caggaaccgt aaaaaggccg cgttgctggc gtttttccat aggctccgcc   3780

cccctgacga gcatcacaaa aatcgacgct caagtcagag gtggcgaaac ccgacaggac   3840

tataaagata ccaggcgttt ccccctggaa gctccctcgt gcgctctcct gttccgaccc   3900

tgccgcttac cggatacctg tccgcctttc tcccttcggg aagcgtggcg ctttctcata   3960
```

```
gctcacgctg taggtatctc agttcggtgt aggtcgttcg ctccaagctg ggctgtgtgc   4020

acgaaccccc cgttcagccc gaccgctgcg ccttatccgg taactatcgt cttgagtcca   4080

acccggtaag acacgactta tcgccactgg cagcagccac tggtaacagg attagcagag   4140

cgaggtatgt aggcggtgct acagagttct tgaagtggtg gcctaactac ggctacacta   4200

gaaggacagt atttggtatc tgcgctctgc tgaagccagt taccttcgga aaaagagttg   4260

gtagctcttg atccggcaaa caaaccaccg ctggtagcgg tggttttttt gtttgcaagc   4320

agcagattac gcgcagaaaa aaaggatctc aagaagatcc tttgatcttt tctacggggt   4380

ctgacgctca gtggaacgaa aactcacgtt aagggatttt ggtcatgaga ttatcaaaaa   4440

ggatcttcac ctagatcctt ttaaattaaa aatgaagttt taaatcaatc taaagtatat   4500

atgagtaaac ttggtctgac agttaccaat gcttaatcag tgaggcacct atctcagcga   4560

tctgtctatt tcgttcatcc atagttgcct gactccccgt cgtgtagata actacgatac   4620

gggagggctt accatctggc cccagtgctg caatgatacc gcgagaccca cgctcaccgg   4680

ctccagattt atcagcaata aaccagccag ccggaagggc cgagcgcaga agtggtcctg   4740

caactttatc cgcctccatc cagtctatta attgttgccg ggaagctaga gtaagtagtt   4800

cgccagttaa tagtttgcgc aacgttgttg ccattgctgc aggcatcgtg gtgtcacgct   4860

cgtcgtttgg tatggcttca ttcagctccg gttcccaacg atcaaggcga gttacatgat   4920

cccccatgtt gtgcaaaaaa gcggttagct ccttcggtcc tccgatcgtt gtcagaagta   4980

agttggccgc agtgttatca ctcatggtta tggcagcact gcataattct cttactgtca   5040

tgccatccgt aagatgcttt tctgtgactg gtgagtactc aaccaagtca ttctgagaat   5100

agtgtatgcg gcgaccgagt tgctcttgcc cggcgtcaac acgggataat accgcgccac   5160

atagcagaac tttaaaagtg ctcatcattg gaaaacgttc ttcggggcga aaactctcaa   5220

ggatcttacc gctgttgaga tccagttcga tgtaacccac tcgtgcaccc aactgatctt   5280

cagcatcttt tactttcacc agcgtttctg ggtgagcaaa aacaggaagg caaaatgccg   5340

caaaaaaggg aataagggcg acacggaaat gttgaatact catactcttc ctttttcaat   5400

attattgaag catttatcag ggttattgtc tcatgagcgg atacatattt gaatgtattt   5460

agaaaaataa acaaataggg gttccgcgca catttccccg aaaagtgcca cctgacgtct   5520

aagaaaccat tattatcatg acattaacct ataaaaatag gcgtatcacg aggccctttc   5580

gtcttcaaga a                                                         5591
```

<210> SEQ ID NO 6
<211> LENGTH: 4789
<212> TYPE: DNA
<213> ORGANISM: Artificial Sequence
<220> FEATURE:
<223> OTHER INFORMATION: Recombinant plasmid pAPSE10274; beta actin sense strand - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)

<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: misc_feature
<222> LOCATION: (990)..(995)
<223> OTHER INFORMATION: restriction endonuclease SphI  recognition site

<400> SEQUENCE: 6
ttctcatgtt tgacagctta tcatcgataa gctttaatgc ggtagtttat cacagttaaa 60
ttgctaacgc agtcaggcac cgtgtatgaa atctaacaat gcgctcatcg tcatcctcgg 120
caccgtcacc ctggatgctg taggcatagg cttggttatg ccggtactgc cgggcctctt 180
gcgggatgaa ttcagatctc gatcccgcga aattaatacg actcactata gggagaccac 240
aacggtttcc ctctagatca caagtttgta caaaaaagca ggctaagaag gagatataca 300
tacgccggcc attcaaacat gaggattacc catgtattta aatacccatg tccaggcgcg 360
ctccgcgatc gcgcacgagg tttttctgtc tagtgagcag tgtccaacct caaaagacaa 420
catgtgtgac gacgatgtag cggctcttgt cgtagacaat ggatccggta tgtgcaaagc 480
cggtttcgca ggagatgacg caccccgtgc cgtcttcccc tcgatcgtcg gtcgcccaag 540
gcatcaagga gtcatggtcg gtatgggaca aaaggactca tacgtaggag atgaagccca 600
aagcaaaaga ggtatcctca ccctgaaata ccccatcgaa cacggtatca tcaccaactg 660
ggatgagttt aaacctttcg gattataaca tcacatctag gcgcgcctga cgatcaacca 720
taccagacgg accgaatacc cggtctgaac gagggcggcc gcggtaccca agaagtactt 780
agagttaatt aaggagttca aacatgagga tcacccatgt cgaagctccc acaccctagc 840
ataacccctt ggggcctcta aacgggtctt gaggggtttt ttgctgaaag gaggaactat 900
atccggatat ccacaggacg ggtgtggtcg ccatgatcgc gtagtcgata gtggctccaa 960
gtagcgaagc gagcaggact gggcggcggg catgcaccat tccttgcggc ggcggtgctc 1020
aacggcctca acctactact gggctgcttc ctaatgcagg agtcgcataa gggagagcgt 1080
cgaccgatgc ccttgagagc cttcaaccca gtcagctcct tccggtgggc gcggggcatg 1140
actatcgtcg ccgcacttat gactgtcttc tttatcatgc aactcgtagg acaggtgccg 1200
gcagcgctct gggtcatttt cggcgaggac cgctttcgct ggagcgcgac gatgatcggc 1260
ctgtcgcttg cggtattcgg aatcttgcac gccctcgctc aagccttcgt cactggtccc 1320
gccaccaaac gtttcggcga gaagcaggcc attatcgccg gcatggcggc cgacgcgctg 1380
ggctacgtct tgctggcgtt cgcgacgcga ggctggatgg ccttccccat tatgattctt 1440
ctcgcttccg gcggcatcgg gatgcccgcg ttgcaggcca tgctgtccag gcaggtagat 1500
gacgaccatc agggacagct tcaaggatcg ctcgcggctc ttaccagcct aacttcgatc 1560
attggaccgc tgatcgtcac ggcgatttat gccgcctcgg cgagcacatg gaacgggttg 1620
gcatggattg taggcgccgc cctatacctt gtctgcctcc ccgcgttgcg tcgcggtgca 1680
tggagccggg ccacctcgac ctgaatggaa gccggcggca cctcgctaac ggattcacca 1740
ctccaagaat tggagccaat caattcttgc ggagaactgt gaatgcgcaa accaaccctt 1800

```
ggcagaacat atccatcgcg tccgccatct ccagcagccg cacgcggcgc atctcgggca   1860
gcgttgggtc ctggccacgg gtgcgcatga tcgtgctcct gtcgttgagg acccggctag   1920
gctggcgggg ttgccttact ggttagcaga atgaatcacc gatacgcgag cgaacgtgaa   1980
gcgactgctg ctgcaaaacg tctgcgacct gagcaacaac atgaatggtc ttcggtttcc   2040
gtgtttcgta aagtctggaa acgcggaagt cagcgccctg caccattatg ttccggatct   2100
gcatcgcagg atgctgctgg ctaccctgtg gaacacctac atctgtatta acgaagcgct   2160
ggcattgacc ctgagtgatt tttctctggt cccgccgcat ccataccgcc agttgtttac   2220
cctcacaacg ttccagtaac cgggcatgtt catcatcagt aacccgtatc gtgagcatcc   2280
tctctcgttt catcggtatc attaccccca tgaacagaaa tcccccttac acggaggcat   2340
cagtgaccaa acaggaaaaa accgccctta acatggcccg ctttatcaga agccagacat   2400
taacgcttct ggagaaactc aacgagctgg acgcggatga acaggcagac atctgtgaat   2460
cgcttcacga ccacgctgat gagctttacc gcagctgcct cgcgcgtttc ggtgatgacg   2520
gtgaaaacct ctgacacatg cagctcccgg agacggtcac agcttgtctg taagcggatg   2580
ccgggagcag acaagcccgt cagggcgcgt cagcgggtgt tggcgggtgt cggggcgcag   2640
ccatgaccca gtcacgtagc gatagcggag tgtatactgg cttaactatg cggcatcaga   2700
gcagattgta ctgagagtgc accatatgcg gtgtgaaata ccgcacagat gcgtaaggag   2760
aaaataccgc atcaggcgct cttccgcttc ctcgctcact gactcgctgc gctcggtcgt   2820
tcggctgcgg cgagcggtat cagctcactc aaaggcggta atacggttat ccacagaatc   2880
aggggataac gcaggaaaga acatgtgagc aaaaggccag caaaaggcca ggaaccgtaa   2940
aaaggccgcg ttgctggcgt ttttccatag gctccgcccc cctgacgagc atcacaaaaa   3000
tcgacgctca agtcagaggt ggcgaaaccc gacaggacta taaagatacc aggcgtttcc   3060
ccctggaagc tccctcgtgc gctctcctgt tccgaccctg ccgcttaccg gatacctgtc   3120
cgcctttctc ccttcgggaa gcgtggcgct ttctcatagc tcacgctgta ggtatctcag   3180
ttcggtgtag gtcgttcgct ccaagctggg ctgtgtgcac gaaccccccg ttcagcccga   3240
ccgctgcgcc ttatccggta actatcgtct tgagtccaac ccggtaagac acgacttatc   3300
gccactggca gcagccactg gtaacaggat tagcagagcg aggtatgtag gcggtgctac   3360
agagttcttg aagtggtggc ctaactacgg ctacactaga aggacagtat ttggtatctg   3420
cgctctgctg aagccagtta ccttcggaaa aagagttggt agctcttgat ccggcaaaca   3480
aaccaccgct ggtagcggtg gtttttttgt ttgcaagcag cagattacgc gcagaaaaaa   3540
aggatctcaa gaagatcctt tgatcttttc tacggggtct gacgctcagt ggaacgaaaa   3600
ctcacgttaa gggattttgg tcatgagatt atcaaaaagg atcttcacct agatcctttt   3660
aaattaaaaa tgaagtttta aatcaatcta aagtatatat gagtaaactt ggtctgacag   3720
ttaccaatgc ttaatcagtg aggcacctat ctcagcgatc tgtctatttc gttcatccat   3780
agttgcctga ctccccgtcg tgtagataac tacgatacgg gagggcttac catctggccc   3840
cagtgctgca atgataccgc gagacccacg ctcaccggct ccagatttat cagcaataaa   3900
ccagccagcc ggaagggccg agcgcagaag tggtcctgca actttatccg cctccatcca   3960
gtctattaat tgttgccggg aagctagagt aagtagttcg ccagttaata gtttgcgcaa   4020
cgttgttgcc attgctgcag gcatcgtggt gtcacgctcg tcgtttggta tggcttcatt   4080
cagctccggt tcccaacgat caaggcgagt tacatgatcc cccatgttgt gcaaaaaagc   4140
```

```
ggttagctcc ttcggtcctc cgatcgttgt cagaagtaag ttggccgcag tgttatcact   4200

catggttatg gcagcactgc ataattctct tactgtcatg ccatccgtaa gatgcttttc   4260

tgtgactggt gagtactcaa ccaagtcatt ctgagaatag tgtatgcggc gaccgagttg   4320

ctcttgcccg gcgtcaacac gggataatac cgcgccacat agcagaactt taaaagtgct   4380

catcattgga aaacgttctt cggggcgaaa actctcaagg atcttaccgc tgttgagatc   4440

cagttcgatg taacccactc gtgcacccaa ctgatcttca gcatctttta ctttcaccag   4500

cgtttctggg tgagcaaaaa caggaaggca aaatgccgca aaaaagggaa taagggcgac   4560

acggaaatgt tgaatactca tactcttcct ttttcaatat tattgaagca tttatcaggg   4620

ttattgtctc atgagcggat acatatttga atgtatttag aaaaataaac aaataggggt   4680

tccgcgcaca tttccccgaa aagtgccacc tgacgtctaa gaaaccatta ttatcatgac   4740

attaacctat aaaaataggc gtatcacgag gccctttcgt cttcaagaa             4789
```

<210> SEQ ID NO 7
<211> LENGTH: 4789
<212> TYPE: DNA
<213> ORGANISM: Artificial Sequence
<220> FEATURE:
<223> OTHER INFORMATION: Recombinant plasmid pAPSE10275; beta actin antisense strand - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin antisense strand gene fragment
<220> FEATURE:
<221> NAME/KEY: misc_feature
<222> LOCATION: (667)..(674)
<223> OTHER INFORMATION: restriction endonuclease PmeI recogntion site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: misc_feature
<222> LOCATION: (990)..(995)
<223> OTHER INFORMATION: restriction endonuclease SphI recognition site

<400> SEQUENCE: 7

```
ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gctcatccca gttggtgatg ataccgtgtt cgatggggta tttcagggtg    420
```

```
aggatacctc ttttgctttg ggcttcatct cctacgtatg agtccttttg tcccataccg    480
accatgactc cttgatgcct tgggcgaccg acgatcgagg ggaagacggc acggggtgcg    540
tcatctcctg cgaaaccggc tttgcacata ccggatccat tgtctacgac aagagccgct    600
acatcgtcgt cacacatgtt gtcttttgag gttggacact gctcactaga cagaaaaacc    660
tcgtgcgttt aaacctttcg gattataaca tcacatctag gcgcgcctga cgatcaacca    720
taccagacgg accgaatacc cggtctgaac gagggcggcc gcggtaccca agaagtactt    780
agagttaatt aaggagttca aacatgagga tcacccatgt cgaagctccc acaccctagc    840
ataacccctt ggggcctcta aacgggtctt gaggggtttt ttgctgaaag gaggaactat    900
atccggatat ccacaggacg ggtgtggtcg ccatgatcgc gtagtcgata gtggctccaa    960
gtagcgaagc gagcaggact gggcggcggg catgcaccat tccttgcggc ggcggtgctc   1020
aacggcctca acctactact gggctgcttc ctaatgcagg agtcgcataa gggagagcgt   1080
cgaccgatgc ccttgagagc cttcaaccca gtcagctcct tccggtgggc gcggggcatg   1140
actatcgtcg ccgcacttat gactgtcttc tttatcatgc aactcgtagg acaggtgccg   1200
gcagcgctct gggtcatttt cggcgaggac cgctttcgct ggagcgcgac gatgatcggc   1260
ctgtcgcttg cggtattcgg aatcttgcac gccctcgctc aagccttcgt cactggtccc   1320
gccaccaaac gtttcggcga gaagcaggcc attatcgccg gcatggcggc cgacgcgctg   1380
ggctacgtct tgctggcgtt cgcgacgcga ggctggatgg ccttccccat tatgattctt   1440
ctcgcttccg gcggcatcgg gatgcccgcg ttgcaggcca tgctgtccag gcaggtagat   1500
gacgaccatc agggacagct tcaaggatcg ctcgcggctc ttaccagcct aacttcgatc   1560
attggaccgc tgatcgtcac ggcgatttat gccgcctcgg cgagcacatg gaacgggttg   1620
gcatggattg taggcgccgc cctatacctt gtctgcctcc ccgcgttgcg tcgcggtgca   1680
tggagccggg ccacctcgac ctgaatggaa gccggcggca cctcgctaac ggattcacca   1740
ctccaagaat tggagccaat caattcttgc ggagaactgt gaatgcgcaa accaaccctt   1800
ggcagaacat atccatcgcg tccgccatct ccagcagccg cacgcggcgc atctcgggca   1860
gcgttgggtc ctggccacgg gtgcgcatga tcgtgctcct gtcgttgagg acccggctag   1920
gctggcgggg ttgccttact ggttagcaga atgaatcacc gatacgcgag cgaacgtgaa   1980
gcgactgctg ctgcaaaacg tctgcgacct gagcaacaac atgaatggtc ttcggtttcc   2040
gtgtttcgta aagtctggaa acgcggaagt cagcgccctg caccattatg ttccggatct   2100
gcatcgcagg atgctgctgg ctaccctgtg gaacacctac atctgtatta acgaagcgct   2160
ggcattgacc ctgagtgatt tttctctggt cccgccgcat ccataccgcc agttgtttac   2220
cctcacaacg ttccagtaac cggcatgtt catcatcagt aacccgtatc gtgagcatcc   2280
tctctcgttt catcggtatc attaccccca tgaacagaaa tcccccttac acggaggcat   2340
cagtgaccaa acaggaaaaa accgccctta acatggcccg ctttatcaga agccagacat   2400
taacgcttct ggagaaactc aacgagctgg acgcggatga acaggcagac atctgtgaat   2460
cgcttcacga ccacgctgat gagctttacc gcagctgcct cgcgcgtttc ggtgatgacg   2520
gtgaaaacct ctgacacatg cagctcccgg agacggtcac agcttgtctg taagcggatg   2580
ccgggagcag acaagcccgt cagggcgcgt cagcgggtgt tggcgggtgt cggggcgcag   2640
ccatgaccca gtcacgtagc gatagcggag tgtatactgg cttaactatg cggcatcaga   2700
gcagattgta ctgagagtgc accatatgcg gtgtgaaata ccgcacagat gcgtaaggag   2760
aaaataccgc atcaggcgct cttccgcttc ctcgctcact gactcgctgc gctcggtcgt   2820
```

```
tcggctgcgg cgagcggtat cagctcactc aaaggcggta atacggttat ccacagaatc   2880

aggggataac gcaggaaaga acatgtgagc aaaaggccag caaaaggcca ggaaccgtaa   2940

aaaggccgcg ttgctggcgt ttttccatag gctccgcccc cctgacgagc atcacaaaaa   3000

tcgacgctca agtcagaggt ggcgaaaccc gacaggacta taaagatacc aggcgtttcc   3060

ccctggaagc tccctcgtgc gctctcctgt tccgaccctg ccgcttaccg gatacctgtc   3120

cgcctttctc ccttcgggaa gcgtggcgct ttctcatagc tcacgctgta ggtatctcag   3180

ttcggtgtag gtcgttcgct ccaagctggg ctgtgtgcac gaaccccccg ttcagcccga   3240

ccgctgcgcc ttatccggta actatcgtct tgagtccaac ccggtaagac acgacttatc   3300

gccactggca gcagccactg gtaacaggat tagcagagcg aggtatgtag gcggtgctac   3360

agagttcttg aagtggtggc ctaactacgg ctacactaga aggacagtat ttggtatctg   3420

cgctctgctg aagccagtta ccttcggaaa aagagttggt agctcttgat ccggcaaaca   3480

aaccaccgct ggtagcggtg gtttttttgt ttgcaagcag cagattacgc gcagaaaaaa   3540

aggatctcaa gaagatcctt tgatcttttc tacggggtct gacgctcagt ggaacgaaaa   3600

ctcacgttaa gggattttgg tcatgagatt atcaaaaagg atcttcacct agatcctttt   3660

aaattaaaaa tgaagtttta aatcaatcta aagtatatat gagtaaactt ggtctgacag   3720

ttaccaatgc ttaatcagtg aggcacctat ctcagcgatc tgtctatttc gttcatccat   3780

agttgcctga ctccccgtcg tgtagataac tacgatacgg gagggcttac catctggccc   3840

cagtgctgca atgataccgc gagacccacg ctcaccggct ccagatttat cagcaataaa   3900

ccagccagcc ggaagggccg agcgcagaag tggtcctgca actttatccg cctccatcca   3960

gtctattaat tgttgccggg aagctagagt aagtagttcg ccagttaata gtttgcgcaa   4020

cgttgttgcc attgctgcag gcatcgtggt gtcacgctcg tcgtttggta tggcttcatt   4080

cagctccggt tcccaacgat caaggcgagt tacatgatcc cccatgttgt gcaaaaaagc   4140

ggttagctcc ttcggtcctc cgatcgttgt cagaagtaag ttggccgcag tgttatcact   4200

catggttatg gcagcactgc ataattctct tactgtcatg ccatccgtaa gatgcttttc   4260

tgtgactggt gagtactcaa ccaagtcatt ctgagaatag tgtatgcggc gaccgagttg   4320

ctcttgcccg gcgtcaacac gggataatac cgcgccacat agcagaactt taaaagtgct   4380

catcattgga aaacgttctt cggggcgaaa actctcaagg atcttaccgc tgttgagatc   4440

cagttcgatg taacccactc gtgcacccaa ctgatcttca gcatctttta ctttcaccag   4500

cgtttctggg tgagcaaaaa caggaaggca aaatgccgca aaaaagggaa taagggcgac   4560

acggaaatgt tgaatactca tactcttcct ttttcaatat tattgaagca tttatcaggg   4620

ttattgtctc atgagcggat acatatttga atgtatttag aaaaataaac aaataggggt   4680

tccgcgcaca tttccccgaa aagtgccacc tgacgtctaa gaaaccatta ttatcatgac   4740

attaacctat aaaaataggc gtatcacgag gccctttcgt cttcaagaa              4789
```

<210> SEQ ID NO 8
<211> LENGTH: 3864
<212> TYPE: DNA
<213> ORGANISM: Artificial Sequence
<220> FEATURE:
<223> OTHER INFORMATION: Recombinant plasmid pAPSE10269; beta actin stem loop + coat protein
<220> FEATURE:
<221> NAME/KEY: promoter
<222> LOCATION: (214)..(232)
<223> OTHER INFORMATION: bacteriophage T7 gene 1 promoter

```
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator

<400> SEQUENCE: 8

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

catgtgtgac gacgatgtag cggctcttgt cgtagacaat ggatccggta tgtgcaaagc    480

cggtttcgca ggagatgacg caccccgtgc cgtcttcccc tcgatcgtcg gtcgcccaag    540

gcatcaagga gtcatggtcg gtatgggaca aaaggactca tacgtaggag atgaagccca    600

aagcaaaaga ggtatcctca ccctgaaata ccccatcgaa cacggtatca tcaccaactg    660

ggatgagttt aaaccctcta gctgctttac aaagtactgg ttccctttcc agcgggatgc    720

tttatctaaa cgcaacatga ggatcaccca tgtcgccaca tcgcttccta gttccgctgg    780

gatccatcgt tggcggccga agccgccatt ccatagtgag ttctggcgcg cctcatccca    840

gttggtgatg ataccgtgtt cgatggggta tttcagggtg aggatacctc ttttgctttg    900

ggcttcatct cctacgtatg agtccttttg tcccataccg accatgactc cttgatgcct    960
```

-continued

```
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg ggcctctaa    1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg tggatccaga tctcgatccc gcgaaattaa tacgactcac   1620
tatagggaga ccacaacggt ttccctctag atcacaagtt tgtacaaaaa agcaggctaa   1680
gaaggagata tacatatggc gtctaacttt acccaattcg ttctggttga taacggcggt   1740
acgggtgacg ttaccgtagc tccgtccaac ttcgccaacg gtgttgcgga atggattagc   1800
tctaacagcc gctctcaggc ctacaaagtc acgtgctccg ttcgtcagtc tagcgcgcag   1860
aatcgcaaat acaccatcaa agttgaagta ccgaaagtcg caacgcagac cgtaggcggc   1920
gtagaactcc cagttgcggc ctggcgctct tacctcaaca tggaactgac tattccgatt   1980
tttgcgacga actccgactg cgaactgatt gttaaggcaa tgcagggcct gctgaaagac   2040
ggtaatccga tcccatctgc aatcgctgct aactctggca tttactaata agcggacgcg   2100
ctgccaccgc tgagcaataa ctagcataac cccttggggc ctctaaacgg gtcttgaggg   2160
gtttttgct gaaaggagga actatatccg gcatgcacca ttccttgcgg cggcggtgct    2220
caacggcctc aacctactac tgggctgctt cctaatgcag gagtcgcata agggagagcg   2280
tcgaccgatg cccttgagag ccttcaaccc agtcagctcc ttccggtggg cgcggggcat   2340
gactatcgtc gccgcactta tgactgtctt ctttatcatg caactcgtag gacaggtgcc   2400
ggcagcgctc tgggtcattt tcggcgagga ccgctttcgc tggagcgcga cgatgatcgg   2460
cctgtcgctt gcggtattcg gaatcttgca cgccctcgct caagccttcg tcactggtcc   2520
cgccaccaaa cgtttcggcg agaagcaggc cattatcgcc ggcatggcgg ccgacgcgct   2580
gggctacgtc ttgctggcgt tcgcgacgcg aggctggatg gccttcccca ttatgattct   2640
tctcgcttcc ggcggcatcg ggatgcccgc gttgcaggcc atgctgtcca ggcaggtaga   2700
tgacgaccat cagggacagc ttcaaggatc gctcgcggct cttaccagcc taacttcgat   2760
cattggaccg ctgatcgtca cggcgattta tgccgcctcg gcgagcacat ggaacgggtt   2820
ggcatggatt gtaggcgccg ccctatacct tgtctgcctc cccgcgttgc gtcgcggtgc   2880
atggagccgg gccacctcga cctgaatgga agccggcggc acctcgctaa cggattcacc   2940
actccaagaa ttggagccaa tcaattcttg cggagaactg tgaatgcgca aaccaaccct   3000
tggcagaaca tatccatcgc gtccgccatc tccagcagcc gcacgcggcg catctcgggc   3060
agcgttgggt cctggccacg ggtgcgcatg atcgtgctcc tgtcgttgag gacccggcta   3120
ggctggcggg gttgccttac tggttagcag aatgaatcac cgatacgcga gcgaacgtga   3180
agcgactgct gctgcaaaac gtctgcgacc tgagcaacaa catgaatggt cttcggtttc   3240
cgtgtttcgt aaagtctgga aacgcggaag tcagcgccct gcaccattat gttccggatc   3300
tgcatcgcag gatgctgctg gctaccctgt ggaacaccta catctgtatt aacgaagcgc   3360
```

```
tggcattgac cctgagtgat ttttctctgg tcccgccgca tccataccgc cagttgttta   3420

ccctcacaac gttccagtaa ccgggcatgt tcatcatcag taacccgtat cgtgagcatc   3480

ctctctcgtt tcatcggtat cattaccccc atgaacagaa atcccccttta cacggaggca   3540

tcagtgacca aacaggaaaa aaccgccctt aacatggccc gctttatcag aagccagaca   3600

ttaacgcttc tggagaaact caacgagctg gacgcggatg aacaggcaga catctgtgaa   3660

tcgcttcacg accacgctga tgagctttac cgcagctgcc tcgcgcgttt cggtgatgac   3720

ggtgaaaacc tctgacacat gcagctcccg gagacggtca cagcttgtct gtaagcggat   3780

gccgggagca gacaagcccg tcagggcgcg tcagcgggtg ttggcgggtg tcggggcgca   3840

gccatgaccc agtcacgtag cgat                                          3864
```

```
<210> SEQ ID NO 9
<211> LENGTH: 5375
<212> TYPE: DNA
<213> ORGANISM: Artificial Sequence
<220> FEATURE:
<223> OTHER INFORMATION: Recombinant plasmid pAPSE10306; beta actin stem
      loop - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1389)..(1394)
<223> OTHER INFORMATION: restriction endonuclease SphI recognition site

<400> SEQUENCE: 9

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300
```

```
tacgccggcc attcaaacat gaggattacc catgtattta aatacccatg tccaggcgcg    360
ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaacatga ggatcaccca tgtcgccaca tcgcttccta gttccgctgg    780
gatccatcgt tggcggccga agccgccatt ccatagtgag ttctggcgcg cctcatccca    840
gttggtgatg ataccgtgtt cgatggggta tttcagggtg aggatacctc ttttgctttg    900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg gggcctctaa   1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg taccattcct tgcggcggcg gtgctcaacg gcctcaacct   1620
actactgggc tgcttcctaa tgcaggagtc gcataaggga gagcgtcgac cgatgccctt   1680
gagagccttc aacccagtca gctccttccg gtgggcgcgg ggcatgacta tcgtcgccgc   1740
acttatgact gtcttcttta tcatgcaact cgtaggacag gtgccggcag cgctctgggt   1800
cattttcggc gaggaccgct ttcgctggag cgcgacgatg atcggcctgt cgcttgcggt   1860
attcggaatc ttgcacgccc tcgctcaagc cttcgtcact ggtcccgcca ccaaacgttt   1920
cggcgagaag caggccatta tcgccggcat ggcggccgac gcgctgggct acgtcttgct   1980
ggcgttcgcg acgcgaggct ggatggcctt ccccattatg attcttctcg cttccggcgg   2040
catcgggatg cccgcgttgc aggccatgct gtccaggcag gtagatgacg accatcaggg   2100
acagcttcaa ggatcgctcg cggctcttac cagcctaact tcgatcattg gaccgctgat   2160
cgtcacggcg atttatgccg cctcggcgag cacatggaac gggttggcat ggattgtagg   2220
cgccgcccta taccttgtct gcctccccgc gttgcgtcgc ggtgcatgga gccgggccac   2280
ctcgacctga atggaagccg gcggcacctc gctaacggat tcaccactcc aagaattgga   2340
gccaatcaat tcttgcggag aactgtgaat gcgcaaacca acccttggca gaacatatcc   2400
atcgcgtccg ccatctccag cagccgcacg cggcgcatct cgggcagcgt tgggtcctgg   2460
ccacgggtgc gcatgatcgt gctcctgtcg ttgaggaccc ggctaggctg gcggggttgc   2520
cttactggtt agcagaatga atcaccgata cgcgagcgaa cgtgaagcga ctgctgctgc   2580
aaaacgtctg cgacctgagc aacaacatga atggtcttcg gtttccgtgt ttcgtaaagt   2640
```

```
ctggaaacgc ggaagtcagc gccctgcacc attatgttcc ggatctgcat cgcaggatgc   2700
tgctggctac cctgtggaac acctacatct gtattaacga agcgctggca ttgaccctga   2760
gtgatttttc tctggtcccg ccgcatccat accgccagtt gtttaccctc acaacgttcc   2820
agtaaccggg catgttcatc atcagtaacc cgtatcgtga gcatcctctc tcgtttcatc   2880
ggtatcatta cccccatgaa cagaaatccc ccttacacgg aggcatcagt gaccaaacag   2940
gaaaaaaccg cccttaacat ggcccgcttt atcagaagcc agacattaac gcttctggag   3000
aaactcaacg agctggacgc ggatgaacag gcagacatct gtgaatcgct tcacgaccac   3060
gctgatgagc tttaccgcag ctgcctcgcg cgtttcggtg atgacggtga aaacctctga   3120
cacatgcagc tcccggagac ggtcacagct tgtctgtaag cggatgccgg gagcagacaa   3180
gcccgtcagg gcgcgtcagc gggtgttggc gggtgtcggg gcgcagccat gacccagtca   3240
cgtagcgata gcggagtgta tactggctta actatgcggc atcagagcag attgtactga   3300
gagtgcacca tatgcggtgt gaaataccgc acagatgcgt aaggagaaaa taccgcatca   3360
ggcgctcttc cgcttcctcg ctcactgact cgctgcgctc ggtcgttcgg ctgcggcgag   3420
cggtatcagc tcactcaaag gcggtaatac ggttatccac agaatcaggg gataacgcag   3480
gaaagaacat gtgagcaaaa ggccagcaaa aggccaggaa ccgtaaaaag gccgcgttgc   3540
tggcgttttt ccataggctc cgcccccctg acgagcatca caaaaatcga cgctcaagtc   3600
agaggtggcg aaacccgaca ggactataaa gataccaggc gtttccccct ggaagctccc   3660
tcgtgcgctc tcctgttccg accctgccgc ttaccggata cctgtccgcc tttctccctt   3720
cgggaagcgt ggcgctttct catagctcac gctgtaggta tctcagttcg gtgtaggtcg   3780
ttcgctccaa gctgggctgt gtgcacgaac cccccgttca gcccgaccgc tgcgccttat   3840
ccggtaacta tcgtcttgag tccaacccgg taagacacga cttatcgcca ctggcagcag   3900
ccactggtaa caggattagc agagcgaggt atgtaggcgg tgctacagag ttcttgaagt   3960
ggtggcctaa ctacggctac actagaagga cagtatttgg tatctgcgct ctgctgaagc   4020
cagttacctt cggaaaaaga gttggtagct cttgatccgg caaacaaacc accgctggta   4080
gcggtggttt ttttgtttgc aagcagcaga ttacgcgcag aaaaaaagga tctcaagaag   4140
atcctttgat cttttctacg gggtctgacg ctcagtggaa cgaaaactca cgttaaggga   4200
ttttggtcat gagattatca aaaaggatct tcacctagat ccttttaaat taaaaatgaa   4260
gttttaaatc aatctaaagt atatatgagt aaacttggtc tgacagttac caatgcttaa   4320
tcagtgaggc acctatctca gcgatctgtc tatttcgttc atccatagtt gcctgactcc   4380
ccgtcgtgta gataactacg atacgggagg gcttaccatc tggccccagt gctgcaatga   4440
taccgcgaga cccacgctca ccggctccag atttatcagc aataaaccag ccagccggaa   4500
gggccgagcg cagaagtggt cctgcaactt tatccgcctc catccagtct attaattgtt   4560
gccgggaagc tagagtaagt agttcgccag ttaatagttt gcgcaacgtt gttgccattg   4620
ctgcaggcat cgtggtgtca cgctcgtcgt ttggtatggc ttcattcagc tccggttccc   4680
aacgatcaag gcgagttaca tgatccccca tgttgtgcaa aaaagcggtt agctccttcg   4740
gtcctccgat cgttgtcaga agtaagttgg ccgcagtgtt atcactcatg gttatggcag   4800
cactgcataa ttctcttact gtcatgccat ccgtaagatg cttttctgtg actggtgagt   4860
actcaaccaa gtcattctga gaatagtgta tgcggcgacc gagttgctct tgcccggcgt   4920
caacacggga taataccgcg ccacatagca gaactttaaa agtgctcatc attggaaaac   4980
gttcttcggg gcgaaaactc tcaaggatct taccgctgtt gagatccagt tcgatgtaac   5040
```

```
ccactcgtgc acccaactga tcttcagcat cttttacttt caccagcgtt tctgggtgag   5100

caaaaacagg aaggcaaaat gccgcaaaaa agggaataag ggcgacacgg aaatgttgaa   5160

tactcatact cttccttttt caatattatt gaagcattta tcagggttat tgtctcatga   5220

gcggatacat atttgaatgt atttagaaaa ataaacaaat aggggttccg cgcacatttc   5280

cccgaaaagt gccacctgac gtctaagaaa ccattattat catgacatta acctataaaa   5340

ataggcgtat cacgaggccc tttcgtcttc aagaa                              5375


<210> SEQ ID NO 10
<211> LENGTH: 5990
<212> TYPE: DNA
<213> ORGANISM: Artificial Sequence
<220> FEATURE:
<223> OTHER INFORMATION: Recombinant plasmid pAPSE10216; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator

<400> SEQUENCE: 10

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360
```

```
ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaatgaga gaggtattcc tcaggccaca tcgcttccta gttccgctgg    780
gatccatcgt tggcggccga agccgccatt ccatagtgag ttctggcgcg cctcatccca    840
gttggtgatg ataccgtgtt cgatggggta tttcagggtg aggatacctc ttttgctttg    900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg gggcctctaa   1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg tggatccaga tctcgatccc gcgaaattaa tacgactcac   1620
tatagggaga ccacaacggt ttccctctag atcacaagtt tgtacaaaaa agcaggctaa   1680
gaaggagata tacatatggc gtctaacttt acccaattcg ttctggttga taacggcggt   1740
acgggtgacg ttaccgtagc tccgtccaac ttcgccaacg gtgttgcgga atggattagc   1800
tctaacagcc gctctcaggc ctacaaagtc acgtgctccg ttcgtcagtc tagcgcgcag   1860
aatcgcaaat acaccatcaa agttgaagta ccgaaagtcg caacgcagac cgtaggcggc   1920
gtagaactcc cagttgcggc ctggcgctct tacctcaaca tggaactgac tattccgatt   1980
tttgcgacga actccgactg cgaactgatt gttaaggcaa tgcagggcct gctgaaagac   2040
ggtaatccga tcccatctgc aatcgctgct aactctggca tttactaata agcggacgcg   2100
ctgccaccgc tgagcaataa ctagcataac cccttggggc ctctaaacgg gtcttgaggg   2160
gttttttgct gaaaggagga actatatccg gcatgcacca ttccttgcgg cggcggtgct   2220
caacggcctc aacctactac tgggctgctt cctaatgcag gagtcgcata agggagagcg   2280
tcgaccgatg cccttgagag ccttcaaccc agtcagctcc ttccggtggg cgcggggcat   2340
gactatcgtc gccgcactta tgactgtctt ctttatcatg caactcgtag gacaggtgcc   2400
ggcagcgctc tgggtcattt tcggcgagga ccgctttcgc tggagcgcga cgatgatcgg   2460
cctgtcgctt gcggtattcg gaatcttgca cgccctcgct caagccttcg tcactggtcc   2520
cgccaccaaa cgtttcggcg agaagcaggc cattatcgcc ggcatggcgg ccgacgcgct   2580
gggctacgtc ttgctggcgt tcgcgacgcg aggctggatg gccttcccca ttatgattct   2640
tctcgcttcc ggcggcatcg ggatgcccgc gttgcaggcc atgctgtcca ggcaggtaga   2700
```

-continued

```
tgacgaccat cagggacagc ttcaaggatc gctcgcggct cttaccagcc taacttcgat   2760
cattggaccg ctgatcgtca cggcgattta tgccgcctcg gcgagcacat ggaacgggtt   2820
ggcatggatt gtaggcgccg ccctatacct tgtctgcctc cccgcgttgc gtcgcggtgc   2880
atggagccgg gccacctcga cctgaatgga agccggcggc acctcgctaa cggattcacc   2940
actccaagaa ttggagccaa tcaattcttg cggagaactg tgaatgcgca aaccaaccct   3000
tggcagaaca tatccatcgc gtccgccatc tccagcagcc gcacgcggcg catctcgggc   3060
agcgttgggt cctggccacg ggtgcgcatg atcgtgctcc tgtcgttgag gacccggcta   3120
ggctggcggg gttgccttac tggttagcag aatgaatcac cgatacgcga gcgaacgtga   3180
agcgactgct gctgcaaaac gtctgcgacc tgagcaacaa catgaatggt cttcggtttc   3240
cgtgtttcgt aaagtctgga aacgcggaag tcagcgccct gcaccattat gttccggatc   3300
tgcatcgcag gatgctgctg gctaccctgt ggaacaccta catctgtatt aacgaagcgc   3360
tggcattgac cctgagtgat ttttctctgg tcccgccgca tccataccgc cagttgttta   3420
ccctcacaac gttccagtaa ccgggcatgt tcatcatcag taacccgtat cgtgagcatc   3480
ctctctcgtt tcatcggtat cattaccccc atgaacagaa atccccctta cacggaggca   3540
tcagtgacca aacaggaaaa aaccgccctt aacatggccc gctttatcag aagccagaca   3600
ttaacgcttc tggagaaact caacgagctg gacgcggatg aacaggcaga catctgtgaa   3660
tcgcttcacg accacgctga tgagctttac cgcagctgcc tcgcgcgttt cggtgatgac   3720
ggtgaaaacc tctgacacat gcagctcccg gagacggtca cagcttgtct gtaagcggat   3780
gccgggagca gacaagcccg tcagggcgcg tcagcgggtg ttggcgggtg tcggggcgca   3840
gccatgaccc agtcacgtag cgatagcgga gtgtatactg gcttaactat gcggcatcag   3900
agcagattgt actgagagtg caccatatgc ggtgtgaaat accgcacaga tgcgtaagga   3960
gaaaataccg catcaggcgc tcttccgctt cctcgctcac tgactcgctg cgctcggtcg   4020
ttcggctgcg gcgagcggta tcagctcact caaaggcggt aatacggtta tccacagaat   4080
caggggataa cgcaggaaag aacatgtgag caaaaggcca gcaaaaggcc aggaaccgta   4140
aaaaggccgc gttgctggcg tttttccata ggctccgccc ccctgacgag catcacaaaa   4200
atcgacgctc aagtcagagg tggcgaaacc cgacaggact ataaagatac caggcgtttc   4260
cccctggaag ctccctcgtg cgctctcctg ttccgaccct gccgcttacc ggatacctgt   4320
ccgcctttct cccttcggga agcgtggcgc tttctcatag ctcacgctgt aggtatctca   4380
gttcggtgta ggtcgttcgc tccaagctgg gctgtgtgca cgaacccccc gttcagcccg   4440
accgctgcgc cttatccggt aactatcgtc ttgagtccaa cccggtaaga cacgacttat   4500
cgccactggc agcagccact ggtaacagga ttagcagagc gaggtatgta ggcggtgcta   4560
cagagttctt gaagtggtgg cctaactacg gctacactag aaggacagta tttggtatct   4620
gcgctctgct gaagccagtt accttcggaa aaagagttgg tagctcttga tccggcaaac   4680
aaaccaccgc tggtagcggt ggtttttttg tttgcaagca gcagattacg cgcagaaaaa   4740
aaggatctca agaagatcct ttgatctttt ctacggggtc tgacgctcag tggaacgaaa   4800
actcacgtta agggattttg gtcatgagat tatcaaaaag gatcttcacc tagatccttt   4860
taaattaaaa atgaagtttt aaatcaatct aaagtatata tgagtaaact tggtctgaca   4920
gttaccaatg cttaatcagt gaggcaccta tctcagcgat ctgtctattt cgttcatcca   4980
tagttgcctg actccccgtc gtgtagataa ctacgatacg ggagggctta ccatctggcc   5040
ccagtgctgc aatgataccg cgagacccac gctcaccggc tccagattta tcagcaataa   5100
```

```
accagccagc cggaagggcc gagcgcagaa gtggtcctgc aactttatcc gcctccatcc   5160

agtctattaa ttgttgccgg gaagctagag taagtagttc gccagttaat agtttgcgca   5220

acgttgttgc cattgctgca ggcatcgtgg tgtcacgctc gtcgtttggt atggcttcat   5280

tcagctccgg ttcccaacga tcaaggcgag ttacatgatc ccccatgttg tgcaaaaaag   5340

cggttagctc cttcggtcct ccgatcgttg tcagaagtaa gttggccgca gtgttatcac   5400

tcatggttat ggcagcactg cataattctc ttactgtcat gccatccgta agatgctttt   5460

ctgtgactgg tgagtactca accaagtcat tctgagaata gtgtatgcgg cgaccgagtt   5520

gctcttgccc ggcgtcaaca cgggataata ccgcgccaca tagcagaact ttaaaagtgc   5580

tcatcattgg aaaacgttct tcggggcgaa aactctcaag gatcttaccg ctgttgagat   5640

ccagttcgat gtaacccact cgtgcaccca actgatcttc agcatctttt actttcacca   5700

gcgtttctgg gtgagcaaaa acaggaaggc aaaatgccgc aaaaaaggga ataagggcga   5760

cacggaaatg ttgaatactc atactcttcc tttttcaata ttattgaagc atttatcagg   5820

gttattgtct catgagcgga tacatatttg aatgtattta gaaaaataaa caaatagggg   5880

ttccgcgcac atttccccga aaagtgccac ctgacgtcta agaaaccatt attatcatga   5940

cattaaccta taaaaatagg cgtatcacga ggccctttcg tcttcaagaa              5990
```

<210> SEQ ID NO 11
<211> LENGTH: 5188
<212> TYPE: DNA
<213> ORGANISM: Artificial Sequence
<220> FEATURE:
<223> OTHER INFORMATION: Recombinant plasmid pAPSE10305; beta actin stem loop - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophageT7 transcription terminator
<220> FEATURE:
<221> NAME/KEY: misc_feature
<222> LOCATION: (1389)..(1394)
<223> OTHER INFORMATION: restriction endonuclease SphI recognition site

<400> SEQUENCE: 11

```
ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180
```

```
gcgggatgaa ttcagatctc gatcccgcga aattaatacg actcactata gggagaccac    240
aacggtttcc ctctagatca caagtttgta caaaaaagca ggctaagaag gagatataca    300
tacgccggcc attcaaacat gaggattacc catgtattta aatacccatg tccaggcgcg    360
ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaatgaga gaggtattcc tcaggccaca tcgcttccta gttccgctgg    780
gatccatcgt tggcggccga agccgccatt ccatagtgag ttctggcgcg cctcatccca    840
gttggtgatg ataccgtgtt cgatggggta tttcagggtg aggatacctc ttttgctttg    900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg ggcctctaa    1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcaccatt ccttgcggcg gcggtgctca acggcctcaa cctactactg   1440
ggctgcttcc taatgcagga gtcgcataag ggagagcgtc gaccgatgcc cttgagagcc   1500
ttcaacccag tcagctcctt ccggtgggcg cggggcatga ctatcgtcgc cgcacttatg   1560
actgtcttct ttatcatgca actcgtagga caggtgccgg cagcgctctg ggtcattttc   1620
ggcgaggacc gctttcgctg gagcgcgacg atgatcggcc tgtcgcttgc ggtattcgga   1680
atcttgcacg ccctcgctca agccttcgtc actggtcccg ccaccaaacg tttcggcgag   1740
aagcaggcca ttatcgccgg catggcggcc gacgcgctgg gctacgtctt gctggcgttc   1800
gcgacgcgag gctggatggc cttccccatt atgattcttc tcgcttccgg cggcatcggg   1860
atgcccgcgt tgcaggccat gctgtccagg caggtagatg acgaccatca gggacagctt   1920
caaggatcgc tcgcggctct taccagccta acttcgatca ttggaccgct gatcgtcacg   1980
gcgatttatg ccgcctcggc gagcacatgg aacgggttgg catggattgt aggcgccgcc   2040
ctataccttg tctgcctccc cgcgttgcgt cgcggtgcat ggagccgggc cacctcgacc   2100
tgaatggaag ccggcggcac ctcgctaacg gattcaccac tccaagaatt ggagccaatc   2160
aattcttgcg gagaactgtg aatgcgcaaa ccaacccttg gcagaacata tccatcgcgt   2220
ccgccatctc cagcagccgc acgcggcgca tctcgggcag cgttgggtcc tggccacggg   2280
tgcgcatgat cgtgctcctg tcgttgagga cccggctagg ctggcggggt tgccttactg   2340
gttagcagaa tgaatcaccg atacgcgagc gaacgtgaag cgactgctgc tgcaaaacgt   2400
ctgcgacctg agcaacaaca tgaatggtct tcggtttccg tgtttcgtaa agtctggaaa   2460
cgcggaagtc agcgccctgc accattatgt tccggatctg catcgcagga tgctgctggc   2520
```

```
taccctgtgg aacacctaca tctgtattaa cgaagcgctg gcattgaccc tgagtgattt   2580
ttctctggtc ccgccgcatc cataccgcca gttgtttacc ctcacaacgt tccagtaacc   2640
gggcatgttc atcatcagta acccgtatcg tgagcatcct ctctcgtttc atcggtatca   2700
ttacccccat gaacagaaat cccccttaca cggaggcatc agtgaccaaa caggaaaaaa   2760
ccgcccttaa catggcccgc tttatcagaa gccagacatt aacgcttctg gagaaactca   2820
acgagctgga cgcggatgaa caggcagaca tctgtgaatc gcttcacgac cacgctgatg   2880
agctttaccg cagctgcctc gcgcgtttcg gtgatgacgg tgaaaacctc tgacacatgc   2940
agctcccgga gacggtcaca gcttgtctgt aagcggatgc cgggagcaga caagcccgtc   3000
agggcgcgtc agcgggtgtt ggcgggtgtc ggggcgcagc catgacccag tcacgtagcg   3060
atagcggagt gtatactggc ttaactatgc ggcatcagag cagattgtac tgagagtgca   3120
ccatatgcgg tgtgaaatac cgcacagatg cgtaaggaga aaataccgca tcaggcgctc   3180
ttccgcttcc tcgctcactg actcgctgcg ctcggtcgtt cggctgcggc gagcggtatc   3240
agctcactca aaggcggtaa tacggttatc cacagaatca ggggataacg caggaaagaa   3300
catgtgagca aaaggccagc aaaaggccag gaaccgtaaa aaggccgcgt tgctggcgtt   3360
tttccatagg ctccgccccc ctgacgagca tcacaaaaat cgacgctcaa gtcagaggtg   3420
gcgaaacccg acaggactat aaagatacca ggcgtttccc cctggaagct ccctcgtgcg   3480
ctctcctgtt ccgaccctgc cgcttaccgg atacctgtcc gcctttctcc cttcgggaag   3540
cgtggcgctt tctcatagct cacgctgtag gtatctcagt tcggtgtagg tcgttcgctc   3600
caagctgggc tgtgtgcacg aaccccccgt tcagcccgac cgctgcgcct tatccggtaa   3660
ctatcgtctt gagtccaacc cggtaagaca cgacttatcg ccactggcag cagccactgg   3720
taacaggatt agcagagcga ggtatgtagg cggtgctaca gagttcttga agtggtggcc   3780
taactacggc tacactagaa ggacagtatt tggtatctgc gctctgctga agccagttac   3840
cttcggaaaa agagttggta gctcttgatc cggcaaacaa accaccgctg gtagcggtgg   3900
tttttttgtt tgcaagcagc agattacgcg cagaaaaaaa ggatctcaag aagatccttt   3960
gatcttttct acggggtctg acgctcagtg gaacgaaaac tcacgttaag ggattttggt   4020
catgagatta tcaaaaagga tcttcaccta gatcctttta aattaaaaat gaagttttaa   4080
atcaatctaa agtatatatg agtaaacttg gtctgacagt taccaatgct taatcagtga   4140
ggcacctatc tcagcgatct gtctatttcg ttcatccata gttgcctgac tccccgtcgt   4200
gtagataact acgatacggg agggcttacc atctggcccc agtgctgcaa tgataccgcg   4260
agacccacgc tcaccggctc cagatttatc agcaataaac cagccagccg gaagggccga   4320
gcgcagaagt ggtcctgcaa ctttatccgc ctccatccag tctattaatt gttgccggga   4380
agctagagta agtagttcgc cagttaatag tttgcgcaac gttgttgcca ttgctgcagg   4440
catcgtggtg tcacgctcgt cgtttggtat ggcttcattc agctccggtt cccaacgatc   4500
aaggcgagtt acatgatccc ccatgttgtg caaaaaagcg gttagctcct tcggtcctcc   4560
gatcgttgtc agaagtaagt tggccgcagt gttatcactc atggttatgg cagcactgca   4620
taattctctt actgtcatgc catccgtaag atgcttttct gtgactggtg agtactcaac   4680
caagtcattc tgagaatagt gtatgcggcg accgagttgc tcttgcccgg cgtcaacacg   4740
ggataatacc gcgccacata gcagaacttt aaaagtgctc atcattggaa aacgttcttc   4800
ggggcgaaaa ctctcaagga tcttaccgct gttgagatcc agttcgatgt aacccactcg   4860
tgcacccaac tgatcttcag catcttttac tttcaccagc gtttctgggt gagcaaaaac   4920
```

```
aggaaggcaa aatgccgcaa aaaagggaat aagggcgaca cggaaatgtt gaatactcat   4980

actcttcctt tttcaatatt attgaagcat ttatcagggt tattgtctca tgagcggata   5040

catatttgaa tgtatttaga aaaataaaca aataggggtt ccgcgcacat ttccccgaaa   5100

agtgccacct gacgtctaag aaaccattat tatcatgaca ttaacctata aaaataggcg   5160

tatcacgagg ccctttcgtc ttcaagaa                                      5188


<210> SEQ ID NO 12
<211> LENGTH: 5657
<212> TYPE: DNA
<213> ORGANISM: Artificial Sequence
<220> FEATURE:
<223> OTHER INFORMATION: Recombinant plasmid pAPSE10219; beta actin stem
      loop + coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
      sequence
<220> FEATURE:
<221> NAME/KEY: misc_feature
<222> LOCATION: (40)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI recognition site
<220> FEATURE:
<221> NAME/KEY: misc_feature
<222> LOCATION: (497)..(791)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: promoter
<222> LOCATION: (1275)..(1293)
<223> OTHER INFORMATION: bacteriophage T7 gene 1 promoter
<220> FEATURE:
<221> NAME/KEY: gene
<222> LOCATION: (1366)..(1755)
<223> OTHER INFORMATION: bacteriophage MS2 coat protein gene
<220> FEATURE:
<221> NAME/KEY: terminator
<222> LOCATION: (1788)..(1835)
<223> OTHER INFORMATION: bacteriophage T7 transcription terminator

<400> SEQUENCE: 12

ttccgaaatt aatacgactc actataggga ggcgatcgcg cacgaggttt ttctgtctag     60

tgagcagtgt ccaacctcaa aagacaacat gtgtgacgac gatgtagcgg ctcttgtcgt    120

agacaatgga tccggtatgt gcaaagccgg tttcgcagga gatgacgcac cccgtgccgt    180

cttcccctcg atcgtcggtc gcccaaggca tcaaggagtc atggtcggta tgggacaaaa    240

ggactcatac gtaggagatg aagcccaaag caaaagaggt atcctcaccc tgaaataccc    300

catcgaacac ggtatcatca ccaactggga tgagtttaaa ccctctagct gctttacaaa    360

gtactggttc cctttccagc gggatgcttt atctaaacgc aatgagagag gtattcctca    420

ggccacatcg cttcctagtt ccgctgggat ccatcgttgg cggccgaagc cgccattcca    480
```

```
tagtgagttc tggcgcgcct catcccagtt ggtgatgata ccgtgttcga tggggtattt    540
cagggtgagg atacctcttt tgctttgggc ttcatctcct acgtatgagt ccttttgtcc    600
cataccgacc atgactcctt gatgccttgg gcgaccgacg atcgagggga agacggcacg    660
gggtgcgtca tctcctgcga aaccggcttt gcacataccg gatccattgt ctacgacaag    720
agccgctaca tcgtcgtcac acatgttgtc ttttgaggtt ggacactgct cactagacag    780
aaaaacctcg tgccggaccg aatacccggt ctgaacgagg gcggccgcgg tacccaagaa    840
gtacttagag ttaattaagg agttcaaaca tgaggatcac ccatgtcgaa gctcccacac    900
cctagcataa ccccttgggg cctctaaacg ggtcttgagg ggttttttgc tgaaaggagg    960
aactatatcc ggatatccac aggacgggtg tggtcgccat gatcgcgtag tcgatagtgg   1020
ctccaagtag cgaagcgagc aggactgggc ggcgggcatg catcgtccat tccgacagca   1080
tcgccagtca ctatggcgtg ctgctagcgc tatatgcgtt gatgcaattt ctatgcgcac   1140
ccgttctcgg agcactgtcc gaccgctttg gccgccgccc agtcctgctc gcttcgctac   1200
ttggagccac tatcgactac gcgatcatgg cgaccacacc cgtcctgtgg atccagatct   1260
cgatcccgcg aaattaatac gactcactat agggagacca caacggtttc cctctagatc   1320
acaagtttgt acaaaaaagc aggctaagaa ggagatatac atatggcgtc taactttacc   1380
caattcgttc tggttgataa cggcggtacg ggtgacgtta ccgtagctcc gtccaacttc   1440
gccaacggtg ttgcggaatg gattagctct aacagccgct ctcaggccta caaagtcacg   1500
tgctccgttc gtcagtctag cgcgcagaat cgcaaataca ccatcaaagt tgaagtaccg   1560
aaagtcgcaa cgcagaccgt aggcggcgta gaactcccag ttgcggcctg gcgctcttac   1620
ctcaacatgg aactgactat tccgattttt gcgacgaact ccgactgcga actgattgtt   1680
aaggcaatgc agggcctgct gaaagacggt aatccgatcc catctgcaat cgctgctaac   1740
tctggcattt actaataagc ggacgcgctg ccaccgctga gcaataacta gcataacccc   1800
ttggggcctc taaacgggtc ttgaggggtt ttttgctgaa aggaggaact atatccggca   1860
tgcaccattc cttgcggcgg cggtgctcaa cggcctcaac ctactactgg gctgcttcct   1920
aatgcaggag tcgcataagg gagagcgtcg accgatgccc ttgagagcct tcaacccagt   1980
cagctccttc cggtgggcgc ggggcatgac tatcgtcgcc gcacttatga ctgtcttctt   2040
tatcatgcaa ctcgtaggac aggtgccggc agcgctctgg gtcattttcg gcgaggaccg   2100
ctttcgctgg agcgcgacga tgatcggcct gtcgcttgcg gtattcggaa tcttgcacgc   2160
cctcgctcaa gccttcgtca ctggtcccgc caccaaacgt ttcggcgaga agcaggccat   2220
tatcgccggc atggcggccg acgcgctggg ctacgtcttg ctggcgttcg cgacgcgagg   2280
ctggatggcc ttccccatta tgattcttct cgcttccggc ggcatcggga tgcccgcgtt   2340
gcaggccatg ctgtccaggc aggtagatga cgaccatcag ggacagcttc aaggatcgct   2400
cgcggctctt accagcctaa cttcgatcat tggaccgctg atcgtcacgg cgatttatgc   2460
cgcctcggcg agcacatgga acgggttggc atggattgta ggcgccgccc tataccttgt   2520
ctgcctcccc gcgttgcgtc gcggtgcatg gagccgggcc acctcgacct gaatggaagc   2580
cggcggcacc tcgctaacgg attcaccact ccaagaattg gagccaatca attcttgcgg   2640
agaactgtga atgcgcaaac caacccttgg cagaacatat ccatcgcgtc cgccatctcc   2700
agcagccgca cgcggcgcat ctcgggcagc gttgggtcct ggccacgggt gcgcatgatc   2760
gtgctcctgt cgttgaggac ccggctaggc tggcggggtt gccttactgg ttagcagaat   2820
gaatcaccga tacgcgagcg aacgtgaagc gactgctgct gcaaaacgtc tgcgacctga   2880
```

```
gcaacaacat gaatggtctt cggtttccgt gtttcgtaaa gtctggaaac gcggaagtca   2940
gcgccctgca ccattatgtt ccggatctgc atcgcaggat gctgctggct accctgtgga   3000
acacctacat ctgtattaac gaagcgctgg cattgaccct gagtgatttt tctctggtcc   3060
cgccgcatcc ataccgccag ttgtttaccc tcacaacgtt ccagtaaccg ggcatgttca   3120
tcatcagtaa cccgtatcgt gagcatcctc tctcgtttca tcggtatcat tacccccatg   3180
aacagaaatc cccttacac ggaggcatca gtgaccaaac aggaaaaaac cgcccttaac   3240
atggcccgct ttatcagaag ccagacatta acgcttctgg agaaactcaa cgagctggac   3300
gcggatgaac aggcagacat ctgtgaatcg cttcacgacc acgctgatga gctttaccgc   3360
agctgcctcg cgcgtttcgg tgatgacggt gaaaacctct gacacatgca gctcccggag   3420
acggtcacag cttgtctgta agcggatgcc gggagcagac aagcccgtca gggcgcgtca   3480
gcgggtgttg gcgggtgtcg gggcgcagcc atgacccagt cacgtagcga tagcggagtg   3540
tatactggct taactatgcg gcatcagagc agattgtact gagagtgcac catatgcggt   3600
gtgaaatacc gcacagatgc gtaaggagaa aataccgcat caggcgctct tccgcttcct   3660
cgctcactga ctcgctgcgc tcggtcgttc ggctgcggcg agcggtatca gctcactcaa   3720
aggcggtaat acggttatcc acagaatcag gggataacgc aggaaagaac atgtgagcaa   3780
aaggccagca aaaggccagg aaccgtaaaa aggccgcgtt gctggcgttt ttccataggc   3840
tccgcccccc tgacgagcat cacaaaaatc gacgctcaag tcagaggtgg cgaaacccga   3900
caggactata aagataccag gcgtttcccc ctggaagctc cctcgtgcgc tctcctgttc   3960
cgaccctgcc gcttaccgga tacctgtccg cctttctccc ttcgggaagc gtggcgcttt   4020
ctcatagctc acgctgtagg tatctcagtt cggtgtaggt cgttcgctcc aagctgggct   4080
gtgtgcacga accccccgtt cagcccgacc gctgcgcctt atccggtaac tatcgtcttg   4140
agtccaaccc ggtaagacac gacttatcgc cactggcagc agccactggt aacaggatta   4200
gcagagcgag gtatgtaggc ggtgctacag agttcttgaa gtggtggcct aactacggct   4260
acactagaag gacagtattt ggtatctgcg ctctgctgaa gccagttacc ttcggaaaaa   4320
gagttggtag ctcttgatcc ggcaaacaaa ccaccgctgg tagcggtggt ttttttgttt   4380
gcaagcagca gattacgcgc agaaaaaaag gatctcaaga agatcctttg atcttttcta   4440
cggggtctga cgctcagtgg aacgaaaact cacgttaagg gattttggtc atgagattat   4500
caaaaaggat cttcacctag atccttttaa attaaaaatg aagttttaaa tcaatctaaa   4560
gtatatatga gtaaacttgg tctgacagtt accaatgctt aatcagtgag gcacctatct   4620
cagcgatctg tctatttcgt tcatccatag ttgcctgact ccccgtcgtg tagataacta   4680
cgatacggga gggcttacca tctggcccca gtgctgcaat gataccgcga gacccacgct   4740
caccggctcc agatttatca gcaataaacc agccagccgg aagggccgag cgcagaagtg   4800
gtcctgcaac tttatccgcc tccatccagt ctattaattg ttgccgggaa gctagagtaa   4860
gtagttcgcc agttaatagt ttgcgcaacg ttgttgccat tgctgcaggc atcgtggtgt   4920
cacgctcgtc gtttggtatg gcttcattca gctccggttc ccaacgatca aggcgagtta   4980
catgatcccc catgttgtgc aaaaaagcgg ttagctcctt cggtcctccg atcgttgtca   5040
gaagtaagtt ggccgcagtg ttatcactca tggttatggc agcactgcat aattctctta   5100
ctgtcatgcc atccgtaaga tgcttttctg tgactggtga gtactcaacc aagtcattct   5160
gagaatagtg tatgcggcga ccgagttgct cttgcccggc gtcaacacgg gataataccg   5220
```

```
cgccacatag cagaacttta aaagtgctca tcattggaaa acgttcttcg gggcgaaaac   5280

tctcaaggat cttaccgctg ttgagatcca gttcgatgta acccactcgt gcacccaact   5340

gatcttcagc atcttttact ttcaccagcg tttctgggtg agcaaaaaca ggaaggcaaa   5400

atgccgcaaa aaagggaata agggcgacac ggaaatgttg aatactcata ctcttccttt   5460

ttcaatatta ttgaagcatt tatcagggtt attgtctcat gagcggatac atatttgaat   5520

gtatttagaa aaataaacaa ataggggttc cgcgcacatt tccccgaaaa gtgccacctg   5580

acgtctaaga aaccattatt atcatgacat taacctataa aaataggcgt atcacgaggc   5640

cctttcgtct tcaagaa                                                  5657
```

```
<210> SEQ ID NO 13
<211> LENGTH: 4855
<212> TYPE: DNA
<213> ORGANISM: Artificial Sequence
<220> FEATURE:
<223> OTHER INFORMATION: Recombinant plasmid pAPSE10304; beta actin stem
      loop - coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (40)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI recognition site
<220> FEATURE:
<221> NAME/KEY: misc_feature
<222> LOCATION: (497)..(791)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: misc_feature
<222> LOCATION: (1056)..(1061)
<223> OTHER INFORMATION: restriction endonuclease SphI recognition site

<400> SEQUENCE: 13

ttccgaaatt aatacgactc actataggga ggcgatcgcg cacgaggttt ttctgtctag     60

tgagcagtgt ccaacctcaa aagacaacat gtgtgacgac gatgtagcgg ctcttgtcgt    120

agacaatgga tccggtatgt gcaaagccgg tttcgcagga gatgacgcac cccgtgccgt    180

cttcccctcg atcgtcggtc gcccaaggca tcaaggagtc atggtcggta tgggacaaaa    240

ggactcatac gtaggagatg aagcccaaag caaaagaggt atcctcaccc tgaaataccc    300

catcgaacac ggtatcatca ccaactggga tgagtttaaa ccctctagct gctttacaaa    360

gtactggttc cctttccagc gggatgcttt atctaaacgc aatgagagag gtattcctca    420

ggccacatcg cttcctagtt ccgctgggat ccatcgttgg cggccgaagc cgccattcca    480

tagtgagttc tggcgcgcct catcccagtt ggtgatgata ccgtgttcga tggggtattt    540

cagggtgagg atacctcttt tgctttgggc ttcatctcct acgtatgagt ccttttgtcc    600
```

```
cataccgacc atgactcctt gatgccttgg gcgaccgacg atcgagggga agacggcacg    660
gggtgcgtca tctcctgcga aaccggcttt gcacataccg gatccattgt ctacgacaag    720
agccgctaca tcgtcgtcac acatgttgtc ttttgaggtt ggacactgct cactagacag    780
aaaaacctcg tgccggaccg aatacccggt ctgaacgagg gcggccgcgg tacccaagaa    840
gtacttagag ttaattaagg agttcaaaca tgaggatcac ccatgtcgaa gctcccacac    900
cctagcataa ccccttgggg cctctaaacg ggtcttgagg ggttttttgc tgaaaggagg    960
aactatatcc ggatatccac aggacgggtg tggtcgccat gatcgcgtag tcgatagtgg   1020
ctccaagtag cgaagcgagc aggactgggc ggcgggcatg caccattcct tgcggcggcg   1080
gtgctcaacg gcctcaacct actactgggc tgcttcctaa tgcaggagtc gcataaggga   1140
gagcgtcgac cgatgccctt gagagccttc aacccagtca gctccttccg gtgggcgcgg   1200
ggcatgacta tcgtcgccgc acttatgact gtcttcttta tcatgcaact cgtaggacag   1260
gtgccggcag cgctctgggt cattttcggc gaggaccgct ttcgctggag cgcgacgatg   1320
atcggcctgt cgcttgcggt attcggaatc ttgcacgccc tcgctcaagc cttcgtcact   1380
ggtcccgcca ccaaacgttt cggcgagaag caggccatta tcgccggcat ggcggccgac   1440
gcgctgggct acgtcttgct ggcgttcgcg acgcgaggct ggatggcctt ccccattatg   1500
attcttctcg cttccggcgg catcgggatg cccgcgttgc aggccatgct gtccaggcag   1560
gtagatgacg accatcaggg acagcttcaa ggatcgctcg cggctcttac cagcctaact   1620
tcgatcattg gaccgctgat cgtcacggcg atttatgccg cctcggcgag cacatggaac   1680
gggttggcat ggattgtagg cgccgcccta taccttgtct gcctccccgc gttgcgtcgc   1740
ggtgcatgga gccgggccac ctcgacctga atggaagccg gcggcacctc gctaacggat   1800
tcaccactcc aagaattgga gccaatcaat tcttgcggag aactgtgaat gcgcaaacca   1860
acccttggca gaacatatcc atcgcgtccg ccatctccag cagccgcacg cggcgcatct   1920
cgggcagcgt tgggtcctgg ccacgggtgc gcatgatcgt gctcctgtcg ttgaggaccc   1980
ggctaggctg gcggggttgc cttactggtt agcagaatga atcaccgata cgcgagcgaa   2040
cgtgaagcga ctgctgctgc aaaacgtctg cgacctgagc aacaacatga atggtcttcg   2100
gtttccgtgt ttcgtaaagt ctggaaacgc ggaagtcagc gccctgcacc attatgttcc   2160
ggatctgcat cgcaggatgc tgctggctac cctgtggaac acctacatct gtattaacga   2220
agcgctggca ttgaccctga gtgatttttc tctggtcccg ccgcatccat accgccagtt   2280
gtttaccctc acaacgttcc agtaaccggg catgttcatc atcagtaacc cgtatcgtga   2340
gcatcctctc tcgtttcatc ggtatcatta cccccatgaa cagaaatccc ccttacacgg   2400
aggcatcagt gaccaaacag gaaaaaaccg cccttaacat ggcccgcttt atcagaagcc   2460
agacattaac gcttctggag aaactcaacg agctggacgc ggatgaacag gcagacatct   2520
gtgaatcgct tcacgaccac gctgatgagc tttaccgcag ctgcctcgcg cgtttcggtg   2580
atgacggtga aaacctctga cacatgcagc tcccggagac ggtcacagct tgtctgtaag   2640
cggatgccgg gagcagacaa gcccgtcagg gcgcgtcagc gggtgttggc gggtgtcggg   2700
gcgcagccat gacccagtca cgtagcgata gcggagtgta tactggctta actatgcggc   2760
atcagagcag attgtactga gagtgcacca tatgcggtgt gaaataccgc acagatgcgt   2820
aaggagaaaa taccgcatca ggcgctcttc cgcttcctcg ctcactgact cgctgcgctc   2880
ggtcgttcgg ctgcggcgag cggtatcagc tcactcaaag gcggtaatac ggttatccac   2940
agaatcaggg gataacgcag gaaagaacat gtgagcaaaa ggccagcaaa aggccaggaa   3000
```

```
ccgtaaaaag gccgcgttgc tggcgttttt ccataggctc cgcccccctg acgagcatca   3060

caaaaatcga cgctcaagtc agaggtggcg aaacccgaca ggactataaa gataccaggc   3120

gtttccccct ggaagctccc tcgtgcgctc tcctgttccg accctgccgc ttaccggata   3180

cctgtccgcc tttctccctt cgggaagcgt ggcgctttct catagctcac gctgtaggta   3240

tctcagttcg gtgtaggtcg ttcgctccaa gctgggctgt gtgcacgaac cccccgttca   3300

gcccgaccgc tgcgccttat ccggtaacta tcgtcttgag tccaacccgg taagacacga   3360

cttatcgcca ctggcagcag ccactggtaa caggattagc agagcgaggt atgtaggcgg   3420

tgctacagag ttcttgaagt ggtggcctaa ctacggctac actagaagga cagtatttgg   3480

tatctgcgct ctgctgaagc cagttacctt cggaaaaaga gttggtagct cttgatccgg   3540

caaacaaacc accgctggta gcggtggttt ttttgtttgc aagcagcaga ttacgcgcag   3600

aaaaaaagga tctcaagaag atcctttgat cttttctacg gggtctgacg ctcagtggaa   3660

cgaaaactca cgttaaggga ttttggtcat gagattatca aaaaggatct tcacctagat   3720

ccttttaaat taaaaatgaa gttttaaatc aatctaaagt atatatgagt aaacttggtc   3780

tgacagttac caatgcttaa tcagtgaggc acctatctca gcgatctgtc tatttcgttc   3840

atccatagtt gcctgactcc ccgtcgtgta gataactacg atacgggagg gcttaccatc   3900

tggccccagt gctgcaatga taccgcgaga cccacgctca ccggctccag atttatcagc   3960

aataaaccag ccagccggaa gggccgagcg cagaagtggt cctgcaactt tatccgcctc   4020

catccagtct attaattgtt gccgggaagc tagagtaagt agttcgccag ttaatagttt   4080

gcgcaacgtt gttgccattg ctgcaggcat cgtggtgtca cgctcgtcgt ttggtatggc   4140

ttcattcagc tccggttccc aacgatcaag gcgagttaca tgatccccca tgttgtgcaa   4200

aaaagcggtt agctccttcg gtcctccgat cgttgtcaga agtaagttgg ccgcagtgtt   4260

atcactcatg gttatggcag cactgcataa ttctcttact gtcatgccat ccgtaagatg   4320

cttttctgtg actggtgagt actcaaccaa gtcattctga gaatagtgta tgcggcgacc   4380

gagttgctct tgcccggcgt caacacggga taataccgcg ccacatagca gaactttaaa   4440

agtgctcatc attggaaaac gttcttcggg gcgaaaactc tcaaggatct taccgctgtt   4500

gagatccagt tcgatgtaac ccactcgtgc acccaactga tcttcagcat cttttacttt   4560

caccagcgtt tctgggtgag caaaaacagg aaggcaaaat gccgcaaaaa agggaataag   4620

ggcgacacgg aaatgttgaa tactcatact cttccttttt caatattatt gaagcattta   4680

tcagggttat tgtctcatga gcggatacat atttgaatgt atttagaaaa ataaacaaat   4740

aggggttccg cgcacatttc cccgaaaagt gccacctgac gtctaagaaa ccattattat   4800

catgacatta acctataaaa ataggcgtat cacgaggccc tttcgtcttc aagaa        4855
```

```
<210> SEQ ID NO 14
<211> LENGTH: 5367
<212> TYPE: DNA
<213> ORGANISM: Artificial Sequence
<220> FEATURE:
<223> OTHER INFORMATION: Recombinant plasmid pAPSE10279; beta actin stem
      loop + capsid
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
```

<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: promoter
<222> LOCATION: (985)..(1003)
<223> OTHER INFORMATION: bacteriophage T7 gene 1 promoter
<220> FEATURE:
<221> NAME/KEY: gene
<222> LOCATION: (1076)..(1465)
<223> OTHER INFORMATION: bacteriophage MS2 coat protein gene
<220> FEATURE:
<221> NAME/KEY: terminator
<222> LOCATION: (1498)..(1545)
<223> OTHER INFORMATION: bacteriophage T7 transcription terminator

<400> SEQUENCE: 14
ttcttagctc cggcaagcaa ttaagaactt ccgaaattaa tacgactcac tatagggagg 60
cgatcgcgca cgaggttttt ctgtctagtg agcagtgtcc aacctcaaaa gacaacatgt 120
gtgacgacga tgtagcggct cttgtcgtag acaatggatc cggtatgtgc aaagccggtt 180
tcgcaggaga tgacgcaccc cgtgccgtct tcccctcgat cgtcggtcgc ccaaggcatc 240
aaggagtcat ggtcggtatg ggacaaaagg actcatacgt aggagatgaa gcccaaagca 300
aaagaggtat cctcaccctg aaatacccca tcgaacacgg tatcatcacc aactgggatg 360
agtttaaacc ctctagctgc tttacaaagt actggttccc tttccagcgg gatgctttat 420
ctaaacgcaa tgagagaggt attcctcagg ccacatcgct tcctagttcc gctgggatcc 480
atcgttggcg gccgaagccg ccattccata gtgagttctg gcgcgcctca tcccagttgg 540
tgatgatacc gtgttcgatg gggtatttca gggtgaggat acctcttttg ctttgggctt 600
catctcctac gtatgagtcc ttttgtccca taccgaccat gactccttga tgccttgggc 660
gaccgacgat cgaggggaag acggcacggg gtgcgtcatc tcctgcgaaa ccggctttgc 720
acataccgga tccattgtct acgacaagag ccgctacatc gtcgtcacac atgttgtctt 780
ttgaggttgg acactgctca ctagacagaa aaacctcgtg ccggaccgaa tacccggtct 840
gaacgaggtt aattaaggta cccaagaagt acttagaggc ggccgcctag cataacccct 900
tggggcctct aaacgggtct tgaggggttt tttgagaaac ggccgaatac acctgttcgg 960
atccagatct cgatcccgcg aaattaatac gactcactat agggagacca caacggtttc 1020
cctctagatc acaagtttgt acaaaaaagc aggctaagaa ggagatatac atatggcgtc 1080
taactttacc caattcgttc tggttgataa cggcggtacg ggtgacgtta ccgtagctcc 1140
gtccaacttc gccaacggtg ttgcggaatg gattagctct aacagccgct ctcaggccta 1200
caaagtcacg tgctccgttc gtcagtctag cgcgcagaat cgcaaataca ccatcaaagt 1260
tgaagtaccg aaagtcgcaa cgcagaccgt aggcggcgta gaactcccag ttgcggcctg 1320
gcgctcttac ctcaacatgg aactgactat tccgattttt gcgacgaact ccgactgcga 1380
actgattgtt aaggcaatgc agggcctgct gaaagacggt aatccgatcc catctgcaat 1440

```
cgctgctaac tctggcattt actaataagc ggacgcgctg ccaccgctga gcaataacta   1500
gcataacccc ttggggcctc taaacgggtc ttgaggggtt ttttgctgaa aggaggaact   1560
atatccggca tgcaccattc cttgcggcgg cggtgctcaa cggcctcaac ctactactgg   1620
gctgcttcct aatgcaggag tcgcataagg gagagcgtcg accgatgccc ttgagagcct   1680
tcaacccagt cagctccttc cggtgggcgc ggggcatgac tatcgtcgcc gcacttatga   1740
ctgtcttctt tatcatgcaa ctcgtaggac aggtgccggc agcgctctgg gtcattttcg   1800
gcgaggaccg ctttcgctgg agcgcgacga tgatcggcct gtcgcttgcg gtattcggaa   1860
tcttgcacgc cctcgctcaa gccttcgtca ctggtcccgc caccaaacgt ttcggcgaga   1920
agcaggccat tatcgccggc atggcggccg acgcgctggg ctacgtcttg ctggcgttcg   1980
cgacgcgagg ctggatggcc ttccccatta tgattcttct cgcttccggc ggcatcggga   2040
tgcccgcgtt gcaggccatg ctgtccaggc aggtagatga cgaccatcag ggacagcttc   2100
aaggatcgct cgcggctctt accagcctaa cttcgatcat tggaccgctg atcgtcacgg   2160
cgatttatgc cgcctcggcg agcacatgga acgggttggc atggattgta ggcgccgccc   2220
tataccttgt ctgcctcccc gcgttgcgtc gcggtgcatg gagccgggcc acctcgacct   2280
gaatggaagc cggcggcacc tcgctaacgg attcaccact ccaagaattg gagccaatca   2340
attcttgcgg agaactgtga atgcgcaaac caacccttgg cagaacatat ccatcgcgtc   2400
cgccatctcc agcagccgca cgcggcgcat ctcgggcagc gttgggtcct ggccacgggt   2460
gcgcatgatc gtgctcctgt cgttgaggac ccggctaggc tggcggggtt gccttactgg   2520
ttagcagaat gaatcaccga tacgcgagcg aacgtgaagc gactgctgct gcaaaacgtc   2580
tgcgacctga gcaacaacat gaatggtctt cggtttccgt gtttcgtaaa gtctggaaac   2640
gcggaagtca gcgccctgca ccattatgtt ccggatctgc atcgcaggat gctgctggct   2700
accctgtgga acacctacat ctgtattaac gaagcgctgg cattgaccct gagtgatttt   2760
tctctggtcc cgccgcatcc ataccgccag ttgtttaccc tcacaacgtt ccagtaaccg   2820
ggcatgttca tcatcagtaa cccgtatcgt gagcatcctc tctcgtttca tcggtatcat   2880
tacccccatg aacagaaatc ccccttacac ggaggcatca gtgaccaaac aggaaaaaac   2940
cgcccttaac atggcccgct ttatcagaag ccagacatta acgcttctgg agaaactcaa   3000
cgagctggac gcggatgaac aggcagacat ctgtgaatcg cttcacgacc acgctgatga   3060
gctttaccgc agctgcctcg cgcgtttcgg tgatgacggt gaaaacctct gacacatgca   3120
gctcccggag acggtcacag cttgtctgta agcggatgcc gggagcagac aagcccgtca   3180
gggcgcgtca gcgggtgttg gcgggtgtcg gggcgcagcc atgacccagt cacgtagcga   3240
tagcggagtg tatactggct taactatgcg gcatcagagc agattgtact gagagtgcac   3300
catatgcggt gtgaaatacc gcacagatgc gtaaggagaa aataccgcat caggcgctct   3360
tccgcttcct cgctcactga ctcgctgcgc tcggtcgttc ggctgcggcg agcggtatca   3420
gctcactcaa aggcggtaat acggttatcc acagaatcag gggataacgc aggaaagaac   3480
atgtgagcaa aaggccagca aaaggccagg aaccgtaaaa aggccgcgtt gctggcgttt   3540
ttccataggc tccgcccccc tgacgagcat cacaaaaatc gacgctcaag tcagaggtgg   3600
cgaaacccga caggactata aagataccag gcgtttcccc ctggaagctc cctcgtgcgc   3660
tctcctgttc cgaccctgcc gcttaccgga tacctgtccg cctttctccc ttcgggaagc   3720
gtggcgcttt ctcatagctc acgctgtagg tatctcagtt cggtgtaggt cgttcgctcc   3780
aagctgggct gtgtgcacga accccccgtt cagcccgacc gctgcgcctt atccggtaac   3840
```

```
tatcgtcttg agtccaaccc ggtaagacac gacttatcgc cactggcagc agccactggt   3900

aacaggatta gcagagcgag gtatgtaggc ggtgctacag agttcttgaa gtggtggcct   3960

aactacggct acactagaag gacagtattt ggtatctgcg ctctgctgaa gccagttacc   4020

ttcggaaaaa gagttggtag ctcttgatcc ggcaaacaaa ccaccgctgg tagcggtggt   4080

tttttgttt gcaagcagca gattacgcgc agaaaaaaag gatctcaaga agatcctttg   4140

atcttttcta cggggtctga cgctcagtgg aacgaaaact cacgttaagg gattttggtc   4200

atgagattat caaaaaggat cttcacctag atccttttaa attaaaaatg aagttttaaa   4260

tcaatctaaa gtatatatga gtaaacttgg tctgacagtt accaatgctt aatcagtgag   4320

gcacctatct cagcgatctg tctatttcgt tcatccatag ttgcctgact ccccgtcgtg   4380

tagataacta cgatacggga gggcttacca tctggcccca gtgctgcaat gataccgcga   4440

gacccacgct caccggctcc agatttatca gcaataaacc agccagccgg aagggccgag   4500

cgcagaagtg gtcctgcaac tttatccgcc tccatccagt ctattaattg ttgccgggaa   4560

gctagagtaa gtagttcgcc agttaatagt ttgcgcaacg ttgttgccat tgctgcaggc   4620

atcgtggtgt cacgctcgtc gtttggtatg gcttcattca gctccggttc ccaacgatca   4680

aggcgagtta catgatcccc catgttgtgc aaaaaagcgg ttagctcctt cggtcctccg   4740

atcgttgtca gaagtaagtt ggccgcagtg ttatcactca tggttatggc agcactgcat   4800

aattctctta ctgtcatgcc atccgtaaga tgcttttctg tgactggtga gtactcaacc   4860

aagtcattct gagaatagtg tatgcggcga ccgagttgct cttgcccggc gtcaacacgg   4920

gataataccg cgccacatag cagaacttta aaagtgctca tcattggaaa acgttcttcg   4980

gggcgaaaac tctcaaggat cttaccgctg ttgagatcca gttcgatgta acccactcgt   5040

gcacccaact gatcttcagc atcttttact ttcaccagcg tttctgggtg agcaaaaaca   5100

ggaaggcaaa atgccgcaaa aaagggaata agggcgacac ggaaatgttg aatactcata   5160

ctcttccttt ttcaatatta ttgaagcatt tatcagggtt attgtctcat gagcggatac   5220

atatttgaat gtatttagaa aaataaacaa ataggggttc cgcgcacatt tccccgaaaa   5280

gtgccacctg acgtctaaga aaccattatt atcatgacat taacctataa aaataggcgt   5340

atcacgaggc cctttcgtct tcaagaa                                        5367
```

```
<210> SEQ ID NO 15
<211> LENGTH: 4764
<212> TYPE: DNA
<213> ORGANISM: Artificial Sequence
<220> FEATURE:
<223> OTHER INFORMATION: Recombinant plasmid pAPSE10303; beta actin stem
      loop - coat protein
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
```

```
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator

<400> SEQUENCE: 15

ttcttagctc cggcaagcaa ttaagaactt ccgaaattaa tacgactcac tatagggagg     60

cgatcgcgca cgaggttttt ctgtctagtg agcagtgtcc aacctcaaaa gacaacatgt    120

gtgacgacga tgtagcggct cttgtcgtag acaatggatc cggtatgtgc aaagccggtt    180

tcgcaggaga tgacgcaccc cgtgccgtct tcccctcgat cgtcggtcgc ccaaggcatc    240

aaggagtcat ggtcggtatg ggacaaaagg actcatacgt aggagatgaa gcccaaagca    300

aaagaggtat cctcaccctg aaatacccca tcgaacacgg tatcatcacc aactgggatg    360

agtttaaacc ctctagctgc tttacaaagt actggttccc tttccagcgg gatgctttat    420

ctaaacgcaa tgagagaggt attcctcagg ccacatcgct tcctagttcc gctgggatcc    480

atcgttggcg gccgaagccg ccattccata gtgagttctg gcgcgcctca tcccagttgg    540

tgatgatacc gtgttcgatg gggtatttca gggtgaggat acctcttttg ctttgggctt    600

catctcctac gtatgagtcc ttttgtccca taccgaccat gactccttga tgccttgggc    660

gaccgacgat cgaggggaag acggcacggg gtgcgtcatc tcctgcgaaa ccggctttgc    720

acataccgga tccattgtct acgacaagag ccgctacatc gtcgtcacac atgttgtctt    780

ttgaggttgg acactgctca ctagacagaa aaacctcgtg ccggaccgaa tacccggtct    840

gaacgaggtt aattaaggta cccaagaagt acttagaggc ggccgcctag cataacccct    900

tggggcctct aaacgggtct tgaggggttt tttgagaaac ggccgaatac acctgttcgg    960

atccagatcc accattcctt gcggcggcgg tgctcaacgg cctcaaccta ctactgggct   1020

gcttcctaat gcaggagtcg cataagggag agcgtcgacc gatgcccttg agagccttca   1080

acccagtcag ctccttccgg tgggcgcggg gcatgactat cgtcgccgca cttatgactg   1140

tcttctttat catgcaactc gtaggacagg tgccggcagc gctctgggtc attttcggcg   1200

aggaccgctt tcgctggagc gcgacgatga tcggcctgtc gcttgcggta ttcggaatct   1260

tgcacgccct cgctcaagcc ttcgtcactg gtcccgccac caaacgtttc ggcgagaagc   1320

aggccattat cgccggcatg gcggccgacg cgctgggcta cgtcttgctg gcgttcgcga   1380

cgcgaggctg gatggccttc cccattatga ttcttctcgc ttccggcggc atcgggatgc   1440

ccgcgttgca ggccatgctg tccaggcagg tagatgacga ccatcaggga cagcttcaag   1500

gatcgctcgc ggctcttacc agcctaactt cgatcattgg accgctgatc gtcacggcga   1560

tttatgccgc ctcggcgagc acatggaacg ggttggcatg gattgtaggc gccgccctat   1620

accttgtctg cctccccgcg ttgcgtcgcg gtgcatggag ccgggccacc tcgacctgaa   1680

tggaagccgg cggcacctcg ctaacggatt caccactcca agaattggag ccaatcaatt   1740

cttgcggaga actgtgaatg cgcaaaccaa cccttggcag aacatatcca tcgcgtccgc   1800

catctccagc agccgcacgc ggcgcatctc gggcagcgtt gggtcctggc cacgggtgcg   1860

catgatcgtg ctcctgtcgt tgaggacccg gctaggctgg cggggttgcc ttactggtta   1920

gcagaatgaa tcaccgatac gcgagcgaac gtgaagcgac tgctgctgca aaacgtctgc   1980

gacctgagca acaacatgaa tggtcttcgg tttccgtgtt tcgtaaagtc tggaaacgcg   2040

gaagtcagcg ccctgcacca ttatgttccg gatctgcatc gcaggatgct gctggctacc   2100
```

```
ctgtggaaca cctacatctg tattaacgaa gcgctggcat tgaccctgag tgatttttct   2160
ctggtcccgc cgcatccata ccgccagttg tttaccctca caacgttcca gtaaccgggc   2220
atgttcatca tcagtaaccc gtatcgtgag catcctctct cgtttcatcg gtatcattac   2280
ccccatgaac agaaatcccc cttacacgga ggcatcagtg accaaacagg aaaaaaccgc   2340
ccttaacatg gcccgcttta tcagaagcca gacattaacg cttctggaga aactcaacga   2400
gctggacgcg gatgaacagg cagacatctg tgaatcgctt cacgaccacg ctgatgagct   2460
ttaccgcagc tgcctcgcgc gtttcggtga tgacggtgaa aacctctgac acatgcagct   2520
cccggagacg gtcacagctt gtctgtaagc ggatgccggg agcagacaag cccgtcaggg   2580
cgcgtcagcg ggtgttggcg ggtgtcgggg cgcagccatg acccagtcac gtagcgatag   2640
cggagtgtat actggcttaa ctatgcggca tcagagcaga ttgtactgag agtgcaccat   2700
atgcggtgtg aaataccgca cagatgcgta aggagaaaat accgcatcag gcgctcttcc   2760
gcttcctcgc tcactgactc gctgcgctcg gtcgttcggc tgcggcgagc ggtatcagct   2820
cactcaaagg cggtaatacg gttatccaca gaatcagggg ataacgcagg aaagaacatg   2880
tgagcaaaag gccagcaaaa ggccaggaac cgtaaaaagg ccgcgttgct ggcgtttttc   2940
cataggctcc gcccccctga cgagcatcac aaaaatcgac gctcaagtca gaggtggcga   3000
aacccgacag gactataaag ataccaggcg tttccccctg gaagctccct cgtgcgctct   3060
cctgttccga ccctgccgct taccggatac ctgtccgcct ttctcccttc gggaagcgtg   3120
gcgctttctc atagctcacg ctgtaggtat ctcagttcgg tgtaggtcgt tcgctccaag   3180
ctgggctgtg tgcacgaacc ccccgttcag cccgaccgct gcgccttatc cggtaactat   3240
cgtcttgagt ccaacccggt aagacacgac ttatcgccac tggcagcagc cactggtaac   3300
aggattagca gagcgaggta tgtaggcggt gctacagagt tcttgaagtg gtggcctaac   3360
tacggctaca ctagaaggac agtatttggt atctgcgctc tgctgaagcc agttaccttc   3420
ggaaaaagag ttggtagctc ttgatccggc aaacaaacca ccgctggtag cggtggtttt   3480
tttgtttgca agcagcagat tacgcgcaga aaaaaaggat ctcaagaaga tcctttgatc   3540
ttttctacgg ggtctgacgc tcagtggaac gaaaactcac gttaagggat tttggtcatg   3600
agattatcaa aaaggatctt cacctagatc cttttaaatt aaaaatgaag ttttaaatca   3660
atctaaagta tatatgagta aacttggtct gacagttacc aatgcttaat cagtgaggca   3720
cctatctcag cgatctgtct atttcgttca tccatagttg cctgactccc cgtcgtgtag   3780
ataactacga tacgggaggg cttaccatct ggccccagtg ctgcaatgat accgcgagac   3840
ccacgctcac cggctccaga tttatcagca ataaaccagc cagccggaag ggccgagcgc   3900
agaagtggtc ctgcaacttt atccgcctcc atccagtcta ttaattgttg ccgggaagct   3960
agagtaagta gttcgccagt taatagtttg cgcaacgttg ttgccattgc tgcaggcatc   4020
gtggtgtcac gctcgtcgtt tggtatggct tcattcagct ccggttccca acgatcaagg   4080
cgagttacat gatcccccat gttgtgcaaa aaagcggtta gctccttcgg tcctccgatc   4140
gttgtcagaa gtaagttggc cgcagtgtta tcactcatgg ttatggcagc actgcataat   4200
tctcttactg tcatgccatc cgtaagatgc ttttctgtga ctggtgagta ctcaaccaag   4260
tcattctgag aatagtgtat gcggcgaccg agttgctctt gcccggcgtc aacacgggat   4320
aataccgcgc cacatagcag aactttaaaa gtgctcatca ttggaaaacg ttcttcgggg   4380
cgaaaactct caaggatctt accgctgttg agatccagtt cgatgtaacc cactcgtgca   4440
cccaactgat cttcagcatc ttttactttc accagcgttt ctgggtgagc aaaaacagga   4500
```

```
aggcaaaatg ccgcaaaaaa gggaataagg gcgacacgga aatgttgaat actcatactc   4560

ttcctttttc aatattattg aagcatttat cagggttatt gtctcatgag cggatacata   4620

tttgaatgta tttagaaaaa taaacaaata ggggttccgc gcacatttcc ccgaaaagtg   4680

ccacctgacg tctaagaaac cattattatc atgacattaa cctataaaaa taggcgtatc   4740

acgaggccct ttcgtcttca agaa                                          4764
```

```
<210> SEQ ID NO 16
<211> LENGTH: 5940
<212> TYPE: DNA
<213> ORGANISM: Artificial Sequence
<220> FEATURE:
<223> OTHER INFORMATION: Recombinant plasmid pAPSE10270; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (782)..(1076)
<223> OTHER INFORMATION: beta actin antisense gene fragment
<220> FEATURE:
<221> NAME/KEY: misc_feature
<222> LOCATION: (1151)..(1169)
<223> OTHER INFORMATION: Bacteriophage MS2 pac sequence
<220> FEATURE:
<221> NAME/KEY: terminator
<222> LOCATION: (1185)..(1232)
<223> OTHER INFORMATION: bacteriophage T7 transcription terminator
<220> FEATURE:
<221> NAME/KEY: promoter
<222> LOCATION: (1558)..(1576)
<223> OTHER INFORMATION: bacteriophage T7 gene 1 promoter
<220> FEATURE:
<221> NAME/KEY: gene
<222> LOCATION: (1649)..(2038)
<223> OTHER INFORMATION: bacteriophage MS2 coat protein gene
<220> FEATURE:
<221> NAME/KEY: terminator
<222> LOCATION: (2071)..(2118)
<223> OTHER INFORMATION: bacteriophage T7 transcription terminator

<400> SEQUENCE: 16

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

catgtgtgac gacgatgtag cggctcttgt cgtagacaat ggatccggta tgtgcaaagc    480

cggtttcgca ggagatgacg caccccgtgc cgtcttcccc tcgatcgtcg gtcgcccaag    540
```

```
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaatgaga gaggtattcc tcaggccaca tcgcttccta gttcggcgcg    780
cctcatccca gttggtgatg ataccgtgtt cgatggggta tttcagggtg aggatacctc    840
ttttgctttg ggcttcatct cctacgtatg agtccttttg tcccataccg accatgactc    900
cttgatgcct tgggcgaccg acgatcgagg ggaagacggc acggggtgcg tcatctcctg    960
cgaaaccggc tttgcacata ccggatccat tgtctacgac aagagccgct acatcgtcgt   1020
cacacatgtt gtcttttgag gttggacact gctcactaga cagaaaaacc tcgtgccgga   1080
ccgaataccc ggtctgaacg agggcggccg cggtacccaa gaagtactta gagttaatta   1140
aggagttcaa acatgaggat cacccatgtc gaagctccca caccctagca taaccccttg   1200
gggcctctaa acgggtcttg aggggttttt tgctgaaagg aggaactata tccggatatc   1260
cacaggacgg gtgtggtcgc catgatcgcg tagtcgatag tggctccaag tagcgaagcg   1320
agcaggactg ggcggcgggc atgcatcgtc cattccgaca gcatcgccag tcactatggc   1380
gtgctgctag cgctatatgc gttgatgcaa tttctatgcg cacccgttct cggagcactg   1440
tccgaccgct ttggccgccg cccagtcctg ctcgcttcgc tacttggagc cactatcgac   1500
tacgcgatca tggcgaccac acccgtcctg tggatccaga tctcgatccc gcgaaattaa   1560
tacgactcac tatagggaga ccacaacggt ttccctctag atcacaagtt tgtacaaaaa   1620
agcaggctaa gaaggagata tacatatggc gtctaacttt acccaattcg ttctggttga   1680
taacggcggt acgggtgacg ttaccgtagc tccgtccaac ttcgccaacg gtgttgcgga   1740
atggattagc tctaacagcc gctctcaggc ctacaaagtc acgtgctccg ttcgtcagtc   1800
tagcgcgcag aatcgcaaat acaccatcaa agttgaagta ccgaaagtcg caacgcagac   1860
cgtaggcggc gtagaactcc cagttgcggc ctggcgctct tacctcaaca tggaactgac   1920
tattccgatt tttgcgacga actccgactg cgaactgatt gttaaggcaa tgcagggcct   1980
gctgaaagac ggtaatccga tcccatctgc aatcgctgct aactctggca tttactaata   2040
agcggacgcg ctgccaccgc tgagcaataa ctagcataac cccttggggc ctctaaacgg   2100
gtcttgaggg gttttttgct gaaaggagga actatatccg gcatgcacca ttccttgcgg   2160
cggcggtgct caacggcctc aacctactac tgggctgctt cctaatgcag gagtcgcata   2220
agggagagcg tcgaccgatg cccttgagag ccttcaaccc agtcagctcc ttccggtggg   2280
cgcggggcat gactatcgtc gccgcactta tgactgtctt ctttatcatg caactcgtag   2340
gacaggtgcc ggcagcgctc tgggtcattt tcggcgagga ccgctttcgc tggagcgcga   2400
cgatgatcgg cctgtcgctt gcggtattcg gaatcttgca cgccctcgct caagccttcg   2460
tcactggtcc cgccaccaaa cgtttcggcg agaagcaggc cattatcgcc ggcatggcgg   2520
ccgacgcgct gggctacgtc ttgctggcgt tcgcgacgcg aggctggatg gccttcccca   2580
ttatgattct tctcgcttcc ggcggcatcg ggatgcccgc gttgcaggcc atgctgtcca   2640
ggcaggtaga tgacgaccat cagggacagc ttcaaggatc gctcgcggct cttaccagcc   2700
taacttcgat cattggaccg ctgatcgtca cggcgattta tgccgcctcg gcgagcacat   2760
ggaacgggtt ggcatggatt gtaggcgccg ccctatacct tgtctgcctc cccgcgttgc   2820
gtcgcggtgc atggagccgg gccacctcga cctgaatgga agccggcggc acctcgctaa   2880
```

```
cggattcacc actccaagaa ttggagccaa tcaattcttg cggagaactg tgaatgcgca   2940

aaccaaccct tggcagaaca tatccatcgc gtccgccatc tccagcagcc gcacgcggcg   3000

catctcgggc agcgttgggt cctggccacg ggtgcgcatg atcgtgctcc tgtcgttgag   3060

gacccggcta ggctggcggg gttgccttac tggttagcag aatgaatcac cgatacgcga   3120

gcgaacgtga agcgactgct gctgcaaaac gtctgcgacc tgagcaacaa catgaatggt   3180

cttcggtttc cgtgtttcgt aaagtctgga aacgcggaag tcagcgccct gcaccattat   3240

gttccggatc tgcatcgcag gatgctgctg gctaccctgt ggaacaccta catctgtatt   3300

aacgaagcgc tggcattgac cctgagtgat ttttctctgg tcccgccgca tccataccgc   3360

cagttgttta ccctcacaac gttccagtaa ccgggcatgt tcatcatcag taacccgtat   3420

cgtgagcatc ctctctcgtt tcatcggtat cattaccccc atgaacagaa atccccctta   3480

cacggaggca tcagtgacca aacaggaaaa aaccgccctt aacatggccc gctttatcag   3540

aagccagaca ttaacgcttc tggagaaact caacgagctg gacgcggatg aacaggcaga   3600

catctgtgaa tcgcttcacg accacgctga tgagctttac cgcagctgcc tcgcgcgttt   3660

cggtgatgac ggtgaaaacc tctgacacat gcagctcccg gagacggtca cagcttgtct   3720

gtaagcggat gccgggagca gacaagcccg tcagggcgcg tcagcgggtg ttggcgggtg   3780

tcggggcgca gccatgaccc agtcacgtag cgatagcgga gtgtatactg gcttaactat   3840

gcggcatcag agcagattgt actgagagtg caccatatgc ggtgtgaaat accgcacaga   3900

tgcgtaagga gaaaataccg catcaggcgc tcttccgctt cctcgctcac tgactcgctg   3960

cgctcggtcg ttcggctgcg gcgagcggta tcagctcact caaaggcggt aatacggtta   4020

tccacagaat caggggataa cgcaggaaag aacatgtgag caaaaggcca gcaaaaggcc   4080

aggaaccgta aaaaggccgc gttgctggcg tttttccata ggctccgccc ccctgacgag   4140

catcacaaaa atcgacgctc aagtcagagg tggcgaaacc cgacaggact ataaagatac   4200

caggcgtttc cccctggaag ctccctcgtg cgctctcctg ttccgaccct gccgcttacc   4260

ggatacctgt ccgcctttct cccttcggga agcgtggcgc tttctcatag ctcacgctgt   4320

aggtatctca gttcggtgta ggtcgttcgc tccaagctgg gctgtgtgca cgaacccccc   4380

gttcagcccg accgctgcgc cttatccggt aactatcgtc ttgagtccaa cccggtaaga   4440

cacgacttat cgccactggc agcagccact ggtaacagga ttagcagagc gaggtatgta   4500

ggcggtgcta cagagttctt gaagtggtgg cctaactacg gctacactag aaggacagta   4560

tttggtatct gcgctctgct gaagccagtt accttcggaa aaagagttgg tagctcttga   4620

tccggcaaac aaaccaccgc tggtagcggt ggtttttttg tttgcaagca gcagattacg   4680

cgcagaaaaa aaggatctca agaagatcct ttgatctttt ctacggggtc tgacgctcag   4740

tggaacgaaa actcacgtta agggattttg gtcatgagat tatcaaaaag gatcttcacc   4800

tagatccttt taaattaaaa atgaagtttt aaatcaatct aaagtatata tgagtaaact   4860

tggtctgaca gttaccaatg cttaatcagt gaggcaccta tctcagcgat ctgtctattt   4920

cgttcatcca tagttgcctg actccccgtc gtgtagataa ctacgatacg ggagggctta   4980

ccatctggcc ccagtgctgc aatgataccg cgagacccac gctcaccggc tccagattta   5040

tcagcaataa accagccagc cggaagggcc gagcgcagaa gtggtcctgc aactttatcc   5100

gcctccatcc agtctattaa ttgttgccgg gaagctagag taagtagttc gccagttaat   5160

agtttgcgca acgttgttgc cattgctgca ggcatcgtgg tgtcacgctc gtcgtttggt   5220

atggcttcat tcagctccgg ttcccaacga tcaaggcgag ttacatgatc ccccatgttg   5280
```

tgcaaaaaag cggttagctc cttcggtcct ccgatcgttg tcagaagtaa gttggccgca 5340
gtgttatcac tcatggttat ggcagcactg cataattctc ttactgtcat gccatccgta 5400
agatgctttt ctgtgactgg tgagtactca accaagtcat tctgagaata gtgtatgcgg 5460
cgaccgagtt gctcttgccc ggcgtcaaca cgggataata ccgcgccaca tagcagaact 5520
ttaaaagtgc tcatcattgg aaaacgttct tcggggcgaa aactctcaag gatcttaccg 5580
ctgttgagat ccagttcgat gtaacccact cgtgcaccca actgatcttc agcatctttt 5640
actttcacca gcgtttctgg gtgagcaaaa acaggaaggc aaaatgccgc aaaaaaggga 5700
ataagggcga cacggaaatg ttgaatactc atactcttcc tttttcaata ttattgaagc 5760
atttatcagg gttattgtct catgagcgga tacatatttg aatgtattta gaaaaataaa 5820
caaatagggg ttccgcgcac atttccccga aaagtgccac ctgacgtcta agaaaccatt 5880
attatcatga cattaaccta taaaaatagg cgtatcacga ggccctttcg tcttcaagaa 5940

<210> SEQ ID NO 17
<211> LENGTH: 5960
<212> TYPE: DNA
<213> ORGANISM: Artificial Sequence
<220> FEATURE:
<223> OTHER INFORMATION: Recombinant plasmid pAPSE10271; beta actin stem loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (802)..(1096)
<223> OTHER INFORMATION: beta actin antisense gene fragment
<220> FEATURE:
<221> NAME/KEY: misc_feature
<222> LOCATION: (1171)..(1189)
<223> OTHER INFORMATION: bacteriophage MS2 pac sequence
<220> FEATURE:
<221> NAME/KEY: terminator
<222> LOCATION: (1205)..(1252)
<223> OTHER INFORMATION: bacteriophage T7 transcription terminator
<220> FEATURE:
<221> NAME/KEY: promoter
<222> LOCATION: (1578)..(1596)
<223> OTHER INFORMATION: bacteriophage T7 gene 1 promoter
<220> FEATURE:
<221> NAME/KEY: gene
<222> LOCATION: (1669)..(2058)
<223> OTHER INFORMATION: bacteriophage MS2 coat protein gene
<220> FEATURE:
<221> NAME/KEY: terminator
<222> LOCATION: (2091)..(2138)
<223> OTHER INFORMATION: bacteriophage T7 transcription terminator

<400> SEQUENCE: 17
ttctcatgtt tgacagctta tcatcgataa gctttaatgc ggtagtttat cacagttaaa 60
ttgctaacgc agtcaggcac cgtgtatgaa atctaacaat gcgctcatcg tcatcctcgg 120
caccgtcacc ctggatgctg taggcatagg cttggttatg ccggtactgc cgggcctctt 180

```
gcgggatgaa ttcagatctc gatcccgcga aattaatacg actcactata gggagaccac    240
aacggtttcc ctctagatca caagtttgta caaaaaagca ggctaagaag gagatataca    300
tacgccggcc attcaaacat gaggattacc catgtattta aatacccatg tccaggcgcg    360
ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaatgaga gaggtattcc tcaggccaca tcgcttccta gttccgctgg    780
gatccatcgt tggcggcgcg cctcatccca gttggtgatg ataccgtgtt cgatggggta    840
tttcagggtg aggatacctc ttttgctttg ggcttcatct cctacgtatg agtccttttg    900
tcccataccg accatgactc cttgatgcct tgggcgaccg acgatcgagg ggaagacggc    960
acggggtgcg tcatctcctg cgaaaccggc tttgcacata ccggatccat tgtctacgac   1020
aagagccgct acatcgtcgt cacacatgtt gtcttttgag gttggacact gctcactaga   1080
cagaaaaacc tcgtgccgga ccgaataccc ggtctgaacg agggcggccg cggtacccaa   1140
gaagtactta gagttaatta aggagttcaa acatgaggat cacccatgtc gaagctccca   1200
caccctagca taaccccttg ggcctctaa acgggtcttg aggggttttt tgctgaaagg   1260
aggaactata tccggatatc cacaggacgg gtgtggtcgc catgatcgcg tagtcgatag   1320
tggctccaag tagcgaagcg agcaggactg ggcggcgggc atgcatcgtc cattccgaca   1380
gcatcgccag tcactatggc gtgctgctag cgctatatgc gttgatgcaa tttctatgcg   1440
cacccgttct cggagcactg tccgaccgct ttggccgccg cccagtcctg ctcgcttcgc   1500
tacttggagc cactatcgac tacgcgatca tggcgaccac acccgtcctg tggatccaga   1560
tctcgatccc gcgaaattaa tacgactcac tatagggaga ccacaacggt ttccctctag   1620
atcacaagtt tgtacaaaaa agcaggctaa gaaggagata tacatatggc gtctaacttt   1680
acccaattcg ttctggttga taacggcggt acgggtgacg ttaccgtagc tccgtccaac   1740
ttcgccaacg gtgttgcgga atggattagc tctaacagcc gctctcaggc ctacaaagtc   1800
acgtgctccg ttcgtcagtc tagcgcgcag aatcgcaaat acaccatcaa agttgaagta   1860
ccgaaagtcg caacgcagac cgtaggcggc gtagaactcc cagttgcggc ctggcgctct   1920
tacctcaaca tggaactgac tattccgatt tttgcgacga actccgactg cgaactgatt   1980
gttaaggcaa tgcagggcct gctgaaagac ggtaatccga tcccatctgc aatcgctgct   2040
aactctggca tttactaata agcggacgcg ctgccaccgc tgagcaataa ctagcataac   2100
cccttggggc ctctaaacgg gtcttgaggg gttttttgct gaaaggagga actatatccg   2160
gcatgcacca ttccttgcgg cggcggtgct caacggcctc aacctactac tgggctgctt   2220
cctaatgcag gagtcgcata agggagagcg tcgaccgatg cccttgagag ccttcaaccc   2280
agtcagctcc ttccggtggg cgcggggcat gactatcgtc gccgcactta tgactgtctt   2340
ctttatcatg caactcgtag gacaggtgcc ggcagcgctc tgggtcattt tcggcgagga   2400
ccgctttcgc tggagcgcga cgatgatcgg cctgtcgctt gcggtattcg gaatcttgca   2460
cgccctcgct caagccttcg tcactggtcc cgccaccaaa cgtttcggcg agaagcaggc   2520
```

-continued

```
cattatcgcc ggcatggcgg ccgacgcgct gggctacgtc ttgctggcgt tcgcgacgcg   2580
aggctggatg gccttcccca ttatgattct tctcgcttcc ggcggcatcg ggatgcccgc   2640
gttgcaggcc atgctgtcca ggcaggtaga tgacgaccat cagggacagc ttcaaggatc   2700
gctcgcggct cttaccagcc taacttcgat cattggaccg ctgatcgtca cggcgattta   2760
tgccgcctcg gcgagcacat ggaacgggtt ggcatggatt gtaggcgccg ccctatacct   2820
tgtctgcctc cccgcgttgc gtcgcggtgc atggagccgg gccacctcga cctgaatgga   2880
agccggcggc acctcgctaa cggattcacc actccaagaa ttggagccaa tcaattcttg   2940
cggagaactg tgaatgcgca aaccaaccct tggcagaaca tatccatcgc gtccgccatc   3000
tccagcagcc gcacgcggcg catctcgggc agcgttgggt cctggccacg ggtgcgcatg   3060
atcgtgctcc tgtcgttgag gacccggcta ggctggcggg gttgccttac tggttagcag   3120
aatgaatcac cgatacgcga gcgaacgtga agcgactgct gctgcaaaac gtctgcgacc   3180
tgagcaacaa catgaatggt cttcggtttc cgtgtttcgt aaagtctgga aacgcggaag   3240
tcagcgccct gcaccattat gttccggatc tgcatcgcag gatgctgctg gctaccctgt   3300
ggaacaccta catctgtatt aacgaagcgc tggcattgac cctgagtgat ttttctctgg   3360
tcccgccgca tccataccgc cagttgttta ccctcacaac gttccagtaa ccgggcatgt   3420
tcatcatcag taacccgtat cgtgagcatc ctctctcgtt tcatcggtat cattaccccc   3480
atgaacagaa atccccctta cacggaggca tcagtgacca aacaggaaaa aaccgccctt   3540
aacatggccc gctttatcag aagccagaca ttaacgcttc tggagaaact caacgagctg   3600
gacgcggatg aacaggcaga catctgtgaa tcgcttcacg accacgctga tgagctttac   3660
cgcagctgcc tcgcgcgttt cggtgatgac ggtgaaaacc tctgacacat gcagctcccg   3720
gagacggtca cagcttgtct gtaagcggat gccgggagca gacaagcccg tcagggcgcg   3780
tcagcgggtg ttggcgggtg tcggggcgca gccatgaccc agtcacgtag cgatagcgga   3840
gtgtatactg gcttaactat gcggcatcag agcagattgt actgagagtg caccatatgc   3900
ggtgtgaaat accgcacaga tgcgtaagga gaaaataccg catcaggcgc tcttccgctt   3960
cctcgctcac tgactcgctg cgctcggtcg ttcggctgcg gcgagcggta tcagctcact   4020
caaaggcggt aatacggtta tccacagaat caggggataa cgcaggaaag aacatgtgag   4080
caaaaggcca gcaaaaggcc aggaaccgta aaaaggccgc gttgctggcg tttttccata   4140
ggctccgccc ccctgacgag catcacaaaa atcgacgctc aagtcagagg tggcgaaacc   4200
cgacaggact ataaagatac caggcgtttc cccctggaag ctccctcgtg cgctctcctg   4260
ttccgaccct gccgcttacc ggatacctgt ccgcctttct cccttcggga agcgtggcgc   4320
tttctcatag ctcacgctgt aggtatctca gttcggtgta ggtcgttcgc tccaagctgg   4380
gctgtgtgca cgaacccccc gttcagcccg accgctgcgc cttatccggt aactatcgtc   4440
ttgagtccaa cccggtaaga cacgacttat cgccactggc agcagccact ggtaacagga   4500
ttagcagagc gaggtatgta ggcggtgcta cagagttctt gaagtggtgg cctaactacg   4560
gctacactag aaggacagta tttggtatct gcgctctgct gaagccagtt accttcggaa   4620
aaagagttgg tagctcttga tccggcaaac aaaccaccgc tggtagcggt ggtttttttg   4680
tttgcaagca gcagattacg cgcagaaaaa aaggatctca agaagatcct ttgatctttt   4740
ctacggggtc tgacgctcag tggaacgaaa actcacgtta agggattttg gtcatgagat   4800
tatcaaaaag gatcttcacc tagatccttt taaattaaaa atgaagtttt aaatcaatct   4860
aaagtatata tgagtaaact tggtctgaca gttaccaatg cttaatcagt gaggcaccta   4920
```

```
tctcagcgat ctgtctattt cgttcatcca tagttgcctg actccccgtc gtgtagataa   4980

ctacgatacg ggagggctta ccatctggcc ccagtgctgc aatgataccg cgagacccac   5040

gctcaccggc tccagattta tcagcaataa accagccagc cggaagggcc gagcgcagaa   5100

gtggtcctgc aactttatcc gcctccatcc agtctattaa ttgttgccgg gaagctagag   5160

taagtagttc gccagttaat agtttgcgca acgttgttgc cattgctgca ggcatcgtgg   5220

tgtcacgctc gtcgtttggt atggcttcat tcagctccgg ttcccaacga tcaaggcgag   5280

ttacatgatc ccccatgttg tgcaaaaaag cggttagctc cttcggtcct ccgatcgttg   5340

tcagaagtaa gttggccgca gtgttatcac tcatggttat ggcagcactg cataattctc   5400

ttactgtcat gccatccgta agatgctttt ctgtgactgg tgagtactca accaagtcat   5460

tctgagaata gtgtatgcgg cgaccgagtt gctcttgccc ggcgtcaaca cgggataata   5520

ccgcgccaca tagcagaact ttaaaagtgc tcatcattgg aaaacgttct tcggggcgaa   5580

aactctcaag gatcttaccg ctgttgagat ccagttcgat gtaacccact cgtgcaccca   5640

actgatcttc agcatctttt actttcacca gcgtttctgg gtgagcaaaa acaggaaggc   5700

aaaatgccgc aaaaaaggga ataagggcga cacggaaatg ttgaatactc atactcttcc   5760

tttttcaata ttattgaagc atttatcagg gttattgtct catgagcgga tacatatttg   5820

aatgtattta gaaaaataaa caaatagggg ttccgcgcac atttccccga aaagtgccac   5880

ctgacgtcta agaaaccatt attatcatga cattaaccta taaaaatagg cgtatcacga   5940

ggccctttcg tcttcaagaa                                                5960


<210> SEQ ID NO 18
<211> LENGTH: 5980
<212> TYPE: DNA
<213> ORGANISM: Artificial Sequence
<220> FEATURE:
<223> OTHER INFORMATION: Recombinant plasmid pAPSE10272; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_features
<222> LOCATION: (317)..(335)
<223> OTHER INFORMATION: bacteriophage MS2 pac sequence
<220> FEATURE:
<221> NAME/KEY: misc_features
<222> LOCATION: (365)..(372)
<223> OTHER INFORMATION: restriction endonuclease AsiSI recognition site
<220> FEATURE:
<221> NAME/KEY: misc_features
<222> LOCATION: (372)..(666)
<223> OTHER INFORMATION: beta actin sense gene fragment
<220> FEATURE:
<221> NAME/KEY: misc_features
<222> LOCATION: (822)..(1116)
<223> OTHER INFORMATION: beta actin antisense gene fragment
<220> FEATURE:
<221> NAME/KEY: misc_feature
<222> LOCATION: (1191)..(1209)
<223> OTHER INFORMATION: bacteriophage MS2 pac sequence
<220> FEATURE:
<221> NAME/KEY: terminator
<222> LOCATION: (1225)..(1272)
<223> OTHER INFORMATION: bacteriophage T7 transcription terminator
<220> FEATURE:
<221> NAME/KEY: promoter
<222> LOCATION: (1598)..(1616)
<223> OTHER INFORMATION: bacteriophage T7 gene 1 promoter
<220> FEATURE:
<221> NAME/KEY: gene
```

```
<222> LOCATION: (1689)..(2078)
<223> OTHER INFORMATION: bacteriophage MS2 coat protein gene
<220> FEATURE:
<221> NAME/KEY: terminator
<222> LOCATION: (2111)..(2158)
<223> OTHER INFORMATION: bacteriophage T7 transcription terminator

<400> SEQUENCE: 18

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

catgtgtgac gacgatgtag cggctcttgt cgtagacaat ggatccggta tgtgcaaagc    480

cggtttcgca ggagatgacg caccccgtgc cgtcttcccc tcgatcgtcg gtcgcccaag    540

gcatcaagga gtcatggtcg gtatgggaca aaaggactca tacgtaggag atgaagccca    600

aagcaaaaga ggtatcctca ccctgaaata ccccatcgaa cacggtatca tcaccaactg    660

ggatgagttt aaaccctcta gctgctttac aaagtactgg ttccctttcc agcgggatgc    720

tttatctaaa cgcaatgaga gaggtattcc tcaggccaca tcgcttccta gttccgctgg    780

gatccatcgt tggcggccga agccgccatt ccatggcgcg cctcatccca gttggtgatg    840

ataccgtgtt cgatggggta tttcagggtg aggatacctc ttttgctttg ggcttcatct    900

cctacgtatg agtccttttg tcccataccg accatgactc cttgatgcct tgggcgaccg    960

acgatcgagg ggaagacggc acggggtgcg tcatctcctg cgaaaccggc tttgcacata   1020

ccggatccat tgtctacgac aagagccgct acatcgtcgt cacacatgtt gtcttttgag   1080

gttggacact gctcactaga cagaaaaacc tcgtgccgga ccgaataccc ggtctgaacg   1140

agggcggccg cggtacccaa gaagtactta gagttaatta aggagttcaa acatgaggat   1200

cacccatgtc gaagctccca caccctagca taaccccttg gggcctctaa acgggtcttg   1260

aggggttttt tgctgaaagg aggaactata tccggatatc cacaggacgg gtgtggtcgc   1320

catgatcgcg tagtcgatag tggctccaag tagcgaagcg agcaggactg ggcggcgggc   1380

atgcatcgtc cattccgaca gcatcgccag tcactatggc gtgctgctag cgctatatgc   1440

gttgatgcaa tttctatgcg cacccgttct cggagcactg tccgaccgct ttggccgccg   1500

cccagtcctg ctcgcttcgc tacttggagc cactatcgac tacgcgatca tggcgaccac   1560

acccgtcctg tggatccaga tctcgatccc gcgaaattaa tacgactcac tatagggaga   1620

ccacaacggt ttccctctag atcacaagtt tgtacaaaaa agcaggctaa gaaggagata   1680

tacatatggc gtctaacttt acccaattcg ttctggttga taacggcggt acgggtgacg   1740

ttaccgtagc tccgtccaac ttcgccaacg gtgttgcgga atggattagc tctaacagcc   1800

gctctcaggc ctacaaagtc acgtgctccg ttcgtcagtc tagcgcgcag aatcgcaaat   1860

acaccatcaa agttgaagta ccgaaagtcg caacgcagac cgtaggcggc gtagaactcc   1920

cagttgcggc ctggcgctct tacctcaaca tggaactgac tattccgatt tttgcgacga   1980

actccgactg cgaactgatt gttaaggcaa tgcagggcct gctgaaagac ggtaatccga   2040

tcccatctgc aatcgctgct aactctggca tttactaata agcggacgcg ctgccaccgc   2100
```

```
tgagcaataa ctagcataac cccttggggc ctctaaacgg gtcttgaggg gttttttgct   2160
gaaaggagga actatatccg gcatgcacca ttccttgcgg cggcggtgct caacggcctc   2220
aacctactac tgggctgctt cctaatgcag gagtcgcata agggagagcg tcgaccgatg   2280
cccttgagag ccttcaaccc agtcagctcc ttccggtggg cgcggggcat gactatcgtc   2340
gccgcactta tgactgtctt ctttatcatg caactcgtag gacaggtgcc ggcagcgctc   2400
tgggtcattt tcggcgagga ccgctttcgc tggagcgcga cgatgatcgg cctgtcgctt   2460
gcggtattcg gaatcttgca cgccctcgct caagccttcg tcactggtcc cgccaccaaa   2520
cgtttcggcg agaagcaggc cattatcgcc ggcatggcgg ccgacgcgct gggctacgtc   2580
ttgctggcgt tcgcgacgcg aggctggatg gccttcccca ttatgattct tctcgcttcc   2640
ggcggcatcg ggatgcccgc gttgcaggcc atgctgtcca ggcaggtaga tgacgaccat   2700
cagggacagc ttcaaggatc gctcgcggct cttaccagcc taacttcgat cattggaccg   2760
ctgatcgtca cggcgattta tgccgcctcg gcgagcacat ggaacgggtt ggcatggatt   2820
gtaggcgccg ccctatacct tgtctgcctc cccgcgttgc gtcgcggtgc atggagccgg   2880
gccacctcga cctgaatgga agccggcggc acctcgctaa cggattcacc actccaagaa   2940
ttggagccaa tcaattcttg cggagaactg tgaatgcgca aaccaaccct tggcagaaca   3000
tatccatcgc gtccgccatc tccagcagcc gcacgcggcg catctcgggc agcgttgggt   3060
cctggccacg ggtgcgcatg atcgtgctcc tgtcgttgag gacccggcta ggctggcggg   3120
gttgccttac tggttagcag aatgaatcac cgatacgcga gcgaacgtga agcgactgct   3180
gctgcaaaac gtctgcgacc tgagcaacaa catgaatggt cttcggtttc cgtgtttcgt   3240
aaagtctgga aacgcggaag tcagcgccct gcaccattat gttccggatc tgcatcgcag   3300
gatgctgctg gctaccctgt ggaacaccta catctgtatt aacgaagcgc tggcattgac   3360
cctgagtgat ttttctctgg tcccgccgca tccataccgc cagttgttta ccctcacaac   3420
gttccagtaa ccgggcatgt tcatcatcag taacccgtat cgtgagcatc ctctctcgtt   3480
tcatcggtat cattaccccc atgaacagaa atccccctta cacggaggca tcagtgacca   3540
aacaggaaaa aaccgccctt aacatggccc gctttatcag aagccagaca ttaacgcttc   3600
tggagaaact caacgagctg gacgcggatg aacaggcaga catctgtgaa tcgcttcacg   3660
accacgctga tgagctttac cgcagctgcc tcgcgcgttt cggtgatgac ggtgaaaacc   3720
tctgacacat gcagctcccg gagacggtca cagcttgtct gtaagcggat gccgggagca   3780
gacaagcccg tcagggcgcg tcagcgggtg ttggcgggtg tcggggcgca gccatgaccc   3840
agtcacgtag cgatagcgga gtgtatactg gcttaactat gcggcatcag agcagattgt   3900
actgagagtg caccatatgc ggtgtgaaat accgcacaga tgcgtaagga gaaaataccg   3960
catcaggcgc tcttccgctt cctcgctcac tgactcgctg cgctcggtcg ttcggctgcg   4020
gcgagcggta tcagctcact caaaggcggt aatacggtta tccacagaat caggggataa   4080
cgcaggaaag aacatgtgag caaaaggcca gcaaaaggcc aggaaccgta aaaaggccgc   4140
gttgctggcg tttttccata ggctccgccc ccctgacgag catcacaaaa atcgacgctc   4200
aagtcagagg tggcgaaacc cgacaggact ataaagatac caggcgtttc cccctggaag   4260
ctccctcgtg cgctctcctg ttccgaccct gccgcttacc ggatacctgt ccgcctttct   4320
cccttcggga agcgtggcgc tttctcatag ctcacgctgt aggtatctca gttcggtgta   4380
ggtcgttcgc tccaagctgg gctgtgtgca cgaacccccc gttcagcccg accgctgcgc   4440
cttatccggt aactatcgtc ttgagtccaa cccggtaaga cacgacttat cgccactggc   4500
```

```
agcagccact ggtaacagga ttagcagagc gaggtatgta ggcggtgcta cagagttctt   4560

gaagtggtgg cctaactacg gctacactag aaggacagta tttggtatct gcgctctgct   4620

gaagccagtt accttcggaa aaagagttgg tagctcttga tccggcaaac aaaccaccgc   4680

tggtagcggt ggtttttttg tttgcaagca gcagattacg cgcagaaaaa aaggatctca   4740

agaagatcct ttgatctttt ctacggggtc tgacgctcag tggaacgaaa actcacgtta   4800

agggattttg gtcatgagat tatcaaaaag gatcttcacc tagatccttt taaattaaaa   4860

atgaagtttt aaatcaatct aaagtatata tgagtaaact tggtctgaca gttaccaatg   4920

cttaatcagt gaggcaccta tctcagcgat ctgtctattt cgttcatcca tagttgcctg   4980

actccccgtc gtgtagataa ctacgatacg ggagggctta ccatctggcc ccagtgctgc   5040

aatgataccg cgagacccac gctcaccggc tccagattta tcagcaataa accagccagc   5100

cggaagggcc gagcgcagaa gtggtcctgc aactttatcc gcctccatcc agtctattaa   5160

ttgttgccgg gaagctagag taagtagttc gccagttaat agtttgcgca acgttgttgc   5220

cattgctgca ggcatcgtgg tgtcacgctc gtcgtttggt atggcttcat tcagctccgg   5280

ttcccaacga tcaaggcgag ttacatgatc ccccatgttg tgcaaaaaag cggttagctc   5340

cttcggtcct ccgatcgttg tcagaagtaa gttggccgca gtgttatcac tcatggttat   5400

ggcagcactg cataattctc ttactgtcat gccatccgta agatgctttt ctgtgactgg   5460

tgagtactca accaagtcat tctgagaata gtgtatgcgg cgaccgagtt gctcttgccc   5520

ggcgtcaaca cgggataata ccgcgccaca tagcagaact ttaaaagtgc tcatcattgg   5580

aaaacgttct tcggggcgaa aactctcaag gatcttaccg ctgttgagat ccagttcgat   5640

gtaacccact cgtgcaccca actgatcttc agcatctttt actttcacca gcgtttctgg   5700

gtgagcaaaa acaggaaggc aaaatgccgc aaaaaaggga ataagggcga cacggaaatg   5760

ttgaatactc atactcttcc tttttcaata ttattgaagc atttatcagg gttattgtct   5820

catgagcgga tacatatttg aatgtattta gaaaaataaa caaatagggg ttccgcgcac   5880

atttccccga aaagtgccac ctgacgtcta agaaaccatt attatcatga cattaaccta   5940

taaaaatagg cgtatcacga ggccctttcg tcttcaagaa                         5980
```

```
<210> SEQ ID NO 19
<211> LENGTH: 6005
<212> TYPE: DNA
<213> ORGANISM: Artificial Sequence
<220> FEATURE:
<223> OTHER INFORMATION: Recombinant plasmid pAPSE10292; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (797)..(1091)
<223> OTHER INFORMATION: beta actin antisense gene fragment
```

<220> FEATURE:
<221> NAME/KEY: misc_feature
<222> LOCATION: (1166)..(1184)
<223> OTHER INFORMATION: bacteriophage MS2 pac sequence
<220> FEATURE:
<221> NAME/KEY: terminator
<222> LOCATION: (1200)..(1247)
<223> OTHER INFORMATION: bacteriophage T7 transcription terminator
<220> FEATURE:
<221> NAME/KEY: promoter
<222> LOCATION: (1573)..(1591)
<223> OTHER INFORMATION: bacteriophage T7 gene 1 promoter
<220> FEATURE:
<221> NAME/KEY: gene
<222> LOCATION: (1664)..(2053)
<223> OTHER INFORMATION: bacteriophage MS2 coat protein gene
<220> FEATURE:
<221> NAME/KEY: terminator
<222> LOCATION: (2086)..(2133)
<223> OTHER INFORMATION: bacteriophage T7 transcription terminator

<400> SEQUENCE: 19

```
ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

catgtgtgac gacgatgtag cggctcttgt cgtagacaat ggatccggta tgtgcaaagc    480

cggtttcgca ggagatgacg caccccgtgc cgtcttcccc tcgatcgtcg gtcgcccaag    540

gcatcaagga gtcatggtcg gtatgggaca aaaggactca tacgtaggag atgaagccca    600

aagcaaaaga ggtatcctca ccctgaaata ccccatcgaa cacggtatca tcaccaactg    660

ggatgagttt aaacgcaatc gcagcaaact ccggcatcta ctaatagacg ccggccattc    720

aacatgagga ttacccatgt aacctaagaa gacaacaaag aagttcaact ctttatgtat    780

tgatcttccg gcgcgcctca tcccagttgg tgatgatacc gtgttcgatg ggtatttca     840

gggtgaggat acctcttttg ctttgggctt catctcctac gtatgagtcc ttttgtccca    900

taccgaccat gactccttga tgccttgggc gaccgacgat cgaggggaag acggcacggg    960

gtgcgtcatc tcctgcgaaa ccggctttgc acataccgga tccattgtct acgacaagag   1020

ccgctacatc gtcgtcacac atgttgtctt ttgaggttgg acactgctca ctagacagaa   1080

aaacctcgtg ccggaccgaa tacccggtct gaacgagggc ggccgcggta cccaagaagt   1140

acttagagtt aattaaggag ttcaaacatg aggatcaccc atgtcgaagc tcccacaccc   1200

tagcataacc ccttggggcc tctaaacggg tcttgagggg ttttttgctg aaaggaggaa   1260

ctatatccgg atatccacag gacgggtgtg gtcgccatga tcgcgtagtc gatagtggct   1320

ccaagtagcg aagcgagcag gactgggcgg cgggcatgca tcgtccattc cgacagcatc   1380

gccagtcact atggcgtgct gctagcgcta tatgcgttga tgcaatttct atgcgcaccc   1440

gttctcggag cactgtccga ccgctttggc cgccgcccag tcctgctcgc ttcgctactt   1500

ggagccacta tcgactacgc gatcatggcg accacacccg tcctgtggat ccagatctcg   1560

atcccgcgaa attaatacga ctcactatag ggagaccaca acggtttccc tctagatcac   1620

aagtttgtac aaaaaagcag gctaagaagg agatatacat atggcgtcta actttaccca   1680
```

-continued

```
attcgttctg gttgataacg gcggtacggg tgacgttacc gtagctccgt ccaacttcgc   1740
caacggtgtt gcggaatgga ttagctctaa cagccgctct caggcctaca aagtcacgtg   1800
ctccgttcgt cagtctagcg cgcagaatcg caaatacacc atcaaagttg aagtaccgaa   1860
agtcgcaacg cagaccgtag gcggcgtaga actcccagtt gcggcctggc gctcttacct   1920
caacatggaa ctgactattc cgatttttgc gacgaactcc gactgcgaac tgattgttaa   1980
ggcaatgcag ggcctgctga aagacggtaa tccgatccca tctgcaatcg ctgctaactc   2040
tggcatttac taataagcgg acgcgctgcc accgctgagc aataactagc ataacccctt   2100
ggggcctcta aacgggtctt gaggggtttt ttgctgaaag gaggaactat atccggcatg   2160
caccattcct tgcggcggcg gtgctcaacg gcctcaacct actactgggc tgcttcctaa   2220
tgcaggagtc gcataaggga gagcgtcgac cgatgccctt gagagccttc aacccagtca   2280
gctccttccg gtgggcgcgg ggcatgacta tcgtcgccgc acttatgact gtcttcttta   2340
tcatgcaact cgtaggacag gtgccggcag cgctctgggt cattttcggc gaggaccgct   2400
ttcgctggag cgcgacgatg atcggcctgt cgcttgcggt attcggaatc ttgcacgccc   2460
tcgctcaagc cttcgtcact ggtcccgcca ccaaacgttt cggcgagaag caggccatta   2520
tcgccggcat ggcggccgac gcgctgggct acgtcttgct ggcgttcgcg acgcgaggct   2580
ggatggcctt ccccattatg attcttctcg cttccggcgg catcgggatg cccgcgttgc   2640
aggccatgct gtccaggcag gtagatgacg accatcaggg acagcttcaa ggatcgctcg   2700
cggctcttac cagcctaact tcgatcattg gaccgctgat cgtcacggcg atttatgccg   2760
cctcggcgag cacatggaac gggttggcat ggattgtagg cgccgcccta taccttgtct   2820
gcctccccgc gttgcgtcgc ggtgcatgga gccgggccac ctcgacctga atggaagccg   2880
gcggcacctc gctaacggat tcaccactcc aagaattgga gccaatcaat tcttgcggag   2940
aactgtgaat gcgcaaacca acccttggca gaacatatcc atcgcgtccg ccatctccag   3000
cagccgcacg cggcgcatct cgggcagcgt tgggtcctgg ccacgggtgc gcatgatcgt   3060
gctcctgtcg ttgaggaccc ggctaggctg gcggggttgc cttactggtt agcagaatga   3120
atcaccgata cgcgagcgaa cgtgaagcga ctgctgctgc aaaacgtctg cgacctgagc   3180
aacaacatga atggtcttcg gtttccgtgt ttcgtaaagt ctggaaacgc ggaagtcagc   3240
gccctgcacc attatgttcc ggatctgcat cgcaggatgc tgctggctac cctgtggaac   3300
acctacatct gtattaacga agcgctggca ttgaccctga gtgatttttc tctggtcccg   3360
ccgcatccat accgccagtt gtttaccctc acaacgttcc agtaaccggg catgttcatc   3420
atcagtaacc cgtatcgtga gcatcctctc tcgtttcatc ggtatcatta cccccatgaa   3480
cagaaatccc ccttacacgg aggcatcagt gaccaaacag gaaaaaaccg cccttaacat   3540
ggcccgcttt atcagaagcc agacattaac gcttctggag aaactcaacg agctggacgc   3600
ggatgaacag gcagacatct gtgaatcgct tcacgaccac gctgatgagc tttaccgcag   3660
ctgcctcgcg cgtttcggtg atgacggtga aaacctctga cacatgcagc tcccggagac   3720
ggtcacagct tgtctgtaag cggatgccgg gagcagacaa gcccgtcagg gcgcgtcagc   3780
gggtgttggc gggtgtcggg gcgcagccat gacccagtca cgtagcgata gcggagtgta   3840
tactggctta actatgcggc atcagagcag attgtactga gagtgcacca tatgcggtgt   3900
gaaataccgc acagatgcgt aaggagaaaa taccgcatca ggcgctcttc cgcttcctcg   3960
ctcactgact cgctgcgctc ggtcgttcgg ctgcggcgag cggtatcagc tcactcaaag   4020
gcggtaatac ggttatccac agaatcaggg gataacgcag gaaagaacat gtgagcaaaa   4080
```

```
ggccagcaaa aggccaggaa ccgtaaaaag gccgcgttgc tggcgttttt ccataggctc   4140
cgcccccctg acgagcatca caaaaatcga cgctcaagtc agaggtggcg aaacccgaca   4200
ggactataaa gataccaggc gtttccccct ggaagctccc tcgtgcgctc tcctgttccg   4260
accctgccgc ttaccggata cctgtccgcc tttctccctt cgggaagcgt ggcgctttct   4320
catagctcac gctgtaggta tctcagttcg gtgtaggtcg ttcgctccaa gctgggctgt   4380
gtgcacgaac cccccgttca gcccgaccgc tgcgccttat ccggtaacta tcgtcttgag   4440
tccaacccgg taagacacga cttatcgcca ctggcagcag ccactggtaa caggattagc   4500
agagcgaggt atgtaggcgg tgctacagag ttcttgaagt ggtggcctaa ctacggctac   4560
actagaagga cagtatttgg tatctgcgct ctgctgaagc cagttacctt cggaaaaaga   4620
gttggtagct cttgatccgg caaacaaacc accgctggta gcggtggttt ttttgtttgc   4680
aagcagcaga ttacgcgcag aaaaaaagga tctcaagaag atcctttgat cttttctacg   4740
gggtctgacg ctcagtggaa cgaaaactca cgttaaggga ttttggtcat gagattatca   4800
aaaaggatct tcacctagat ccttttaaat taaaaatgaa gttttaaatc aatctaaagt   4860
atatatgagt aaacttggtc tgacagttac caatgcttaa tcagtgaggc acctatctca   4920
gcgatctgtc tatttcgttc atccatagtt gcctgactcc ccgtcgtgta gataactacg   4980
atacgggagg gcttaccatc tggccccagt gctgcaatga taccgcgaga cccacgctca   5040
ccggctccag atttatcagc aataaaccag ccagccggaa gggccgagcg cagaagtggt   5100
cctgcaactt tatccgcctc catccagtct attaattgtt gccgggaagc tagagtaagt   5160
agttcgccag ttaatagttt gcgcaacgtt gttgccattg ctgcaggcat cgtggtgtca   5220
cgctcgtcgt ttggtatggc ttcattcagc tccggttccc aacgatcaag gcgagttaca   5280
tgatccccca tgttgtgcaa aaaagcggtt agctccttcg gtcctccgat cgttgtcaga   5340
agtaagttgg ccgcagtgtt atcactcatg gttatggcag cactgcataa ttctcttact   5400
gtcatgccat ccgtaagatg cttttctgtg actggtgagt actcaaccaa gtcattctga   5460
gaatagtgta tgcggcgacc gagttgctct tgcccggcgt caacacggga taataccgcg   5520
ccacatagca gaactttaaa agtgctcatc attggaaaac gttcttcggg gcgaaaactc   5580
tcaaggatct taccgctgtt gagatccagt tcgatgtaac ccactcgtgc acccaactga   5640
tcttcagcat cttttacttt caccagcgtt tctgggtgag caaaaacagg aaggcaaaat   5700
gccgcaaaaa agggaataag ggcgacacgg aaatgttgaa tactcatact cttccttttt   5760
caatattatt gaagcattta tcagggttat tgtctcatga gcggatacat atttgaatgt   5820
atttagaaaa ataaacaaat aggggttccg cgcacatttc cccgaaaagt gccacctgac   5880
gtctaagaaa ccattattat catgacatta acctataaaa ataggcgtat cacgaggccc   5940
tttcgtcttc aagaacatta acctataaaa ataggcgtat cacgaggccc tttcgtcttc   6000
aagaa                                                               6005
```

<210> SEQ ID NO 20
<211> LENGTH: 5966
<212> TYPE: DNA
<213> ORGANISM: Artificial Sequence
<220> FEATURE:
<223> OTHER INFORMATION: Recombinant plasmid pAPSE10291; beta actin stem loop + coat protein
<220> FEATURE:
<221> NAME/KEY: promoter
<222> LOCATION: (214)..(232)
<223> OTHER INFORMATION: bacteriophage T7 gene 1 promoter

```
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (808)..(1102)
<223> OTHER INFORMATION: beta actin antisense gene fragment
<220> FEATURE:
<221> NAME/KEY: misc_feature
<222> LOCATION: (1177)..(1195)
<223> OTHER INFORMATION: bacteriophage MS2 pac sequence
<220> FEATURE:
<221> NAME/KEY: terminator
<222> LOCATION: (1211)..(1258)
<223> OTHER INFORMATION: bacteriophage T7 transcription terminator
<220> FEATURE:
<221> NAME/KEY: promoter
<222> LOCATION: (1584)..(1602)
<223> OTHER INFORMATION: bacteriophage T7 gene 1 promoter
<220> FEATURE:
<221> NAME/KEY: gene
<222> LOCATION: (1675)..(2064)
<223> OTHER INFORMATION: bacteriophage MS2 coat protein gene
<220> FEATURE:
<221> NAME/KEY: terminator
<222> LOCATION: (2097)..(2144)
<223> OTHER INFORMATION: bacteriophage T7 transcription terminator

<400> SEQUENCE: 20

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

catgtgtgac gacgatgtag cggctcttgt cgtagacaat ggatccggta tgtgcaaagc    480

cggtttcgca ggagatgacg caccccgtgc cgtcttcccc tcgatcgtcg gtcgcccaag    540

gcatcaagga gtcatggtcg gtatgggaca aaaggactca tacgtaggag atgaagccca    600

aagcaaaaga ggtatcctca ccctgaaata ccccatcgaa cacggtatca tcaccaactg    660

ggatgagttt aaacttaagc ggaacaccag gcggaacgaa gaggagatag agaactagat    720

tgattagaat caaatactag aactactaaa tcgaatcgat acgctaacga aaggacctgg    780

acacgtcgac gagccgctgg ggcgcgcctc atcccagttg gtgatgatac cgtgttcgat    840

ggggtatttc agggtgagga tacctctttt gctttgggct tcatctccta cgtatgagtc    900

cttttgtccc ataccgacca tgactccttg atgccttggg cgaccgacga tcgaggggaa    960

gacggcacgg ggtgcgtcat ctcctgcgaa accggctttg cacataccgg atccattgtc   1020

tacgacaaga gccgctacat cgtcgtcaca catgttgtct tttgaggttg gacactgctc   1080

actagacaga aaaacctcgt gccggaccga atacccggtc tgaacgaggg cggccgcggt   1140

acccaagaag tacttagagt taattaagga gttcaaacat gaggatcacc catgtcgaag   1200
```

-continued

```
ctcccacacc ctagcataac cccttggggc ctctaaacgg gtcttgaggg gttttttgct   1260
gaaaggagga actatatccg gatatccaca ggacgggtgt ggtcgccatg atcgcgtagt   1320
cgatagtggc tccaagtagc gaagcgagca ggactgggcg gcgggcatgc atcgtccatt   1380
ccgacagcat cgccagtcac tatggcgtgc tgctagcgct atatgcgttg atgcaatttc   1440
tatgcgcacc cgttctcgga gcactgtccg accgctttgg ccgccgccca gtcctgctcg   1500
cttcgctact tggagccact atcgactacg cgatcatggc gaccacaccc gtcctgtgga   1560
tccagatctc gatcccgcga aattaatacg actcactata gggagaccac aacggtttcc   1620
ctctagatca caagtttgta caaaaaagca ggctaagaag gagatataca tatggcgtct   1680
aactttaccc aattcgttct ggttgataac ggcggtacgg gtgacgttac cgtagctccg   1740
tccaacttcg ccaacggtgt tgcggaatgg attagctcta acagccgctc tcaggcctac   1800
aaagtcacgt gctccgttcg tcagtctagc gcgcagaatc gcaaatacac catcaaagtt   1860
gaagtaccga aagtcgcaac gcagaccgta ggcggcgtag aactcccagt tgcggcctgg   1920
cgctcttacc tcaacatgga actgactatt ccgatttttg cgacgaactc cgactgcgaa   1980
ctgattgtta aggcaatgca gggcctgctg aaagacggta atccgatccc atctgcaatc   2040
gctgctaact ctggcattta ctaataagcg gacgcgctgc caccgctgag caataactag   2100
cataacccct tggggcctct aaacgggtct tgaggggttt tttgctgaaa ggaggaacta   2160
tatccggcat gcaccattcc ttgcggcggc ggtgctcaac ggcctcaacc tactactggg   2220
ctgcttccta atgcaggagt cgcataaggg agagcgtcga ccgatgccct tgagagcctt   2280
caacccagtc agctccttcc ggtgggcgcg gggcatgact atcgtcgccg cacttatgac   2340
tgtcttcttt atcatgcaac tcgtaggaca ggtgccggca gcgctctggg tcattttcgg   2400
cgaggaccgc tttcgctgga gcgcgacgat gatcggcctg tcgcttgcgg tattcggaat   2460
cttgcacgcc ctcgctcaag ccttcgtcac tggtcccgcc accaaacgtt tcggcgagaa   2520
gcaggccatt atcgccggca tggcggccga cgcgctgggc tacgtcttgc tggcgttcgc   2580
gacgcgaggc tggatggcct tccccattat gattcttctc gcttccggcg gcatcgggat   2640
gcccgcgttg caggccatgc tgtccaggca ggtagatgac gaccatcagg gacagcttca   2700
aggatcgctc gcggctctta ccagcctaac ttcgatcatt ggaccgctga tcgtcacggc   2760
gatttatgcc gcctcggcga gcacatggaa cgggttggca tggattgtag gcgccgccct   2820
ataccttgtc tgcctccccg cgttgcgtcg cggtgcatgg agccgggcca cctcgacctg   2880
aatggaagcc ggcggcacct cgctaacgga ttcaccactc caagaattgg agccaatcaa   2940
ttcttgcgga gaactgtgaa tgcgcaaacc aacccttggc agaacatatc catcgcgtcc   3000
gccatctcca gcagccgcac gcggcgcatc tcgggcagcg ttgggtcctg gccacgggtg   3060
cgcatgatcg tgctcctgtc gttgaggacc cggctaggct ggcggggttg ccttactggt   3120
tagcagaatg aatcaccgat acgcgagcga acgtgaagcg actgctgctg caaaacgtct   3180
gcgacctgag caacaacatg aatggtcttc ggtttccgtg tttcgtaaag tctggaaacg   3240
cggaagtcag cgccctgcac cattatgttc cggatctgca tcgcaggatg ctgctggcta   3300
ccctgtggaa cacctacatc tgtattaacg aagcgctggc attgaccctg agtgattttt   3360
ctctggtccc gccgcatcca taccgccagt tgtttaccct cacaacgttc cagtaaccgg   3420
gcatgttcat catcagtaac ccgtatcgtg agcatcctct ctcgtttcat cggtatcatt   3480
acccccatga acagaaatcc cccttacacg gaggcatcag tgaccaaaca ggaaaaaacc   3540
gcccttaaca tggcccgctt tatcagaagc cagacattaa cgcttctgga gaaactcaac   3600
```

```
gagctggacg cggatgaaca ggcagacatc tgtgaatcgc ttcacgacca cgctgatgag   3660
ctttaccgca gctgcctcgc gcgtttcggt gatgacggtg aaaacctctg acacatgcag   3720
ctcccggaga cggtcacagc ttgtctgtaa gcggatgccg ggagcagaca agcccgtcag   3780
ggcgcgtcag cgggtgttgg cgggtgtcgg ggcgcagcca tgacccagtc acgtagcgat   3840
agcggagtgt atactggctt aactatgcgg catcagagca gattgtactg agagtgcacc   3900
atatgcggtg tgaaataccg cacagatgcg taaggagaaa ataccgcatc aggcgctctt   3960
ccgcttcctc gctcactgac tcgctgcgct cggtcgttcg gctgcggcga gcggtatcag   4020
ctcactcaaa ggcggtaata cggttatcca cagaatcagg ggataacgca ggaaagaaca   4080
tgtgagcaaa aggccagcaa aaggccagga accgtaaaaa ggccgcgttg ctggcgtttt   4140
tccataggct ccgcccccct gacgagcatc acaaaaatcg acgctcaagt cagaggtggc   4200
gaaacccgac aggactataa agataccagg cgtttccccc tggaagctcc ctcgtgcgct   4260
ctcctgttcc gaccctgccg cttaccggat acctgtccgc ctttctccct tcgggaagcg   4320
tggcgctttc tcatagctca cgctgtaggt atctcagttc ggtgtaggtc gttcgctcca   4380
agctgggctg tgtgcacgaa ccccccgttc agcccgaccg ctgcgcctta tccggtaact   4440
atcgtcttga gtccaacccg gtaagacacg acttatcgcc actggcagca gccactggta   4500
acaggattag cagagcgagg tatgtaggcg gtgctacaga gttcttgaag tggtggccta   4560
actacggcta cactagaagg acagtatttg gtatctgcgc tctgctgaag ccagttacct   4620
tcggaaaaag agttggtagc tcttgatccg gcaaacaaac caccgctggt agcggtggtt   4680
tttttgtttg caagcagcag attacgcgca gaaaaaaagg atctcaagaa gatcctttga   4740
tcttttctac ggggtctgac gctcagtgga acgaaaactc acgttaaggg attttggtca   4800
tgagattatc aaaaaggatc ttcacctaga tccttttaaa ttaaaaatga agttttaaat   4860
caatctaaag tatatatgag taaacttggt ctgacagtta ccaatgctta atcagtgagg   4920
cacctatctc agcgatctgt ctatttcgtt catccatagt tgcctgactc cccgtcgtgt   4980
agataactac gatacgggag ggcttaccat ctggccccag tgctgcaatg ataccgcgag   5040
acccacgctc accggctcca gatttatcag caataaacca gccagccgga agggccgagc   5100
gcagaagtgg tcctgcaact ttatccgcct ccatccagtc tattaattgt tgccgggaag   5160
ctagagtaag tagttcgcca gttaatagtt tgcgcaacgt tgttgccatt gctgcaggca   5220
tcgtggtgtc acgctcgtcg tttggtatgg cttcattcag ctccggttcc caacgatcaa   5280
ggcgagttac atgatccccc atgttgtgca aaaaagcggt tagctccttc ggtcctccga   5340
tcgttgtcag aagtaagttg gccgcagtgt tatcactcat ggttatggca gcactgcata   5400
attctcttac tgtcatgcca tccgtaagat gcttttctgt gactggtgag tactcaacca   5460
agtcattctg agaatagtgt atgcggcgac cgagttgctc ttgcccggcg tcaacacggg   5520
ataataccgc gccacatagc agaactttaa aagtgctcat cattggaaaa cgttcttcgg   5580
ggcgaaaact ctcaaggatc ttaccgctgt tgagatccag ttcgatgtaa cccactcgtg   5640
cacccaactg atcttcagca tcttttactt tcaccagcgt ttctgggtga gcaaaaacag   5700
gaaggcaaaa tgccgcaaaa aagggaataa gggcgacacg gaaatgttga atactcatac   5760
tcttcctttt tcaatattat tgaagcattt atcagggtta ttgtctcatg agcggataca   5820
tatttgaatg tatttagaaa aataaacaaa taggggttcc gcgcacattt ccccgaaaag   5880
tgccacctga cgtctaagaa accattatta tcatgacatt aacctataaa aataggcgta   5940
```

```
tcacgaggcc ctttcgtctt caagaa                                      5966


<210> SEQ ID NO 21
<211> LENGTH: 5502
<212> TYPE: DNA
<213> ORGANISM: Artificial Sequence
<220> FEATURE:
<223> OTHER INFORMATION: Recombinant plasmid pAPSE10276; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(422)
<223> OTHER INFORMATION: beta actin sense gene fragment
<220> FEATURE:
<221> NAME/KEY: misc_feature
<222> LOCATION: (588)..(638)
<223> OTHER INFORMATION: beta actin antisense gene fragment
<220> FEATURE:
<221> NAME/KEY: misc_feature
<222> LOCATION: (713)..(731)
<223> OTHER INFORMATION: bacteriophage MS2 pac sequence
<220> FEATURE:
<221> NAME/KEY: terminator
<222> LOCATION: (747)..(794)
<223> OTHER INFORMATION: bacteriophage T7 transcription terminator
<220> FEATURE:
<221> NAME/KEY: promoter
<222> LOCATION: (1120)..(1138)
<223> OTHER INFORMATION: bacteriophage T7 gene 1 promoter
<220> FEATURE:
<221> NAME/KEY: gene
<222> LOCATION: (1211)..(1600)
<223> OTHER INFORMATION: bacteriophage MS2 coat protein gene
<220> FEATURE:
<221> NAME/KEY: terminator
<222> LOCATION: (1633)..(1680)
<223> OTHER INFORMATION: bacteriophage T7 transcription terminator

<400> SEQUENCE: 21

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

cagtttaaac cctctagctg ctttacaaag tactggttcc ctttccagcg ggatgcttta    480

tctaaacgca atgagagagg tattcctcag gccacatcgc ttcctagttc cgctgggatc    540

catcgttggc ggccgaagcc gccattccat agtgagttct ggcgcgcctg ttgtcttttg    600

aggttggaca ctgctcacta gacagaaaaa cctcgtgccg gaccgaatac ccggtctgaa    660

cgagggcggc cgcggtaccc aagaagtact tagagttaat taaggagttc aaacatgagg    720

atcacccatg tcgaagctcc cacaccctag cataacccct tggggcctct aaacgggtct    780
```

```
tgaggggttt tttgctgaaa ggaggaacta tatccggata tccacaggac gggtgtggtc    840
gccatgatcg cgtagtcgat agtggctcca agtagcgaag cgagcaggac tgggcggcgg    900
gcatgcatcg tccattccga cagcatcgcc agtcactatg gcgtgctgct agcgctatat    960
gcgttgatgc aatttctatg cgcacccgtt ctcggagcac tgtccgaccg ctttggccgc   1020
cgcccagtcc tgctcgcttc gctacttgga gccactatcg actacgcgat catggcgacc   1080
acacccgtcc tgtggatcca gatctcgatc ccgcgaaatt aatacgactc actataggga   1140
gaccacaacg gtttccctct agatcacaag tttgtacaaa aaagcaggct aagaaggaga   1200
tatacatatg gcgtctaact ttacccaatt cgttctggtt gataacggcg gtacgggtga   1260
cgttaccgta gctccgtcca acttcgccaa cggtgttgcg gaatggatta gctctaacag   1320
ccgctctcag gcctacaaag tcacgtgctc cgttcgtcag tctagcgcgc agaatcgcaa   1380
atacaccatc aaagttgaag taccgaaagt cgcaacgcag accgtaggcg gcgtagaact   1440
cccagttgcg gcctggcgct cttacctcaa catggaactg actattccga tttttgcgac   1500
gaactccgac tgcgaactga ttgttaaggc aatgcagggc ctgctgaaag acggtaatcc   1560
gatcccatct gcaatcgctg ctaactctgg catttactaa taagcggacg cgctgccacc   1620
gctgagcaat aactagcata accccttggg gcctctaaac gggtcttgag gggttttttg   1680
ctgaaaggag gaactatatc cggcatgcac cattccttgc ggcggcggtg ctcaacggcc   1740
tcaacctact actgggctgc ttcctaatgc aggagtcgca taagggagag cgtcgaccga   1800
tgcccttgag agccttcaac ccagtcagct ccttccggtg ggcgcggggc atgactatcg   1860
tcgccgcact tatgactgtc ttctttatca tgcaactcgt aggacaggtg ccggcagcgc   1920
tctgggtcat tttcggcgag gaccgctttc gctggagcgc gacgatgatc ggcctgtcgc   1980
ttgcggtatt cggaatcttg cacgccctcg ctcaagcctt cgtcactggt cccgccacca   2040
aacgtttcgg cgagaagcag gccattatcg ccggcatggc ggccgacgcg ctgggctacg   2100
tcttgctggc gttcgcgacg cgaggctgga tggccttccc cattatgatt cttctcgctt   2160
ccggcggcat cgggatgccc gcgttgcagg ccatgctgtc caggcaggta gatgacgacc   2220
atcagggaca gcttcaagga tcgctcgcgg ctcttaccag cctaacttcg atcattggac   2280
cgctgatcgt cacggcgatt tatgccgcct cggcgagcac atggaacggg ttggcatgga   2340
ttgtaggcgc cgccctatac cttgtctgcc tccccgcgtt gcgtcgcggt gcatggagcc   2400
gggccacctc gacctgaatg gaagccggcg gcacctcgct aacggattca ccactccaag   2460
aattggagcc aatcaattct tgcggagaac tgtgaatgcg caaaccaacc cttggcagaa   2520
catatccatc gcgtccgcca tctccagcag ccgcacgcgg cgcatctcgg gcagcgttgg   2580
gtcctggcca cgggtgcgca tgatcgtgct cctgtcgttg aggacccggc taggctggcg   2640
gggttgcctt actggttagc agaatgaatc accgatacgc gagcgaacgt gaagcgactg   2700
ctgctgcaaa acgtctgcga cctgagcaac aacatgaatg gtcttcggtt tccgtgtttc   2760
gtaaagtctg gaaacgcgga agtcagcgcc ctgcaccatt atgttccgga tctgcatcgc   2820
aggatgctgc tggctaccct gtggaacacc tacatctgta ttaacgaagc gctggcattg   2880
accctgagtg atttttctct ggtcccgccg catccatacc gccagttgtt taccctcaca   2940
acgttccagt aaccgggcat gttcatcatc agtaacccgt atcgtgagca tcctctctcg   3000
tttcatcggt atcattaccc ccatgaacag aaatccccct tacacggagg catcagtgac   3060
caaacaggaa aaaaccgccc ttaacatggc ccgctttatc agaagccaga cattaacgct   3120
tctggagaaa ctcaacgagc tggacgcgga tgaacaggca gacatctgtg aatcgcttca   3180
```

```
cgaccacgct gatgagcttt accgcagctg cctcgcgcgt ttcggtgatg acggtgaaaa   3240
cctctgacac atgcagctcc cggagacggt cacagcttgt ctgtaagcgg atgccgggag   3300
cagacaagcc cgtcagggcg cgtcagcggg tgttggcggg tgtcggggcg cagccatgac   3360
ccagtcacgt agcgatagcg gagtgtatac tggcttaact atgcggcatc agagcagatt   3420
gtactgagag tgcaccatat gcggtgtgaa ataccgcaca gatgcgtaag gagaaaatac   3480
cgcatcaggc gctcttccgc ttcctcgctc actgactcgc tgcgctcggt cgttcggctg   3540
cggcgagcgg tatcagctca ctcaaaggcg gtaatacggt tatccacaga atcaggggat   3600
aacgcaggaa agaacatgtg agcaaaaggc cagcaaaagg ccaggaaccg taaaaaggcc   3660
gcgttgctgg cgtttttcca taggctccgc ccccctgacg agcatcacaa aaatcgacgc   3720
tcaagtcaga ggtggcgaaa cccgacagga ctataaagat accaggcgtt tccccctgga   3780
agctccctcg tgcgctctcc tgttccgacc ctgccgctta ccggatacct gtccgccttt   3840
ctcccttcgg gaagcgtggc gctttctcat agctcacgct gtaggtatct cagttcggtg   3900
taggtcgttc gctccaagct gggctgtgtg cacgaacccc ccgttcagcc cgaccgctgc   3960
gccttatccg gtaactatcg tcttgagtcc aacccggtaa gacacgactt atcgccactg   4020
gcagcagcca ctggtaacag gattagcaga gcgaggtatg taggcggtgc tacagagttc   4080
ttgaagtggt ggcctaacta cggctacact agaaggacag tatttggtat ctgcgctctg   4140
ctgaagccag ttaccttcgg aaaaagagtt ggtagctctt gatccggcaa acaaaccacc   4200
gctggtagcg gtggtttttt tgtttgcaag cagcagatta cgcgcagaaa aaaaggatct   4260
caagaagatc ctttgatctt ttctacgggg tctgacgctc agtggaacga aaactcacgt   4320
taagggattt tggtcatgag attatcaaaa aggatcttca cctagatcct tttaaattaa   4380
aaatgaagtt ttaaatcaat ctaaagtata tatgagtaaa cttggtctga cagttaccaa   4440
tgcttaatca gtgaggcacc tatctcagcg atctgtctat ttcgttcatc catagttgcc   4500
tgactccccg tcgtgtagat aactacgata cgggagggct taccatctgg ccccagtgct   4560
gcaatgatac cgcgagaccc acgctcaccg gctccagatt tatcagcaat aaaccagcca   4620
gccggaaggg ccgagcgcag aagtggtcct gcaactttat ccgcctccat ccagtctatt   4680
aattgttgcc gggaagctag agtaagtagt tcgccagtta atagtttgcg caacgttgtt   4740
gccattgctg caggcatcgt ggtgtcacgc tcgtcgtttg gtatggcttc attcagctcc   4800
ggttcccaac gatcaaggcg agttacatga tcccccatgt tgtgcaaaaa agcggttagc   4860
tccttcggtc ctccgatcgt tgtcagaagt aagttggccg cagtgttatc actcatggtt   4920
atggcagcac tgcataattc tcttactgtc atgccatccg taagatgctt ttctgtgact   4980
ggtgagtact caaccaagtc attctgagaa tagtgtatgc ggcgaccgag ttgctcttgc   5040
ccggcgtcaa cacgggataa taccgcgcca catagcagaa ctttaaaagt gctcatcatt   5100
ggaaaacgtt cttcggggcg aaaactctca aggatcttac cgctgttgag atccagttcg   5160
atgtaaccca ctcgtgcacc caactgatct tcagcatctt ttactttcac cagcgtttct   5220
gggtgagcaa aaacaggaag gcaaaatgcc gcaaaaaagg gaataagggc gacacggaaa   5280
tgttgaatac tcatactctt cctttttcaa tattattgaa gcatttatca gggttattgt   5340
ctcatgagcg gatacatatt tgaatgtatt tagaaaaata aacaaatagg ggttccgcgc   5400
acatttcccc gaaaagtgcc acctgacgtc taagaaacca ttattatcat gacattaacc   5460
tataaaaata ggcgtatcac gaggcccttt cgtcttcaag aa                      5502
```

<210> SEQ ID NO 22
<211> LENGTH: 5552
<212> TYPE: DNA
<213> ORGANISM: Artificial Sequence
<220> FEATURE:
<223> OTHER INFORMATION: Recombinant plasmid pAPSE10277; beta actin stem loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(447)
<223> OTHER INFORMATION: beta actin sense gene fragment
<220> FEATURE:
<221> NAME/KEY: misc_feature
<222> LOCATION: (613)..(688)
<223> OTHER INFORMATION: beta actin antisense gene fragment
<220> FEATURE:
<221> NAME/KEY: misc_feature
<222> LOCATION: (763)..(781)
<223> OTHER INFORMATION: bacteriophage MS2 pac sequence
<220> FEATURE:
<221> NAME/KEY: terminator
<222> LOCATION: (797)..(844)
<223> OTHER INFORMATION: bacteriophage T7 transcription terminator
<220> FEATURE:
<221> NAME/KEY: promoter
<222> LOCATION: (1170)..(1188)
<223> OTHER INFORMATION: bacteriophage T7 gene 1 promoter
<220> FEATURE:
<221> NAME/KEY: gene
<222> LOCATION: (1261)..(1650)
<223> OTHER INFORMATION: bacteriophage MS2 coat protein gene
<220> FEATURE:
<221> NAME/KEY: terminator
<222> LOCATION: (1683)..(1730)
<223> OTHER INFORMATION: bacteriophage T7 transcription terminator

<400> SEQUENCE: 22
ttctcatgtt tgacagctta tcatcgataa gctttaatgc ggtagtttat cacagttaaa 60
ttgctaacgc agtcaggcac cgtgtatgaa atctaacaat gcgctcatcg tcatcctcgg 120
caccgtcacc ctggatgctg taggcatagg cttggttatg ccggtactgc cgggcctctt 180
gcgggatgaa ttcagatctc gatcccgcga aattaatacg actcactata gggagaccac 240
aacggtttcc ctctagatca caagtttgta caaaaaagca ggctaagaag gagatataca 300
tacgccggcc attcaaacat gaggattacc catgtattta aatacccatg tccaggcgcg 360
ctccgcgatc gcgcacgagg tttttctgtc tagtgagcag tgtccaacct caaaagacaa 420
catgtgtgac gacgatgtag cggctctgtt taaaccctct agctgcttta caaagtactg 480
gttccctttc cagcgggatg ctttatctaa acgcaatgag agaggtattc ctcaggccac 540
atcgcttcct agttccgctg ggatccatcg ttggcggccg aagccgccat tccatagtga 600
gttctggcgc gccagagccg ctacatcgtc gtcacacatg ttgtcttttg aggttggaca 660
ctgctcacta gacagaaaaa cctcgtgccg gaccgaatac ccggtctgaa cgagggcggc 720
cgcggtaccc aagaagtact tagagttaat taaggagttc aaacatgagg atcacccatg 780
tcgaagctcc cacaccctag cataaccccct tggggcctct aaacgggtct tgaggggttt 840

```
tttgctgaaa ggaggaacta tatccggata tccacaggac gggtgtggtc gccatgatcg     900

cgtagtcgat agtggctcca agtagcgaag cgagcaggac tgggcggcgg gcatgcatcg     960

tccattccga cagcatcgcc agtcactatg gcgtgctgct agcgctatat gcgttgatgc    1020

aatttctatg cgcacccgtt ctcggagcac tgtccgaccg ctttggccgc cgcccagtcc    1080

tgctcgcttc gctacttgga gccactatcg actacgcgat catggcgacc acacccgtcc    1140

tgtggatcca gatctcgatc ccgcgaaatt aatacgactc actataggga gaccacaacg    1200

gtttccctct agatcacaag tttgtacaaa aaagcaggct aagaaggaga tatacatatg    1260

gcgtctaact ttacccaatt cgttctggtt gataacggcg gtacgggtga cgttaccgta    1320

gctccgtcca acttcgccaa cggtgttgcg gaatggatta gctctaacag ccgctctcag    1380

gcctacaaag tcacgtgctc cgttcgtcag tctagcgcgc agaatcgcaa atacaccatc    1440

aaagttgaag taccgaaagt cgcaacgcag accgtaggcg gcgtagaact cccagttgcg    1500

gcctggcgct cttacctcaa catggaactg actattccga tttttgcgac gaactccgac    1560

tgcgaactga ttgttaaggc aatgcagggc ctgctgaaag acggtaatcc gatcccatct    1620

gcaatcgctg ctaactctgg catttactaa taagcggacg cgctgccacc gctgagcaat    1680

aactagcata accccttggg gcctctaaac gggtcttgag gggttttttg ctgaaaggag    1740

gaactatatc cggcatgcac cattccttgc ggcggcggtg ctcaacggcc tcaacctact    1800

actgggctgc ttcctaatgc aggagtcgca taagggagag cgtcgaccga tgcccttgag    1860

agccttcaac ccagtcagct ccttccggtg ggcgcggggc atgactatcg tcgccgcact    1920

tatgactgtc ttctttatca tgcaactcgt aggacaggtg ccggcagcgc tctgggtcat    1980

tttcggcgag gaccgctttc gctggagcgc gacgatgatc ggcctgtcgc ttgcggtatt    2040

cggaatcttg cacgccctcg ctcaagcctt cgtcactggt cccgccacca aacgtttcgg    2100

cgagaagcag gccattatcg ccggcatggc ggccgacgcg ctgggctacg tcttgctggc    2160

gttcgcgacg cgaggctgga tggccttccc cattatgatt cttctcgctt ccggcggcat    2220

cgggatgccc gcgttgcagg ccatgctgtc caggcaggta gatgacgacc atcagggaca    2280

gcttcaagga tcgctcgcgg ctcttaccag cctaacttcg atcattggac cgctgatcgt    2340

cacggcgatt tatgccgcct cggcgagcac atggaacggg ttggcatgga ttgtaggcgc    2400

cgccctatac cttgtctgcc tccccgcgtt gcgtcgcggt gcatggagcc gggccacctc    2460

gacctgaatg gaagccggcg gcacctcgct aacggattca ccactccaag aattggagcc    2520

aatcaattct tgcggagaac tgtgaatgcg caaaccaacc cttggcagaa catatccatc    2580

gcgtccgcca tctccagcag ccgcacgcgg cgcatctcgg gcagcgttgg gtcctggcca    2640

cgggtgcgca tgatcgtgct cctgtcgttg aggacccggc taggctggcg gggttgcctt    2700

actggttagc agaatgaatc accgatacgc gagcgaacgt gaagcgactg ctgctgcaaa    2760

acgtctgcga cctgagcaac aacatgaatg gtcttcggtt tccgtgtttc gtaaagtctg    2820

gaaacgcgga agtcagcgcc ctgcaccatt atgttccgga tctgcatcgc aggatgctgc    2880

tggctaccct gtggaacacc tacatctgta ttaacgaagc gctggcattg accctgagtg    2940

atttttctct ggtcccgccg catccatacc gccagttgtt taccctcaca acgttccagt    3000

aaccgggcat gttcatcatc agtaacccgt atcgtgagca tcctctctcg tttcatcggt    3060

atcattaccc ccatgaacag aaatccccct tacacggagg catcagtgac caaacaggaa    3120

aaaaccgccc ttaacatggc ccgctttatc agaagccaga cattaacgct tctggagaaa    3180

ctcaacgagc tggacgcgga tgaacaggca gacatctgtg aatcgcttca cgaccacgct    3240
```

```
gatgagcttt accgcagctg cctcgcgcgt ttcggtgatg acggtgaaaa cctctgacac   3300
atgcagctcc cggagacggt cacagcttgt ctgtaagcgg atgccgggag cagacaagcc   3360
cgtcagggcg cgtcagcggg tgttggcggg tgtcggggcg cagccatgac ccagtcacgt   3420
agcgatagcg gagtgtatac tggcttaact atgcggcatc agagcagatt gtactgagag   3480
tgcaccatat gcggtgtgaa ataccgcaca gatgcgtaag gagaaaatac cgcatcaggc   3540
gctcttccgc ttcctcgctc actgactcgc tgcgctcggt cgttcggctg cggcgagcgg   3600
tatcagctca ctcaaaggcg gtaatacggt tatccacaga atcaggggat aacgcaggaa   3660
agaacatgtg agcaaaaggc cagcaaaagg ccaggaaccg taaaaaggcc gcgttgctgg   3720
cgtttttcca taggctccgc ccccctgacg agcatcacaa aaatcgacgc tcaagtcaga   3780
ggtggcgaaa cccgacagga ctataaagat accaggcgtt tccccctgga agctccctcg   3840
tgcgctctcc tgttccgacc ctgccgctta ccggatacct gtccgccttt ctcccttcgg   3900
gaagcgtggc gctttctcat agctcacgct gtaggtatct cagttcggtg taggtcgttc   3960
gctccaagct gggctgtgtg cacgaacccc ccgttcagcc cgaccgctgc gccttatccg   4020
gtaactatcg tcttgagtcc aacccggtaa gacacgactt atcgccactg gcagcagcca   4080
ctggtaacag gattagcaga gcgaggtatg taggcggtgc tacagagttc ttgaagtggt   4140
ggcctaacta cggctacact agaaggacag tatttggtat ctgcgctctg ctgaagccag   4200
ttaccttcgg aaaaagagtt ggtagctctt gatccggcaa acaaaccacc gctggtagcg   4260
gtggtttttt tgtttgcaag cagcagatta cgcgcagaaa aaaaggatct caagaagatc   4320
ctttgatctt ttctacgggg tctgacgctc agtggaacga aaactcacgt taagggattt   4380
tggtcatgag attatcaaaa aggatcttca cctagatcct tttaaattaa aaatgaagtt   4440
ttaaatcaat ctaaagtata tatgagtaaa cttggtctga cagttaccaa tgcttaatca   4500
gtgaggcacc tatctcagcg atctgtctat ttcgttcatc catagttgcc tgactccccg   4560
tcgtgtagat aactacgata cgggagggct taccatctgg ccccagtgct gcaatgatac   4620
cgcgagaccc acgctcaccg gctccagatt tatcagcaat aaaccagcca gccggaaggg   4680
ccgagcgcag aagtggtcct gcaactttat ccgcctccat ccagtctatt aattgttgcc   4740
gggaagctag agtaagtagt tcgccagtta atagtttgcg caacgttgtt gccattgctg   4800
caggcatcgt ggtgtcacgc tcgtcgtttg gtatggcttc attcagctcc ggttcccaac   4860
gatcaaggcg agttacatga tcccccatgt tgtgcaaaaa agcggttagc tccttcggtc   4920
ctccgatcgt tgtcagaagt aagttggccg cagtgttatc actcatggtt atggcagcac   4980
tgcataattc tcttactgtc atgccatccg taagatgctt ttctgtgact ggtgagtact   5040
caaccaagtc attctgagaa tagtgtatgc ggcgaccgag ttgctcttgc ccggcgtcaa   5100
cacgggataa taccgcgcca catagcagaa ctttaaaagt gctcatcatt ggaaaacgtt   5160
cttcggggcg aaaactctca aggatcttac cgctgttgag atccagttcg atgtaaccca   5220
ctcgtgcacc caactgatct tcagcatctt ttactttcac cagcgtttct gggtgagcaa   5280
aaacaggaag gcaaaatgcc gcaaaaaagg gaataagggc gacacggaaa tgttgaatac   5340
tcatactctt cctttttcaa tattattgaa gcatttatca gggttattgt ctcatgagcg   5400
gatacatatt tgaatgtatt tagaaaaata aacaaatagg ggttccgcgc acatttcccc   5460
gaaaagtgcc acctgacgtc taagaaacca ttattatcat gacattaacc tataaaaata   5520
ggcgtatcac gaggcccttt cgtcttcaag aa                                 5552
```

<210> SEQ ID NO 23
<211> LENGTH: 4667
<212> TYPE: DNA
<213> ORGANISM: Artificial Sequence
<220> FEATURE:
<223> OTHER INFORMATION: Recombinant plasmid pAPSE10149; coat protein
<220> FEATURE:
<221> NAME/KEY: promoter
<222> LOCATION: (1896)..(1914)
<223> OTHER INFORMATION: bacteriophage T7 gene 1 promoter
<220> FEATURE:
<221> NAME/KEY: gene
<222> LOCATION: (1987)..(2376)
<223> OTHER INFORMATION: bacteriophage MS2 coat protein
<220> FEATURE:
<221> NAME/KEY: terminator
<222> LOCATION: (2409)..(2456)
<223> OTHER INFORMATION: bacteriophage T7 transcription terminator

<400> SEQUENCE: 23
gaattccgga tgagcattca tcaggcgggc aagaatgtga ataaaggccg gataaaactt 60
gtgcttattt ttctttacgg tctttaaaaa ggccgtaata tccagctgaa cggtctggtt 120
ataggtacat tgagcaactg actgaaatgc ctcaaaatgt tctttacgat gccattggga 180
tatatcaacg gtggtatatc cagtgatttt tttctccatt ttagcttcct tagctcctga 240
aaatctcgat aactcaaaaa atacgcccgg tagtgatctt atttcattat ggtgaaagtt 300
ggaacctctt acgtgccgat caacgtctca ttttcgccaa aagttggccc agggcttccc 360
ggtatcaaca gggacaccag gatttattta ttctgcgaag tgatcttccg tcacaggtat 420
ttattcggcg caaagtgcgt cgggtgatgc tgccaactta ctgatttagt gtatgatggt 480
gtttttgagg tgctccagtg gcttctgttt ctatcagctg tccctcctgt tcagctactg 540
acggggtggt gcgtaacggc aaaagcaccg ccggacatca gcgctagcgg agtgtatact 600
ggcttactat gttggcactg atgagggtgt cagtgaagtg cttcatgtgg caggagaaaa 660
aaggctgcac cggtgcgtca gcagaatatg tgatacagga tatattccgc ttcctcgctc 720
actgactcgc tacgctcggt cgttcgactg cggcgagcgg aaatggctta cgaacggggc 780
ggagatttcc tggaagatgc caggaagata cttaacaggg aagtgagagg gccgcggcaa 840
agccgttttt ccataggctc cgcccccctg acaagcatca cgaaatctga cgctcaaatc 900
agtggtggcg aaacccgaca ggactataaa gataccaggc gtttccccct ggcggctccc 960
tcgtgcgctc tcctgttcct gcctttcggt ttaccggtgt cattccgctg ttatggccgc 1020
gtttgtctca ttccacgcct gacactcagt tccgggtagg cagttcgctc caagctggac 1080
tgtatgcacg aaccccccgt tcagtccgac cgctgcgcct tatccggtaa ctatcgtctt 1140
gagtccaacc cggaaagaca tgcaaaagca ccactggcag cagccactgg taattgattt 1200
agaggagtta gtcttgaagt catgcgccgg ttaaggctaa actgaaagga caagttttgg 1260
tgactgcgct cctccaagcc agttacctcg gttcaaagag ttggtagctc agagaacctt 1320
cgaaaaaccg ccctgcaagg cggttttttc gttttcagag caagagatta cgcgcagacc 1380
aaaacgatct caagaagatc atcttattaa tcagataaaa tatttctaga tttcagtgca 1440
atttatctct tcaaatgtag cacctgaagt cagccccata cgatataagt tgtaattctc 1500
atgtttgaca gcttatcatc gataagcttt aatgcggtag tttatcacag ttaaattgct 1560
aacgcagtca ggcaccgtgt atgaaatcta acaatgcgct catcgtcatc ctcggcaccg 1620
tcaccctgga tgctgtaggc ataggcttgg ttatgccggt actgccgggc ctcttgcggg 1680
atatcgtcca ttccgacagc atcgccagtc actatggcgt gctgctagcg ctatatgcgt 1740

```
tgatgcaatt tctatgcgca cccgttctcg gagcactgtc cgaccgcttt ggccgccgcc   1800
cagtcctgct cgcttcgcta cttggagcca ctatcgacta cgcgatcatg gcgaccacac   1860
ccgtcctgtg gatccagatc tcgatcccgc gaaattaata cgactcacta tagggagacc   1920
acaacggttt ccctctagat cacaagtttg tacaaaaaag caggctaaga aggagatata   1980
catatggcgt ctaactttac ccaattcgtt ctggttgata acggcggtac gggtgacgtt   2040
accgtagctc cgtccaactt cgccaacggt gttgcggaat ggattagctc taacagccgc   2100
tctcaggcct acaaagtcac gtgctccgtt cgtcagtcta gcgcgcagaa tcgcaaatac   2160
accatcaaag ttgaagtacc gaaagtcgca acgcagaccg taggcggcgt agaactccca   2220
gttgcggcct ggcgctctta cctcaacatg gaactgacta ttccgatttt tgcgacgaac   2280
tccgactgcg aactgattgt taaggcaatg cagggcctgc tgaaagacgg taatccgatc   2340
ccatctgcaa tcgctgctaa ctctggcatt tactaataag cggacgcgct gccaccgctg   2400
agcaataact agcataaccc cttggggcct ctaaacgggt cttgaggggt tttttgctga   2460
aaggaggaac tatatccggc atgcaccatt ccttgcggcg gcggtgctca acggcctcaa   2520
cctactactg ggctgcttcc taatgcagga gtcgcataag ggagagcgtc gaccgatgcc   2580
cttgagagcc ttcaacccag tcagctcctt ccggtgggcg cggggcatga ctatcgtcgc   2640
cgcacttatg actgtcttct ttatcatgca actcgtagga caggtgccgg cagcgctctg   2700
ggtcattttc ggcgaggacc gctttcgctg gagcgcgacg atgatcggcc tgtcgcttgc   2760
ggtattcgga atcttgcacg ccctcgctca agccttcgtc actggtcccg ccaccaaacg   2820
tttcggcgag aagcaggcca ttatcgccgg catggcggcc gacgcgctgg gctacgtctt   2880
gctggcgttc gcgacgcgag gctggatggc cttccccatt atgattcttc tcgcttccgg   2940
cggcatcggg atgcccgcgt tgcaggccat gctgtccagg caggtagatg acgaccatca   3000
gggacagctt caaggatcgc tcgcggctct taccagccta acttcgatca ttggaccgct   3060
gatcgtcacg gcgatttatg ccgcctcggc gagcacatgg aacgggttgg catggattgt   3120
aggcgccgcc ctataccttg tctgcctccc cgcgttgcgt cgcggtgcat ggagccgggc   3180
cacctcgacc tgaatggaag ccggcggcac ctcgctaacg gattcaccac tccaagaatt   3240
ggagccaatc aattcttgcg gagaactgtg aatgcgcaaa ccaacccttg gcagaacata   3300
tccatcgcgt ccgccatctc cagcagccgc acgcggcgca tctcgggcag cgttgggtcc   3360
tggccacggg tgcgcatgat cgtgctcctg tcgttgagga cccggctagg ctggcggggt   3420
tgccttactg gttagcagaa tgaatcaccg atacgcgagc gaacgtgaag cgactgctgc   3480
tgcaaaacgt ctgcgacctg agcaacaaca tgaatggtct tcggtttccg tgtttcgtaa   3540
agtctggaaa cgcggaagtc ccctacgtgc tgctgaagtt gcccgcaaca gagagtggaa   3600
ccaaccggtg ataccacgat actatgactg agagtcaacg ccatgagcgg cctcatttct   3660
tattctgagt tacaacagtc cgcaccgctg tccggtagct ccttccggtg ggcgcggggc   3720
atgactatcg tcgccgcact tatgactgtc ttctttatca tgcaactcgt aggacaggtg   3780
ccggcagcgc ccaacagtcc cccggccacg gggcctgcca ccatacccac gccgaaacaa   3840
gcgccctgca ccattatgtt ccggatctgc atcgcaggat gctgctggct accctgtgga   3900
acacctacat ctgtattaac gaagcgctaa ccgtttttat caggctctgg gaggcagaat   3960
aaatgatcat atcgtcaatt attacctcca cggggagagc ctgagcaaac tggcctcagg   4020
catttgagaa gcacacggtc acactgcttc cggtagtcaa taaaccggta aaccagcaat   4080
```

```
agacataagc ggctatttaa cgaccctgcc ctgaaccgac gaccgggtcg aatttgcttt   4140

cgaatttctg ccattcatcc gcttattatc acttattcag gcgtagcacc aggcgtttaa   4200

gggcaccaat aactgcctta aaaaaattac gccccgccct gccactcatc gcagtactgt   4260

tgtaattcat taagcattct gccgacatgg aagccatcac agacggcatg atgaacctga   4320

atcgccagcg gcatcagcac cttgtcgcct tgcgtataat atttgcccat ggtgaaaacg   4380

ggggcgaaga agttgtccat attggccacg tttaaatcaa aactggtgaa actcacccag   4440

ggattggctg agacgaaaaa catattctca ataaaccctt tagggaaata ggccaggttt   4500

tcaccgtaac acgccacatc ttgcgaatat atgtgtagaa actgccggaa atcgtcgtgg   4560

tattcactcc agagcgatga aaacgtttca gtttgctcat ggaaaacggt gtaacaaggg   4620

tgaacactat cccatatcac cagctcaccg tctttcattg ccatacg                 4667
```

```
<210> SEQ ID NO 24
<211> LENGTH: 6228
<212> TYPE: DNA
<213> ORGANISM: Artificial Sequence
<220> FEATURE:
<223> OTHER INFORMATION: Recombinant plasmid pAPSE10366; beta actin stem
      loop + eGFP protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1696)..(2415)
<223> OTHER INFORMATION: bacteriophage MS2 coat protein gene
<220> FEATURE:
<221> NAME/KEY: terminator
<222> LOCATION: (2448)..(2495)
<223> OTHER INFORMATION: bacteriophage T7 transcription terminator

<400> SEQUENCE: 24

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240
```

```
aacggtttcc ctctagatca caagtttgta caaaaaagca ggctaagaag gagatataca    300
tacgccggcc attcaaacat gaggattacc catgtattta aatacccatg tccaggcgcg    360
ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaatgaga gaggtattcc tcaggccaca tcgcttccta gttccgctgg    780
gatccatcgt tggcggccga agccgccatt ccatagtgag ttctggcgcg cctcatccca    840
gttggtgatg ataccgtgtt cgatggggta tttcagggtg aggatacctc ttttgctttg    900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg ggcctctaa    1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg tggatccaga tctcgatccc gcgaaattaa tacgactcac   1620
tatagggaga ccacaacggt ttccctctag atcacaagtt tgtacaaaaa agcaggctaa   1680
gaaggagata tacatatggt gagcaagggc gaggagctgt tcaccggggt ggtgcccatc   1740
ctggtcgagc tggacggcga cgtaaacggc cacaagttca gcgtgtccgg cgagggcgag   1800
ggcgatgcca cctacggcaa gctgaccctg aagttcatct gcaccaccgg caagctgccc   1860
gtgccctggc ccaccctcgt gaccaccctg acctacggcg tgcagtgctt cagccgctac   1920
cccgaccaca tgaagcagca cgacttcttc aagtccgcca tgcccgaagg ctacgtccag   1980
gagcgcacca tcttcttcaa ggacgacggc aactacaaga cccgcgccga ggtgaagttc   2040
gagggcgaca ccctggtgaa ccgcatcgag ctgaagggca tcgacttcaa ggaggacggc   2100
aacatcctgg ggcacaagct ggagtacaac tacaacagcc acaacgtcta tatcatggcc   2160
gacaagcaga agaacggcat caaggtgaac ttcaagatcc gccacaacat cgaggacggc   2220
agcgtgcagc tcgccgacca ctaccagcag aacaccccca tcggcgacgg ccccgtgctg   2280
ctgcccgaca accactacct gagcacccag tccgccctga gcaaagaccc caacgagaag   2340
cgcgatcaca tggtcctgct ggagttcgtg accgccgccg ggatcactct cggcatggac   2400
gagctgtaca agtaataagc ggacgcgctg ccaccgctga gcaataacta gcataacccc   2460
ttggggcctc taaacgggtc ttgaggggtt ttttgctgaa aggaggaact atatccggtc   2520
gaccgatgcc cttgagagcc ttcaacccag tcagctcctt ccggtgggcg cggggcatga   2580
ctatcgtcgc cgcacttatg actgtcttct ttatcatgca actcgtagga caggtgccgg   2640
```

```
cagcgctctg ggtcattttc ggcgaggacc gctttcgctg gagcgcgacg atgatcggcc   2700
tgtcgcttgc ggtattcgga atcttgcacg ccctcgctca agccttcgtc actggtcccg   2760
ccaccaaacg tttcggcgag aagcaggcca ttatcgccgg catggcggcc gacgcgctgg   2820
gctacgtctt gctggcgttc gcgacgcgag gctggatggc cttccccatt atgattcttc   2880
tcgcttccgg cggcatcggg atgcccgcgt tgcaggccat gctgtccagg caggtagatg   2940
acgaccatca gggacagctt caaggatcgc tcgcggctct taccagccta acttcgatca   3000
ttggaccgct gatcgtcacg gcgatttatg ccgcctcggc gagcacatgg aacgggttgg   3060
catggattgt aggcgccgcc ctataccttg tctgcctccc cgcgttgcgt cgcggtgcat   3120
ggagccgggc cacctcgacc tgaatggaag ccggcggcac ctcgctaacg gattcaccac   3180
tccaagaatt ggagccaatc aattcttgcg gagaactgtg aatgcgcaaa ccaacccttg   3240
gcagaacata tccatcgcgt ccgccatctc cagcagccgc acgcggcgca tctcgggcag   3300
cgttgggtcc tggccacggg tgcgcatgat cgtgctcctg tcgttgagga cccggctagg   3360
ctggcggggt tgccttactg gttagcagaa tgaatcaccg atacgcgagc gaacgtgaag   3420
cgactgctgc tgcaaaacgt ctgcgacctg agcaacaaca tgaatggtct tcggtttccg   3480
tgtttcgtaa agtctggaaa cgcggaagtc agcgccctgc accattatgt tccggatctg   3540
catcgcagga tgctgctggc taccctgtgg aacacctaca tctgtattaa cgaagcgctg   3600
gcattgaccc tgagtgattt ttctctggtc ccgccgcatc cataccgcca gttgtttacc   3660
ctcacaacgt tccagtaacc gggcatgttc atcatcagta acccgtatcg tgagcatcct   3720
ctctcgtttc atcggtatca ttacccccat gaacagaaat cccccttaca cggaggcatc   3780
agtgaccaaa caggaaaaaa ccgcccttaa catggcccgc tttatcagaa gccagacatt   3840
aacgcttctg gagaaactca acgagctgga cgcggatgaa caggcagaca tctgtgaatc   3900
gcttcacgac cacgctgatg agctttaccg cagctgcctc gcgcgtttcg gtgatgacgg   3960
tgaaaacctc tgacacatgc agctcccgga gacggtcaca gcttgtctgt aagcggatgc   4020
cgggagcaga caagcccgtc agggcgcgtc agcgggtgtt ggcgggtgtc ggggcgcagc   4080
catgacccag tcacgtagcg atagcggagt gtatactggc ttaactatgc ggcatcagag   4140
cagattgtac tgagagtgca ccatatgcgg tgtgaaatac cgcacagatg cgtaaggaga   4200
aaataccgca tcaggcgctc ttccgcttcc tcgctcactg actcgctgcg ctcggtcgtt   4260
cggctgcggc gagcggtatc agctcactca aaggcggtaa tacggttatc cacagaatca   4320
ggggataacg caggaaagaa catgtgagca aaaggccagc aaaaggccag gaaccgtaaa   4380
aaggccgcgt tgctggcgtt tttccatagg ctccgccccc ctgacgagca tcacaaaaat   4440
cgacgctcaa gtcagaggtg gcgaaacccg acaggactat aaagatacca ggcgtttccc   4500
cctggaagct ccctcgtgcg ctctcctgtt ccgaccctgc cgcttaccgg atacctgtcc   4560
gcctttctcc cttcgggaag cgtggcgctt tctcatagct cacgctgtag gtatctcagt   4620
tcggtgtagg tcgttcgctc caagctgggc tgtgtgcacg aaccccccgt tcagcccgac   4680
cgctgcgcct tatccggtaa ctatcgtctt gagtccaacc cggtaagaca cgacttatcg   4740
ccactggcag cagccactgg taacaggatt agcagagcga ggtatgtagg cggtgctaca   4800
gagttcttga agtggtggcc taactacggc tacactagaa ggacagtatt tggtatctgc   4860
gctctgctga agccagttac cttcggaaaa agagttggta gctcttgatc cggcaaacaa   4920
accaccgctg gtagcggtgg tttttttgtt tgcaagcagc agattacgcg cagaaaaaaa   4980
```

```
ggatctcaag aagatccttt gatcttttct acggggtctg acgctcagtg gaacgaaaac   5040

tcacgttaag ggattttggt catgagatta tcaaaaagga tcttcaccta gatcctttta   5100

aattaaaaat gaagttttaa atcaatctaa agtatatatg agtaaacttg gtctgacagt   5160

taccaatgct taatcagtga ggcacctatc tcagcgatct gtctatttcg ttcatccata   5220

gttgcctgac tccccgtcgt gtagataact acgatacggg agggcttacc atctggcccc   5280

agtgctgcaa tgataccgcg agacccacgc tcaccggctc cagatttatc agcaataaac   5340

cagccagccg gaagggccga gcgcagaagt ggtcctgcaa ctttatccgc ctccatccag   5400

tctattaatt gttgccggga agctagagta agtagttcgc cagttaatag tttgcgcaac   5460

gttgttgcca ttgctgcagg catcgtggtg tcacgctcgt cgtttggtat ggcttcattc   5520

agctccggtt cccaacgatc aaggcgagtt acatgatccc ccatgttgtg caaaaaagcg   5580

gttagctcct tcggtcctcc gatcgttgtc agaagtaagt tggccgcagt gttatcactc   5640

atggttatgg cagcactgca taattctctt actgtcatgc catccgtaag atgcttttct   5700

gtgactggtg agtactcaac caagtcattc tgagaatagt gtatgcggcg accgagttgc   5760

tcttgcccgg cgtcaacacg ggataatacc gcgccacata gcagaacttt aaaagtgctc   5820

atcattggaa aacgttcttc ggggcgaaaa ctctcaagga tcttaccgct gttgagatcc   5880

agttcgatgt aacccactcg tgcacccaac tgatcttcag catcttttac tttcaccagc   5940

gtttctgggt gagcaaaaac aggaaggcaa aatgccgcaa aaaagggaat aagggcgaca   6000

cggaaatgtt gaatactcat actcttcctt tttcaatatt attgaagcat ttatcagggt   6060

tattgtctca tgagcggata catatttgaa tgtatttaga aaaataaaca aataggggtt   6120

ccgcgcacat ttccccgaaa agtgccacct gacgtctaag aaaccattat tatcatgaca   6180

ttaacctata aaaataggcg tatcacgagg ccctttcgtc ttcaagaa                6228
```

```
<210> SEQ ID NO 25
<211> LENGTH: 5499
<212> TYPE: DNA
<213> ORGANISM: Artificial Sequence
<220> FEATURE:
<223> OTHER INFORMATION: Recombinant plasmid pAPSE10359; beta actin stem
      loop + Qbeta coat protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (46)..(65)
<223> OTHER INFORMATION: bacteriophage Qbeta pac sequence
<220> FEATURE:
<221> NAME/KEY: misc_feature
<222> LOCATION: (66)..(73)
<223> OTHER INFORMATION: restriction endonuclease AsiSI recognition site
<220> FEATURE:
<221> NAME/KEY: misc_feature
<222> LOCATION: (74)..(367)
<223> OTHER INFORMATION: beta actin sense strand gene fragment
<220> FEATURE:
<221> NAME/KEY: misc_feature
<222> LOCATION: (534)..(827)
<223> OTHER INFORMATION: beta actin antisense strand gene fragment
<220> FEATURE:
<221> NAME/KEY: misc_feature
<222> LOCATION: (872)..(891)
<223> OTHER INFORMATION: bacteriophage Qbeta pac sequence
<220> FEATURE:
<221> NAME/KEY: terminator
<222> LOCATION: (907)..(954)
<223> OTHER INFORMATION: bacteriophage T7 transcription terminator
<220> FEATURE:
```

<221> NAME/KEY: promoter
<222> LOCATION: (1108)..(1126)
<223> OTHER INFORMATION: bacteriophage T7 gene 1 promoter
<220> FEATURE:
<221> NAME/KEY: gene
<222> LOCATION: (1196)..(1597)
<223> OTHER INFORMATION: bacteriophage Qbeta coat protein
<220> FEATURE:
<221> NAME/KEY: terminator
<222> LOCATION: (1630)..(1677)
<223> OTHER INFORMATION: bacteriophage T7 transcription terminator

<400> SEQUENCE: 25

```
ttcagatctc gatcccgcga aattaatacg actcactata gggagatgca tgtctaagac     60
agcatgcgat cgcgcacgag gtttttctgt ctagtgagca gtgtccaacc tcaaaagaca    120
acatgtgtga cgacgatgta gcggctcttg tcgtagacaa tggatccggt atgtgcaaag    180
ccggtttcgc aggagatgac gcaccccgtg ccgtcttccc ctcgatcgtc ggtcgcccaa    240
ggcatcaagg agtcatggtc ggtatgggac aaaaggactc atacgtagga gatgaagccc    300
aaagcaaaag aggtatcctc accctgaaat accccatcga acacggtatc atcaccaact    360
gggatgagtt taaaccctct agctgcttta caaagtactg gttccctttc cagcgggatg    420
ctttatctaa acgcaatgag agaggtattc ctcaggccac atcgcttcct agttccgctg    480
ggatccatcg ttggcggccg aagccgccat tccatagtga gttctggcgc gcctcatccc    540
agttggtgat gataccgtgt tcgatggggt atttcagggt gaggatacct cttttgcttt    600
gggcttcatc tcctacgtat gagtcctttt gtcccatacc gaccatgact ccttgatgcc    660
ttgggcgacc gacgatcgag gggaagacgg cacggggtgc gtcatctcct gcgaaaccgg    720
ctttgcacat accggatcca ttgtctacga caagagccgc tacatcgtcg tcacacatgt    780
tgtcttttga ggttggacac tgctcactag acagaaaaac ctcgtgccgg accgaatacc    840
cggtctgaac gagggcggcc gcggagttca aatgcatgtc taagacagca tcgaagctcc    900
cacaccctag cataacccct tggggcctct aaacgggtct tgaggggttt tttgctgaaa    960
ggaggaacta tatccggata tccacaggac gggtgtggtc gccatgatcg cgtagtcgat   1020
agtggctcca agtagcgaag cgagcaggac tgggcggcgg gcatgcgcct ccgcctttag   1080
gggatccaga tctcgatccc gcgaaattaa tacgactcac tatagggaga ccacaacggt   1140
ttccctctag atcacaagtt tgtacaaaaa agcaggctaa gaaggagata tacatatggc   1200
aaaattagag actgttactt taggtaacat cgggaaagat ggaaaacaaa ctctggtcct   1260
caatccgcgt ggggtaaatc ccactaacgg cgttgcctcg ctttcacaag cgggtgcagt   1320
tcctgcgctg gagaagcgtg ttaccgtttc ggtatctcag ccttctcgca atcgtaagaa   1380
ctacaaggtc caggttaaga tccagaaccc gaccgcttgc actgcaaacg gttcttgtga   1440
cccatccgtt actcgccagg catatgctga cgtgaccttt tcgttcacgc agtatagtac   1500
cgatgaggaa cgagcttttg ttcgtacaga gcttactgct ctgctcgcta gtcctctgct   1560
gatcgatgct attgatcagc tgaacccagc gtattaataa gcggacgcgc tgccaccgct   1620
gagcaataac tagcataacc ccttggggcc tctaaacggg tcttgagggg ttttttgctg   1680
aaaggaggaa ctatatccgg catgcaccat tccttgcggc ggcggtgctc aacggcctca   1740
acctactact gggctgcttc ctaatgcagg agtcgcataa gggagagcgt cgaccgatgc   1800
ccttgagagc cttcaaccca gtcagctcct tccggtgggc gcggggcatg actatcgtcg   1860
ccgcacttat gactgtcttc tttatcatgc aactcgtagg acaggtgccg gcagcgctct   1920
gggtcatttt cggcgaggac cgctttcgct ggagcgcgac gatgatcggc ctgtcgcttg   1980
```

```
cggtattcgg aatcttgcac gccctcgctc aagccttcgt cactggtccc gccaccaaac   2040
gtttcggcga gaagcaggcc attatcgccg gcatggcggc cgacgcgctg ggctacgtct   2100
tgctggcgtt cgcgacgcga ggctggatgg ccttccccat tatgattctt ctcgcttccg   2160
gcggcatcgg gatgcccgcg ttgcaggcca tgctgtccag gcaggtagat gacgaccatc   2220
agggacagct tcaaggatcg ctcgcggctc ttaccagcct aacttcgatc attggaccgc   2280
tgatcgtcac ggcgatttat gccgcctcgg cgagcacatg gaacgggttg gcatggattg   2340
taggcgccgc cctatacctt gtctgcctcc ccgcgttgcg tcgcggtgca tggagccggg   2400
ccacctcgac ctgaatggaa gccggcggca cctcgctaac ggattcacca ctccaagaat   2460
tggagccaat caattcttgc ggagaactgt gaatgcgcaa accaaccctt ggcagaacat   2520
atccatcgcg tccgccatct ccagcagccg cacgcggcgc atctcgggca gcgttgggtc   2580
ctggccacgg gtgcgcatga tcgtgctcct gtcgttgagg acccggctag gctggcgggg   2640
ttgccttact ggttagcaga atgaatcacc gatacgcgag cgaacgtgaa gcgactgctg   2700
ctgcaaaacg tctgcgacct gagcaacaac atgaatggtc ttcggtttcc gtgtttcgta   2760
aagtctggaa acgcggaagt cagcgccctg caccattatg ttccggatct gcatcgcagg   2820
atgctgctgg ctaccctgtg gaacacctac atctgtatta acgaagcgct ggcattgacc   2880
ctgagtgatt tttctctggt cccgccgcat ccataccgcc agttgtttac cctcacaacg   2940
ttccagtaac cgggcatgtt catcatcagt aacccgtatc gtgagcatcc tctctcgttt   3000
catcggtatc attaccccca tgaacagaaa tcccccttac acggaggcat cagtgaccaa   3060
acaggaaaaa accgccctta acatggcccg ctttatcaga agccagacat taacgcttct   3120
ggagaaactc aacgagctgg acgcggatga acaggcagac atctgtgaat cgcttcacga   3180
ccacgctgat gagctttacc gcagctgcct cgcgcgtttc ggtgatgacg gtgaaaacct   3240
ctgacacatg cagctcccgg agacggtcac agcttgtctg taagcggatg ccgggagcag   3300
acaagcccgt cagggcgcgt cagcgggtgt tggcgggtgt cggggcgcag ccatgaccca   3360
gtcacgtagc gatagcggag tgtatactgg cttaactatg cggcatcaga gcagattgta   3420
ctgagagtgc accatatgcg gtgtgaaata ccgcacagat gcgtaaggag aaaataccgc   3480
atcaggcgct cttccgcttc ctcgctcact gactcgctgc gctcggtcgt tcggctgcgg   3540
cgagcggtat cagctcactc aaaggcggta atacggttat ccacagaatc aggggataac   3600
gcaggaaaga acatgtgagc aaaaggccag caaaaggcca ggaaccgtaa aaaggccgcg   3660
ttgctggcgt ttttccatag gctccgcccc cctgacgagc atcacaaaaa tcgacgctca   3720
agtcagaggt ggcgaaaccc gacaggacta taaagatacc aggcgtttcc ccctggaagc   3780
tccctcgtgc gctctcctgt tccgaccctg ccgcttaccg gatacctgtc cgcctttctc   3840
ccttcgggaa gcgtggcgct ttctcatagc tcacgctgta ggtatctcag ttcggtgtag   3900
gtcgttcgct ccaagctggg ctgtgtgcac gaaccccccg ttcagcccga ccgctgcgcc   3960
ttatccggta actatcgtct tgagtccaac ccggtaagac acgacttatc gccactggca   4020
gcagccactg gtaacaggat tagcagagcg aggtatgtag gcggtgctac agagttcttg   4080
aagtggtggc ctaactacgg ctacactaga aggacagtat ttggtatctg cgctctgctg   4140
aagccagtta ccttcggaaa aagagttggt agctcttgat ccggcaaaca aaccaccgct   4200
ggtagcggtg gtttttttgt ttgcaagcag cagattacgc gcagaaaaaa aggatctcaa   4260
gaagatcctt tgatcttttc tacggggtct gacgctcagt ggaacgaaaa ctcacgttaa   4320
```

```
gggattttgg tcatgagatt atcaaaaagg atcttcacct agatcctttt aaattaaaaa   4380
tgaagtttta aatcaatcta aagtatatat gagtaaactt ggtctgacag ttaccaatgc   4440
ttaatcagtg aggcacctat ctcagcgatc tgtctatttc gttcatccat agttgcctga   4500
ctccccgtcg tgtagataac tacgatacgg gagggcttac catctggccc cagtgctgca   4560
atgataccgc gagacccacg ctcaccggct ccagatttat cagcaataaa ccagccagcc   4620
ggaagggccg agcgcagaag tggtcctgca actttatccg cctccatcca gtctattaat   4680
tgttgccggg aagctagagt aagtagttcg ccagttaata gtttgcgcaa cgttgttgcc   4740
attgctgcag gcatcgtggt gtcacgctcg tcgtttggta tggcttcatt cagctccggt   4800
tcccaacgat caaggcgagt tacatgatcc cccatgttgt gcaaaaaagc ggttagctcc   4860
ttcggtcctc cgatcgttgt cagaagtaag ttggccgcag tgttatcact catggttatg   4920
gcagcactgc ataattctct tactgtcatg ccatccgtaa gatgcttttc tgtgactggt   4980
gagtactcaa ccaagtcatt ctgagaatag tgtatgcggc gaccgagttg ctcttgcccg   5040
gcgtcaacac gggataatac cgcgccacat agcagaactt taaaagtgct catcattgga   5100
aaacgttctt cggggcgaaa actctcaagg atcttaccgc tgttgagatc cagttcgatg   5160
taacccactc gtgcacccaa ctgatcttca gcatctttta ctttcaccag cgtttctggg   5220
tgagcaaaaa caggaaggca aaatgccgca aaaaagggaa taagggcgac acggaaatgt   5280
tgaatactca tactcttcct ttttcaatat tattgaagca tttatcaggg ttattgtctc   5340
atgagcggat acatatttga atgtatttag aaaaataaac aaataggggt tccgcgcaca   5400
tttccccgaa aagtgccacc tgacgtctaa gaaaccatta ttatcatgac attaacctat   5460
aaaaataggc gtatcacgag gccctttcgt cttcaagaa                          5499
```

<210> SEQ ID NO 26
<211> LENGTH: 5413
<212> TYPE: DNA
<213> ORGANISM: Artificial Sequence
<220> FEATURE:
<223> OTHER INFORMATION: Recombinant plasmid pAPSE10357; beta actin stem loop + U1A protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (41)..(66)
<223> OTHER INFORMATION: U1A binding site sequence
<220> FEATURE:
<221> NAME/KEY: misc_feature
<222> LOCATION: (67)..(74)
<223> OTHER INFORMATION: restriction endonuclease AsiSI recognition site
<220> FEATURE:
<221> NAME/KEY: misc_feature
<222> LOCATION: (75)..(368)
<223> OTHER INFORMATION: beta actin sense strand gene fragment
<220> FEATURE:
<221> NAME/KEY: misc_feature
<222> LOCATION: (535)..(828)
<223> OTHER INFORMATION: beta actin antisense strand gene fragment
<220> FEATURE:
<221> NAME/KEY: misc_feature
<222> LOCATION: (873)..(898)
<223> OTHER INFORMATION: U1A binding site sequence
<220> FEATURE:
<221> NAME/KEY: terminator
<222> LOCATION: (914)..(961)
<223> OTHER INFORMATION: bacteriophage T7 transcription terminator
<220> FEATURE:
<221> NAME/KEY: promoter
<222> LOCATION: (1115)..(1133)

<223> OTHER INFORMATION: bacteriophage T7 gene 1 promoter
<220> FEATURE:
<221> NAME/KEY: gene
<222> LOCATION: (1203)..(1511)
<223> OTHER INFORMATION: human U1A protein gene
<220> FEATURE:
<221> NAME/KEY: terminator
<222> LOCATION: (1544)..(1591)
<223> OTHER INFORMATION: bacteriophage T7 transcription terminator

<400> SEQUENCE: 26

```
ttcagatctc gatcccgcga aattaatacg actcactata gggtatccat tgcactccgg     60
atgcccgcga tcgcgcacga ggtttttctg tctagtgagc agtgtccaac ctcaaaagac    120
aacatgtgtg acgacgatgt agcggctctt gtcgtagaca atggatccgg tatgtgcaaa    180
gccggtttcg caggagatga cgcaccccgt gccgtcttcc cctcgatcgt cggtcgccca    240
aggcatcaag gagtcatggt cggtatggga caaaaggact catacgtagg agatgaagcc    300
caaagcaaaa gaggtatcct caccctgaaa taccccatcg aacacggtat catcaccaac    360
tgggatgagt ttaaaccctc tagctgcttt acaaagtact ggttcccttt ccagcgggat    420
gctttatcta aacgcaatga gagaggtatt cctcaggcca catcgcttcc tagttccgct    480
gggatccatc gttggcggcc gaagccgcca ttccatagtg agttctggcg cgcctcatcc    540
cagttggtga tgataccgtg ttcgatgggg tatttcaggg tgaggatacc tcttttgctt    600
tgggcttcat ctcctacgta tgagtccttt tgtcccatac cgaccatgac tccttgatgc    660
cttgggcgac cgacgatcga ggggaagacg gcacggggtg cgtcatctcc tgcgaaaccg    720
gctttgcaca taccggatcc attgtctacg acaagagccg ctacatcgtc gtcacacatg    780
ttgtcttttg aggttggaca ctgctcacta gacagaaaaa cctcgtgccg gaccgaatac    840
ccggtctgaa cgagggcggc cgcggagttc aagggtatcc attgcactcc ggatgccccg    900
aagctcccac accctagcat aaccccttgg ggcctctaaa cggtcttga ggggtttttt    960
gctgaaagga ggaactatat ccggatatcc acaggacggg tgtggtcgcc atgatcgcgt   1020
agtcgatagt ggctccaagt agcgaagcga gcaggactgg gcggcgggca tgcgcctccg   1080
cctttagggg atccagatct cgatcccgcg aaattaatac gactcactat agggagacca   1140
caacggtttc cctctagatc acaagtttgt acaaaaaagc aggctaagaa ggagatatac   1200
atatggcagt tcccgagacc cgccctaacc acactattta tatcaacaac ctcaatgaga   1260
agatcaagaa ggatgagcta aaaaagtccc tgtacgccat cttctcccag tttggccaga   1320
tcctggatat cctggtatca cggagcctga agatgagggg ccaggccttt gtcatcttca   1380
aggaggtcag cagcgccacc aacgccctgc gctccatgca gggtttccct ttctatgaca   1440
aacctatgcg tatccagtat gccaagaccg actcagatat cattgccaag atgaaaggca   1500
ccttcgtgta ataagcggac gcgctgccac cgctgagcaa taactagcat aaccccttgg   1560
ggcctctaaa cgggtcttga ggggtttttt gctgaaagga ggaactatat ccggcatgca   1620
ccattccttg cggcggcggt gctcaacggc ctcaacctac tactgggctg cttcctaatg   1680
caggagtcgc ataagggaga gcgtcgaccg atgcccttga gagccttcaa cccagtcagc   1740
tccttccggt gggcgcgggg catgactatc gtcgccgcac ttatgactgt cttctttatc   1800
atgcaactcg taggacaggt gccggcagcg ctctgggtca ttttcggcga ggaccgcttt   1860
cgctggagcg cgacgatgat cggcctgtcg cttgcggtat tcggaatctt gcacgccctc   1920
gctcaagcct tcgtcactgg tcccgccacc aaacgtttcg gcgagaagca ggccattatc   1980
gccggcatgg cggccgacgc gctgggctac gtcttgctgg cgttcgcgac gcgaggctgg   2040
```

```
atggccttcc ccattatgat tcttctcgct tccggcggca tcgggatgcc cgcgttgcag   2100
gccatgctgt ccaggcaggt agatgacgac catcagggac agcttcaagg atcgctcgcg   2160
gctcttacca gcctaacttc gatcattgga ccgctgatcg tcacggcgat ttatgccgcc   2220
tcggcgagca catggaacgg gttggcatgg attgtaggcg ccgccctata ccttgtctgc   2280
ctccccgcgt tgcgtcgcgg tgcatggagc cgggccacct cgacctgaat ggaagccggc   2340
ggcacctcgc taacggattc accactccaa gaattggagc caatcaattc ttgcggagaa   2400
ctgtgaatgc gcaaaccaac ccttggcaga acatatccat cgcgtccgcc atctccagca   2460
gccgcacgcg gcgcatctcg ggcagcgttg ggtcctggcc acgggtgcgc atgatcgtgc   2520
tcctgtcgtt gaggacccgg ctaggctggc ggggttgcct tactggttag cagaatgaat   2580
caccgatacg cgagcgaacg tgaagcgact gctgctgcaa aacgtctgcg acctgagcaa   2640
caacatgaat ggtcttcggt ttccgtgttt cgtaaagtct ggaaacgcgg aagtcagcgc   2700
cctgcaccat tatgttccgg atctgcatcg caggatgctg ctggctaccc tgtggaacac   2760
ctacatctgt attaacgaag cgctggcatt gaccctgagt gatttttctc tggtcccgcc   2820
gcatccatac cgccagttgt ttaccctcac aacgttccag taaccgggca tgttcatcat   2880
cagtaacccg tatcgtgagc atcctctctc gtttcatcgg tatcattacc cccatgaaca   2940
gaaatccccc ttacacggag gcatcagtga ccaaacagga aaaaaccgcc cttaacatgg   3000
cccgctttat cagaagccag acattaacgc ttctggagaa actcaacgag ctggacgcgg   3060
atgaacaggc agacatctgt gaatcgcttc acgaccacgc tgatgagctt taccgcagct   3120
gcctcgcgcg tttcggtgat gacggtgaaa acctctgaca catgcagctc ccggagacgg   3180
tcacagcttg tctgtaagcg gatgccggga gcagacaagc ccgtcagggc gcgtcagcgg   3240
gtgttggcgg gtgtcggggc gcagccatga cccagtcacg tagcgatagc ggagtgtata   3300
ctggcttaac tatgcggcat cagagcagat tgtactgaga gtgcaccata tgcggtgtga   3360
aataccgcac agatgcgtaa ggagaaaata ccgcatcagg cgctcttccg cttcctcgct   3420
cactgactcg ctgcgctcgg tcgttcggct gcggcgagcg gtatcagctc actcaaaggc   3480
ggtaatacgg ttatccacag aatcagggga taacgcagga aagaacatgt gagcaaaagg   3540
ccagcaaaag gccaggaacc gtaaaaaggc cgcgttgctg gcgtttttcc ataggctccg   3600
cccccctgac gagcatcaca aaaatcgacg ctcaagtcag aggtggcgaa acccgacagg   3660
actataaaga taccaggcgt ttccccctgg aagctccctc gtgcgctctc ctgttccgac   3720
cctgccgctt accggatacc tgtccgcctt tctcccttcg ggaagcgtgg cgctttctca   3780
tagctcacgc tgtaggtatc tcagttcggt gtaggtcgtt cgctccaagc tgggctgtgt   3840
gcacgaaccc cccgttcagc ccgaccgctg cgccttatcc ggtaactatc gtcttgagtc   3900
caacccggta agacacgact tatcgccact ggcagcagcc actggtaaca ggattagcag   3960
agcgaggtat gtaggcggtg ctacagagtt cttgaagtgg tggcctaact acggctacac   4020
tagaaggaca gtatttggta tctgcgctct gctgaagcca gttaccttcg gaaaaagagt   4080
tggtagctct tgatccggca aacaaaccac cgctggtagc ggtggttttt ttgtttgcaa   4140
gcagcagatt acgcgcagaa aaaaaggatc tcaagaagat cctttgatct tttctacggg   4200
gtctgacgct cagtggaacg aaaactcacg ttaagggatt ttggtcatga gattatcaaa   4260
aaggatcttc acctagatcc ttttaaatta aaaatgaagt tttaaatcaa tctaaagtat   4320
atatgagtaa acttggtctg acagttacca atgcttaatc agtgaggcac ctatctcagc   4380
```

```
gatctgtcta tttcgttcat ccatagttgc ctgactcccc gtcgtgtaga taactacgat   4440

acgggagggc ttaccatctg gccccagtgc tgcaatgata ccgcgagacc cacgctcacc   4500

ggctccagat ttatcagcaa taaaccagcc agccggaagg gccgagcgca gaagtggtcc   4560

tgcaacttta tccgcctcca tccagtctat taattgttgc cgggaagcta gagtaagtag   4620

ttcgccagtt aatagtttgc gcaacgttgt tgccattgct gcaggcatcg tggtgtcacg   4680

ctcgtcgttt ggtatggctt cattcagctc cggttcccaa cgatcaaggc gagttacatg   4740

atcccccatg ttgtgcaaaa aagcggttag ctccttcggt cctccgatcg ttgtcagaag   4800

taagttggcc gcagtgttat cactcatggt tatggcagca ctgcataatt ctcttactgt   4860

catgccatcc gtaagatgct tttctgtgac tggtgagtac tcaaccaagt cattctgaga   4920

atagtgtatg cggcgaccga gttgctcttg cccggcgtca acacgggata ataccgcgcc   4980

acatagcaga actttaaaag tgctcatcat tggaaaacgt tcttcggggc gaaaactctc   5040

aaggatctta ccgctgttga gatccagttc gatgtaaccc actcgtgcac ccaactgatc   5100

ttcagcatct tttactttca ccagcgtttc tgggtgagca aaaacaggaa ggcaaaatgc   5160

cgcaaaaaag ggaataaggg cgacacggaa atgttgaata ctcatactct tcctttttca   5220

atattattga agcatttatc agggttattg tctcatgagc ggatacatat ttgaatgtat   5280

ttagaaaaat aaacaaatag gggttccgcg cacatttccc cgaaaagtgc cacctgacgt   5340

ctaagaaacc attattatca tgacattaac ctataaaaat aggcgtatca cgaggccctt   5400

tcgtcttcaa gaa                                                      5413
```

<210> SEQ ID NO 27
<211> LENGTH: 5504
<212> TYPE: DNA
<213> ORGANISM: Artificial Sequence
<220> FEATURE:
<223> OTHER INFORMATION: Recombinant plasmid pAPSE10372; beta actin stem loop + truncated coat protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (127)..(145)
<223> OTHER INFORMATION: bacteriophage MS2 pac sequence
<220> FEATURE:
<221> NAME/KEY: misc_feature
<222> LOCATION: (175)..(182)
<223> OTHER INFORMATION: restriction endonuclease AsiSI recognition site
<220> FEATURE:
<221> NAME/KEY: misc_feature
<222> LOCATION: (179)..(384)
<223> OTHER INFORMATION: ErkA sense strand gene fragment
<220> FEATURE:
<221> NAME/KEY: misc_feature
<222> LOCATION: (436)..(454)
<223> OTHER INFORMATION: bacteriophage MS2 pac sequence
<220> FEATURE:
<221> NAME/KEY: misc_feature
<222> LOCATION: (504)..(511)
<223> OTHER INFORMATION: restriction endonuclease NotI recognition site
<220> FEATURE:
<221> NAME/KEY: misc_feature
<222> LOCATION: (505)..(696)
<223> OTHER INFORMATION: ErkA antisense strand gene fragment
<220> FEATURE:
<221> NAME/KEY: misc_feature
<222> LOCATION: (692)..(699)
<223> OTHER INFORMATION: restriction endonuclease PacI recognition site
<220> FEATURE:
<221> NAME/KEY: misc_feature
<222> LOCATION: (728)..(746)

<223> OTHER INFORMATION: bacteriophage MS2 pac sequence
<220> FEATURE:
<221> NAME/KEY: terminator
<222> LOCATION: (762)..(809)
<223> OTHER INFORMATION: bacteriophage T7 transcription terminator
<220> FEATURE:
<221> NAME/KEY: promoter
<222> LOCATION: (1135)..(1153)
<223> OTHER INFORMATION: bacteriophage T7 gene 1 promoter
<220> FEATURE:
<221> NAME/KEY: misc_feature
<222> LOCATION: (1223)..(1429)
<223> OTHER INFORMATION: bacteriophage MS2 coat protein N-terminal fragment
<220> FEATURE:
<221> NAME/KEY: terminator
<222> LOCATION: (1635)..(1682)
<223> OTHER INFORMATION: bacteriophage T7 transcription terminator

<400> SEQUENCE: 27

```
ttcagatctc gatcccgcga aattaatacg actcactata gggagaccac aacggtttcc     60

ctctagatca caagtttgta caaaaaagca ggctaagaag gagatataca tacgccggcc    120

attcaaacat gaggattacc catgtaacct aaggccggtg tccaggcgcg ctccgcgatc    180

gcacgcggac aaagttcctc aatctaatgc tgaagttata aggggacaaa tatttgaagt    240

tggtcctagg tatattaaac tcgcctatat aggtgaagga gcttatggca tggttgtgtc    300

tgcggatgac acgctaacaa accaaagagt tgcaataaaa aaaatatcgc cctttgaaca    360

ccaaacttat tgctactaca gtttaaacgc aatcgcagca aactccggca tctactaata    420

gacgccggcc attcaacatg aggattaccc atgtaaccta agaagacaac aaagaagttc    480

aactctttat gtattgatct tccgcggccg cggtaccggg gcaataagtt tggtgttcaa    540

agggcgatat ttttttatt gcaactcttt ggtttgttag cgtgtcatcc gcagacacaa    600

ccatgccata agctccttca cctatatagg cgagtttaat atacctagga ccaacttcaa    660

atatttgtcc ccttataact tcagcattag attgaggaac tatacgaaaa ttaattaagg    720

agttcaaaca tgaggatcac ccatgtcgaa gctcccacac cctagcataa ccccttgggg    780

cctctaaacg ggtcttgagg ggttttttgc tgaaaggagg aactatatcc ggatatccac    840

aggacgggtg tggtcgccat gatcgcgtag tcgatagtgg ctccaagtag cgaagcgagc    900

aggactgggc ggcgggcatg catcgtccat tccgacagca tcgccagtca ctatggcgtg    960

ctgctagcgc tatatgcgtt gatgcaattt ctatgcgcac ccgttctcgg agcactgtcc   1020

gaccgctttg gccgccgccc agtcctgctc gcttcgctac ttggagccac tatcgactac   1080

gcgatcatgg cgaccacacc cgtcctgtgg atccagatct cgatcccgcg aaattaatac   1140

gactcactat agggagacca caacggtttc cctctagatc acaagtttgt acaaaaaagc   1200

aggctaagaa ggagatatac atatggcgtc taactttacc caattcgttc tggttgataa   1260

cggcggtacg ggtgacgtta ccgtagctcc gtccaacttc gccaacggtg ttgcggaatg   1320

gattagctct aacagccgct ctcagggtgc tccgttcgtc agtctagcgc gcagaatcgc   1380

aaatacacca tcaaagttga agtaccgaaa gtcgcaacgc agaccgtagg cggcgtagaa   1440

ctcccagttg cggcctggcg ctcttacctc aacatggaac tgactattcc gatttttgcg   1500

acgaactccg actgcgaact gattgttaag gcaatgcagg gcctgctgaa agacggtaat   1560

ccgatcccat ctgcaatcgc tgctaactct ggcatttact aataagcgga cgcgctgcca   1620

ccgctgagca ataactagca taaccccttg gggcctctaa acgggtcttg aggggttttt   1680

tgctgaaagg aggaactata tccggcatgc accattcctt gcggcggcgg tgctcaacgg   1740
```

```
cctcaaccta ctactgggct gcttcctaat gcaggagtcg cataagggag agcgtcgacc   1800
gatgcccttg agagccttca acccagtcag ctccttccgg tgggcgcggg gcatgactat   1860
cgtcgccgca cttatgactg tcttctttat catgcaactc gtaggacagg tgccggcagc   1920
gctctgggtc attttcggcg aggaccgctt tcgctggagc gcgacgatga tcggcctgtc   1980
gcttgcggta ttcggaatct tgcacgccct cgctcaagcc ttcgtcactg gtcccgccac   2040
caaacgtttc ggcgagaagc aggccattat cgccggcatg gcggccgacg cgctgggcta   2100
cgtcttgctg gcgttcgcga cgcgaggctg gatggccttc cccattatga ttcttctcgc   2160
ttccggcggc atcgggatgc ccgcgttgca ggccatgctg tccaggcagg tagatgacga   2220
ccatcaggga cagcttcaag gatcgctcgc ggctcttacc agcctaactt cgatcattgg   2280
accgctgatc gtcacggcga tttatgccgc ctcggcgagc acatggaacg ggttggcatg   2340
gattgtaggc gccgccctat accttgtctg cctccccgcg ttgcgtcgcg gtgcatggag   2400
ccgggccacc tcgacctgaa tggaagccgg cggcacctcg ctaacggatt caccactcca   2460
agaattggag ccaatcaatt cttgcggaga actgtgaatg cgcaaaccaa cccttggcag   2520
aacatatcca tcgcgtccgc catctccagc agccgcacgc ggcgcatctc gggcagcgtt   2580
gggtcctggc cacgggtgcg catgatcgtg ctcctgtcgt tgaggacccg gctaggctgg   2640
cggggttgcc ttactggtta gcagaatgaa tcaccgatac gcgagcgaac gtgaagcgac   2700
tgctgctgca aaacgtctgc gacctgagca acaacatgaa tggtcttcgg tttccgtgtt   2760
tcgtaaagtc tggaaacgcg gaagtcagcg ccctgcacca ttatgttccg gatctgcatc   2820
gcaggatgct gctggctacc ctgtggaaca cctacatctg tattaacgaa gcgctggcat   2880
tgaccctgag tgatttttct ctggtcccgc cgcatccata ccgccagttg tttaccctca   2940
caacgttcca gtaaccgggc atgttcatca tcagtaaccc gtatcgtgag catcctctct   3000
cgtttcatcg gtatcattac ccccatgaac agaaatcccc cttacacgga ggcatcagtg   3060
accaaacagg aaaaaaccgc ccttaacatg gcccgcttta tcagaagcca gacattaacg   3120
cttctggaga aactcaacga gctggacgcg gatgaacagg cagacatctg tgaatcgctt   3180
cacgaccacg ctgatgagct ttaccgcagc tgcctcgcgc gtttcggtga tgacggtgaa   3240
aacctctgac acatgcagct cccggagacg gtcacagctt gtctgtaagc ggatgccggg   3300
agcagacaag cccgtcaggg cgcgtcagcg ggtgttggcg ggtgtcgggg cgcagccatg   3360
acccagtcac gtagcgatag cggagtgtat actggcttaa ctatgcggca tcagagcaga   3420
ttgtactgag agtgcaccat atgcggtgtg aaataccgca cagatgcgta aggagaaaat   3480
accgcatcag gcgctcttcc gcttcctcgc tcactgactc gctgcgctcg gtcgttcggc   3540
tgcggcgagc ggtatcagct cactcaaagg cggtaatacg gttatccaca gaatcagggg   3600
ataacgcagg aaagaacatg tgagcaaaag gccagcaaaa ggccaggaac cgtaaaaagg   3660
ccgcgttgct ggcgtttttc cataggctcc gcccccctga cgagcatcac aaaaatcgac   3720
gctcaagtca gaggtggcga aacccgacag gactataaag ataccaggcg tttccccctg   3780
gaagctccct cgtgcgctct cctgttccga ccctgccgct taccggatac ctgtccgcct   3840
ttctcccttc gggaagcgtg gcgctttctc atagctcacg ctgtaggtat ctcagttcgg   3900
tgtaggtcgt tcgctccaag ctgggctgtg tgcacgaacc ccccgttcag cccgaccgct   3960
gcgccttatc cggtaactat cgtcttgagt ccaacccggt aagacacgac ttatcgccac   4020
tggcagcagc cactggtaac aggattagca gagcgaggta tgtaggcggt gctacagagt   4080
tcttgaagtg gtggcctaac tacggctaca ctagaaggac agtatttggt atctgcgctc   4140
```

```
tgctgaagcc agttaccttc ggaaaaagag ttggtagctc ttgatccggc aaacaaacca   4200

ccgctggtag cggtggtttt tttgtttgca agcagcagat tacgcgcaga aaaaaaggat   4260

ctcaagaaga tcctttgatc ttttctacgg ggtctgacgc tcagtggaac gaaaactcac   4320

gttaagggat tttggtcatg agattatcaa aaaggatctt cacctagatc cttttaaatt   4380

aaaaatgaag ttttaaatca atctaaagta tatatgagta aacttggtct gacagttacc   4440

aatgcttaat cagtgaggca cctatctcag cgatctgtct atttcgttca tccatagttg   4500

cctgactccc cgtcgtgtag ataactacga tacgggaggg cttaccatct ggccccagtg   4560

ctgcaatgat accgcgagac ccacgctcac cggctccaga tttatcagca ataaaccagc   4620

cagccggaag ggccgagcgc agaagtggtc ctgcaacttt atccgcctcc atccagtcta   4680

ttaattgttg ccgggaagct agagtaagta gttcgccagt taatagtttg cgcaacgttg   4740

ttgccattgc tgcaggcatc gtggtgtcac gctcgtcgtt tggtatggct tcattcagct   4800

ccggttccca acgatcaagg cgagttacat gatcccccat gttgtgcaaa aaagcggtta   4860

gctccttcgg tcctccgatc gttgtcagaa gtaagttggc cgcagtgtta tcactcatgg   4920

ttatggcagc actgcataat tctcttactg tcatgccatc cgtaagatgc ttttctgtga   4980

ctggtgagta ctcaaccaag tcattctgag aatagtgtat gcggcgaccg agttgctctt   5040

gcccggcgtc aacacgggat aataccgcgc cacatagcag aactttaaaa gtgctcatca   5100

ttggaaaacg ttcttcgggg cgaaaactct caaggatctt accgctgttg agatccagtt   5160

cgatgtaacc cactcgtgca cccaactgat cttcagcatc ttttactttc accagcgttt   5220

ctgggtgagc aaaaacagga aggcaaaatg ccgcaaaaaa gggaataagg gcgacacgga   5280

aatgttgaat actcatactc ttcctttttc aatattattg aagcatttat cagggttatt   5340

gtctcatgag cggatacata tttgaatgta tttagaaaaa taaacaaata ggggttccgc   5400

gcacatttcc ccgaaaagtg ccacctgacg tctaagaaac cattattatc atgacattaa   5460

cctataaaaa taggcgtatc acgaggccct ttcgtcttca agaa                    5504
```

```
<210> SEQ ID NO 28
<211> LENGTH: 68
<212> TYPE: PRT
<213> ORGANISM: Artificial Sequence
<220> FEATURE:
<223> OTHER INFORMATION: N-terminus truncated bacteriophage MS2 coat
      protein sequence

<400> SEQUENCE: 28

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Gly Ala Pro Phe Val Ser Leu
        35                  40                  45

Ala Arg Arg Ile Ala Asn Thr Pro Ser Lys Leu Lys Tyr Arg Lys Ser
    50                  55                  60

Gln Arg Arg Pro
65


<210> SEQ ID NO 29
<211> LENGTH: 8339
<212> TYPE: DNA
<213> ORGANISM: Artificial Sequence
<220> FEATURE:
```

<223> OTHER INFORMATION: Recombinant plasmid pAPSE10429; C. glutamicum
      rnc deletion plasmid
<220> FEATURE:
<221> NAME/KEY: gene
<222> LOCATION: (346)..(1140)
<223> OTHER INFORMATION: Kanamycin resistance gene
<220> FEATURE:
<221> NAME/KEY: promoter
<222> LOCATION: (1186)..(1631)
<223> OTHER INFORMATION: sacB promoter
<220> FEATURE:
<221> NAME/KEY: gene
<222> LOCATION: (1632)..(3053)
<223> OTHER INFORMATION: sacB gene
<220> FEATURE:
<221> NAME/KEY: misc_feature
<222> LOCATION: (5504)..(5510)
<223> OTHER INFORMATION: restriction endonuclease BamHI recognition site
<220> FEATURE:
<221> NAME/KEY: misc_feature
<222> LOCATION: (5511)..(8136)
<223> OTHER INFORMATION: PCR fragment comprising 1.5 kb of chromosomal
      sequencedownstream of rnc gene (5511-7012) and 1.2 kb of
      chromosomal sequence upstream of rnc gene (7013-8136).
<220> FEATURE:
<221> NAME/KEY: misc_feature
<222> LOCATION: (8136)..(8141)
<223> OTHER INFORMATION: restrcition endonuclease SalI recognition site

<400> SEQUENCE: 29
tgccgcaagc actcagggcg caagggctgc taaaggaagc ggaacacgta gaaagccagt 60
ccgcagaaac ggtgctgacc ccggatgaat gtcagctact gggctatctg gacaagggaa 120
aacgcaagcg caaagagaaa gcaggtagct tgcagtgggc ttacatggcg atagctagac 180
tgggcggttt tatggacagc aagcgaaccg gaattgccag ctggggcgcc ctctggtaag 240
gttgggaagc cctgcaaagt aaactggatg gctttcttgc cgccaaggat ctgatggcgc 300
aggggatcaa gatctgatca agagacagga tgaggatcgt ttcgcatgat tgaacaagat 360
ggattgcacg caggttctcc ggccgcttgg gtggagaggc tattcggcta tgactgggca 420
caacagacaa tcggctgctc tgatgccgcc gtgttccggc tgtcagcgca ggggcgcccg 480
gttctttttg tcaagaccga cctgtccggt gccctgaatg aactccaaga cgaggcagcg 540
cggctatcgt ggctggccac gacgggcgtt ccttgcgcag ctgtgctcga cgttgtcact 600
gaagcgggaa gggactggct gctattgggc gaagtgccgg ggcaggatct cctgtcatct 660
caccttgctc ctgccgagaa agtatccatc atggctgatg caatgcggcg gctgcatacg 720
cttgatccgg ctacctgccc attcgaccac caagcgaaac atcgcatcga gcgagcacgt 780
actcggatgg aagccggtct tgtcgatcag gatgatctgg acgaagagca tcaggggctc 840
gcgccagccg aactgttcgc caggctcaag gcgcggatgc ccgacggcga ggatctcgtc 900
gtgacccatg gcgatgcctg cttgccgaat atcatggtgg aaaatggccg cttttctgga 960
ttcatcgact gtggccggct gggtgtggcg gaccgctatc aggacatagc gttggctacc 1020
cgtgatattg ctgaagagct tggcggcgaa tgggctgacc gcttcctcgt gctttacggt 1080
atcgccgctc ccgattcgca gcgcatcgcc ttctatcgcc ttcttgacga gttcttctga 1140
gcgggactct ggggttcgct agaggatcga tcctttttaa cccatcacat atacctgccg 1200
ttcactatta tttagtgaaa tgagatatta tgatattttc tgaattgtga ttaaaaaggc 1260
aactttatgc ccatgcaaca gaaactataa aaaatacaga gaatgaaaag aaacagatag 1320
attttttagt tctttaggcc cgtagtctgc aaatcctttt atgattttct atcaaacaaa 1380
agaggaaaat agaccagttg caatccaaac gagagtctaa tagaatgagg tcgaaaagta 1440

```
aatcgcgcgg gtttgttact gataaagcag gcaagaccta aaatgtgtaa agggcaaagt   1500
gtatactttg gcgtcacccc ttacatattt taggtctttt tttattgtgc gtaactaact   1560
tgccatcttc aaacaggagg gctggaagaa gcagaccgct aacacagtac ataaaaaagg   1620
agacatgaac gatgaacatc aaaaagtttg caaaacaagc aacagtatta acctttacta   1680
ccgcactgct ggcaggaggc gcaactcaag cgtttgcgaa agaaacgaac caaaagccat   1740
ataaggaaac atacggcatt tcccatatta cacgccatga tatgctgcaa atccctgaac   1800
agcaaaaaaa tgaaaaatat caagtttctg aatttgattc gtccacaatt aaaaatatct   1860
cttctgcaaa aggcctggac gtttgggaca gctggccatt acaaaacgct gacggcactg   1920
tcgcaaacta tcacggctac cacatcgtct ttgcattagc cggagatcct aaaaatgcgg   1980
atgacacatc gatttacatg ttctatcaaa aagtcggcga aacttctatt gacagctgga   2040
aaaacgctgg ccgcgtcttt aaagacagcg acaaattcga tgcaaatgat tctatcctaa   2100
aagaccaaac acaagaatgg tcaggttcag ccacatttac atctgacgga aaaatccgtt   2160
tattctacac tgatttctcc ggtaaacatt acggcaaaca aacactgaca actgcacaag   2220
ttaacgtatc agcatcagac agctctttga acatcaacgg tgtagaggat tataaatcaa   2280
tctttgacgg tgacggaaaa acgtatcaaa atgtacagca gttcatcgat gaaggcaact   2340
acagctcagg cgacaaccat acgctgagag atcctcacta cgtagaagat aaaggccaca   2400
aatacttagt atttgaagca aacactggaa ctgaagatgg ctaccaaggc gaagaatctt   2460
tatttaacaa agcatactat ggcaaaagca catcattctt ccgtcaagaa agtcaaaaac   2520
ttctgcaaag cgataaaaaa cgcacggctg agttagcaaa cggcgctctc ggtatgattg   2580
agctaaacga tgattacaca ctgaaaaaag tgatgaaacc gctgattgca tctaacacag   2640
taacagatga aattgaacgc gcgaacgtct ttaaaatgaa cggcaaatgg tacctgttca   2700
ctgactcccg cggatcaaaa atgacgattg acggcattac gtctaacgat atttacatgc   2760
ttggttatgt ttctaattct ttaactggcc catacaagcc gctgaacaaa actggccttg   2820
tgttaaaaat ggatcttgat cctaacgatg taacctttac ttactcacac ttcgctgtac   2880
ctcaagcgaa aggaaacaat gtcgtgatta caagctatat gacaaacaga ggattctacg   2940
cagacaaaca atcaacgttt gcgccgagct tcctgctgaa catcaaaggc aagaaaacat   3000
ctgttgtcaa agacagcatc cttgaacaag gacaattaac agttaacaaa taaaaacgca   3060
aaagaaaatg ccgatgggta ccgagcgaaa tgaccgacca agcgacgccc aacctgccat   3120
cacgagattt cgattccacc gccgccttct atgaaaggtt gggcttcgga atcgttttcc   3180
gggacgccct cgcggacgtg ctcatagtcc acgacgcccg tgattttgta gccctggccg   3240
acggccagca ggtaggccga caggctcatg ccggccgccg ccgccttttc ctcaatcgct   3300
cttcgttcgt ctggaaggca gtacaccttg ataggtgggc tgcccttcct ggttggcttg   3360
gtttcatcag ccatccgctt gccctcatct gttacgccgg cggtagccgg ccagcctcgc   3420
agagcaggat tcccgttgag caccgccagg tgcgaataag ggacagtgaa gaaggaacac   3480
ccgctcgcgg gtgggcctac ttcacctatc ctgcccggct gacgccgttg gatacaccaa   3540
ggaaagtcta cacgaaccct ttggcaaaat cctgtatatc gtgcgaaaaa ggatggatat   3600
accgaaaaaa tcgctataat gaccccgaag cagggttatg cagcggaaaa gcgctgcttc   3660
cctgctgttt tgtggaatat ctaccgactg gaaacaggca aatgcaggaa attactgaac   3720
tgaggggaca ggcgagagac gatgccaaag agctcctgaa aatctcgata actcaaaaaa   3780
tacgcccggt agtgatctta tttcattatg gtgaaagttg gaacctctta cgtgccgatc   3840
```

```
aacgtctcat tttcgccaaa agttggccca gggcttcccg gtatcaacag ggacaccagg   3900

atttatttat tctgcgaagt gatcttccgt cacaggtatt tattcggcgc aaagtgcgtc   3960

gggtgatgct gccaacttac tgatttagtg tatgatggtg tttttgaggt gctccagtgg   4020

cttctgtttc tatcagctcc tgaaaatctc gataactcaa aaaatacgcc cggtagtgat   4080

cttatttcat tatggtgaaa gttggaacct cttacgtgcc gatcaacgtc tcattttcgc   4140

caaaagttgg cccagggctt cccggtatca acagggacac caggatttat ttattctgcg   4200

aagtgatctt ccgtcacagg tatttattcg gcgcaaagtg cgtcgggtga tgctgccaac   4260

ttactgattt agtgtatgat ggtgtttttg aggtgctcca gtggcttctg tttctatcag   4320

ggctggatga tcctccagcg cggggatctc atgctggagt tcttcgccca ccccaaaagg   4380

atctaggtga agatcctttt tgataatctc atgaccaaaa tcccttaacg tgagttttcg   4440

ttccactgag cgtcagaccc cgtagaaaag atcaaaggat cttcttgaga tccttttttt   4500

ctgcgcgtaa tctgctgctt gcaaacaaaa aaaccaccgc taccagcggt ggtttgtttg   4560

ccggatcaag agctaccaac tctttttccg aaggtaactg gcttcagcag agcgcagata   4620

ccaaatactg ttcttctagt gtagccgtag ttaggccacc acttcaagaa ctctgtagca   4680

ccgcctacat acctcgctct gctaatcctg ttaccagtgg ctgctgccag tggcgataag   4740

tcgtgtctta ccgggttgga ctcaagacga tagttaccgg ataaggcgca gcggtcgggc   4800

tgaacggggg gttcgtgcac acagcccagc ttggagcgaa cgacctacac cgaactgaga   4860

tacctacagc gtgagctatg agaaagcgcc acgcttcccg aagggagaaa ggcggacagg   4920

tatccggtaa gcggcagggt cggaacagga gagcgcacga gggagcttcc agggggaaac   4980

gcctggtatc tttatagtcc tgtcgggttt cgccacctct gacttgagcg tcgatttttg   5040

tgatgctcgt caggggggcg gagcctatgg aaaaacgcca gcaacgcggc ctttttacgg   5100

ttcctggcct tttgctggcc ttttgctcac atgttctttc ctgcgttatc ccctgattct   5160

gtggataacc gtattaccgc ctttgagtga gctgataccg ctcgccgcag ccgaacgacc   5220

gagcgcagcg agtcagtgag cgaggaagcg gaagagcgcc caatacgcaa accgcctctc   5280

cccgcgcgtt ggccgattca ttaatgcagc tggcacgaca ggtttcccga ctggaaagcg   5340

ggcagtgagc gcaacgcaat taatgtgagt tagctcactc attaggcacc ccaggcttta   5400

cactttatgc ttccggctcg tatgttgtgt ggaattgtga gcggataaca atttcacaca   5460

ggaaacagct atgacatgat tacgaattcg agctcggtac ccggggatcc caaatccaga   5520

aaagctcata ctgctcccct aatcgatggc ttccccagca agggctttgg aggcgaggcg   5580

ttcttcctca ctgacttccc acacctcgtg agcggcgtgc agtgcgagca gaatgatgaa   5640

acaacctagg atcaaatctg gccatccaga cgtcgtccat gcggtaatta aggccatcat   5700

gatgatggca atgttgatca ggacgtcatt tcgggcggat aggaaggcag cttggccaag   5760

cgagccacca tgttgtcgca ctcgagaaat aatgatggca ctcgcgccgt tgatcacgac   5820

ggcgcccaga gaagcgacga tgatcggaaa cacttcgggc gcttgcggtg cggaaaaccg   5880

ttgaatcgct gcccacgcag caaaagcagc aggtgcaaga atcacaatcg ccataagttt   5940

gcccatcact gcgcgcctcg ccaacggcca tcctagggca atgaaaatga gcaggttgat   6000

ggaggtgtct tcaagaaaat cgacactgtc agccagtaga gaaacggagc ctgcgcttaa   6060

tgcaataaag aattctacaa agaaataagc gaagttaagc agcgcgacgg tgagcacagc   6120

tttgcgcact ttggttgcat caaaagcttc gctcatcagc tagcgccgct tctggcagtt   6180
```

```
tgggcagtag tgggagccgc ggttcatgaa actctcccgg atgattaatg ttccgcagcg   6240
tccgcacggc tccccggttt gcgcataagc attcaatgac agcgcaaagt agccggagtt   6300
gccattgacg ttgacataga gcgcgtcgaa agaggtgcca ccttgagcaa gtgctttggt   6360
catcacgtct ttgccagctt gaagaagttc ttccaagcga gctagggaca gtcgatcggc   6420
acgttgcaat gggtgaattt ttgcttgcca gagcatttca tcggcataga tatttccgat   6480
gccggagacg atctcttggt taagcaggag gcgtttgatc tccgatttcc gagatttcaa   6540
attccgcgca atcgcagaga aatcagcaga ctcatccaat acatctgtgg caatgtgaga   6600
gacgcgttcg ggtactccat caactaggtc gccgagccac caataaccga aggtgcgttg   6660
atcgacaaac cacacttcat cgccattatc tagctcgact ttggctcgaa ggtgtggact   6720
aattggtgca tctggttctt tgatgagcat ttgtccactc atcccaaggt gaaccagtag   6780
ccctaaatcg ggacgggttt cgccggaggg tgcgtcgata agctcaagcc agaggaattt   6840
gccgcgtcgc ttggcagcgc tgaccctaag ccctgcgatg ttggcctcga tttcggggcc   6900
accgccgagt tgattgcggg ctgcgcgcgg gtgaagcact gtggcggaca cgatggtgtg   6960
gccgaccata tgatcttcta aaccgcggcg caccacctca acttcaggca gtaggaactt   7020
ctccaaacca gcccagcgcg gatcgacctt ttcctcgtct tctacttctt cagagacacc   7080
gtcaggagct ggcgtttcat catcctggca tgcgccgtac ccaagttctt cgcagacagg   7140
gttaaacggc aaggtcagac cagcttcatc aatgacagac tgaagcagat caatctggtc   7200
ttggttaacc attggcagct catcttcgtc atctgctgca tcttcaccag taacaaagtc   7260
tggatcggca gcaaaaacct cagagacgtg cagcgtcttg gttggggtga gttcgcggag   7320
gcagcgggag cactgtccca gaagctgcgc ttcgatatct gcttcgacgg ccaggcctcc   7380
accgagtgga atgatctggg cttctacgat aacttttccg ccctcgggga tcgcgatcat   7440
ttccggacca atgcgggtcg ggcttggacc tgattgggtg aggtgttccg gaagggcact   7500
tccacgaagg agtgcggcga catcaaaaat aaatggagat ttcatgacca ggaagatcct   7560
actcgtacct catcgtgact acatacatca gatgaggatc gctagacgga aaggtgaaaa   7620
agcctaaatg gtttcttgga aactagtagt ctcgatcgtc gcgttcgtag cctcgttcat   7680
aatcacgctc gtagtcccgc tcatattcac cacgcgctgc cggttgctca tcgcgcagct   7740
cgcggccagt agctccagct cctcggcgta gtgcggaacg atcagcagtg acagaacgca   7800
acgtggtgga cagcgaggtt tcaaactctg ccaacttggt atccacgtag tcatcgcatt   7860
cattgcgcag cttgttggag tcagcgtgcg ctgcatccac aatgcggtgt gcttcttccg   7920
tggagcgacg caccacttct gcctcgctga ccaggcgatc ctgctcggcc tggccttcag   7980
caaccgcgcg gcgatacgca tcattgccgg agttgaccag gcgctcagat tcagcctggg   8040
cgcgctcggt gacgctgttt gcttctcgac gagcgtcact cacgatgcga tccgctgtgt   8100
cattagcctt agcaacgaca gaatgcgcat gcttgggtcg acctgcaggc atgcaagctt   8160
ggcactggcc gtcgttttac aacgtcgtga ctgggaaaac cctggcgtta cccaacttaa   8220
tcgccttgca gcacatcccc ctttcgccag ctggcgtaat agcgaagagg cccgcaccga   8280
tcgcccttcc caacagttgc gcagcctgaa tggcgaatgg cgataagcta gcttcacgc    8339
```

<210> SEQ ID NO 30
<211> LENGTH: 3343
<212> TYPE: DNA
<213> ORGANISM: Artificial Sequence
<220> FEATURE:
<223> OTHER INFORMATION: synthetic DNA

```
<220> FEATURE:
<221> NAME/KEY: misc_feature
<222> LOCATION: (1)..(301)
<223> OTHER INFORMATION: pCG1 origin of replication
<220> FEATURE:
<221> NAME/KEY: gene
<222> LOCATION: (2269)..(3063)
<223> OTHER INFORMATION: kanamycin resistance gene

<400> SEQUENCE: 30

ccatggtcgt cacagagctg gaagcggcag cgagaattat ccgcgatcgt ggcgcggtgc     60

ccgcaggcat gacaaacatc gtaaatgccg cgtttcgtgt ggccgtggcc gcccaggacg    120

tgtcagcgcc gccaccacct gcaccgaatc ggcagcagcg tcgcgcgtcg aaaaagcgca    180

caggcggcaa gaagcgataa gctgcacgaa tacctgaaaa atgttgaacg ccccgtgagc    240

ggtaactcac agggcgtcgg ctaaccccca gtccaaacct gggagaaagc gctcaaaaat    300

gactctagcg gattcacgag acattgacac accggcctgg aaattttccg ctgatctgtt    360

cgacacccat cccgagctcg cgctgcgatc acgtggctgg acgagcgaag accgccgcga    420

attcctcgct cacctgggca gagaaaattt ccagggcagc aagacccgcg acttcgccag    480

cgcttggatc aaagacccgg acacgggaga aacacagccg aagttatacc gagttggttc    540

aaaatcgctt gcccggtgcc agtatgttgc tctgacgcac gcgcagcacg cagccgtgct    600

tgtcctggac attgatgtgc cgagccacca ggccggcggg aaaatcgagc acgtaaaccc    660

cgaggtctac gcgattttgg agcgctgggc acgcctggaa aaagcgccag cttggatcgg    720

cgtgaatcca ctgagcggga aatgccagct catctggctc attgatccgg tgtatgccgc    780

agcaggcatg agcagcccga atatgcgcct gctggctgca acgaccgagg aaatgacccg    840

cgttttcggc gctgaccagg ctttttcaca taggctgagc cggtggccac tgcacgtctc    900

cgacgatccc accgcgtacc gctggcatgc ccagcacaat cgcgtggatc gcctagctga    960

tcttatggag gttgctcgca tgatctcagg cacagaaaaa cctaaaaaac gctatgagca   1020

ggagttttct agcggacggg cacgtatcga agcggcaaga aaagccactg cggaagcaaa   1080

agcacttgcc acgcttgaag caagcctgcc gagcgccgct gaagcgtctg gagagctgat   1140

cgacggcgtc cgtgtcctct ggactgctcc agggcgtgcc gcccgtgatg agacggcttt   1200

tcgccacgct ttgactgtgg gataccagtt aaaagcggct ggtgagcgcc taaaagacac   1260

caagatcatc gacgcctacg agcgtgccta caccgtcgct caggcggtcg gagcagacgg   1320

ccgtgagcct gatctgccgc cgatgcgtga ccgccagacg atggcgcgac gtgtgcgcgg   1380

ctacgtcgct aaaggccagc cagtcgtccc tgctcgtcag acagagacgc agagcagccg   1440

agggcgaaaa gctctggcca ctatgggaag acgtggcggt aaaaaggccg cagaacgctg   1500

gaaagaccca aacagtgagt acgcccgagc acagcgagaa aaactagcta agtccagtca   1560

acgacaagct aggaaagcta aaggaaatcg cttgaccatt gcaggttggt ttatgactgt   1620

tgagggagag actggctcgt ggcgacaatc aatgaagcta tgtctgaatt tagcgtgtca   1680

cgtcagaccg tgaatagagc acttaagtct gcgggcattg aacttccacg aggacgccgt   1740

aaagcttccc agtaaatgtg ccatctcgta ggcagaaaac ggttcccccc gtaggggtct   1800

ctctcttggc ctcctttcta ggtcgggctg attgctcttg aagctctcta gggggctca    1860

caccataggc agataacggt tccccaccgg ctcacctcgt aagcgcacaa ggactgctcc   1920

caatgccgca agcactcagg gcgcaagggc tgctaaagga agcggaacac gtagaaagcc   1980

agtccgcaga aacggtgctg accccggatg aatgtcagct actgggctat ctggacaagg   2040
```

```
gaaaacgcaa gcgcaaagag aaagcaggta gcttgcagtg ggcttacatg gcgatagcta   2100

gactgggcgg ttttatggac agcaagcgaa ccggaattgc cagctggggc gccctctggt   2160

aaggttggga agccctgcaa agtaaactgg atggctttct tgccgccaag gatctgatgg   2220

cgcaggggat caagatctga tcaagagaca ggatgaggat cgtttcgcat gattgaacaa   2280

gatggattgc acgcaggttc tccggccgct tgggtggaga ggctattcgg ctatgactgg   2340

gcacaacaga caatcggctg ctctgatgcc gccgtgttcc ggctgtcagc gcaggggcgc   2400

ccggttcttt ttgtcaagac cgacctgtcc ggtgccctga atgaactcca agacgaggca   2460

gcgcggctat cgtggctggc cacgacgggc gttccttgcg cagctgtgct cgacgttgtc   2520

actgaagcgg gaagggactg gctgctattg ggcgaagtgc cggggcagga tctcctgtca   2580

tctcaccttg ctcctgccga gaaagtatcc atcatggctg atgcaatgcg gcggctgcat   2640

acgcttgatc cggctacctg cccattcgac caccaagcga aacatcgcat cgagcgagca   2700

cgtactcgga tggaagccgg tcttgtcgat caggatgatc tggacgaaga gcatcagggg   2760

ctcgcgccag ccgaactgtt cgccaggctc aaggcgcgga tgcccgacgg cgaggatctc   2820

gtcgtgaccc atggcgatgc ctgcttgccg aatatcatgg tggaaaatgg ccgcttttct   2880

ggattcatcg actgtggccg gctgggtgtg gcggaccgct atcaggacat agcgttggct   2940

acccgtgata ttgctgaaga gcttggcggc gaatgggctg accgcttcct cgtgctttac   3000

ggtatcgccg ctcccgattc gcagcgcatc gccttctatc gccttcttga cgagttcttc   3060

tgagcgggac tctggggttc gctagaggat cgatcctttt taacccatca catatacctg   3120

ccgttcacta ttatttagtg aaatgagata ttatgatatt ttctgaattg tgattaaaaa   3180

ggcaacttta tgcccatgca acagaaacta taaaaaatac agagaatgaa aagaaacaga   3240

tagatttttt agttctttag gcccgtagtc tgcaaatcct tttatgattt tctatcaaac   3300

aaaagaggaa aatagaccag ttgcaatcca aacgagagtc taa                      3343
```

```
<210> SEQ ID NO 31
<211> LENGTH: 8710
<212> TYPE: DNA
<213> ORGANISM: Artificial Sequence
<220> FEATURE:
<223> OTHER INFORMATION: Recombinant plasmid pAPSE10430; beta actin
      hairpin + coat protein
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: promoter
<222> LOCATION: (985)..(1003)
```

```
<223> OTHER INFORMATION: bacteriophage T7 gene 1 promoter
<220> FEATURE:
<221> NAME/KEY: gene
<222> LOCATION: (1076)..(1465)
<223> OTHER INFORMATION: bacteriophage MS2 coat protein gene
<220> FEATURE:
<221> NAME/KEY: terminator
<222> LOCATION: (1498)..(1545)
<223> OTHER INFORMATION: bacteriophage T7 transcription terminator
<220> FEATURE:
<221> NAME/KEY: misc_feature
<222> LOCATION: (1981)..(5324)
<223> OTHER INFORMATION: synthetic DNA (SEQ ID NO: 30)

<400> SEQUENCE: 31

ttcttagctc cggcaagcaa ttaagaactt ccgaaattaa tacgactcac tatagggagg     60

cgatcgcgca cgaggttttt ctgtctagtg agcagtgtcc aacctcaaaa gacaacatgt    120

gtgacgacga tgtagcggct cttgtcgtag acaatggatc cggtatgtgc aaagccggtt    180

tcgcaggaga tgacgcaccc cgtgccgtct tcccctcgat cgtcggtcgc ccaaggcatc    240

aaggagtcat ggtcggtatg ggacaaaagg actcatacgt aggagatgaa gcccaaagca    300

aaagaggtat cctcaccctg aaatacccca tcgaacacgg tatcatcacc aactgggatg    360

agtttaaacc ctctagctgc tttacaaagt actggttccc tttccagcgg gatgctttat    420

ctaaacgcaa tgagagaggt attcctcagg ccacatcgct tcctagttcc gctgggatcc    480

atcgttggcg gccgaagccg ccattccata gtgagttctg gcgcgcctca tcccagttgg    540

tgatgatacc gtgttcgatg ggtatttca gggtgaggat acctcttttg ctttgggctt    600

catctcctac gtatgagtcc ttttgtccca taccgaccat gactccttga tgccttgggc    660

gaccgacgat cgaggggaag acggcacggg gtgcgtcatc tcctgcgaaa ccggctttgc    720

acataccgga tccattgtct acgacaagag ccgctacatc gtcgtcacac atgttgtctt    780

ttgaggttgg acactgctca ctagacagaa aaacctcgtg ccggaccgaa tacccggtct    840

gaacgaggtt aattaaggta cccaagaagt acttagaggc ggccgcctag cataacccct    900

tggggcctct aaacgggtct tgaggggttt tttgagaaac ggccgaatac acctgttcgg    960

atccagatct cgatcccgcg aaattaatac gactcactat agggagacca caacggtttc   1020

cctctagatc acaagtttgt acaaaaaagc aggctaagaa ggagatatac atatggcgtc   1080

taactttacc caattcgttc tggttgataa cggcggtacg ggtgacgtta ccgtagctcc   1140

gtccaacttc gccaacggtg ttgcggaatg gattagctct aacagccgct ctcaggccta   1200

caaagtcacg tgctccgttc gtcagtctag cgcgcagaat cgcaaataca ccatcaaagt   1260

tgaagtaccg aaagtcgcaa cgcagaccgt aggcggcgta gaactcccag ttgcggcctg   1320

gcgctcttac ctcaacatgg aactgactat tccgattttt gcgacgaact ccgactgcga   1380

actgattgtt aaggcaatgc agggcctgct gaaagacggt aatccgatcc catctgcaat   1440

cgctgctaac tctggcattt actaataagc ggacgcgctg ccaccgctga gcaataacta   1500

gcataacccc ttggggcctc taaacgggtc ttgaggggtt ttttgctgaa aggaggaact   1560

atatccggca tgcaccattc cttgcggcgg cggtgctcaa cggcctcaac ctactactgg   1620

gctgcttcct aatgcaggag tcgcataagg gagagcgtcg accgatgccc ttgagagcct   1680

tcaacccagt cagctccttc cggtgggcgc ggggcatgac tatcgtcgcc gcacttatga   1740

ctgtcttctt tatcatgcaa ctcgtaggac aggtgccggc agcgctctgg gtcattttcg   1800

gcgaggaccg ctttcgctgg agcgcgacga tgatcggcct gtcgcttgcg gtattcggaa   1860

tcttgcacgc cctcgctcaa gccttcgtca ctggtcccgc caccaaacgt ttcggcgaga   1920
```

```
agcaggccat tatcgccggc atggcggccg acgcgctggg ctacgtcttg ctggcgttcg   1980
ccatggtcgt cacagagctg gaagcggcag cgagaattat ccgcgatcgt ggcgcggtgc   2040
ccgcaggcat gacaaacatc gtaaatgccg cgtttcgtgt ggccgtggcc gcccaggacg   2100
tgtcagcgcc gccaccacct gcaccgaatc ggcagcagcg tcgcgcgtcg aaaaagcgca   2160
caggcggcaa gaagcgataa gctgcacgaa tacctgaaaa atgttgaacg ccccgtgagc   2220
ggtaactcac agggcgtcgg ctaacccccca gtccaaacct gggagaaagc gctcaaaaat   2280
gactctagcg gattcacgag acattgacac accggcctgg aaattttccg ctgatctgtt   2340
cgacacccat cccgagctcg cgctgcgatc acgtggctgg acgagcgaag accgccgcga   2400
attcctcgct cacctgggca gagaaaattt ccagggcagc aagacccgcg acttcgccag   2460
cgcttggatc aaagacccgg acacgggaga aacacagccg aagttatacc gagttggttc   2520
aaaatcgctt gcccggtgcc agtatgttgc tctgacgcac gcgcagcacg cagccgtgct   2580
tgtcctggac attgatgtgc cgagccacca ggccggcggg aaaatcgagc acgtaaaccc   2640
cgaggtctac gcgattttgg agcgctgggc acgcctggaa aaagcgccag cttggatcgg   2700
cgtgaatcca ctgagcggga aatgccagct catctggctc attgatccgg tgtatgccgc   2760
agcaggcatg agcagcccga atatgcgcct gctggctgca acgaccgagg aaatgacccg   2820
cgttttcggc gctgaccagg ctttttcaca taggctgagc cggtggccac tgcacgtctc   2880
cgacgatccc accgcgtacc gctggcatgc ccagcacaat cgcgtggatc gcctagctga   2940
tcttatggag gttgctcgca tgatctcagg cacagaaaaa cctaaaaaac gctatgagca   3000
ggagttttct agcggacggg cacgtatcga agcggcaaga aaagccactg cggaagcaaa   3060
agcacttgcc acgcttgaag caagcctgcc gagcgccgct gaagcgtctg gagagctgat   3120
cgacggcgtc cgtgtcctct ggactgctcc agggcgtgcc gcccgtgatg agacggcttt   3180
tcgccacgct ttgactgtgg gataccagtt aaaagcggct ggtgagcgcc taaaagacac   3240
caagatcatc gacgcctacg agcgtgccta caccgtcgct caggcggtcg gagcagacgg   3300
ccgtgagcct gatctgccgc cgatgcgtga ccgccagacg atggcgcgac gtgtgcgcgg   3360
ctacgtcgct aaaggccagc cagtcgtccc tgctcgtcag acagagacgc agagcagccg   3420
agggcgaaaa gctctggcca ctatgggaag acgtggcggt aaaaaggccg cagaacgctg   3480
gaaagaccca aacagtgagt acgcccgagc acagcgagaa aaactagcta agtccagtca   3540
acgacaagct aggaaagcta aggaaatcg cttgaccatt gcaggttggt ttatgactgt   3600
tgagggagag actggctcgt ggcgacaatc aatgaagcta tgtctgaatt tagcgtgtca   3660
cgtcagaccg tgaatagagc acttaagtct gcgggcattg aacttccacg aggacgccgt   3720
aaagcttccc agtaaatgtg ccatctcgta ggcagaaaac ggttcccccc gtaggggtct   3780
ctctcttggc ctcctttcta ggtcgggctg attgctcttg aagctctcta ggggggctca   3840
caccataggc agataacggt tccccaccgg ctcacctcgt aagcgcacaa ggactgctcc   3900
caatgccgca agcactcagg gcgcaagggc tgctaaagga agcggaacac gtagaaagcc   3960
agtccgcaga aacggtgctg accccggatg aatgtcagct actgggctat ctggacaagg   4020
gaaaacgcaa gcgcaaagag aaagcaggta gcttgcagtg ggcttacatg gcgatagcta   4080
gactgggcgg ttttatggac agcaagcgaa ccggaattgc cagctggggc gccctctggt   4140
aaggttggga agccctgcaa agtaaactgg atggctttct tgccgccaag gatctgatgg   4200
cgcaggggat caagatctga tcaagagaca ggatgaggat cgtttcgcat gattgaacaa   4260
```

```
gatggattgc acgcaggttc tccggccgct tgggtggaga ggctattcgg ctatgactgg   4320
gcacaacaga caatcggctg ctctgatgcc gccgtgttcc ggctgtcagc gcaggggcgc   4380
ccggttcttt ttgtcaagac cgacctgtcc ggtgccctga atgaactcca agacgaggca   4440
gcgcggctat cgtggctggc cacgacgggc gttccttgcg cagctgtgct cgacgttgtc   4500
actgaagcgg gaagggactg gctgctattg ggcgaagtgc cggggcagga tctcctgtca   4560
tctcaccttg ctcctgccga gaaagtatcc atcatggctg atgcaatgcg gcggctgcat   4620
acgcttgatc cggctacctg cccattcgac caccaagcga aacatcgcat cgagcgagca   4680
cgtactcgga tggaagccgg tcttgtcgat caggatgatc tggacgaaga gcatcagggg   4740
ctcgcgccag ccgaactgtt cgccaggctc aaggcgcgga tgcccgacgg cgaggatctc   4800
gtcgtgaccc atggcgatgc ctgcttgccg aatatcatgg tggaaaatgg ccgcttttct   4860
ggattcatcg actgtggccg gctgggtgtg gcggaccgct atcaggacat agcgttggct   4920
acccgtgata ttgctgaaga gcttggcggc gaatgggctg accgcttcct cgtgctttac   4980
ggtatcgccg ctcccgattc gcagcgcatc gccttctatc gccttcttga cgagttcttc   5040
tgagcgggac tctggggttc gctagaggat cgatcctttt taacccatca catatacctg   5100
ccgttcacta ttatttagtg aaatgagata ttatgatatt ttctgaattg tgattaaaaa   5160
ggcaacttta tgcccatgca acagaaacta taaaaaatac agagaatgaa aagaaacaga   5220
tagatttttt agttctttag gcccgtagtc tgcaaatcct tttatgattt tctatcaaac   5280
aaaagaggaa aatagaccag ttgcaatcca aacgagagtc taacgacgcg aggctggatg   5340
gccttcccca ttatgattct tctcgcttcc ggcggcatcg ggatgcccgc gttgcaggcc   5400
atgctgtcca ggcaggtaga tgacgaccat cagggacagc ttcaaggatc gctcgcggct   5460
cttaccagcc taacttcgat cattggaccg ctgatcgtca cggcgattta tgccgcctcg   5520
gcgagcacat ggaacgggtt ggcatggatt gtaggcgccg ccctatacct tgtctgcctc   5580
cccgcgttgc gtcgcggtgc atggagccgg gccacctcga cctgaatgga agccggcggc   5640
acctcgctaa cggattcacc actccaagaa ttggagccaa tcaattcttg cggagaactg   5700
tgaatgcgca aaccaaccct tggcagaaca tatccatcgc gtccgccatc tccagcagcc   5760
gcacgcggcg catctcgggc agcgttgggt cctggccacg ggtgcgcatg atcgtgctcc   5820
tgtcgttgag gacccggcta ggctggcggg gttgccttac tggttagcag aatgaatcac   5880
cgatacgcga gcgaacgtga agcgactgct gctgcaaaac gtctgcgacc tgagcaacaa   5940
catgaatggt cttcggtttc cgtgtttcgt aaagtctgga aacgcggaag tcagcgccct   6000
gcaccattat gttccggatc tgcatcgcag gatgctgctg gctaccctgt ggaacaccta   6060
catctgtatt aacgaagcgc tggcattgac cctgagtgat ttttctctgg tcccgccgca   6120
tccataccgc cagttgttta ccctcacaac gttccagtaa ccgggcatgt tcatcatcag   6180
taacccgtat cgtgagcatc ctctctcgtt tcatcggtat cattaccccc atgaacagaa   6240
atccccctta cacggaggca tcagtgacca aacaggaaaa aaccgccctt aacatggccc   6300
gctttatcag aagccagaca ttaacgcttc tggagaaact caacgagctg gacgcggatg   6360
aacaggcaga catctgtgaa tcgcttcacg accacgctga tgagctttac cgcagctgcc   6420
tcgcgcgttt cggtgatgac ggtgaaaacc tctgacacat gcagctcccg gagacggtca   6480
cagcttgtct gtaagcggat gccgggagca gacaagcccg tcagggcgcg tcagcgggtg   6540
ttggcgggtg tcggggcgca gccatgaccc agtcacgtag cgatagcgga gtgtatactg   6600
gcttaactat gcggcatcag agcagattgt actgagagtg caccatatgc ggtgtgaaat   6660
```

```
accgcacaga tgcgtaagga gaaaataccg catcaggcgc tcttccgctt cctcgctcac   6720
tgactcgctg cgctcggtcg ttcggctgcg gcgagcggta tcagctcact caaaggcggt   6780
aatacggtta tccacagaat caggggataa cgcaggaaag aacatgtgag caaaaggcca   6840
gcaaaaggcc aggaaccgta aaaaggccgc gttgctggcg tttttccata ggctccgccc   6900
ccctgacgag catcacaaaa atcgacgctc aagtcagagg tggcgaaacc cgacaggact   6960
ataaagatac caggcgtttc cccctggaag ctccctcgtg cgctctcctg ttccgaccct   7020
gccgcttacc ggatacctgt ccgcctttct cccttcggga agcgtggcgc tttctcatag   7080
ctcacgctgt aggtatctca gttcggtgta ggtcgttcgc tccaagctgg gctgtgtgca   7140
cgaacccccc gttcagcccg accgctgcgc cttatccggt aactatcgtc ttgagtccaa   7200
cccggtaaga cacgacttat cgccactggc agcagccact ggtaacagga ttagcagagc   7260
gaggtatgta ggcggtgcta cagagttctt gaagtggtgg cctaactacg gctacactag   7320
aaggacagta tttggtatct gcgctctgct gaagccagtt accttcggaa aaagagttgg   7380
tagctcttga tccggcaaac aaaccaccgc tggtagcggt ggtttttttg tttgcaagca   7440
gcagattacg cgcagaaaaa aaggatctca agaagatcct ttgatctttt ctacggggtc   7500
tgacgctcag tggaacgaaa actcacgtta agggattttg gtcatgagat tatcaaaaag   7560
gatcttcacc tagatccttt taaattaaaa atgaagtttt aaatcaatct aaagtatata   7620
tgagtaaact tggtctgaca gttaccaatg cttaatcagt gaggcaccta tctcagcgat   7680
ctgtctattt cgttcatcca tagttgcctg actccccgtc gtgtagataa ctacgatacg   7740
ggagggctta ccatctggcc ccagtgctgc aatgataccg cgagacccac gctcaccggc   7800
tccagattta tcagcaataa accagccagc cggaagggcc gagcgcagaa gtggtcctgc   7860
aactttatcc gcctccatcc agtctattaa ttgttgccgg gaagctagag taagtagttc   7920
gccagttaat agtttgcgca acgttgttgc cattgctgca ggcatcgtgg tgtcacgctc   7980
gtcgtttggt atggcttcat tcagctccgg ttcccaacga tcaaggcgag ttacatgatc   8040
ccccatgttg tgcaaaaaag cggttagctc cttcggtcct ccgatcgttg tcagaagtaa   8100
gttggccgca gtgttatcac tcatggttat ggcagcactg cataattctc ttactgtcat   8160
gccatccgta agatgctttt ctgtgactgg tgagtactca accaagtcat tctgagaata   8220
gtgtatgcgg cgaccgagtt gctcttgccc ggcgtcaaca cgggataata ccgcgccaca   8280
tagcagaact ttaaaagtgc tcatcattgg aaaacgttct tcggggcgaa aactctcaag   8340
gatcttaccg ctgttgagat ccagttcgat gtaacccact cgtgcaccca actgatcttc   8400
agcatctttt actttcacca gcgtttctgg gtgagcaaaa acaggaaggc aaaatgccgc   8460
aaaaaaggga ataagggcga cacggaaatg ttgaatactc atactcttcc tttttcaata   8520
ttattgaagc atttatcagg gttattgtct catgagcgga tacatatttg aatgtattta   8580
gaaaaataaa caaatagggg ttccgcgcac atttccccga aaagtgccac ctgacgtcta   8640
agaaaccatt attatcatga cattaaccta taaaaatagg cgtatcacga ggccctttcg   8700
tcttcaagaa                                                          8710
```

<210> SEQ ID NO 32
<211> LENGTH: 8107
<212> TYPE: DNA
<213> ORGANISM: Artificial Sequence
<220> FEATURE:
<223> OTHER INFORMATION: Recombinant plasmid pAPSE10431; beta actin stem loop - coat protein

```
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: misc_feature
<222> LOCATION: (1378)..(4721)
<223> OTHER INFORMATION: synthetic DNA (SEQ ID NO: 30)

<400> SEQUENCE: 32

ttcttagctc cggcaagcaa ttaagaactt ccgaaattaa tacgactcac tatagggagg     60

cgatcgcgca cgaggttttt ctgtctagtg agcagtgtcc aacctcaaaa gacaacatgt    120

gtgacgacga tgtagcggct cttgtcgtag acaatggatc cggtatgtgc aaagccggtt    180

tcgcaggaga tgacgcaccc cgtgccgtct tcccctcgat cgtcggtcgc ccaaggcatc    240

aaggagtcat ggtcggtatg ggacaaaagg actcatacgt aggagatgaa gcccaaagca    300

aaagaggtat cctcaccctg aaatacccca tcgaacacgg tatcatcacc aactgggatg    360

agtttaaacc ctctagctgc tttacaaagt actggttccc tttccagcgg gatgctttat    420

ctaaacgcaa tgagagaggt attcctcagg ccacatcgct tcctagttcc gctgggatcc    480

atcgttggcg gccgaagccg ccattccata gtgagttctg gcgcgcctca tcccagttgg    540

tgatgatacc gtgttcgatg ggtatttca gggtgaggat acctcttttg ctttgggctt     600

catctcctac gtatgagtcc ttttgtccca taccgaccat gactccttga tgccttgggc    660

gaccgacgat cgaggggaag acggcacggg gtgcgtcatc tcctgcgaaa ccggctttgc    720

acataccgga tccattgtct acgacaagag ccgctacatc gtcgtcacac atgttgtctt    780

ttgaggttgg acactgctca ctagacagaa aaacctcgtg ccggaccgaa tacccggtct    840

gaacgaggtt aattaaggta cccaagaagt acttagaggc ggccgcctag cataacccct    900

tggggcctct aaacgggtct tgaggggttt tttgagaaac ggccgaatac acctgttcgg    960

atccagatcc accattcctt gcggcggcgg tgctcaacgg cctcaaccta ctactgggct   1020

gcttcctaat gcaggagtcg cataagggag agcgtcgacc gatgcccttg agagccttca   1080

acccagtcag ctccttccgg tgggcgcggg gcatgactat cgtcgccgca cttatgactg   1140

tcttctttat catgcaactc gtaggacagg tgccggcagc gctctgggtc attttcggcg   1200

aggaccgctt tcgctggagc gcgacgatga tcggcctgtc gcttgcggta ttcggaatct   1260

tgcacgccct cgctcaagcc ttcgtcactg gtcccgccac caaacgtttc ggcgagaagc   1320

aggccattat cgccggcatg gcggccgacg cgctgggcta cgtcttgctg gcgttcgcca   1380

tggtcgtcac agagctggaa gcggcagcga gaattatccg cgatcgtggc gcggtgcccg   1440
```

```
caggcatgac aaacatcgta aatgccgcgt ttcgtgtggc cgtggccgcc caggacgtgt   1500
cagcgccgcc accacctgca ccgaatcggc agcagcgtcg cgcgtcgaaa aagcgcacag   1560
gcggcaagaa gcgataagct gcacgaatac ctgaaaaatg ttgaacgccc cgtgagcggt   1620
aactcacagg gcgtcggcta acccccagtc caaacctggg agaaagcgct caaaaatgac   1680
tctagcggat tcacgagaca ttgacacacc ggcctggaaa ttttccgctg atctgttcga   1740
cacccatccc gagctcgcgc tgcgatcacg tggctggacg agcgaagacc gccgcgaatt   1800
cctcgctcac ctgggcagag aaaatttcca gggcagcaag acccgcgact tcgccagcgc   1860
ttggatcaaa gacccggaca cgggagaaac acagccgaag ttataccgag ttggttcaaa   1920
atcgcttgcc cggtgccagt atgttgctct gacgcacgcg cagcacgcag ccgtgcttgt   1980
cctggacatt gatgtgccga gccaccaggc cggcgggaaa atcgagcacg taaaccccga   2040
ggtctacgcg attttggagc gctgggcacg cctggaaaaa gcgccagctt ggatcggcgt   2100
gaatccactg agcgggaaat gccagctcat ctggctcatt gatccggtgt atgccgcagc   2160
aggcatgagc agcccgaata tgcgcctgct ggctgcaacg accgaggaaa tgacccgcgt   2220
tttcggcgct gaccaggctt tttcacatag gctgagccgg tggccactgc acgtctccga   2280
cgatcccacc gcgtaccgct ggcatgccca gcacaatcgc gtggatcgcc tagctgatct   2340
tatggaggtt gctcgcatga tctcaggcac agaaaaacct aaaaaacgct atgagcagga   2400
gttttctagc ggacgggcac gtatcgaagc ggcaagaaaa gccactgcgg aagcaaaagc   2460
acttgccacg cttgaagcaa gcctgccgag cgccgctgaa gcgtctggag agctgatcga   2520
cggcgtccgt gtcctctgga ctgctccagg gcgtgccgcc cgtgatgaga cggcttttcg   2580
ccacgctttg actgtgggat accagttaaa agcggctggt gagcgcctaa aagacaccaa   2640
gatcatcgac gcctacgagc gtgcctacac cgtcgctcag gcggtcggag cagacggccg   2700
tgagcctgat ctgccgccga tgcgtgaccg ccagacgatg gcgcgacgtg tgcgcggcta   2760
cgtcgctaaa ggccagccag tcgtccctgc tcgtcagaca gagacgcaga gcagccgagg   2820
gcgaaaagct ctggccacta tgggaagacg tggcggtaaa aaggccgcag aacgctggaa   2880
agacccaaac agtgagtacg cccgagcaca gcgagaaaaa ctagctaagt ccagtcaacg   2940
acaagctagg aaagctaaag gaaatcgctt gaccattgca ggttggttta tgactgttga   3000
gggagagact ggctcgtggc gacaatcaat gaagctatgt ctgaatttag cgtgtcacgt   3060
cagaccgtga atagagcact taagtctgcg ggcattgaac ttccacgagg acgccgtaaa   3120
gcttcccagt aaatgtgcca tctcgtaggc agaaaacggt tcccccgta ggggtctctc   3180
tcttggcctc ctttctaggt cgggctgatt gctcttgaag ctctctaggg gggctcacac   3240
cataggcaga taacggttcc ccaccggctc acctcgtaag cgcacaagga ctgctcccaa   3300
tgccgcaagc actcagggcg caagggctgc taaaggaagc ggaacacgta gaaagccagt   3360
ccgcagaaac ggtgctgacc ccggatgaat gtcagctact gggctatctg gacaagggaa   3420
aacgcaagcg caaagagaaa gcaggtagct tgcagtgggc ttacatggcg atagctagac   3480
tgggcggttt tatggacagc aagcgaaccg gaattgccag ctggggcgcc ctctggtaag   3540
gttgggaagc cctgcaaagt aaactggatg gctttcttgc cgccaaggat ctgatggcgc   3600
aggggatcaa gatctgatca agagacagga tgaggatcgt ttcgcatgat tgaacaagat   3660
ggattgcacg caggttctcc ggccgcttgg gtggagaggc tattcggcta tgactgggca   3720
caacagacaa tcggctgctc tgatgccgcc gtgttccggc tgtcagcgca ggggcgcccg   3780
gttctttttg tcaagaccga cctgtccggt gccctgaatg aactccaaga cgaggcagcg   3840
```

```
cggctatcgt ggctggccac gacgggcgtt ccttgcgcag ctgtgctcga cgttgtcact   3900
gaagcgggaa gggactggct gctattgggc gaagtgccgg ggcaggatct cctgtcatct   3960
caccttgctc ctgccgagaa agtatccatc atggctgatg caatgcggcg gctgcatacg   4020
cttgatccgg ctacctgccc attcgaccac caagcgaaac atcgcatcga gcgagcacgt   4080
actcggatgg aagccggtct tgtcgatcag gatgatctgg acgaagagca tcaggggctc   4140
gcgccagccg aactgttcgc caggctcaag gcgcggatgc ccgacggcga ggatctcgtc   4200
gtgacccatg gcgatgcctg cttgccgaat atcatggtgg aaaatggccg cttttctgga   4260
ttcatcgact gtggccggct gggtgtggcg gaccgctatc aggacatagc gttggctacc   4320
cgtgatattg ctgaagagct tggcggcgaa tgggctgacc gcttcctcgt gctttacggt   4380
atcgccgctc ccgattcgca gcgcatcgcc ttctatcgcc ttcttgacga gttcttctga   4440
gcgggactct ggggttcgct agaggatcga tcctttttaa cccatcacat atacctgccg   4500
ttcactatta tttagtgaaa tgagatatta tgatattttc tgaattgtga ttaaaaaggc   4560
aactttatgc ccatgcaaca gaaactataa aaaatacaga gaatgaaaag aaacagatag   4620
atttttagt tctttaggcc cgtagtctgc aaatcctttt atgattttct atcaaacaaa   4680
agaggaaaat agaccagttg caatccaaac gagagtctaa cgacgcgagg ctggatggcc   4740
ttccccatta tgattcttct cgcttccggc ggcatcggga tgcccgcgtt gcaggccatg   4800
ctgtccaggc aggtagatga cgaccatcag ggacagcttc aaggatcgct cgcggctctt   4860
accagcctaa cttcgatcat tggaccgctg atcgtcacgg cgatttatgc cgcctcggcg   4920
agcacatgga acgggttggc atggattgta ggcgccgccc tataccttgt ctgcctcccc   4980
gcgttgcgtc gcggtgcatg gagccgggcc acctcgacct gaatggaagc cggcggcacc   5040
tcgctaacgg attcaccact ccaagaattg gagccaatca attcttgcgg agaactgtga   5100
atgcgcaaac caacccttgg cagaacatat ccatcgcgtc cgccatctcc agcagccgca   5160
cgcggcgcat ctcgggcagc gttgggtcct ggccacgggt gcgcatgatc gtgctcctgt   5220
cgttgaggac ccggctaggc tggcggggtt gccttactgg ttagcagaat gaatcaccga   5280
tacgcgagcg aacgtgaagc gactgctgct gcaaaacgtc tgcgacctga gcaacaacat   5340
gaatggtctt cggtttccgt gtttcgtaaa gtctggaaac gcggaagtca gcgccctgca   5400
ccattatgtt ccggatctgc atcgcaggat gctgctggct accctgtgga acacctacat   5460
ctgtattaac gaagcgctgg cattgaccct gagtgatttt tctctggtcc cgccgcatcc   5520
ataccgccag ttgtttaccc tcacaacgtt ccagtaaccg ggcatgttca tcatcagtaa   5580
cccgtatcgt gagcatcctc tctcgtttca tcggtatcat tacccccatg aacagaaatc   5640
cccettacac ggaggcatca gtgaccaaac aggaaaaaac cgcccttaac atggcccgct   5700
ttatcagaag ccagacatta acgcttctgg agaaactcaa cgagctggac gcggatgaac   5760
aggcagacat ctgtgaatcg cttcacgacc acgctgatga gctttaccgc agctgcctcg   5820
cgcgtttcgg tgatgacggt gaaaacctct gacacatgca gctcccggag acggtcacag   5880
cttgtctgta agcggatgcc gggagcagac aagcccgtca gggcgcgtca gcgggtgttg   5940
gcgggtgtcg gggcgcagcc atgacccagt cacgtagcga tagcggagtg tatactggct   6000
taactatgcg gcatcagagc agattgtact gagagtgcac catatgcggt gtgaaatacc   6060
gcacagatgc gtaaggagaa aataccgcat caggcgctct tccgcttcct cgctcactga   6120
ctcgctgcgc tcggtcgttc ggctgcggcg agcggtatca gctcactcaa aggcggtaat   6180
```

```
acggttatcc acagaatcag gggataacgc aggaaagaac atgtgagcaa aaggccagca   6240

aaaggccagg aaccgtaaaa aggccgcgtt gctggcgttt ttccataggc tccgcccccc   6300

tgacgagcat cacaaaaatc gacgctcaag tcagaggtgg cgaaacccga caggactata   6360

aagataccag gcgtttcccc ctggaagctc cctcgtgcgc tctcctgttc cgaccctgcc   6420

gcttaccgga tacctgtccg cctttctccc ttcgggaagc gtggcgcttt ctcatagctc   6480

acgctgtagg tatctcagtt cggtgtaggt cgttcgctcc aagctgggct gtgtgcacga   6540

accccccgtt cagcccgacc gctgcgcctt atccggtaac tatcgtcttg agtccaaccc   6600

ggtaagacac gacttatcgc cactggcagc agccactggt aacaggatta gcagagcgag   6660

gtatgtaggc ggtgctacag agttcttgaa gtggtggcct aactacggct acactagaag   6720

gacagtattt ggtatctgcg ctctgctgaa gccagttacc ttcggaaaaa gagttggtag   6780

ctcttgatcc ggcaaacaaa ccaccgctgg tagcggtggt ttttttgttt gcaagcagca   6840

gattacgcgc agaaaaaaag gatctcaaga agatcctttg atcttttcta cggggtctga   6900

cgctcagtgg aacgaaaact cacgttaagg gattttggtc atgagattat caaaaaggat   6960

cttcacctag atccttttaa attaaaaatg aagttttaaa tcaatctaaa gtatatatga   7020

gtaaacttgg tctgacagtt accaatgctt aatcagtgag gcacctatct cagcgatctg   7080

tctatttcgt tcatccatag ttgcctgact ccccgtcgtg tagataacta cgatacggga   7140

gggcttacca tctggcccca gtgctgcaat gataccgcga gacccacgct caccggctcc   7200

agatttatca gcaataaacc agccagccgg aagggccgag cgcagaagtg gtcctgcaac   7260

tttatccgcc tccatccagt ctattaattg ttgccgggaa gctagagtaa gtagttcgcc   7320

agttaatagt ttgcgcaacg ttgttgccat tgctgcaggc atcgtggtgt cacgctcgtc   7380

gtttggtatg gcttcattca gctccggttc ccaacgatca aggcgagtta catgatcccc   7440

catgttgtgc aaaaaagcgg ttagctcctt cggtcctccg atcgttgtca gaagtaagtt   7500

ggccgcagtg ttatcactca tggttatggc agcactgcat aattctctta ctgtcatgcc   7560

atccgtaaga tgcttttctg tgactggtga gtactcaacc aagtcattct gagaatagtg   7620

tatgcggcga ccgagttgct cttgcccggc gtcaacacgg gataataccg cgccacatag   7680

cagaacttta aaagtgctca tcattggaaa acgttcttcg gggcgaaaac tctcaaggat   7740

cttaccgctg ttgagatcca gttcgatgta acccactcgt gcacccaact gatcttcagc   7800

atcttttact ttcaccagcg tttctgggtg agcaaaaaca ggaaggcaaa atgccgcaaa   7860

aaagggaata agggcgacac ggaaatgttg aatactcata ctcttccttt ttcaatatta   7920

ttgaagcatt tatcagggtt attgtctcat gagcggatac atatttgaat gtatttagaa   7980

aaataaacaa ataggggttc cgcgcacatt tccccgaaaa gtgccacctg acgtctaaga   8040

aaccattatt atcatgacat taacctataa aaataggcgt atcacgaggc cctttcgtct   8100

tcaagaa                                                             8107
```

<210> SEQ ID NO 33
<211> LENGTH: 9000
<212> TYPE: DNA
<213> ORGANISM: Artificial Sequence
<220> FEATURE:
<223> OTHER INFORMATION: Recombinant plasmid pAPSE10432; beta actin hairpin + coat protein
<220> FEATURE:
<221> NAME/KEY: promoter
<222> LOCATION: (10)..(28)
<223> OTHER INFORMATION: bacteriophage T7 gene 1 promoter
<220> FEATURE:

<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (41)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI recognition site
<220> FEATURE:
<221> NAME/KEY: misc_feature
<222> LOCATION: (498)..(793)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: promoter
<222> LOCATION: (1275)..(1293)
<223> OTHER INFORMATION: bacteriophage T7 gene 1 promoter
<220> FEATURE:
<221> NAME/KEY: gene
<222> LOCATION: (1366)..(1755)
<223> OTHER INFORMATION: bacteriophage MS2 coat protein gene
<220> FEATURE:
<221> NAME/KEY: terminator
<222> LOCATION: (1788)..(1835)
<223> OTHER INFORMATION: bacteriophage T7 transcription terminator
<220> FEATURE:
<221> NAME/KEY: misc_feature
<222> LOCATION: (2272)..(5614)
<223> OTHER INFORMATION: synthetic DNA (SEQ ID NO: 30)

<400> SEQUENCE: 33
ttccgaaatt aatacgactc actataggga ggcgatcgcg cacgaggttt ttctgtctag 60
tgagcagtgt ccaacctcaa aagacaacat gtgtgacgac gatgtagcgg ctcttgtcgt 120
agacaatgga tccggtatgt gcaaagccgg tttcgcagga gatgacgcac cccgtgccgt 180
cttcccctcg atcgtcggtc gcccaaggca tcaaggagtc atggtcggta tgggacaaaa 240
ggactcatac gtaggagatg aagcccaaag caaaagaggt atcctcaccc tgaaataccc 300
catcgaacac ggtatcatca ccaactggga tgagtttaaa ccctctagct gctttacaaa 360
gtactggttc cctttccagc gggatgcttt atctaaacgc aatgagagag gtattcctca 420
ggccacatcg cttcctagtt ccgctgggat ccatcgttgg cggccgaagc cgccattcca 480
tagtgagttc tggcgcgcct catcccagtt ggtgatgata ccgtgttcga tggggtattt 540
cagggtgagg atacctcttt tgctttgggc ttcatctcct acgtatgagt ccttttgtcc 600
cataccgacc atgactcctt gatgccttgg gcgaccgacg atcgagggga agacggcacg 660
gggtgcgtca tctcctgcga aaccggcttt gcacataccg gatccattgt ctacgacaag 720
agccgctaca tcgtcgtcac acatgttgtc ttttgaggtt ggacactgct cactagacag 780
aaaaacctcg tgccggaccg aatacccggt ctgaacgagg gcggccgcgg tacccaagaa 840
gtacttagag ttaattaagg agttcaaaca tgaggatcac ccatgtcgaa gctcccacac 900
cctagcataa ccccttgggg cctctaaacg ggtcttgagg ggttttttgc tgaaaggagg 960
aactatatcc ggatatccac aggacgggtg tggtcgccat gatcgcgtag tcgatagtgg 1020
ctccaagtag cgaagcgagc aggactgggc ggcgggcatg catcgtccat tccgacagca 1080
tcgccagtca ctatggcgtg ctgctagcgc tatatgcgtt gatgcaattt ctatgcgcac 1140

```
ccgttctcgg agcactgtcc gaccgctttg gccgccgccc agtcctgctc gcttcgctac   1200
ttggagccac tatcgactac gcgatcatgg cgaccacacc cgtcctgtgg atccagatct   1260
cgatcccgcg aaattaatac gactcactat agggagacca caacggtttc cctctagatc   1320
acaagtttgt acaaaaaagc aggctaagaa ggagatatac atatggcgtc taactttacc   1380
caattcgttc tggttgataa cggcggtacg ggtgacgtta ccgtagctcc gtccaacttc   1440
gccaacggtg ttgcggaatg gattagctct aacagccgct ctcaggccta caaagtcacg   1500
tgctccgttc gtcagtctag cgcgcagaat cgcaaataca ccatcaaagt tgaagtaccg   1560
aaagtcgcaa cgcagaccgt aggcggcgta gaactcccag ttgcggcctg gcgctcttac   1620
ctcaacatgg aactgactat tccgattttt gcgacgaact ccgactgcga actgattgtt   1680
aaggcaatgc agggcctgct gaaagacggt aatccgatcc catctgcaat cgctgctaac   1740
tctggcattt actaataagc ggacgcgctg ccaccgctga gcaataacta gcataacccc   1800
ttggggcctc taaacgggtc ttgaggggtt ttttgctgaa aggaggaact atatccggca   1860
tgcaccattc cttgcggcgg cggtgctcaa cggcctcaac ctactactgg gctgcttcct   1920
aatgcaggag tcgcataagg gagagcgtcg accgatgccc ttgagagcct tcaacccagt   1980
cagctccttc cggtgggcgc ggggcatgac tatcgtcgcc gcacttatga ctgtcttctt   2040
tatcatgcaa ctcgtaggac aggtgccggc agcgctctgg gtcattttcg gcgaggaccg   2100
ctttcgctgg agcgcgacga tgatcggcct gtcgcttgcg gtattcggaa tcttgcacgc   2160
cctcgctcaa gccttcgtca ctggtcccgc caccaaacgt ttcggcgaga agcaggccat   2220
tatcgccggc atggcggccg acgcgctggg ctacgtcttg ctggcgttcg ccatggtcgt   2280
cacagagctg gaagcggcag cgagaattat ccgcgatcgt ggcgcggtgc ccgcaggcat   2340
gacaaacatc gtaaatgccg cgtttcgtgt ggccgtggcc gcccaggacg tgtcagcgcc   2400
gccaccacct gcaccgaatc ggcagcagcg tcgcgcgtcg aaaaagcgca caggcggcaa   2460
gaagcgataa gctgcacgaa tacctgaaaa atgttgaacg ccccgtgagc ggtaactcac   2520
agggcgtcgg ctaacccccca gtccaaacct gggagaaagc gctcaaaaat gactctagcg   2580
gattcacgag acattgacac accggcctgg aaattttccg ctgatctgtt cgacacccat   2640
cccgagctcg cgctgcgatc acgtggctgg acgagcgaag accgccgcga attcctcgct   2700
cacctgggca gagaaaattt ccagggcagc aagacccgcg acttcgccag cgcttggatc   2760
aaagacccgg acacgggaga aacacagccg aagttatacc gagttggttc aaaatcgctt   2820
gcccggtgcc agtatgttgc tctgacgcac gcgcagcacg cagccgtgct tgtcctggac   2880
attgatgtgc cgagccacca ggccggcggg aaaatcgagc acgtaaaccc cgaggtctac   2940
gcgattttgg agcgctgggc acgcctggaa aaagcgccag cttggatcgg cgtgaatcca   3000
ctgagcggga aatgccagct catctggctc attgatccgg tgtatgccgc agcaggcatg   3060
agcagcccga atatgcgcct gctggctgca acgaccgagg aaatgacccg cgttttcggc   3120
gctgaccagg ctttttcaca taggctgagc cggtggccac tgcacgtctc cgacgatccc   3180
accgcgtacc gctggcatgc ccagcacaat cgcgtggatc gcctagctga tcttatggag   3240
gttgctcgca tgatctcagg cacagaaaaa cctaaaaaac gctatgagca ggagttttct   3300
agcggacggg cacgtatcga agcggcaaga aaagccactg cggaagcaaa agcacttgcc   3360
acgcttgaag caagcctgcc gagcgccgct gaagcgtctg gagagctgat cgacggcgtc   3420
cgtgtcctct ggactgctcc agggcgtgcc gcccgtgatg agacggcttt tcgccacgct   3480
```

```
ttgactgtgg gataccagtt aaaagcggct ggtgagcgcc taaaagacac caagatcatc   3540
gacgcctacg agcgtgccta caccgtcgct caggcggtcg gagcagacgg ccgtgagcct   3600
gatctgccgc cgatgcgtga ccgccagacg atggcgcgac gtgtgcgcgg ctacgtcgct   3660
aaaggccagc cagtcgtccc tgctcgtcag acagagacgc agagcagccg agggcgaaaa   3720
gctctggcca ctatgggaag acgtggcggt aaaaaggccg cagaacgctg gaaagaccca   3780
aacagtgagt acgcccgagc acagcgagaa aaactagcta agtccagtca acgacaagct   3840
aggaaagcta aaggaaatcg cttgaccatt gcaggttggt ttatgactgt tgagggagag   3900
actggctcgt ggcgacaatc aatgaagcta tgtctgaatt tagcgtgtca cgtcagaccg   3960
tgaatagagc acttaagtct gcgggcattg aacttccacg aggacgccgt aaagcttccc   4020
agtaaatgtg ccatctcgta ggcagaaaac ggttcccccc gtaggggtct ctctcttggc   4080
ctcctttcta ggtcgggctg attgctcttg aagctctcta gggggggctca caccataggc   4140
agataacggt tccccaccgg ctcacctcgt aagcgcacaa ggactgctcc caatgccgca   4200
agcactcagg gcgcaagggc tgctaaagga agcggaacac gtagaaagcc agtccgcaga   4260
aacggtgctg accccggatg aatgtcagct actgggctat ctggacaagg gaaaacgcaa   4320
gcgcaaagag aaagcaggta gcttgcagtg ggcttacatg gcgatagcta gactgggcgg   4380
ttttatggac agcaagcgaa ccggaattgc cagctggggc gccctctggt aaggttggga   4440
agccctgcaa agtaaactgg atggctttct tgccgccaag gatctgatgg cgcaggggat   4500
caagatctga tcaagagaca ggatgaggat cgtttcgcat gattgaacaa gatggattgc   4560
acgcaggttc tccggccgct tgggtggaga ggctattcgg ctatgactgg gcacaacaga   4620
caatcggctg ctctgatgcc gccgtgttcc ggctgtcagc gcaggggcgc ccggttcttt   4680
ttgtcaagac cgacctgtcc ggtgccctga atgaactcca agacgaggca gcgcggctat   4740
cgtggctggc cacgacgggc gttccttgcg cagctgtgct cgacgttgtc actgaagcgg   4800
gaagggactg gctgctattg ggcgaagtgc cggggcagga tctcctgtca tctcaccttg   4860
ctcctgccga gaaagtatcc atcatggctg atgcaatgcg gcggctgcat acgcttgatc   4920
cggctacctg cccattcgac caccaagcga aacatcgcat cgagcgagca cgtactcgga   4980
tggaagccgg tcttgtcgat caggatgatc tggacgaaga gcatcagggg ctcgcgccag   5040
ccgaactgtt cgccaggctc aaggcgcgga tgcccgacgg cgaggatctc gtcgtgaccc   5100
atggcgatgc ctgcttgccg aatatcatgg tggaaaatgg ccgcttttct ggattcatcg   5160
actgtggccg gctgggtgtg gcggaccgct atcaggacat agcgttggct acccgtgata   5220
ttgctgaaga gcttggcggc gaatgggctg accgcttcct cgtgctttac ggtatcgccg   5280
ctcccgattc gcagcgcatc gccttctatc gccttcttga cgagttcttc tgagcgggac   5340
tctggggttc gctagaggat cgatcctttt taacccatca catatacctg ccgttcacta   5400
ttatttagtg aaatgagata ttatgatatt ttctgaattg tgattaaaaa ggcaacttta   5460
tgcccatgca acagaaacta taaaaaatac agagaatgaa aagaaacaga tagatttttt   5520
agttctttag gcccgtagtc tgcaaatcct tttatgattt tctatcaaac aaaagaggaa   5580
aatagaccag ttgcaatcca aacgagagtc taacgacgcg aggctggatg gccttcccca   5640
ttatgattct tctcgcttcc ggcggcatcg ggatgcccgc gttgcaggcc atgctgtcca   5700
ggcaggtaga tgacgaccat cagggacagc ttcaaggatc gctcgcggct cttaccagcc   5760
taacttcgat cattggaccg ctgatcgtca cggcgattta tgccgcctcg gcgagcacat   5820
ggaacgggtt ggcatggatt gtaggcgccg ccctatacct tgtctgcctc cccgcgttgc   5880
```

```
gtcgcggtgc atggagccgg gccacctcga cctgaatgga agccggcggc acctcgctaa   5940
cggattcacc actccaagaa ttggagccaa tcaattcttg cggagaactg tgaatgcgca   6000
aaccaaccct tggcagaaca tatccatcgc gtccgccatc tccagcagcc gcacgcggcg   6060
catctcgggc agcgttgggt cctggccacg ggtgcgcatg atcgtgctcc tgtcgttgag   6120
gacccggcta ggctggcggg gttgccttac tggttagcag aatgaatcac cgatacgcga   6180
gcgaacgtga agcgactgct gctgcaaaac gtctgcgacc tgagcaacaa catgaatggt   6240
cttcggtttc cgtgtttcgt aaagtctgga aacgcggaag tcagcgccct gcaccattat   6300
gttccggatc tgcatcgcag gatgctgctg gctaccctgt ggaacaccta catctgtatt   6360
aacgaagcgc tggcattgac cctgagtgat ttttctctgg tcccgccgca tccataccgc   6420
cagttgttta ccctcacaac gttccagtaa ccgggcatgt tcatcatcag taacccgtat   6480
cgtgagcatc ctctctcgtt tcatcggtat cattaccccc atgaacagaa atccccctta   6540
cacggaggca tcagtgacca aacaggaaaa aaccgccctt aacatggccc gctttatcag   6600
aagccagaca ttaacgcttc tggagaaact caacgagctg gacgcggatg aacaggcaga   6660
catctgtgaa tcgcttcacg accacgctga tgagctttac cgcagctgcc tcgcgcgttt   6720
cggtgatgac ggtgaaaacc tctgacacat gcagctcccg gagacggtca cagcttgtct   6780
gtaagcggat gccgggagca gacaagcccg tcagggcgcg tcagcgggtg ttggcgggtg   6840
tcggggcgca gccatgaccc agtcacgtag cgatagcgga gtgtatactg gcttaactat   6900
gcggcatcag agcagattgt actgagagtg caccatatgc ggtgtgaaat accgcacaga   6960
tgcgtaagga gaaaataccg catcaggcgc tcttccgctt cctcgctcac tgactcgctg   7020
cgctcggtcg ttcggctgcg gcgagcggta tcagctcact caaaggcggt aatacggtta   7080
tccacagaat caggggataa cgcaggaaag aacatgtgag caaaaggcca gcaaaaggcc   7140
aggaaccgta aaaaggccgc gttgctggcg tttttccata ggctccgccc ccctgacgag   7200
catcacaaaa atcgacgctc aagtcagagg tggcgaaacc cgacaggact ataaagatac   7260
caggcgtttc cccctggaag ctccctcgtg cgctctcctg ttccgaccct gccgcttacc   7320
ggatacctgt ccgcctttct cccttcggga agcgtggcgc tttctcatag ctcacgctgt   7380
aggtatctca gttcggtgta ggtcgttcgc tccaagctgg gctgtgtgca cgaacccccc   7440
gttcagcccg accgctgcgc cttatccggt aactatcgtc ttgagtccaa cccggtaaga   7500
cacgacttat cgccactggc agcagccact ggtaacagga ttagcagagc gaggtatgta   7560
ggcggtgcta cagagttctt gaagtggtgg cctaactacg gctacactag aaggacagta   7620
tttggtatct gcgctctgct gaagccagtt accttcggaa aaagagttgg tagctcttga   7680
tccggcaaac aaaccaccgc tggtagcggt ggtttttttg tttgcaagca gcagattacg   7740
cgcagaaaaa aaggatctca agaagatcct ttgatctttt ctacggggtc tgacgctcag   7800
tggaacgaaa actcacgtta agggattttg gtcatgagat tatcaaaaag gatcttcacc   7860
tagatccttt taaattaaaa atgaagtttt aaatcaatct aaagtatata tgagtaaact   7920
tggtctgaca gttaccaatg cttaatcagt gaggcaccta tctcagcgat ctgtctattt   7980
cgttcatcca tagttgcctg actccccgtc gtgtagataa ctacgatacg ggagggctta   8040
ccatctggcc ccagtgctgc aatgataccg cgagacccac gctcaccggc tccagattta   8100
tcagcaataa accagccagc cggaagggcc gagcgcagaa gtggtcctgc aactttatcc   8160
gcctccatcc agtctattaa ttgttgccgg gaagctagag taagtagttc gccagttaat   8220
```

```
agtttgcgca acgttgttgc cattgctgca ggcatcgtgg tgtcacgctc gtcgtttggt   8280

atggcttcat tcagctccgg ttcccaacga tcaaggcgag ttacatgatc ccccatgttg   8340

tgcaaaaaag cggttagctc cttcggtcct ccgatcgttg tcagaagtaa gttggccgca   8400

gtgttatcac tcatggttat ggcagcactg cataattctc ttactgtcat gccatccgta   8460

agatgctttt ctgtgactgg tgagtactca accaagtcat tctgagaata gtgtatgcgg   8520

cgaccgagtt gctcttgccc ggcgtcaaca cgggataata ccgcgccaca tagcagaact   8580

ttaaaagtgc tcatcattgg aaaacgttct tcggggcgaa aactctcaag gatcttaccg   8640

ctgttgagat ccagttcgat gtaacccact cgtgcaccca actgatcttc agcatctttt   8700

actttcacca gcgtttctgg gtgagcaaaa acaggaaggc aaaatgccgc aaaaaaggga   8760

ataagggcga cacggaaatg ttgaatactc atactcttcc tttttcaata ttattgaagc   8820

atttatcagg gttattgtct catgagcgga tacatatttg aatgtattta gaaaaataaa   8880

caaatagggg ttccgcgcac atttccccga aaagtgccac ctgacgtcta agaaaccatt   8940

attatcatga cattaaccta taaaaatagg cgtatcacga ggccctttcg tcttcaagaa   9000
```

```
<210> SEQ ID NO 34
<211> LENGTH: 8198
<212> TYPE: DNA
<213> ORGANISM: Artificial Sequence
<220> FEATURE:
<223> OTHER INFORMATION: Recombinant plasmid pAPSE10433; beta actin
      hairpin - coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (41)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI site
<220> FEATURE:
<221> NAME/KEY: misc_feature
<222> LOCATION: (498)..(793)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: misc_feature
<222> LOCATION: (1470)..(4812)
<223> OTHER INFORMATION: bacteriophage T7 transcription terminator

<400> SEQUENCE: 34

ttccgaaatt aatacgactc actataggga ggcgatcgcg cacgaggttt ttctgtctag     60

tgagcagtgt ccaacctcaa aagacaacat gtgtgacgac gatgtagcgg ctcttgtcgt    120

agacaatgga tccggtatgt gcaaagccgg tttcgcagga gatgacgcac cccgtgccgt    180

cttcccctcg atcgtcggtc gcccaaggca tcaaggagtc atggtcggta tgggacaaaa    240

ggactcatac gtaggagatg aagcccaaag caaaagaggt atcctcaccc tgaaataccc    300
```

```
catcgaacac ggtatcatca ccaactggga tgagtttaaa ccctctagct gctttacaaa    360
gtactggttc cctttccagc gggatgcttt atctaaacgc aatgagagag gtattcctca    420
ggccacatcg cttcctagtt ccgctgggat ccatcgttgg cggccgaagc cgccattcca    480
tagtgagttc tggcgcgcct catcccagtt ggtgatgata ccgtgttcga tggggtattt    540
cagggtgagg atacctcttt tgctttgggc ttcatctcct acgtatgagt ccttttgtcc    600
cataccgacc atgactcctt gatgccttgg gcgaccgacg atcgagggga agacggcacg    660
gggtgcgtca tctcctgcga aaccggcttt gcacataccg gatccattgt ctacgacaag    720
agccgctaca tcgtcgtcac acatgttgtc ttttgaggtt ggacactgct cactagacag    780
aaaaacctcg tgccggaccg aatacccggt ctgaacgagg gcggccgcgg tacccaagaa    840
gtacttagag ttaattaagg agttcaaaca tgaggatcac ccatgtcgaa gctcccacac    900
cctagcataa ccccttgggg cctctaaacg ggtcttgagg ggttttttgc tgaaaggagg    960
aactatatcc ggatatccac aggacgggtg tggtcgccat gatcgcgtag tcgatagtgg   1020
ctccaagtag cgaagcgagc aggactgggc ggcgggcatg caccattcct tgcggcggcg   1080
gtgctcaacg gcctcaacct actactgggc tgcttcctaa tgcaggagtc gcataaggga   1140
gagcgtcgac cgatgccctt gagagccttc aacccagtca gctccttccg gtgggcgcgg   1200
ggcatgacta tcgtcgccgc acttatgact gtcttcttta tcatgcaact cgtaggacag   1260
gtgccggcag cgctctgggt cattttcggc gaggaccgct ttcgctggag cgcgacgatg   1320
atcggcctgt cgcttgcggt attcggaatc ttgcacgccc tcgctcaagc cttcgtcact   1380
ggtcccgcca ccaaacgttt cggcgagaag caggccatta tcgccggcat ggcggccgac   1440
gcgctgggct acgtcttgct ggcgttcgcc atggtcgtca cagagctgga agcggcagcg   1500
agaattatcc gcgatcgtgg cgcggtgccc gcaggcatga caaacatcgt aaatgccgcg   1560
tttcgtgtgg ccgtggccgc ccaggacgtg tcagcgccgc caccacctgc accgaatcgg   1620
cagcagcgtc gcgcgtcgaa aaagcgcaca ggcggcaaga agcgataagc tgcacgaata   1680
cctgaaaaat gttgaacgcc ccgtgagcgg taactcacag ggcgtcggct aacccccagt   1740
ccaaacctgg gagaaagcgc tcaaaaatga ctctagcgga ttcacgagac attgacacac   1800
cggcctggaa attttccgct gatctgttcg acacccatcc cgagctcgcg ctgcgatcac   1860
gtggctggac gagcgaagac cgccgcgaat tcctcgctca cctgggcaga gaaaatttcc   1920
agggcagcaa gacccgcgac ttcgccagcg cttggatcaa agacccggac acgggagaaa   1980
cacagccgaa gttataccga gttggttcaa aatcgcttgc ccggtgccag tatgttgctc   2040
tgacgcacgc gcagcacgca gccgtgcttg tcctggacat tgatgtgccg agccaccagg   2100
ccggcgggaa aatcgagcac gtaaaccccg aggtctacgc gattttggag cgctgggcac   2160
gcctggaaaa agcgccagct tggatcggcg tgaatccact gagcgggaaa tgccagctca   2220
tctggctcat tgatccggtg tatgccgcag caggcatgag cagcccgaat atgcgcctgc   2280
tggctgcaac gaccgaggaa atgacccgcg ttttcggcgc tgaccaggct tttcacata   2340
ggctgagccg gtggccactg cacgtctccg acgatcccac cgcgtaccgc tggcatgccc   2400
agcacaatcg cgtggatcgc ctagctgatc ttatggaggt tgctcgcatg atctcaggca   2460
cagaaaaacc taaaaaacgc tatgagcagg agttttctag cggacgggca cgtatcgaag   2520
cggcaagaaa agccactgcg gaagcaaaag cacttgccac gcttgaagca agcctgccga   2580
gcgccgctga agcgtctgga gagctgatcg acggcgtccg tgtcctctgg actgctccag   2640
ggcgtgccgc ccgtgatgag acggcttttc gccacgcttt gactgtggga taccagttaa   2700
```

```
aagcggctgg tgagcgccta aaagacacca agatcatcga cgcctacgag cgtgcctaca   2760
ccgtcgctca ggcggtcgga gcagacggcc gtgagcctga tctgccgccg atgcgtgacc   2820
gccagacgat ggcgcgacgt gtgcgcggct acgtcgctaa aggccagcca gtcgtccctg   2880
ctcgtcagac agagacgcag agcagccgag ggcgaaaagc tctggccact atgggaagac   2940
gtggcggtaa aaaggccgca gaacgctgga aagacccaaa cagtgagtac gcccgagcac   3000
agcgagaaaa actagctaag tccagtcaac gacaagctag gaaagctaaa ggaaatcgct   3060
tgaccattgc aggttggttt atgactgttg agggagagac tggctcgtgg cgacaatcaa   3120
tgaagctatg tctgaattta gcgtgtcacg tcagaccgtg aatagagcac ttaagtctgc   3180
gggcattgaa cttccacgag gacgccgtaa agcttcccag taaatgtgcc atctcgtagg   3240
cagaaaacgg ttcccccccgt aggggtctct ctcttggcct cctttctagg tcgggctgat   3300
tgctcttgaa gctctctagg ggggctcaca ccataggcag ataacggttc cccaccggct   3360
cacctcgtaa gcgcacaagg actgctccca atgccgcaag cactcagggc gcaagggctg   3420
ctaaaggaag cggaacacgt agaaagccag tccgcagaaa cggtgctgac cccggatgaa   3480
tgtcagctac tgggctatct ggacaaggga aaacgcaagc gcaaagagaa agcaggtagc   3540
ttgcagtggg cttacatggc gatagctaga ctgggcggtt ttatggacag caagcgaacc   3600
ggaattgcca gctggggcgc cctctggtaa ggttgggaag ccctgcaaag taaactggat   3660
ggctttcttg ccgccaagga tctgatggcg caggggatca agatctgatc aagagacagg   3720
atgaggatcg tttcgcatga ttgaacaaga tggattgcac gcaggttctc cggccgcttg   3780
ggtggagagg ctattcggct atgactgggc acaacagaca atcggctgct ctgatgccgc   3840
cgtgttccgg ctgtcagcgc aggggcgccc ggttcttttt gtcaagaccg acctgtccgg   3900
tgccctgaat gaactccaag acgaggcagc gcggctatcg tggctggcca cgacgggcgt   3960
tccttgcgca gctgtgctcg acgttgtcac tgaagcggga agggactggc tgctattggg   4020
cgaagtgccg gggcaggatc tcctgtcatc tcaccttgct cctgccgaga aagtatccat   4080
catggctgat gcaatgcggc ggctgcatac gcttgatccg gctacctgcc cattcgacca   4140
ccaagcgaaa catcgcatcg agcgagcacg tactcggatg gaagccggtc ttgtcgatca   4200
ggatgatctg gacgaagagc atcaggggct cgcgccagcc gaactgttcg ccaggctcaa   4260
ggcgcggatg cccgacggcg aggatctcgt cgtgacccat ggcgatgcct gcttgccgaa   4320
tatcatggtg gaaaatggcc gcttttctgg attcatcgac tgtggccggc tgggtgtggc   4380
ggaccgctat caggacatag cgttggctac ccgtgatatt gctgaagagc ttggcggcga   4440
atgggctgac cgcttcctcg tgctttacgg tatcgccgct cccgattcgc agcgcatcgc   4500
cttctatcgc cttcttgacg agttcttctg agcgggactc tggggttcgc tagaggatcg   4560
atccttttta acccatcaca tatacctgcc gttcactatt atttagtgaa atgagatatt   4620
atgatatttt ctgaattgtg attaaaaagg caactttatg cccatgcaac agaaactata   4680
aaaaatacag agaatgaaaa gaaacagata gattttttag ttctttaggc ccgtagtctg   4740
caaatccttt tatgattttc tatcaaacaa aagaggaaaa tagaccagtt gcaatccaaa   4800
cgagagtcta acgacgcgag gctggatggc cttccccatt atgattcttc tcgcttccgg   4860
cggcatcggg atgcccgcgt tgcaggccat gctgtccagg caggtagatg acgaccatca   4920
gggacagctt caaggatcgc tcgcggctct taccagccta acttcgatca ttggaccgct   4980
gatcgtcacg gcgatttatg ccgcctcggc gagcacatgg aacgggttgg catggattgt   5040
```

```
aggcgccgcc ctataccttg tctgcctccc cgcgttgcgt cgcggtgcat ggagccgggc   5100
cacctcgacc tgaatggaag ccggcggcac ctcgctaacg gattcaccac tccaagaatt   5160
ggagccaatc aattcttgcg gagaactgtg aatgcgcaaa ccaacccttg gcagaacata   5220
tccatcgcgt ccgccatctc cagcagccgc acgcggcgca tctcgggcag cgttgggtcc   5280
tggccacggg tgcgcatgat cgtgctcctg tcgttgagga cccggctagg ctggcggggt   5340
tgccttactg gttagcagaa tgaatcaccg atacgcgagc gaacgtgaag cgactgctgc   5400
tgcaaaacgt ctgcgacctg agcaacaaca tgaatggtct tcggtttccg tgtttcgtaa   5460
agtctggaaa cgcggaagtc agcgccctgc accattatgt tccggatctg catcgcagga   5520
tgctgctggc taccctgtgg aacacctaca tctgtattaa cgaagcgctg gcattgaccc   5580
tgagtgattt ttctctggtc ccgccgcatc cataccgcca gttgtttacc ctcacaacgt   5640
tccagtaacc gggcatgttc atcatcagta acccgtatcg tgagcatcct ctctcgtttc   5700
atcggtatca ttacccccat gaacagaaat cccccttaca cggaggcatc agtgaccaaa   5760
caggaaaaaa ccgcccttaa catggcccgc tttatcagaa gccagacatt aacgcttctg   5820
gagaaactca acgagctgga cgcggatgaa caggcagaca tctgtgaatc gcttcacgac   5880
cacgctgatg agctttaccg cagctgcctc gcgcgtttcg gtgatgacgg tgaaaacctc   5940
tgacacatgc agctcccgga gacggtcaca gcttgtctgt aagcggatgc cgggagcaga   6000
caagcccgtc agggcgcgtc agcgggtgtt ggcgggtgtc ggggcgcagc catgacccag   6060
tcacgtagcg atagcggagt gtatactggc ttaactatgc ggcatcagag cagattgtac   6120
tgagagtgca ccatatgcgg tgtgaaatac cgcacagatg cgtaaggaga aaataccgca   6180
tcaggcgctc ttccgcttcc tcgctcactg actcgctgcg ctcggtcgtt cggctgcggc   6240
gagcggtatc agctcactca aaggcggtaa tacggttatc cacagaatca ggggataacg   6300
caggaaagaa catgtgagca aaaggccagc aaaaggccag gaaccgtaaa aaggccgcgt   6360
tgctggcgtt tttccatagg ctccgccccc ctgacgagca tcacaaaaat cgacgctcaa   6420
gtcagaggtg gcgaaacccg acaggactat aaagatacca ggcgtttccc cctggaagct   6480
ccctcgtgcg ctctcctgtt ccgaccctgc cgcttaccgg atacctgtcc gcctttctcc   6540
cttcgggaag cgtggcgctt tctcatagct cacgctgtag gtatctcagt tcggtgtagg   6600
tcgttcgctc caagctgggc tgtgtgcacg aaccccccgt tcagcccgac cgctgcgcct   6660
tatccggtaa ctatcgtctt gagtccaacc cggtaagaca cgacttatcg ccactggcag   6720
cagccactgg taacaggatt agcagagcga ggtatgtagg cggtgctaca gagttcttga   6780
agtggtggcc taactacggc tacactagaa ggacagtatt tggtatctgc gctctgctga   6840
agccagttac cttcggaaaa agagttggta gctcttgatc cggcaaacaa accaccgctg   6900
gtagcggtgg tttttttgtt tgcaagcagc agattacgcg cagaaaaaaa ggatctcaag   6960
aagatccttt gatcttttct acggggtctg acgctcagtg gaacgaaaac tcacgttaag   7020
ggattttggt catgagatta tcaaaaagga tcttcaccta gatcctttta aattaaaaat   7080
gaagttttaa atcaatctaa agtatatatg agtaaacttg gtctgacagt taccaatgct   7140
taatcagtga ggcacctatc tcagcgatct gtctatttcg ttcatccata gttgcctgac   7200
tccccgtcgt gtagataact acgatacggg agggcttacc atctggcccc agtgctgcaa   7260
tgataccgcg agacccacgc tcaccggctc cagatttatc agcaataaac cagccagccg   7320
gaagggccga gcgcagaagt ggtcctgcaa ctttatccgc ctccatccag tctattaatt   7380
gttgccggga agctagagta agtagttcgc cagttaatag tttgcgcaac gttgttgcca   7440
```

```
ttgctgcagg catcgtggtg tcacgctcgt cgtttggtat ggcttcattc agctccggtt   7500

cccaacgatc aaggcgagtt acatgatccc ccatgttgtg caaaaaagcg gttagctcct   7560

tcggtcctcc gatcgttgtc agaagtaagt tggccgcagt gttatcactc atggttatgg   7620

cagcactgca taattctctt actgtcatgc catccgtaag atgcttttct gtgactggtg   7680

agtactcaac caagtcattc tgagaatagt gtatgcggcg accgagttgc tcttgcccgg   7740

cgtcaacacg ggataatacc gcgccacata gcagaacttt aaaagtgctc atcattggaa   7800

aacgttcttc ggggcgaaaa ctctcaagga tcttaccgct gttgagatcc agttcgatgt   7860

aacccactcg tgcacccaac tgatcttcag catcttttac tttcaccagc gtttctgggt   7920

gagcaaaaac aggaaggcaa aatgccgcaa aaaagggaat aagggcgaca cggaaatgtt   7980

gaatactcat actcttcctt tttcaatatt attgaagcat ttatcagggt tattgtctca   8040

tgagcggata catatttgaa tgtatttaga aaaataaaca aataggggtt ccgcgcacat   8100

ttccccgaaa agtgccacct gacgtctaag aaaccattat tatcatgaca ttaacctata   8160

aaaataggcg tatcacgagg ccctttcgtc ttcaagaa                           8198
```

```
<210> SEQ ID NO 35
<211> LENGTH: 9327
<212> TYPE: DNA
<213> ORGANISM: Artificial Sequence
<220> FEATURE:
<223> OTHER INFORMATION: Recombinant plasmid pAPSE10434; beta actin
      hairpin + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1602)..(1620)
<223> OTHER INFORMATION: bacteriophage T7 gene 1 promoter
<220> FEATURE:
<221> NAME/KEY: gene
<222> LOCATION: (1693)..(2082)
<223> OTHER INFORMATION: bacteriophage MS2 coat protein gene
<220> FEATURE:
<221> NAME/KEY: terminator
<222> LOCATION: (2115)..(2162)
<223> OTHER INFORMATION: bacteriophage T7 transcription terminator
```

```
<220> FEATURE:
<221> NAME/KEY: misc_feature
<222> LOCATION: (2599)..(5941)
<223> OTHER INFORMATION: synthetic DNA (SEQ ID NO: 30)

<400> SEQUENCE: 35

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

catgtgtgac gacgatgtag cggctcttgt cgtagacaat ggatccggta tgtgcaaagc    480

cggtttcgca ggagatgacg caccccgtgc cgtcttcccc tcgatcgtcg gtcgcccaag    540

gcatcaagga gtcatggtcg gtatgggaca aaaggactca tacgtaggag atgaagccca    600

aagcaaaaga ggtatcctca ccctgaaata ccccatcgaa cacggtatca tcaccaactg    660

ggatgagttt aaaccctcta gctgctttac aaagtactgg ttccctttcc agcgggatgc    720

tttatctaaa cgcaatgaga gaggtattcc tcaggccaca tcgcttccta gttccgctgg    780

gatccatcgt tggcggccga agccgccatt ccatagtgag ttctggcgcg cctcatccca    840

gttggtgatg ataccgtgtt cgatggggta tttcagggtg aggatacctc ttttgctttg    900

ggcttcatct cctacgtatg agtccttttg tcccataccg accatgactc cttgatgcct    960

tgggcgaccg acgatcgagg ggaagacggc acggggtgcg tcatctcctg cgaaaccggc   1020

tttgcacata ccggatccat tgtctacgac aagagccgct acatcgtcgt cacacatgtt   1080

gtcttttgag gttggacact gctcactaga cagaaaaacc tcgtgccgga ccgaataccc   1140

ggtctgaacg agggcggccg cggtacccaa gaagtactta gagttaatta aggagttcaa   1200

acatgaggat cacccatgtc gaagctccca caccctagca taaccccttg gggcctctaa   1260

acgggtcttg aggggttttt tgctgaaagg aggaactata tccgcacagg acgggtgtgg   1320

tcgccatgat cgcgtagtcg atagtggctc caagtagcga agcgagcagg actgggcggc   1380

gggcatgcat cgtccattcc gacagcatcg ccagtcacta tggcgtgctg ctagcgctat   1440

atgcgttgat gcaatttcta tgcgcacccg ttctcggagc actgtccgac cgctttggcc   1500

gccgcccagt cctgctcgct tcgctacttg gagccactat cgactacgcg atcatggcga   1560

ccacacccgt cctgtggatc cagatctcga tcccgcgaaa ttaatacgac tcactatagg   1620

gagaccacaa cggtttccct ctagatcaca agtttgtaca aaaaagcagg ctaagaagga   1680

gatatacata tggcgtctaa ctttacccaa ttcgttctgg ttgataacgg cggtacgggt   1740

gacgttaccg tagctccgtc caacttcgcc aacggtgttg cggaatggat tagctctaac   1800

agccgctctc aggcctacaa agtcacgtgc tccgttcgtc agtctagcgc gcagaatcgc   1860

aaatacacca tcaaagttga agtaccgaaa gtcgcaacgc agaccgtagg cggcgtagaa   1920

ctcccagttg cggcctggcg ctcttacctc aacatggaac tgactattcc gatttttgcg   1980

acgaactccg actgcgaact gattgttaag gcaatgcagg gcctgctgaa agacggtaat   2040

ccgatcccat ctgcaatcgc tgctaactct ggcatttact aataagcgga cgcgctgcca   2100

ccgctgagca ataactagca taaccccttg gggcctctaa acgggtcttg aggggttttt   2160
```

```
tgctgaaagg aggaactata tccggcatgc accattcctt gcggcggcgg tgctcaacgg   2220
cctcaaccta ctactgggct gcttcctaat gcaggagtcg cataagggag agcgtcgacc   2280
gatgcccttg agagccttca acccagtcag ctccttccgg tgggcgcggg gcatgactat   2340
cgtcgccgca cttatgactg tcttctttat catgcaactc gtaggacagg tgccggcagc   2400
gctctgggtc attttcggcg aggaccgctt tcgctggagc gcgacgatga tcggcctgtc   2460
gcttgcggta ttcggaatct tgcacgccct cgctcaagcc ttcgtcactg gtcccgccac   2520
caaacgtttc ggcgagaagc aggccattat cgccggcatg gcggccgacg cgctgggcta   2580
cgtcttgctg gcgttcgcca tggtcgtcac agagctggaa gcggcagcga gaattatccg   2640
cgatcgtggc gcggtgcccg caggcatgac aaacatcgta aatgccgcgt ttcgtgtggc   2700
cgtggccgcc caggacgtgt cagcgccgcc accacctgca ccgaatcggc agcagcgtcg   2760
cgcgtcgaaa aagcgcacag gcggcaagaa gcgataagct gcacgaatac ctgaaaaatg   2820
ttgaacgccc cgtgagcggt aactcacagg gcgtcggcta acccccagtc caaacctggg   2880
agaaagcgct caaaaatgac tctagcggat tcacgagaca ttgacacacc ggcctggaaa   2940
ttttccgctg atctgttcga cacccatccc gagctcgcgc tgcgatcacg tggctggacg   3000
agcgaagacc gccgcgaatt cctcgctcac ctgggcagag aaaatttcca gggcagcaag   3060
acccgcgact tcgccagcgc ttggatcaaa gacccggaca cgggagaaac acagccgaag   3120
ttataccgag ttggttcaaa atcgcttgcc cggtgccagt atgttgctct gacgcacgcg   3180
cagcacgcag ccgtgcttgt cctggacatt gatgtgccga gccaccaggc cggcgggaaa   3240
atcgagcacg taaaccccga ggtctacgcg attttggagc gctgggcacg cctggaaaaa   3300
gcgccagctt ggatcggcgt gaatccactg agcgggaaat gccagctcat ctggctcatt   3360
gatccggtgt atgccgcagc aggcatgagc agcccgaata tgcgcctgct ggctgcaacg   3420
accgaggaaa tgacccgcgt tttcggcgct gaccaggctt tttcacatag gctgagccgg   3480
tggccactgc acgtctccga cgatcccacc gcgtaccgct ggcatgccca gcacaatcgc   3540
gtggatcgcc tagctgatct tatggaggtt gctcgcatga tctcaggcac agaaaaacct   3600
aaaaaacgct atgagcagga gttttctagc ggacgggcac gtatcgaagc ggcaagaaaa   3660
gccactgcgg aagcaaaagc acttgccacg cttgaagcaa gcctgccgag cgccgctgaa   3720
gcgtctggag agctgatcga cggcgtccgt gtcctctgga ctgctccagg gcgtgccgcc   3780
cgtgatgaga cggcttttcg ccacgctttg actgtgggat accagttaaa agcggctggt   3840
gagcgcctaa aagacaccaa gatcatcgac gcctacgagc gtgcctacac cgtcgctcag   3900
gcggtcggag cagacggccg tgagcctgat ctgccgccga tgcgtgaccg ccagacgatg   3960
gcgcgacgtg tgcgcggcta cgtcgctaaa ggccagccag tcgtccctgc tcgtcagaca   4020
gagacgcaga gcagccgagg gcgaaaagct ctggccacta tgggaagacg tggcggtaaa   4080
aaggccgcag aacgctggaa agacccaaac agtgagtacg cccgagcaca gcgagaaaaa   4140
ctagctaagt ccagtcaacg acaagctagg aaagctaaag gaaatcgctt gaccattgca   4200
ggttggttta tgactgttga gggagagact ggctcgtggc gacaatcaat gaagctatgt   4260
ctgaatttag cgtgtcacgt cagaccgtga atagagcact taagtctgcg ggcattgaac   4320
ttccacgagg acgccgtaaa gcttcccagt aaatgtgcca tctcgtaggc agaaaacggt   4380
tcccccgta ggggtctctc tcttggcctc ctttctaggt cgggctgatt gctcttgaag   4440
ctctctaggg gggctcacac cataggcaga taacggttcc ccaccggctc acctcgtaag   4500
cgcacaagga ctgctcccaa tgccgcaagc actcagggcg caagggctgc taaaggaagc   4560
```

```
ggaacacgta gaaagccagt ccgcagaaac ggtgctgacc ccggatgaat gtcagctact   4620
gggctatctg gacaagggaa aacgcaagcg caaagagaaa gcaggtagct tgcagtgggc   4680
ttacatggcg atagctagac tggcggttt tatggacagc aagcgaaccg gaattgccag   4740
ctggggcgcc ctctggtaag gttgggaagc cctgcaaagt aaactggatg gctttcttgc   4800
cgccaaggat ctgatggcgc aggggatcaa gatctgatca agagacagga tgaggatcgt   4860
ttcgcatgat tgaacaagat ggattgcacg caggttctcc ggccgcttgg gtggagaggc   4920
tattcggcta tgactgggca caacagacaa tcggctgctc tgatgccgcc gtgttccggc   4980
tgtcagcgca ggggcgcccg gttctttttg tcaagaccga cctgtccggt gccctgaatg   5040
aactccaaga cgaggcagcg cggctatcgt ggctggccac gacgggcgtt ccttgcgcag   5100
ctgtgctcga cgttgtcact gaagcgggaa gggactggct gctattgggc gaagtgccgg   5160
ggcaggatct cctgtcatct caccttgctc ctgccgagaa agtatccatc atggctgatg   5220
caatgcggcg gctgcatacg cttgatccgg ctacctgccc attcgaccac caagcgaaac   5280
atcgcatcga gcgagcacgt actcggatgg aagccggtct tgtcgatcag gatgatctgg   5340
acgaagagca tcaggggctc gcgccagccg aactgttcgc caggctcaag gcgcggatgc   5400
ccgacggcga ggatctcgtc gtgacccatg gcgatgcctg cttgccgaat atcatggtgg   5460
aaaatggccg cttttctgga ttcatcgact gtggccggct gggtgtggcg gaccgctatc   5520
aggacatagc gttggctacc cgtgatattg ctgaagagct tggcggcgaa tgggctgacc   5580
gcttcctcgt gctttacggt atcgccgctc ccgattcgca gcgcatcgcc ttctatcgcc   5640
ttcttgacga gttcttctga gcgggactct ggggttcgct agaggatcga tcctttttaa   5700
cccatcacat atacctgccg ttcactatta tttagtgaaa tgagatatta tgatattttc   5760
tgaattgtga ttaaaaaggc aactttatgc ccatgcaaca gaaactataa aaaatacaga   5820
gaatgaaaag aaacagatag attttttagt tctttaggcc cgtagtctgc aaatcctttt   5880
atgattttct atcaaacaaa agaggaaaat agaccagttg caatccaaac gagagtctaa   5940
cgacgcgagg ctggatggcc ttccccatta tgattcttct cgcttccggc ggcatcggga   6000
tgcccgcgtt gcaggccatg ctgtccaggc aggtagatga cgaccatcag ggacagcttc   6060
aaggatcgct cgcggctctt accagcctaa cttcgatcat tggaccgctg atcgtcacgg   6120
cgatttatgc cgcctcggcg agcacatgga acgggttggc atggattgta ggcgccgccc   6180
tataccttgt ctgcctcccc gcgttgcgtc gcggtgcatg gagccgggcc acctcgacct   6240
gaatggaagc cggcggcacc tcgctaacgg attcaccact ccaagaattg gagccaatca   6300
attcttgcgg agaactgtga atgcgcaaac caacccttgg cagaacatat ccatcgcgtc   6360
cgccatctcc agcagccgca cgcggcgcat ctcgggcagc gttgggtcct ggccacgggt   6420
gcgcatgatc gtgctcctgt cgttgaggac ccggctaggc tggcggggtt gccttactgg   6480
ttagcagaat gaatcaccga tacgcgagcg aacgtgaagc gactgctgct gcaaaacgtc   6540
tgcgacctga gcaacaacat gaatggtctt cggtttccgt gtttcgtaaa gtctggaaac   6600
gcggaagtca gcgccctgca ccattatgtt ccggatctgc atcgcaggat gctgctggct   6660
accctgtgga acacctacat ctgtattaac gaagcgctgg cattgaccct gagtgatttt   6720
tctctggtcc cgccgcatcc ataccgccag ttgtttaccc tcacaacgtt ccagtaaccg   6780
ggcatgttca tcatcagtaa cccgtatcgt gagcatcctc tctcgtttca tcggtatcat   6840
tacccccatg aacagaaatc ccccttacac ggaggcatca gtgaccaaac aggaaaaaac   6900
```

```
cgccccttaac atggcccgct ttatcagaag ccagacatta acgcttctgg agaaactcaa   6960
cgagctggac gcggatgaac aggcagacat ctgtgaatcg cttcacgacc acgctgatga   7020
gctttaccgc agctgcctcg cgcgtttcgg tgatgacggt gaaaacctct gacacatgca   7080
gctcccggag acggtcacag cttgtctgta agcggatgcc gggagcagac aagcccgtca   7140
gggcgcgtca gcgggtgttg gcgggtgtcg gggcgcagcc atgacccagt cacgtagcga   7200
tagcggagtg tatactggct taactatgcg gcatcagagc agattgtact gagagtgcac   7260
catatgcggt gtgaaatacc gcacagatgc gtaaggagaa aataccgcat caggcgctct   7320
tccgcttcct cgctcactga ctcgctgcgc tcggtcgttc ggctgcggcg agcggtatca   7380
gctcactcaa aggcggtaat acggttatcc acagaatcag gggataacgc aggaaagaac   7440
atgtgagcaa aaggccagca aaaggccagg aaccgtaaaa aggccgcgtt gctggcgttt   7500
ttccataggc tccgcccccc tgacgagcat cacaaaaatc gacgctcaag tcagaggtgg   7560
cgaaacccga caggactata aagataccag gcgtttcccc ctggaagctc cctcgtgcgc   7620
tctcctgttc cgaccctgcc gcttaccgga tacctgtccg cctttctccc ttcgggaagc   7680
gtggcgcttt ctcatagctc acgctgtagg tatctcagtt cggtgtaggt cgttcgctcc   7740
aagctgggct gtgtgcacga accccccgtt cagcccgacc gctgcgcctt atccggtaac   7800
tatcgtcttg agtccaaccc ggtaagacac gacttatcgc cactggcagc agccactggt   7860
aacaggatta gcagagcgag gtatgtaggc ggtgctacag agttcttgaa gtggtggcct   7920
aactacggct acactagaag gacagtattt ggtatctgcg ctctgctgaa gccagttacc   7980
ttcggaaaaa gagttggtag ctcttgatcc ggcaaacaaa ccaccgctgg tagcggtggt   8040
tttttgttt gcaagcagca gattacgcgc agaaaaaaag gatctcaaga agatcctttg   8100
atcttttcta cggggtctga cgctcagtgg aacgaaaact cacgttaagg gattttggtc   8160
atgagattat caaaaaggat cttcacctag atccttttaa attaaaaatg aagttttaaa   8220
tcaatctaaa gtatatatga gtaaacttgg tctgacagtt accaatgctt aatcagtgag   8280
gcacctatct cagcgatctg tctatttcgt tcatccatag ttgcctgact ccccgtcgtg   8340
tagataacta cgatacggga gggcttacca tctggcccca gtgctgcaat gataccgcga   8400
gacccacgct caccggctcc agatttatca gcaataaacc agccagccgg aagggccgag   8460
cgcagaagtg gtcctgcaac tttatccgcc tccatccagt ctattaattg ttgccgggaa   8520
gctagagtaa gtagttcgcc agttaatagt ttgcgcaacg ttgttgccat tgctgcaggc   8580
atcgtggtgt cacgctcgtc gtttggtatg gcttcattca gctccggttc ccaacgatca   8640
aggcgagtta catgatcccc catgttgtgc aaaaaagcgg ttagctcctt cggtcctccg   8700
atcgttgtca gaagtaagtt ggccgcagtg ttatcactca tggttatggc agcactgcat   8760
aattctctta ctgtcatgcc atccgtaaga tgcttttctg tgactggtga gtactcaacc   8820
aagtcattct gagaatagtg tatgcggcga ccgagttgct cttgcccggc gtcaacacgg   8880
gataataccg cgccacatag cagaacttta aaagtgctca tcattggaaa acgttcttcg   8940
gggcgaaaac tctcaaggat cttaccgctg ttgagatcca gttcgatgta acccactcgt   9000
gcacccaact gatcttcagc atcttttact ttcaccagcg tttctgggtg agcaaaaaca   9060
ggaaggcaaa atgccgcaaa aaagggaata agggcgacac ggaaatgttg aatactcata   9120
ctcttccttt ttcaatatta ttgaagcatt tatcagggtt attgtctcat gagcggatac   9180
atatttgaat gtatttagaa aaataaacaa ataggggttc cgcgcacatt tccccgaaaa   9240
gtgccacctg acgtctaaga aaccattatt atcatgacat taacctataa aaataggcgt   9300
```

atcacgaggc cctttcgtct tcaagaa 9327

<210> SEQ ID NO 36
<211> LENGTH: 8531
<212> TYPE: DNA
<213> ORGANISM: Artificial Sequence
<220> FEATURE:
<223> OTHER INFORMATION: Recombinant plasmid pAPSE10435; beta actin hairpin - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1803)..(5145)
<223> OTHER INFORMATION: synthetic DNA (SEQ ID NO: 30)

<400> SEQUENCE: 36
ttctcatgtt tgacagctta tcatcgataa gctttaatgc ggtagtttat cacagttaaa 60
ttgctaacgc agtcaggcac cgtgtatgaa atctaacaat gcgctcatcg tcatcctcgg 120
caccgtcacc ctggatgctg taggcatagg cttggttatg ccggtactgc cgggcctctt 180
gcgggatgaa ttcagatctc gatcccgcga aattaatacg actcactata gggagaccac 240
aacggtttcc ctctagatca caagtttgta caaaaaagca ggctaagaag gagatataca 300
tacgccggcc attcaaacat gaggattacc catgtattta aatacccatg tccaggcgcg 360
ctccgcgatc gcgcacgagg tttttctgtc tagtgagcag tgtccaacct caaaagacaa 420
catgtgtgac gacgatgtag cggctcttgt cgtagacaat ggatccggta tgtgcaaagc 480
cggtttcgca ggagatgacg caccccgtgc cgtcttcccc tcgatcgtcg gtcgcccaag 540
gcatcaagga gtcatggtcg gtatgggaca aaaggactca tacgtaggag atgaagccca 600
aagcaaaaga ggtatcctca ccctgaaata ccccatcgaa cacggtatca tcaccaactg 660
ggatgagttt aaaccctcta gctgctttac aaagtactgg ttccctttcc agcgggatgc 720
tttatctaaa cgcaatgaga gaggtattcc tcaggccaca tcgcttccta gttccgctgg 780
gatccatcgt tggcggccga agccgccatt ccatagtgag ttctggcgcg cctcatccca 840
gttggtgatg ataccgtgtt cgatggggta tttcagggtg aggatacctc ttttgctttg 900

```
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg ggcctctaa    1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcaccatt ccttgcggcg gcggtgctca acggcctcaa cctactactg   1440
ggctgcttcc taatgcagga gtcgcataag ggagagcgtc gaccgatgcc cttgagagcc   1500
ttcaacccag tcagctcctt ccggtgggcg cggggcatga ctatcgtcgc cgcacttatg   1560
actgtcttct ttatcatgca actcgtagga caggtgccgg cagcgctctg ggtcattttc   1620
ggcgaggacc gctttcgctg gagcgcgacg atgatcggcc tgtcgcttgc ggtattcgga   1680
atcttgcacg ccctcgctca agccttcgtc actggtcccg ccaccaaacg tttcggcgag   1740
aagcaggcca ttatcgccgg catggcggcc gacgcgctgg gctacgtctt gctggcgttc   1800
gccatggtcg tcacagagct ggaagcggca gcgagaatta tccgcgatcg tggcgcggtg   1860
cccgcaggca tgacaaacat cgtaaatgcc gcgtttcgtg tggccgtggc cgcccaggac   1920
gtgtcagcgc cgccaccacc tgcaccgaat cggcagcagc gtcgcgcgtc gaaaaagcgc   1980
acaggcggca agaagcgata agctgcacga atacctgaaa aatgttgaac gccccgtgag   2040
cggtaactca cagggcgtcg gctaaccccc agtccaaacc tgggagaaag cgctcaaaaa   2100
tgactctagc ggattcacga gacattgaca caccggcctg gaaattttcc gctgatctgt   2160
tcgacaccca tcccgagctc gcgctgcgat cacgtggctg gacgagcgaa gaccgccgcg   2220
aattcctcgc tcacctgggc agagaaaatt tccagggcag caagacccgc gacttcgcca   2280
gcgcttggat caaagacccg gacacgggag aaacacagcc gaagttatac cgagttggtt   2340
caaaatcgct tgcccggtgc cagtatgttg ctctgacgca cgcgcagcac gcagccgtgc   2400
ttgtcctgga cattgatgtg ccgagccacc aggccggcgg gaaaatcgag cacgtaaacc   2460
ccgaggtcta cgcgattttg gagcgctggg cacgcctgga aaaagcgcca gcttggatcg   2520
gcgtgaatcc actgagcggg aaatgccagc tcatctggct cattgatccg gtgtatgccg   2580
cagcaggcat gagcagcccg aatatgcgcc tgctggctgc aacgaccgag gaaatgaccc   2640
gcgttttcgg cgctgaccag gctttttcac ataggctgag ccggtggcca ctgcacgtct   2700
ccgacgatcc caccgcgtac cgctggcatg cccagcacaa tcgcgtggat cgcctagctg   2760
atcttatgga ggttgctcgc atgatctcag gcacagaaaa acctaaaaaa cgctatgagc   2820
aggagttttc tagcggacgg gcacgtatcg aagcggcaag aaaagccact gcggaagcaa   2880
aagcacttgc cacgcttgaa gcaagcctgc cgagcgccgc tgaagcgtct ggagagctga   2940
tcgacggcgt ccgtgtcctc tggactgctc cagggcgtgc cgcccgtgat gagacggctt   3000
ttcgccacgc tttgactgtg ggataccagt taaaagcggc tggtgagcgc ctaaaagaca   3060
ccaagatcat cgacgcctac gagcgtgcct acaccgtcgc tcaggcggtc ggagcagacg   3120
gccgtgagcc tgatctgccg ccgatgcgtg accgccagac gatggcgcga cgtgtgcgcg   3180
gctacgtcgc taaaggccag ccagtcgtcc ctgctcgtca gacagagacg cagagcagcc   3240
```

```
gagggcgaaa agctctggcc actatgggaa gacgtggcgg taaaaaggcc gcagaacgct   3300
ggaaagaccc aaacagtgag tacgcccgag cacagcgaga aaaactagct aagtccagtc   3360
aacgacaagc taggaaagct aaaggaaatc gcttgaccat tgcaggttgg tttatgactg   3420
ttgagggaga gactggctcg tggcgacaat caatgaagct atgtctgaat ttagcgtgtc   3480
acgtcagacc gtgaatagag cacttaagtc tgcgggcatt gaacttccac gaggacgccg   3540
taaagcttcc cagtaaatgt gccatctcgt aggcagaaaa cggttccccc cgtaggggtc   3600
tctctcttgg cctcctttct aggtcgggct gattgctctt gaagctctct agggggggctc   3660
acaccatagg cagataacgg ttccccaccg gctcacctcg taagcgcaca aggactgctc   3720
ccaatgccgc aagcactcag ggcgcaaggg ctgctaaagg aagcggaaca cgtagaaagc   3780
cagtccgcag aaacggtgct gaccccggat gaatgtcagc tactgggcta tctggacaag   3840
ggaaaacgca agcgcaaaga gaaagcaggt agcttgcagt gggcttacat ggcgatagct   3900
agactgggcg gttttatgga cagcaagcga accggaattg ccagctgggg cgccctctgg   3960
taaggttggg aagccctgca aagtaaactg gatggctttc ttgccgccaa ggatctgatg   4020
gcgcagggga tcaagatctg atcaagagac aggatgagga tcgtttcgca tgattgaaca   4080
agatggattg cacgcaggtt ctccggccgc ttgggtggag aggctattcg gctatgactg   4140
ggcacaacag acaatcggct gctctgatgc cgccgtgttc cggctgtcag cgcaggggcg   4200
cccggttctt tttgtcaaga ccgacctgtc cggtgccctg aatgaactcc aagacgaggc   4260
agcgcggcta tcgtggctgg ccacgacggg cgttccttgc gcagctgtgc tcgacgttgt   4320
cactgaagcg ggaagggact ggctgctatt gggcgaagtg ccggggcagg atctcctgtc   4380
atctcacctt gctcctgccg agaaagtatc catcatggct gatgcaatgc ggcggctgca   4440
tacgcttgat ccggctacct gcccattcga ccaccaagcg aaacatcgca tcgagcgagc   4500
acgtactcgg atggaagccg gtcttgtcga tcaggatgat ctggacgaag agcatcaggg   4560
gctcgcgcca gccgaactgt tcgccaggct caaggcgcgg atgcccgacg gcgaggatct   4620
cgtcgtgacc catggcgatg cctgcttgcc gaatatcatg gtggaaaatg gccgcttttc   4680
tggattcatc gactgtggcc ggctgggtgt ggcggaccgc tatcaggaca tagcgttggc   4740
tacccgtgat attgctgaag agcttggcgg cgaatgggct gaccgcttcc tcgtgcttta   4800
cggtatcgcc gctcccgatt cgcagcgcat cgccttctat cgccttcttg acgagttctt   4860
ctgagcggga ctctggggtt cgctagagga tcgatccttt ttaacccatc acatatacct   4920
gccgttcact attatttagt gaaatgagat attatgatat tttctgaatt gtgattaaaa   4980
aggcaacttt atgcccatgc aacagaaact ataaaaaata cagagaatga aaagaaacag   5040
atagattttt tagttcttta ggcccgtagt ctgcaaatcc ttttatgatt ttctatcaaa   5100
caaaagagga aaatagacca gttgcaatcc aaacgagagt ctaacgacgc gaggctggat   5160
ggccttcccc attatgattc ttctcgcttc cggcggcatc gggatgcccg cgttgcaggc   5220
catgctgtcc aggcaggtag atgacgacca tcagggacag cttcaaggat cgctcgcggc   5280
tcttaccagc ctaacttcga tcattggacc gctgatcgtc acggcgattt atgccgcctc   5340
ggcgagcaca tggaacgggt tggcatggat tgtaggcgcc gccctatacc ttgtctgcct   5400
ccccgcgttg cgtcgcggtg catggagccg ggccacctcg acctgaatgg aagccggcgg   5460
cacctcgcta acggattcac cactccaaga attggagcca atcaattctt gcggagaact   5520
gtgaatgcgc aaaccaaccc ttggcagaac atatccatcg cgtccgccat ctccagcagc   5580
cgcacgcggc gcatctcggg cagcgttggg tcctggccac gggtgcgcat gatcgtgctc   5640
```

```
ctgtcgttga ggacccggct aggctggcgg ggttgcctta ctggttagca gaatgaatca   5700
ccgatacgcg agcgaacgtg aagcgactgc tgctgcaaaa cgtctgcgac ctgagcaaca   5760
acatgaatgg tcttcggttt ccgtgtttcg taaagtctgg aaacgcggaa gtcagcgccc   5820
tgcaccatta tgttccggat ctgcatcgca ggatgctgct ggctaccctg tggaacacct   5880
acatctgtat taacgaagcg ctggcattga ccctgagtga tttttctctg gtcccgccgc   5940
atccataccg ccagttgttt accctcacaa cgttccagta accgggcatg ttcatcatca   6000
gtaacccgta tcgtgagcat cctctctcgt ttcatcggta tcattacccc catgaacaga   6060
aatccccctt acacggaggc atcagtgacc aaacaggaaa aaaccgccct taacatggcc   6120
cgctttatca gaagccagac attaacgctt ctggagaaac tcaacgagct ggacgcggat   6180
gaacaggcag acatctgtga atcgcttcac gaccacgctg atgagcttta ccgcagctgc   6240
ctcgcgcgtt tcggtgatga cggtgaaaac ctctgacaca tgcagctccc ggagacggtc   6300
acagcttgtc tgtaagcgga tgccgggagc agacaagccc gtcagggcgc gtcagcgggt   6360
gttggcgggt gtcggggcgc agccatgacc cagtcacgta gcgatagcgg agtgtatact   6420
ggcttaacta tgcggcatca gagcagattg tactgagagt gcaccatatg cggtgtgaaa   6480
taccgcacag atgcgtaagg agaaaatacc gcatcaggcg ctcttccgct tcctcgctca   6540
ctgactcgct gcgctcggtc gttcggctgc ggcgagcggt atcagctcac tcaaaggcgg   6600
taatacggtt atccacagaa tcaggggata acgcaggaaa gaacatgtga gcaaaaggcc   6660
agcaaaaggc caggaaccgt aaaaaggccg cgttgctggc gtttttccat aggctccgcc   6720
cccctgacga gcatcacaaa aatcgacgct caagtcagag gtggcgaaac ccgacaggac   6780
tataaagata ccaggcgttt ccccctggaa gctccctcgt gcgctctcct gttccgaccc   6840
tgccgcttac cggatacctg tccgcctttc tcccttcggg aagcgtggcg ctttctcata   6900
gctcacgctg taggtatctc agttcggtgt aggtcgttcg ctccaagctg ggctgtgtgc   6960
acgaaccccc cgttcagccc gaccgctgcg ccttatccgg taactatcgt cttgagtcca   7020
acccggtaag acacgactta tcgccactgg cagcagccac tggtaacagg attagcagag   7080
cgaggtatgt aggcggtgct acagagttct tgaagtggtg gcctaactac ggctacacta   7140
gaaggacagt atttggtatc tgcgctctgc tgaagccagt taccttcgga aaaagagttg   7200
gtagctcttg atccggcaaa caaaccaccg ctggtagcgg tggttttttt gtttgcaagc   7260
agcagattac gcgcagaaaa aaaggatctc aagaagatcc tttgatcttt tctacggggt   7320
ctgacgctca gtggaacgaa aactcacgtt aagggatttt ggtcatgaga ttatcaaaaa   7380
ggatcttcac ctagatcctt ttaaattaaa aatgaagttt taaatcaatc taaagtatat   7440
atgagtaaac ttggtctgac agttaccaat gcttaatcag tgaggcacct atctcagcga   7500
tctgtctatt tcgttcatcc atagttgcct gactccccgt cgtgtagata actacgatac   7560
gggagggctt accatctggc cccagtgctg caatgatacc gcgagaccca cgctcaccgg   7620
ctccagattt atcagcaata aaccagccag ccggaagggc cgagcgcaga agtggtcctg   7680
caactttatc cgcctccatc cagtctatta attgttgccg ggaagctaga gtaagtagtt   7740
cgccagttaa tagtttgcgc aacgttgttg ccattgctgc aggcatcgtg gtgtcacgct   7800
cgtcgtttgg tatggcttca ttcagctccg gttcccaacg atcaaggcga gttacatgat   7860
cccccatgtt gtgcaaaaaa gcggttagct ccttcggtcc tccgatcgtt gtcagaagta   7920
agttggccgc agtgttatca ctcatggtta tggcagcact gcataattct cttactgtca   7980
```

```
tgccatccgt aagatgcttt tctgtgactg gtgagtactc aaccaagtca ttctgagaat   8040

agtgtatgcg gcgaccgagt tgctcttgcc cggcgtcaac acgggataat accgcgccac   8100

atagcagaac tttaaaagtg ctcatcattg gaaaacgttc ttcggggcga aaactctcaa   8160

ggatcttacc gctgttgaga tccagttcga tgtaacccac tcgtgcaccc aactgatctt   8220

cagcatcttt tactttcacc agcgtttctg ggtgagcaaa aacaggaagg caaaatgccg   8280

caaaaaaggg aataagggcg acacggaaat gttgaatact catactcttc ctttttcaat   8340

attattgaag catttatcag ggttattgtc tcatgagcgg atacatattt gaatgtattt   8400

agaaaaataa acaaataggg gttccgcgca catttccccg aaaagtgcca cctgacgtct   8460

aagaaaccat tattatcatg acattaacct ataaaaatag gcgtatcacg aggccctttc   8520

gtcttcaaga a                                                        8531
```

<210> SEQ ID NO 37
<211> LENGTH: 9520
<212> TYPE: DNA
<213> ORGANISM: Artificial Sequence
<220> FEATURE:
<223> OTHER INFORMATION: Recombinant plasmid pAPSE10436; beta actin hairpin + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (665)..(672)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator
<220> FEATURE:
<221> NAME/KEY: misc_feature
<222> LOCATION: (2792)..(6134)

<223> OTHER INFORMATION: synthetic DNA (SEQ ID NO: 30)

<400> SEQUENCE: 37

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatgaa ttcagatctc gatcccgcga aattaatacg actcactata gggagaccac    240
aacggtttcc ctctagatca caagtttgta caaaaaagca ggctaagaag gagatataca    300
tacgccggcc attcaaacat gaggattacc catgtattta aatacccatg tccaggcgcg    360
ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaacatga ggatcaccca tgtcgccaca tcgcttccta gttccgctgg    780
gatccatcgt tggcggccga agccgccatt ccatagtgag ttctggcgcg cctcatccca    840
gttggtgatg ataccgtgtt cgatggggta tttcagggtg aggatacctc ttttgctttg    900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg gggcctctaa   1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg tggatccaga tctcgatccc gcgaaattaa tacgactcac   1620
tatagggaga ccacaacggt ttccctctag atcacaagtt tgtacaaaaa agcaggctaa   1680
gaaggagata tacatatggc gtctaacttt acccaattcg ttctggttga taacggcggt   1740
acgggtgacg ttaccgtagc tccgtccaac ttcgccaacg gtgttgcgga atggattagc   1800
tctaacagcc gctctcaggc ctacaaagtc acgtgctccg ttcgtcagtc tagcgcgcag   1860
aatcgcaaat acaccatcaa agttgaagta ccgaaagtcg caacgcagac cgtaggcggc   1920
gtagaactcc cagttgcggc ctggcgctct tacctcaaca tggaactgac tattccgatt   1980
tttgcgacga actccgactg cgaactgatt gttaaggcaa tgcagggcct gctgaaagac   2040
ggtaatccga tcccatctgc aatcgctgct aactctggca tttactaata agcggacgcg   2100
ctgccaccgc tgagcaataa ctagcataac cccttggggc ctctaaacgg gtcttgaggg   2160
gttttttgct gaaaggagga actatatccg gcatgcatcg tccattccga cagcatcgcc   2220
agtcactatg gcgtgctgct agcgctatat gcgttgatgc aatttctatg cgcacccgtt   2280
```

```
ctcggagcac tgtccgaccg ctttggccgc cgcccagtcc tgctcgcttc gctacttgga   2340
gccactatcg actacgcgat catggcgacc acacccgtcc tgtaccattc cttgcggcgg   2400
cggtgctcaa cggcctcaac ctactactgg gctgcttcct aatgcaggag tcgcataagg   2460
gagagcgtcg accgatgccc ttgagagcct tcaacccagt cagctccttc cggtgggcgc   2520
ggggcatgac tatcgtcgcc gcacttatga ctgtcttctt tatcatgcaa ctcgtaggac   2580
aggtgccggc agcgctctgg gtcattttcg gcgaggaccg ctttcgctgg agcgcgacga   2640
tgatcggcct gtcgcttgcg gtattcggaa tcttgcacgc cctcgctcaa gccttcgtca   2700
ctggtcccgc caccaaacgt ttcggcgaga agcaggccat tatcgccggc atggcggccg   2760
acgcgctggg ctacgtcttg ctggcgttcg ccatggtcgt cacagagctg gaagcggcag   2820
cgagaattat ccgcgatcgt ggcgcggtgc ccgcaggcat gacaaacatc gtaaatgccg   2880
cgtttcgtgt ggccgtggcc gcccaggacg tgtcagcgcc gccaccacct gcaccgaatc   2940
ggcagcagcg tcgcgcgtcg aaaaagcgca caggcggcaa gaagcgataa gctgcacgaa   3000
tacctgaaaa atgttgaacg ccccgtgagc ggtaactcac agggcgtcgg ctaaccccca   3060
gtccaaacct gggagaaagc gctcaaaaat gactctagcg gattcacgag acattgacac   3120
accggcctgg aaattttccg ctgatctgtt cgacacccat cccgagctcg cgctgcgatc   3180
acgtggctgg acgagcgaag accgccgcga attcctcgct cacctgggca gagaaaattt   3240
ccagggcagc aagacccgcg acttcgccag cgcttggatc aaagacccgg acacgggaga   3300
aacacagccg aagttatacc gagttggttc aaaatcgctt gcccggtgcc agtatgttgc   3360
tctgacgcac gcgcagcacg cagccgtgct tgtcctggac attgatgtgc cgagccacca   3420
ggccggcggg aaaatcgagc acgtaaaccc cgaggtctac gcgattttgg agcgctgggc   3480
acgcctggaa aaagcgccag cttggatcgg cgtgaatcca ctgagcggga aatgccagct   3540
catctggctc attgatccgg tgtatgccgc agcaggcatg agcagcccga atatgcgcct   3600
gctggctgca acgaccgagg aaatgacccg cgttttcggc gctgaccagg ctttttcaca   3660
taggctgagc cggtggccac tgcacgtctc cgacgatccc accgcgtacc gctggcatgc   3720
ccagcacaat cgcgtggatc gcctagctga tcttatggag gttgctcgca tgatctcagg   3780
cacagaaaaa cctaaaaaac gctatgagca ggagttttct agcggacggg cacgtatcga   3840
agcggcaaga aaagccactg cggaagcaaa agcacttgcc acgcttgaag caagcctgcc   3900
gagcgccgct gaagcgtctg gagagctgat cgacggcgtc cgtgtcctct ggactgctcc   3960
agggcgtgcc gcccgtgatg agacggcttt tcgccacgct ttgactgtgg gataccagtt   4020
aaaagcggct ggtgagcgcc taaaagacac caagatcatc gacgcctacg agcgtgccta   4080
caccgtcgct caggcggtcg gagcagacgg ccgtgagcct gatctgccgc cgatgcgtga   4140
ccgccagacg atggcgcgac gtgtgcgcgg ctacgtcgct aaaggccagc cagtcgtccc   4200
tgctcgtcag acagagacgc agagcagccg agggcgaaaa gctctggcca ctatgggaag   4260
acgtggcggt aaaaaggccg cagaacgctg gaaagaccca aacagtgagt acgcccgagc   4320
acagcgagaa aaactagcta agtccagtca acgacaagct aggaaagcta aaggaaatcg   4380
cttgaccatt gcaggttggt ttatgactgt tgagggagag actggctcgt ggcgacaatc   4440
aatgaagcta tgtctgaatt tagcgtgtca cgtcagaccg tgaatagagc acttaagtct   4500
gcgggcattg aacttccacg aggacgccgt aaagcttccc agtaaatgtg ccatctcgta   4560
ggcagaaaac ggttcccccc gtaggggtct ctctcttggc ctcctttcta ggtcgggctg   4620
```

```
attgctcttg aagctctcta ggggggctca caccataggc agataacggt tccccaccgg   4680
ctcacctcgt aagcgcacaa ggactgctcc caatgccgca agcactcagg gcgcaagggc   4740
tgctaaagga agcggaacac gtagaaagcc agtccgcaga aacggtgctg accccggatg   4800
aatgtcagct actgggctat ctggacaagg gaaaacgcaa gcgcaaagag aaagcaggta   4860
gcttgcagtg ggcttacatg gcgatagcta gactgggcgg ttttatggac agcaagcgaa   4920
ccggaattgc cagctggggc gccctctggt aaggttggga agccctgcaa agtaaactgg   4980
atggctttct tgccgccaag gatctgatgg cgcaggggat caagatctga tcaagagaca   5040
ggatgaggat cgtttcgcat gattgaacaa gatggattgc acgcaggttc tccggccgct   5100
tgggtggaga ggctattcgg ctatgactgg gcacaacaga caatcggctg ctctgatgcc   5160
gccgtgttcc ggctgtcagc gcaggggcgc ccggttcttt ttgtcaagac cgacctgtcc   5220
ggtgccctga atgaactcca agacgaggca gcgcggctat cgtggctggc cacgacgggc   5280
gttccttgcg cagctgtgct cgacgttgtc actgaagcgg gaagggactg gctgctattg   5340
ggcgaagtgc cggggcagga tctcctgtca tctcaccttg ctcctgccga gaaagtatcc   5400
atcatggctg atgcaatgcg gcggctgcat acgcttgatc cggctacctg cccattcgac   5460
caccaagcga aacatcgcat cgagcgagca cgtactcgga tggaagccgg tcttgtcgat   5520
caggatgatc tggacgaaga gcatcagggg ctcgcgccag ccgaactgtt cgccaggctc   5580
aaggcgcgga tgcccgacgg cgaggatctc gtcgtgaccc atggcgatgc ctgcttgccg   5640
aatatcatgg tggaaaatgg ccgcttttct ggattcatcg actgtggccg gctgggtgtg   5700
gcggaccgct atcaggacat agcgttggct acccgtgata ttgctgaaga gcttggcggc   5760
gaatgggctg accgcttcct cgtgctttac ggtatcgccg ctcccgattc gcagcgcatc   5820
gccttctatc gccttcttga cgagttcttc tgagcgggac tctggggttc gctagaggat   5880
cgatcctttt taacccatca catatacctg ccgttcacta ttatttagtg aaatgagata   5940
ttatgatatt ttctgaattg tgattaaaaa ggcaacttta tgcccatgca acagaaacta   6000
taaaaaatac agagaatgaa aagaaacaga tagatttttt agttctttag gcccgtagtc   6060
tgcaaatcct tttatgattt tctatcaaac aaaagaggaa aatagaccag ttgcaatcca   6120
aacgagagtc taacgacgcg aggctggatg gccttcccca ttatgattct tctcgcttcc   6180
ggcggcatcg ggatgcccgc gttgcaggcc atgctgtcca ggcaggtaga tgacgaccat   6240
cagggacagc ttcaaggatc gctcgcggct cttaccagcc taacttcgat cattggaccg   6300
ctgatcgtca cggcgattta tgccgcctcg gcgagcacat ggaacgggtt ggcatggatt   6360
gtaggcgccg ccctatacct tgtctgcctc cccgcgttgc gtcgcggtgc atggagccgg   6420
gccacctcga cctgaatgga agccggcggc acctcgctaa cggattcacc actccaagaa   6480
ttggagccaa tcaattcttg cggagaactg tgaatgcgca aaccaaccct tggcagaaca   6540
tatccatcgc gtccgccatc tccagcagcc gcacgcggcg catctcgggc agcgttgggt   6600
cctggccacg ggtgcgcatg atcgtgctcc tgtcgttgag gacccggcta ggctggcggg   6660
gttgccttac tggttagcag aatgaatcac cgatacgcga gcgaacgtga agcgactgct   6720
gctgcaaaac gtctgcgacc tgagcaacaa catgaatggt cttcggtttc cgtgtttcgt   6780
aaagtctgga aacgcggaag tcagcgccct gcaccattat gttccggatc tgcatcgcag   6840
gatgctgctg gctaccctgt ggaacaccta catctgtatt aacgaagcgc tggcattgac   6900
cctgagtgat ttttctctgg tcccgccgca tccataccgc cagttgttta ccctcacaac   6960
gttccagtaa ccgggcatgt tcatcatcag taacccgtat cgtgagcatc ctctctcgtt   7020
```

```
tcatcggtat cattaccccc atgaacagaa atccccctta cacggaggca tcagtgacca   7080
aacaggaaaa aaccgccctt aacatggccc gctttatcag aagccagaca ttaacgcttc   7140
tggagaaact caacgagctg gacgcggatg aacaggcaga catctgtgaa tcgcttcacg   7200
accacgctga tgagctttac cgcagctgcc tcgcgcgttt cggtgatgac ggtgaaaacc   7260
tctgacacat gcagctcccg gagacggtca cagcttgtct gtaagcggat gccgggagca   7320
gacaagcccg tcagggcgcg tcagcgggtg ttggcgggtg tcggggcgca gccatgaccc   7380
agtcacgtag cgatagcgga gtgtatactg gcttaactat gcggcatcag agcagattgt   7440
actgagagtg caccatatgc ggtgtgaaat accgcacaga tgcgtaagga gaaaataccg   7500
catcaggcgc tcttccgctt cctcgctcac tgactcgctg cgctcggtcg ttcggctgcg   7560
gcgagcggta tcagctcact caaaggcggt aatacggtta tccacagaat caggggataa   7620
cgcaggaaag aacatgtgag caaaaggcca gcaaaaggcc aggaaccgta aaaaggccgc   7680
gttgctggcg tttttccata ggctccgccc ccctgacgag catcacaaaa atcgacgctc   7740
aagtcagagg tggcgaaacc cgacaggact ataaagatac caggcgtttc cccctggaag   7800
ctccctcgtg cgctctcctg ttccgaccct gccgcttacc ggatacctgt ccgcctttct   7860
cccttcggga agcgtggcgc tttctcatag ctcacgctgt aggtatctca gttcggtgta   7920
ggtcgttcgc tccaagctgg gctgtgtgca cgaacccccc gttcagcccg accgctgcgc   7980
cttatccggt aactatcgtc ttgagtccaa cccggtaaga cacgacttat cgccactggc   8040
agcagccact ggtaacagga ttagcagagc gaggtatgta ggcggtgcta cagagttctt   8100
gaagtggtgg cctaactacg gctacactag aaggacagta tttggtatct gcgctctgct   8160
gaagccagtt accttcggaa aaagagttgg tagctcttga tccggcaaac aaaccaccgc   8220
tggtagcggt ggtttttttg tttgcaagca gcagattacg cgcagaaaaa aaggatctca   8280
agaagatcct ttgatctttt ctacggggtc tgacgctcag tggaacgaaa actcacgtta   8340
agggattttg gtcatgagat tatcaaaaag gatcttcacc tagatccttt taaattaaaa   8400
atgaagtttt aaatcaatct aaagtatata tgagtaaact tggtctgaca gttaccaatg   8460
cttaatcagt gaggcaccta tctcagcgat ctgtctattt cgttcatcca tagttgcctg   8520
actccccgtc gtgtagataa ctacgatacg ggagggctta ccatctggcc ccagtgctgc   8580
aatgataccg cgagacccac gctcaccggc tccagattta tcagcaataa accagccagc   8640
cggaagggcc gagcgcagaa gtggtcctgc aactttatcc gcctccatcc agtctattaa   8700
ttgttgccgg gaagctagag taagtagttc gccagttaat agtttgcgca acgttgttgc   8760
cattgctgca ggcatcgtgg tgtcacgctc gtcgtttggt atggcttcat tcagctccgg   8820
ttcccaacga tcaaggcgag ttacatgatc ccccatgttg tgcaaaaaag cggttagctc   8880
cttcggtcct ccgatcgttg tcagaagtaa gttggccgca gtgttatcac tcatggttat   8940
ggcagcactg cataattctc ttactgtcat gccatccgta agatgctttt ctgtgactgg   9000
tgagtactca accaagtcat tctgagaata gtgtatgcgg cgaccgagtt gctcttgccc   9060
ggcgtcaaca cgggataata ccgcgccaca tagcagaact ttaaaagtgc tcatcattgg   9120
aaaacgttct tcggggcgaa aactctcaag gatcttaccg ctgttgagat ccagttcgat   9180
gtaacccact cgtgcaccca actgatcttc agcatctttt actttcacca gcgtttctgg   9240
gtgagcaaaa acaggaaggc aaaatgccgc aaaaaaggga ataagggcga cacggaaatg   9300
ttgaatactc atactcttcc tttttcaata ttattgaagc atttatcagg gttattgtct   9360
```

```
catgagcgga tacatatttg aatgtattta gaaaaataaa caaatagggg ttccgcgcac   9420

atttccccga aaagtgccac ctgacgtcta agaaaccatt attatcatga cattaaccta   9480

taaaaatagg cgtatcacga ggccctttcg tcttcaagaa                         9520


<210> SEQ ID NO 38
<211> LENGTH: 8718
<212> TYPE: DNA
<213> ORGANISM: Artificial Sequence
<220> FEATURE:
<223> OTHER INFORMATION: Recombinant plasmid pAPSE10437; beta actin
      hairpin - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1990)..(5332)
<223> OTHER INFORMATION: synthetic DNA (SEQ ID NO: 30)

<400> SEQUENCE: 38

ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatgaa ttcagatctc gatcccgcga aattaatacg actcactata gggagaccac    240

aacggtttcc ctctagatca caagtttgta caaaaaagca ggctaagaag gagatataca    300

tacgccggcc attcaaacat gaggattacc catgtattta aatacccatg tccaggcgcg    360

ctccgcgatc gcgcacgagg tttttctgtc tagtgagcag tgtccaacct caaaagacaa    420

catgtgtgac gacgatgtag cggctcttgt cgtagacaat ggatccggta tgtgcaaagc    480

cggtttcgca ggagatgacg caccccgtgc cgtcttcccc tcgatcgtcg gtcgcccaag    540

gcatcaagga gtcatggtcg gtatgggaca aaaggactca tacgtaggag atgaagccca    600

aagcaaaaga ggtatcctca ccctgaaata ccccatcgaa cacggtatca tcaccaactg    660
```

-continued

```
ggatgagttt aaaccctcta gctgctttac aaagtactgg ttccctttcc agcgggatgc    720
tttatctaaa cgcaacatga ggatcaccca tgtcgccaca tcgcttccta gttccgctgg    780
gatccatcgt tggcggccga agccgccatt ccatagtgag ttctggcgcg cctcatccca    840
gttggtgatg ataccgtgtt cgatggggta tttcagggtg aggatacctc ttttgctttg    900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg ggcctctaa    1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg taccattcct tgcggcggcg gtgctcaacg gcctcaacct   1620
actactgggc tgcttcctaa tgcaggagtc gcataaggga gagcgtcgac cgatgccctt   1680
gagagccttc aacccagtca gctccttccg gtgggcgcgg ggcatgacta tcgtcgccgc   1740
acttatgact gtcttcttta tcatgcaact cgtaggacag gtgccggcag cgctctgggt   1800
cattttcggc gaggaccgct ttcgctggag cgcgacgatg atcggcctgt cgcttgcggt   1860
attcggaatc ttgcacgccc tcgctcaagc cttcgtcact ggtcccgcca ccaaacgttt   1920
cggcgagaag caggccatta tcgccggcat ggcggccgac gcgctgggct acgtcttgct   1980
ggcgttcgcc atggtcgtca cagagctgga agcggcagcg agaattatcc gcgatcgtgg   2040
cgcggtgccc gcaggcatga caaacatcgt aaatgccgcg tttcgtgtgg ccgtggccgc   2100
ccaggacgtg tcagcgccgc caccacctgc accgaatcgg cagcagcgtc gcgcgtcgaa   2160
aaagcgcaca ggcggcaaga agcgataagc tgcacgaata cctgaaaaat gttgaacgcc   2220
ccgtgagcgg taactcacag ggcgtcggct aacccccagt ccaaacctgg gagaaagcgc   2280
tcaaaaatga ctctagcgga ttcacgagac attgacacac cggcctggaa attttccgct   2340
gatctgttcg acacccatcc cgagctcgcg ctgcgatcac gtggctggac gagcgaagac   2400
cgccgcgaat tcctcgctca cctgggcaga gaaaatttcc agggcagcaa gacccgcgac   2460
ttcgccagcg cttggatcaa agacccggac acgggagaaa cacagccgaa gttataccga   2520
gttggttcaa aatcgcttgc ccggtgccag tatgttgctc tgacgcacgc gcagcacgca   2580
gccgtgcttg tcctggacat tgatgtgccg agccaccagg ccggcgggaa aatcgagcac   2640
gtaaaccccg aggtctacgc gattttggag cgctgggcac gcctggaaaa agcgccagct   2700
tggatcggcg tgaatccact gagcgggaaa tgccagctca tctggctcat tgatccggtg   2760
tatgccgcag caggcatgag cagcccgaat atgcgcctgc tggctgcaac gaccgaggaa   2820
atgacccgcg ttttcggcgc tgaccaggct tttcacatag gctgagccgg gtggccactg   2880
cacgtctccg acgatcccac cgcgtaccgc tggcatgccc agcacaatcg cgtggatcgc   2940
ctagctgatc ttatggaggt tgctcgcatg atctcaggca cagaaaaacc taaaaaacgc   3000
tatgagcagg agttttctag cggacgggca cgtatcgaag cggcaagaaa agccactgcg   3060
```

```
gaagcaaaag cacttgccac gcttgaagca agcctgccga gcgccgctga agcgtctgga   3120
gagctgatcg acggcgtccg tgtcctctgg actgctccag ggcgtgccgc ccgtgatgag   3180
acggcttttc gccacgcttt gactgtggga taccagttaa aagcggctgg tgagcgccta   3240
aaagacacca agatcatcga cgcctacgag cgtgcctaca ccgtcgctca ggcggtcgga   3300
gcagacggcc gtgagcctga tctgccgccg atgcgtgacc gccagacgat ggcgcgacgt   3360
gtgcgcggct acgtcgctaa aggccagcca gtcgtccctg ctcgtcagac agagacgcag   3420
agcagccgag ggcgaaaagc tctggccact atgggaagac gtggcggtaa aaaggccgca   3480
gaacgctgga aagacccaaa cagtgagtac gcccgagcac agcgagaaaa actagctaag   3540
tccagtcaac gacaagctag gaaagctaaa ggaaatcgct tgaccattgc aggttggttt   3600
atgactgttg agggagagac tggctcgtgg cgacaatcaa tgaagctatg tctgaattta   3660
gcgtgtcacg tcagaccgtg aatagagcac ttaagtctgc gggcattgaa cttccacgag   3720
gacgccgtaa agcttcccag taaatgtgcc atctcgtagg cagaaaacgg ttcccccgt    3780
aggggtctct ctcttggcct cctttctagg tcgggctgat tgctcttgaa gctctctagg   3840
ggggctcaca ccataggcag ataacggttc cccaccggct cacctcgtaa gcgcacaagg   3900
actgctccca atgccgcaag cactcagggc gcaagggctg ctaaaggaag cggaacacgt   3960
agaaagccag tccgcagaaa cggtgctgac cccggatgaa tgtcagctac tgggctatct   4020
ggacaaggga aaacgcaagc gcaaagagaa agcaggtagc ttgcagtggg cttacatggc   4080
gatagctaga ctgggcggtt ttatggacag caagcgaacc ggaattgcca gctggggcgc   4140
cctctggtaa ggttgggaag ccctgcaaag taaactggat ggctttcttg ccgccaagga   4200
tctgatggcg caggggatca agatctgatc aagagacagg atgaggatcg tttcgcatga   4260
ttgaacaaga tggattgcac gcaggttctc cggccgcttg ggtggagagg ctattcggct   4320
atgactgggc acaacagaca atcggctgct ctgatgccgc cgtgttccgg ctgtcagcgc   4380
aggggcgccc ggttcttttt gtcaagaccg acctgtccgg tgccctgaat gaactccaag   4440
acgaggcagc gcggctatcg tggctggcca cgacgggcgt tccttgcgca gctgtgctcg   4500
acgttgtcac tgaagcggga agggactggc tgctattggg cgaagtgccg gggcaggatc   4560
tcctgtcatc tcaccttgct cctgccgaga aagtatccat catggctgat gcaatgcggc   4620
ggctgcatac gcttgatccg gctacctgcc cattcgacca ccaagcgaaa catcgcatcg   4680
agcgagcacg tactcggatg gaagccggtc ttgtcgatca ggatgatctg gacgaagagc   4740
atcaggggct cgcgccagcc gaactgttcg ccaggctcaa ggcgcggatg cccgacggcg   4800
aggatctcgt cgtgacccat ggcgatgcct gcttgccgaa tatcatggtg gaaaatggcc   4860
gcttttctgg attcatcgac tgtggccggc tgggtgtggc ggaccgctat caggacatag   4920
cgttggctac ccgtgatatt gctgaagagc ttggcggcga atgggctgac cgcttcctcg   4980
tgctttacgg tatcgccgct cccgattcgc agcgcatcgc cttctatcgc cttcttgacg   5040
agttcttctg agcgggactc tggggttcgc tagaggatcg atccttttta acccatcaca   5100
tatacctgcc gttcactatt atttagtgaa atgagatatt atgatatttt ctgaattgtg   5160
attaaaaagg caactttatg cccatgcaac agaaactata aaaaatacag agaatgaaaa   5220
gaaacagata gatttttag ttctttaggc ccgtagtctg caaatccttt tatgattttc   5280
tatcaaacaa aagaggaaaa tagaccagtt gcaatccaaa cgagagtcta acgacgcgag   5340
gctggatggc cttccccatt atgattcttc tcgcttccgg cggcatcggg atgcccgcgt   5400
```

```
tgcaggccat gctgtccagg caggtagatg acgaccatca gggacagctt caaggatcgc   5460
tcgcggctct taccagccta acttcgatca ttggaccgct gatcgtcacg gcgatttatg   5520
ccgcctcggc gagcacatgg aacgggttgg catggattgt aggcgccgcc ctataccttg   5580
tctgcctccc cgcgttgcgt cgcggtgcat ggagccgggc cacctcgacc tgaatggaag   5640
ccggcggcac ctcgctaacg gattcaccac tccaagaatt ggagccaatc aattcttgcg   5700
gagaactgtg aatgcgcaaa ccaacccttg gcagaacata tccatcgcgt ccgccatctc   5760
cagcagccgc acgcggcgca tctcgggcag cgttgggtcc tggccacggg tgcgcatgat   5820
cgtgctcctg tcgttgagga cccggctagg ctggcggggt tgccttactg gttagcagaa   5880
tgaatcaccg atacgcgagc gaacgtgaag cgactgctgc tgcaaaacgt ctgcgacctg   5940
agcaacaaca tgaatggtct tcggtttccg tgtttcgtaa agtctggaaa cgcggaagtc   6000
agcgccctgc accattatgt tccggatctg catcgcagga tgctgctggc taccctgtgg   6060
aacacctaca tctgtattaa cgaagcgctg gcattgaccc tgagtgattt ttctctggtc   6120
ccgccgcatc cataccgcca gttgtttacc ctcacaacgt tccagtaacc gggcatgttc   6180
atcatcagta acccgtatcg tgagcatcct ctctcgtttc atcggtatca ttacccccat   6240
gaacagaaat cccccttaca cggaggcatc agtgaccaaa caggaaaaaa ccgcccttaa   6300
catggcccgc tttatcagaa gccagacatt aacgcttctg gagaaactca acgagctgga   6360
cgcggatgaa caggcagaca tctgtgaatc gcttcacgac cacgctgatg agctttaccg   6420
cagctgcctc gcgcgtttcg gtgatgacgg tgaaaacctc tgacacatgc agctcccgga   6480
gacggtcaca gcttgtctgt aagcggatgc cgggagcaga caagcccgtc agggcgcgtc   6540
agcgggtgtt ggcgggtgtc ggggcgcagc catgacccag tcacgtagcg atagcggagt   6600
gtatactggc ttaactatgc ggcatcagag cagattgtac tgagagtgca ccatatgcgg   6660
tgtgaaatac cgcacagatg cgtaaggaga aaataccgca tcaggcgctc ttccgcttcc   6720
tcgctcactg actcgctgcg ctcggtcgtt cggctgcggc gagcggtatc agctcactca   6780
aaggcggtaa tacggttatc cacagaatca ggggataacg caggaaagaa catgtgagca   6840
aaaggccagc aaaaggccag gaaccgtaaa aaggccgcgt tgctggcgtt tttccatagg   6900
ctccgccccc ctgacgagca tcacaaaaat cgacgctcaa gtcagaggtg gcgaaacccg   6960
acaggactat aaagatacca ggcgtttccc cctggaagct ccctcgtgcg ctctcctgtt   7020
ccgaccctgc cgcttaccgg atacctgtcc gcctttctcc cttcgggaag cgtggcgctt   7080
tctcatagct cacgctgtag gtatctcagt tcggtgtagg tcgttcgctc caagctgggc   7140
tgtgtgcacg aaccccccgt tcagcccgac cgctgcgcct tatccggtaa ctatcgtctt   7200
gagtccaacc cggtaagaca cgacttatcg ccactggcag cagccactgg taacaggatt   7260
agcagagcga ggtatgtagg cggtgctaca gagttcttga agtggtggcc taactacggc   7320
tacactagaa ggacagtatt tggtatctgc gctctgctga agccagttac cttcggaaaa   7380
agagttggta gctcttgatc cggcaaacaa accaccgctg gtagcggtgg tttttttgtt   7440
tgcaagcagc agattacgcg cagaaaaaaa ggatctcaag aagatccttt gatcttttct   7500
acggggtctg acgctcagtg gaacgaaaac tcacgttaag ggattttggt catgagatta   7560
tcaaaaagga tcttcaccta gatcctttta aattaaaaat gaagttttaa atcaatctaa   7620
agtatatatg agtaaacttg gtctgacagt taccaatgct taatcagtga ggcacctatc   7680
tcagcgatct gtctatttcg ttcatccata gttgcctgac tccccgtcgt gtagataact   7740
acgatacggg agggcttacc atctggcccc agtgctgcaa tgataccgcg agacccacgc   7800
```

```
tcaccggctc cagatttatc agcaataaac cagccagccg gaagggccga gcgcagaagt   7860

ggtcctgcaa ctttatccgc ctccatccag tctattaatt gttgccggga agctagagta   7920

agtagttcgc cagttaatag tttgcgcaac gttgttgcca ttgctgcagg catcgtggtg   7980

tcacgctcgt cgtttggtat ggcttcattc agctccggtt cccaacgatc aaggcgagtt   8040

acatgatccc ccatgttgtg caaaaaagcg gttagctcct tcggtcctcc gatcgttgtc   8100

agaagtaagt tggccgcagt gttatcactc atggttatgg cagcactgca taattctctt   8160

actgtcatgc catccgtaag atgcttttct gtgactggtg agtactcaac caagtcattc   8220

tgagaatagt gtatgcggcg accgagttgc tcttgcccgg cgtcaacacg ggataatacc   8280

gcgccacata gcagaacttt aaaagtgctc atcattggaa aacgttcttc ggggcgaaaa   8340

ctctcaagga tcttaccgct gttgagatcc agttcgatgt aacccactcg tgcacccaac   8400

tgatcttcag catcttttac tttcaccagc gtttctgggt gagcaaaaac aggaaggcaa   8460

aatgccgcaa aaaagggaat aagggcgaca cggaaatgtt gaatactcat actcttcctt   8520

tttcaatatt attgaagcat ttatcagggt tattgtctca tgagcggata catatttgaa   8580

tgtatttaga aaaataaaca aataggggtt ccgcgcacat ttccccgaaa agtgccacct   8640

gacgtctaag aaaccattat tatcatgaca ttaacctata aaaataggcg tatcacgagg   8700

ccctttcgtc ttcaagaa                                                 8718
```

<210> SEQ ID NO 39
<211> LENGTH: 7250
<212> TYPE: DNA
<213> ORGANISM: Artificial Sequence
<220> FEATURE:
<223> OTHER INFORMATION: Recombinant plasmid pAPSE10439; beta actin hairpin - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional prmoter
<220> FEATURE:
<221> NAME/KEY: misc_feature
<222> LOCATION: (2844)..(2851)
<223> OTHER INFORMATION: restriction endonuclease AsiSI recognition sequence
<220> FEATURE:
<221> NAME/KEY: misc_feature
<222> LOCATION: (2852)..(3146)
<223> OTHER INFORMATION: beta actin sense gene fragment
<220> FEATURE:
<221> NAME/KEY: misc_feature
<222> LOCATION: (3146)..(3153)
<223> OTHER INFORMATION: restriction endonuclease PmeI recognition site
<220> FEATURE:
<221> NAME/KEY: misc_feature
<222> LOCATION: (3311)..(3605)
<223> OTHER INFORMATION: beta actin antisense strand gene fragment
<220> FEATURE:

<221> NAME/KEY: terminator
<222> LOCATION: (3657)..(3846)
<223> OTHER INFORMATION: yeast CYC1 terminator
<220> FEATURE:
<221> NAME/KEY: misc_feature
<222> LOCATION: (5840)..(7182)
<223> OTHER INFORMATION: yeast 2 micron ori

<400> SEQUENCE: 39

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctcaga tcttatcgtc   2100
```

```
gtcatccttg taatccatcg atactagtgc ggccgccctt tagtgagggt tgaattcgaa   2160
ttttcaaaaa ttcttacttt ttttttggat ggacgcaaag aagtttaata atcatattac   2220
atggcattac caccatatac atatccatat acatatccat atctaatctt acttatatgt   2280
tgtggaaatg taaagagccc cattatctta gcctaaaaaa accttctctt tggaactttc   2340
agtaatacgc ttaactgctc attgctatat tgaagtacgg attagaagcc gccgagcggg   2400
tgacagccct ccgaaggaag actctcctcc gtgcgtcctc gtcttcaccg gtcgcgttcc   2460
tgaaacgcag atgtgcctcg cgccgcactg ctccgaacaa taaagattct acaatactag   2520
cttttatggt tatgaagagg aaaaattggc agtaacctgg ccccacaaac cttcaaatga   2580
acgaatcaaa ttaacaacca taggatgata atgcgattag ttttttagcc ttatttctgg   2640
ggtaattaat cagcgaagcg atgatttttg atctattaac agatatataa atgcaaaaac   2700
tgcataacca ctttaactaa tactttcaac attttcggtt tgtattactt cttattcaaa   2760
tgtaataaaa gtatcaacaa aaaattgtta atatacctct atactttaac gtcaaggaga   2820
aaaaaccccg gatccattta aatgcgatcg cgcacgaggt ttttctgtct agtgagcagt   2880
gtccaacctc aaaagacaac atgtgtgacg acgatgtagc ggctcttgtc gtagacaatg   2940
gatccggtat gtgcaaagcc ggtttcgcag gagatgacgc accccgtgcc gtcttcccct   3000
cgatcgtcgg tcgcccaagg catcaaggag tcatggtcgg tatgggacaa aaggactcat   3060
acgtaggaga tgaagcccaa agcaaaagag gtatcctcac cctgaaatac cccatcgaac   3120
acggtatcat caccaactgg gatgagttta aaccctctag ctgctttaca aagtactggt   3180
tccctttcca gcgggatgct ttatctaaac gcaatgagag aggtattcct caggccacat   3240
cgcttcctag ttccgctggg atccatcgtt ggcggccgaa gccgccattc catagtgagt   3300
tctggcgcgc ctcatcccag ttggtgatga taccgtgttc gatggggtat ttcagggtga   3360
ggatacctct tttgctttgg gcttcatctc ctacgtatga gtccttttgt cccataccga   3420
ccatgactcc ttgatgcctt gggcgaccga cgatcgaggg gaagacggca cggggtgcgt   3480
catctcctgc gaaaccggct ttgcacatac cggatccatt gtctacgaca agagccgcta   3540
catcgtcgtc acacatgttg tcttttgagg ttggacactg ctcactagac agaaaaacct   3600
cgtgccggac cgaatacccg gtctgaacga gggcggccgc ccgcgggcta gctaagatcc   3660
gctctaaccg aaaaggaagg agttagacaa cctgaagtct aggtccctat ttattttttt   3720
atagttatgt tagtattaag aacgttattt atatttcaaa tttttctttt ttttctgtac   3780
agacgcgtgt acgcatgtaa cattatactg aaaaccttgc ttgagaaggt tttgggacgc   3840
tcgaagatcc agctgcatta atgaatcggc caacgcgcgg ggagaggcgg tttgcgtatt   3900
gggcgctctt ccgcttcctc gctcactgac tcgctgcgct cggtcgttcg gctgcggcga   3960
gcggtatcag ctcactcaaa ggcggtaata cggttatcca cagaatcagg ggataacgca   4020
ggaaagaaca tgtgagcaaa aggccagcaa aaggccagga accgtaaaaa ggccgcgttg   4080
ctggcgtttt tccataggct ccgcccccct gacgagcatc acaaaaatcg acgctcaagt   4140
cagaggtggc gaaacccgac aggactataa agataccagg cgtttccccc tggaagctcc   4200
ctcgtgcgct ctcctgttcc gaccctgccg cttaccggat acctgtccgc ctttctccct   4260
tcgggaagcg tggcgctttc tcatagctca cgctgtaggt atctcagttc ggtgtaggtc   4320
gttcgctcca agctgggctg tgtgcacgaa ccccccgttc agcccgaccg ctgcgcctta   4380
tccggtaact atcgtcttga gtccaacccg gtaagacacg acttatcgcc actggcagca   4440
```

-continued

```
gccactggta acaggattag cagagcgagg tatgtaggcg gtgctacaga gttcttgaag   4500
tggtggccta actacggcta cactagaagg acagtatttg gtatctgcgc tctgctgaag   4560
ccagttacct tcggaaaaag agttggtagc tcttgatccg gcaaacaaac caccgctggt   4620
agcggtggtt tttttgtttg caagcagcag attacgcgca gaaaaaaagg atctcaagaa   4680
gatcctttga tcttttctac ggggtctgac gctcagtgga acgaaaactc acgttaaggg   4740
attttggtca tgagattatc aaaaaggatc ttcacctaga tccttttaaa ttaaaaatga   4800
agttttaaat caatctaaag tatatatgag taaacttggt ctgacagtta ccaatgctta   4860
atcagtgagg cacctatctc agcgatctgt ctatttcgtt catccatagt tgcctgactc   4920
cccgtcgtgt agataactac gatacgggag ggcttaccat ctggccccag tgctgcaatg   4980
ataccgcgag acccacgctc accggctcca gatttatcag caataaacca gccagccgga   5040
agggccgagc gcagaagtgg tcctgcaact ttatccgcct ccatccagtc tattaattgt   5100
tgccgggaag ctagagtaag tagttcgcca gttaatagtt tgcgcaacgt tgttgccatt   5160
gctacaggca tcgtggtgtc acgctcgtcg tttggtatgg cttcattcag ctccggttcc   5220
caacgatcaa ggcgagttac atgatccccc atgttgtgca aaaaagcggt tagctccttc   5280
ggtcctccga tcgttgtcag aagtaagttg gccgcagtgt tatcactcat ggttatggca   5340
gcactgcata attctcttac tgtcatgcca tccgtaagat gcttttctgt gactggtgag   5400
tactcaacca agtcattctg agaatagtgt atgcggcgac cgagttgctc ttgcccggcg   5460
tcaatacggg ataataccgc gccacatagc agaactttaa aagtgctcat cattggaaaa   5520
cgttcttcgg ggcgaaaact ctcaaggatc ttaccgctgt tgagatccag ttcgatgtaa   5580
cccactcgtg cacccaactg atcttcagca tcttttactt tcaccagcgt ttctgggtga   5640
gcaaaaacag gaaggcaaaa tgccgcaaaa aagggaataa gggcgacacg gaaatgttga   5700
atactcatac tcttcctttt tcaatattat tgaagcattt atcagggtta ttgtctcatg   5760
agcggataca tatttgaatg tatttagaaa aataaacaaa taggggttcc gcgcacattt   5820
ccccgaaaag tgccacctga acgaagcatc tgtgcttcat tttgtagaac aaaaatgcaa   5880
cgcgagagcg ctaatttttc aaacaaagaa tctgagctgc atttttacag aacagaaatg   5940
caacgcgaaa gcgctatttt accaacgaag aatctgtgct tcatttttgt aaaacaaaaa   6000
tgcaacgcga gagcgctaat ttttcaaaca aagaatctga gctgcatttt tacagaacag   6060
aaatgcaacg cgagagcgct attttaccaa caaagaatct atacttcttt tttgttctac   6120
aaaaatgcat cccgagagcg ctatttttct aacaaagcat cttagattac tttttttctc   6180
ctttgtgcgc tctataatgc agtctcttga taactttttg cactgtaggt ccgttaaggt   6240
tagaagaagg ctactttggt gtctattttc tcttccataa aaaaagcctg actccacttc   6300
ccgcgtttac tgattactag cgaagctgcg ggtgcatttt ttcaagataa aggcatcccc   6360
gattatattc tataccgatg tggattgcgc atactttgtg aacagaaagt gatagcgttg   6420
atgattcttc attggtcaga aaattatgaa cggtttcttc tattttgtct ctatatacta   6480
cgtataggaa atgtttacat ttcgtattg ttttcgattc actctatgaa tagttcttac    6540
tacaattttt ttgtctaaag agtaatacta gagataaaca taaaaaatgt agaggtcgag   6600
tttagatgca agttcaagga gcgaaaggtg gatgggtagg ttatataggg atatagcaca   6660
gagatatata gcaaagagat acttttgagc aatgtttgtg gaagcggtat tcgcaatatt   6720
ttagtagctc gttacagtcc ggtgcgtttt tggttttttg aaagtgcgtc ttcagagcgc   6780
ttttggtttt caaaagcgct ctgaagttcc tatactttct agagaatagg aacttcggaa   6840
```

```
taggaacttc aaagcgtttc cgaaaacgag cgcttccgaa aatgcaacgc gagctgcgca   6900

catacagctc actgttcacg tcgcacctat atctgcgtgt tgcctgtata tatatataca   6960

tgagaagaac ggcatagtgc gtgtttatgc ttaaatgcgt acttatatgc gtctatttat   7020

gtaggatgaa aggtagtcta gtacctcctg tgatattatc ccattccatg cggggtatcg   7080

tatgcttcct tcagcactac cctttagctg ttctatatgc tgccactcct caattggatt   7140

agtctcatcc ttcaatgcta tcatttcctt tgatattgga tcatattaag aaaccattat   7200

tatcatgaca ttaacctata aaaataggcg tatcacgagg ccctttcgtc             7250
```

<210> SEQ ID NO 40
<211> LENGTH: 7582
<212> TYPE: DNA
<213> ORGANISM: Artificial Sequence
<220> FEATURE:
<223> OTHER INFORMATION: Recombinant plasmid pAPSE1440; beta actin hairpin + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3183)
<223> OTHER INFORMATION: restriction endonuclease AsiSI recognition sequence
<220> FEATURE:
<221> NAME/KEY: misc_feature
<222> LOCATION: (3185)..(3478)
<223> OTHER INFORMATION: beta actin sense gene fragment
<220> FEATURE:
<221> NAME/KEY: misc_feature
<222> LOCATION: (3478)..(3485)
<223> OTHER INFORMATION: restriction endonuclease PmeI recognition site
<220> FEATURE:
<221> NAME/KEY: misc_feature
<222> LOCATION: (3643)..(3937)
<223> OTHER INFORMATION: beta actin antisense strand gene fragment
<220> FEATURE:
<221> NAME/KEY: terminator
<222> LOCATION: (3989)..(4178)
<223> OTHER INFORMATION: yeast CYC1 terminator
<220> FEATURE:
<221> NAME/KEY: misc_feature
<222> LOCATION: (6172)..(7514)
<223> OTHER INFORMATION: yeast 2 micron ori

<400> SEQUENCE: 40

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120
```

```
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct ttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaatttc gttttaaaac    1860
ctaagagtca ctttaaaatt tgtatacact tattttttt ataacttatt taataataaa    1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctctta ttagtaaatg   2100
ccagagttag cagcgattgc agatgggatc ggattaccgt ctttcagcag gccctgcatt   2160
gccttaacaa tcagttcgca gtcggagttc gtcgcaaaaa tcggaatagt cagttccatg   2220
ttgaggtaag agcgccaggc cgcaactggg agttctacgc cgcctacggt ctgcgttgcg   2280
actttcggta cttcaacttt gatggtgtat ttgcgattct gcgcgctaga ctgacgaacg   2340
gagcacgtga ctttgtaggc ctgagagcgg ctgttagagc taatccattc cgcaacaccg   2400
ttggcgaagt tggacggagc tacggtaacg tcacccgtac cgccgttatc aaccagaacg   2460
aattgggtaa agttagacgc catgaattcg aattttcaaa aattcttact ttttttttgg   2520
```

```
atggacgcaa agaagtttaa taatcatatt acatggcatt accaccatat acatatccat   2580
atacatatcc atatctaatc ttacttatat gttgtggaaa tgtaaagagc cccattatct   2640
tagcctaaaa aaaccttctc tttggaactt tcagtaatac gcttaactgc tcattgctat   2700
attgaagtac ggattagaag ccgccgagcg ggtgacagcc ctccgaagga agactctcct   2760
ccgtgcgtcc tcgtcttcac cggtcgcgtt cctgaaacgc agatgtgcct cgcgccgcac   2820
tgctccgaac aataaagatt ctacaatact agcttttatg gttatgaaga ggaaaaattg   2880
gcagtaacct ggccccacaa accttcaaat gaacgaatca aattaacaac cataggatga   2940
taatgcgatt agttttttag ccttatttct ggggtaatta atcagcgaag cgatgatttt   3000
tgatctatta acagatatat aaatgcaaaa actgcataac cactttaact aatactttca   3060
acattttcgg tttgtattac ttcttattca aatgtaataa aagtatcaac aaaaaattgt   3120
taatatacct ctatacttta acgtcaagga gaaaaaaccc cggatccatt taaatgcgat   3180
cgcgcacgag gtttttctgt ctagtgagca gtgtccaacc tcaaaagaca acatgtgtga   3240
cgacgatgta gcggctcttg tcgtagacaa tggatccggt atgtgcaaag ccggtttcgc   3300
aggagatgac gcaccccgtg ccgtcttccc ctcgatcgtc ggtcgcccaa ggcatcaagg   3360
agtcatggtc ggtatgggac aaaaggactc atacgtagga gatgaagccc aaagcaaaag   3420
aggtatcctc accctgaaat accccatcga acacggtatc atcaccaact gggatgagtt   3480
taaaccctct agctgcttta caaagtactg gttccctttc cagcgggatg ctttatctaa   3540
acgcaatgag agaggtattc ctcaggccac atcgcttcct agttccgctg ggatccatcg   3600
ttggcggccg aagccgccat tccatagtga gttctggcgc gcctcatccc agttggtgat   3660
gataccgtgt tcgatggggt atttcagggt gaggatacct cttttgcttt gggcttcatc   3720
tcctacgtat gagtcctttt gtcccatacc gaccatgact ccttgatgcc ttgggcgacc   3780
gacgatcgag gggaagacgg cacggggtgc gtcatctcct gcgaaaccgg ctttgcacat   3840
accggatcca ttgtctacga caagagccgc tacatcgtcg tcacacatgt tgtcttttga   3900
ggttggacac tgctcactag acagaaaaac ctcgtgccgg accgaatacc cggtctgaac   3960
gagggcggcc gcccgcgggc tagctaagat ccgctctaac cgaaaaggaa ggagttagac   4020
aacctgaagt ctaggtccct atttattttt ttatagttat gttagtatta agaacgttat   4080
ttatatttca aatttttctt ttttttctgt acagacgcgt gtacgcatgt aacattatac   4140
tgaaaacctt gcttgagaag gttttgggac gctcgaagat ccagctgcat taatgaatcg   4200
gccaacgcgc ggggagaggc ggtttgcgta ttgggcgctc ttccgcttcc tcgctcactg   4260
actcgctgcg ctcggtcgtt cggctgcggc gagcggtatc agctcactca aaggcggtaa   4320
tacggttatc cacagaatca ggggataacg caggaaagaa catgtgagca aaaggccagc   4380
aaaaggccag gaaccgtaaa aaggccgcgt tgctggcgtt tttccatagg ctccgccccc   4440
ctgacgagca tcacaaaaat cgacgctcaa gtcagaggtg gcgaaacccg acaggactat   4500
aaagatacca ggcgtttccc cctggaagct ccctcgtgcg ctctcctgtt ccgaccctgc   4560
cgcttaccgg atacctgtcc gcctttctcc cttcgggaag cgtggcgctt tctcatagct   4620
cacgctgtag gtatctcagt tcggtgtagg tcgttcgctc caagctgggc tgtgtgcacg   4680
aaccccccgt tcagcccgac cgctgcgcct tatccggtaa ctatcgtctt gagtccaacc   4740
cggtaagaca cgacttatcg ccactggcag cagccactgg taacaggatt agcagagcga   4800
ggtatgtagg cggtgctaca gagttcttga agtggtggcc taactacggc tacactagaa   4860
```

```
ggacagtatt tggtatctgc gctctgctga agccagttac cttcggaaaa agagttggta   4920
gctcttgatc cggcaaacaa accaccgctg gtagcggtgg tttttttgtt tgcaagcagc   4980
agattacgcg cagaaaaaaa ggatctcaag aagatccttt gatcttttct acggggtctg   5040
acgctcagtg gaacgaaaac tcacgttaag ggattttggt catgagatta tcaaaaagga   5100
tcttcaccta gatcctttta aattaaaaat gaagttttaa atcaatctaa agtatatatg   5160
agtaaacttg gtctgacagt taccaatgct taatcagtga ggcacctatc tcagcgatct   5220
gtctatttcg ttcatccata gttgcctgac tccccgtcgt gtagataact acgatacggg   5280
agggcttacc atctggcccc agtgctgcaa tgataccgcg agacccacgc tcaccggctc   5340
cagatttatc agcaataaac cagccagccg gaagggccga gcgcagaagt ggtcctgcaa   5400
ctttatccgc ctccatccag tctattaatt gttgccggga agctagagta agtagttcgc   5460
cagttaatag tttgcgcaac gttgttgcca ttgctacagg catcgtggtg tcacgctcgt   5520
cgtttggtat ggcttcattc agctccggtt cccaacgatc aaggcgagtt acatgatccc   5580
ccatgttgtg caaaaaagcg gttagctcct tcggtcctcc gatcgttgtc agaagtaagt   5640
tggccgcagt gttatcactc atggttatgg cagcactgca taattctctt actgtcatgc   5700
catccgtaag atgcttttct gtgactggtg agtactcaac caagtcattc tgagaatagt   5760
gtatgcggcg accgagttgc tcttgcccgg cgtcaatacg ggataatacc gcgccacata   5820
gcagaacttt aaaagtgctc atcattggaa aacgttcttc ggggcgaaaa ctctcaagga   5880
tcttaccgct gttgagatcc agttcgatgt aacccactcg tgcacccaac tgatcttcag   5940
catcttttac tttcaccagc gtttctgggt gagcaaaaac aggaaggcaa aatgccgcaa   6000
aaaagggaat aagggcgaca cggaaatgtt gaatactcat actcttcctt tttcaatatt   6060
attgaagcat ttatcagggt tattgtctca tgagcggata catatttgaa tgtatttaga   6120
aaaataaaca aataggggtt ccgcgcacat ttccccgaaa agtgccacct gaacgaagca   6180
tctgtgcttc attttgtaga acaaaaatgc aacgcgagag cgctaatttt tcaaacaaag   6240
aatctgagct gcatttttac agaacagaaa tgcaacgcga aagcgctatt ttaccaacga   6300
agaatctgtg cttcattttt gtaaaacaaa aatgcaacgc gagagcgcta atttttcaaa   6360
caaagaatct gagctgcatt tttacagaac agaaatgcaa cgcgagagcg ctattttacc   6420
aacaaagaat ctatacttct tttttgttct acaaaaatgc atcccgagag cgctattttt   6480
ctaacaaagc atcttagatt actttttttc tcctttgtgc gctctataat gcagtctctt   6540
gataactttt tgcactgtag gtccgttaag gttagaagaa ggctactttg gtgtctattt   6600
tctcttccat aaaaaaagcc tgactccact tcccgcgttt actgattact agcgaagctg   6660
cgggtgcatt ttttcaagat aaaggcatcc ccgattatat tctataccga tgtggattgc   6720
gcatactttg tgaacagaaa gtgatagcgt tgatgattct tcattggtca gaaaattatg   6780
aacggtttct tctattttgt ctctatatac tacgtatagg aaatgtttac attttcgtat   6840
tgttttcgat tcactctatg aatagttctt actacaattt ttttgtctaa agagtaatac   6900
tagagataaa cataaaaaat gtagaggtcg agtttagatg caagttcaag gagcgaaagg   6960
tggatgggta ggttatatag ggatatagca cagagatata tagcaaagag atacttttga   7020
gcaatgtttg tggaagcggt attcgcaata ttttagtagc tcgttacagt ccggtgcgtt   7080
tttggttttt tgaaagtgcg tcttcagagc gcttttggtt ttcaaaagcg ctctgaagtt   7140
cctatacttt ctagagaata ggaacttcgg aataggaact tcaaagcgtt tccgaaaacg   7200
agcgcttccg aaaatgcaac gcgagctgcg cacatacagc tcactgttca cgtcgcacct   7260
```

```
atatctgcgt gttgcctgta tatatatata catgagaaga acggcatagt gcgtgtttat   7320

gcttaaatgc gtacttatat gcgtctattt atgtaggatg aaaggtagtc tagtacctcc   7380

tgtgatatta tcccattcca tgcggggtat cgtatgcttc cttcagcact accctttagc   7440

tgttctatat gctgccactc ctcaattgga ttagtctcat ccttcaatgc tatcatttcc   7500

tttgatattg gatcatatta agaaaccatt attatcatga cattaaccta taaaaatagg   7560

cgtatcacga ggccctttcg tc                                            7582
```

<210> SEQ ID NO 41
<211> LENGTH: 7269
<212> TYPE: DNA
<213> ORGANISM: Artificial Sequence
<220> FEATURE:
<223> OTHER INFORMATION: Recombinant plasmid pAPSE10441; beta actin stem loop - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional promoter
<220> FEATURE:
<221> NAME/KEY: misc_feature
<222> LOCATION: (2844)..(2851)
<223> OTHER INFORMATION: restriction endonuclease AsiSI recognition sequence
<220> FEATURE:
<221> NAME/KEY: misc_feature
<222> LOCATION: (2852)..(3146)
<223> OTHER INFORMATION: beta actin sense gene fragment
<220> FEATURE:
<221> NAME/KEY: misc_feature
<222> LOCATION: (3146)..(3153)
<223> OTHER INFORMATION: restriction endonuclease PmeI recognition site
<220> FEATURE:
<221> NAME/KEY: misc_feature
<222> LOCATION: (3311)..(3605)
<223> OTHER INFORMATION: beta actin antisense strand gene fragment
<220> FEATURE:
<221> NAME/KEY: misc_feature
<222> LOCATION: (3641)..(3659)
<223> OTHER INFORMATION: bacteriophage MS2 pac sequence
<220> FEATURE:
<221> NAME/KEY: terminator
<222> LOCATION: (3676)..(3865)
<223> OTHER INFORMATION: yeast CYC1 terminator
<220> FEATURE:
<221> NAME/KEY: misc_feature
<222> LOCATION: (5859)..(7201)
<223> OTHER INFORMATION: yeast 2 micron ori

<400> SEQUENCE: 41

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180
```

```
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctcaga tcttatcgtc   2100
gtcatccttg taatccatcg atactagtgc ggccgccctt tagtgagggt tgaattcgaa   2160
ttttcaaaaa ttcttacttt ttttttggat ggacgcaaag aagtttaata atcatattac   2220
atggcattac caccatatac atatccatat acatatccat atctaatctt acttatatgt   2280
tgtggaaatg taaagagccc cattatctta gcctaaaaaa accttctctt tggaactttc   2340
agtaatacgc ttaactgctc attgctatat tgaagtacgg attagaagcc gccgagcggg   2400
tgacagccct ccgaaggaag actctcctcc gtgcgtcctc gtcttcaccg gtcgcgttcc   2460
tgaaacgcag atgtgcctcg cgccgcactg ctccgaacaa taaagattct acaatactag   2520
cttttatggt tatgaagagg aaaaattggc agtaacctgg ccccacaaac cttcaaatga   2580
```

```
acgaatcaaa ttaacaacca taggatgata atgcgattag ttttttagcc ttatttctgg   2640

ggtaattaat cagcgaagcg atgatttttg atctattaac agatatataa atgcaaaaac   2700

tgcataacca ctttaactaa tactttcaac attttcggtt tgtattactt cttattcaaa   2760

tgtaataaaa gtatcaacaa aaaattgtta atatacctct atactttaac gtcaaggaga   2820

aaaaaccccg gatccattta aatgcgatcg cgcacgaggt tttctgtct agtgagcagt   2880

gtccaacctc aaaagacaac atgtgtgacg acgatgtagc ggctcttgtc gtagacaatg   2940

gatccggtat gtgcaaagcc ggtttcgcag gagatgacgc accccgtgcc gtcttcccct   3000

cgatcgtcgg tcgcccaagg catcaaggag tcatggtcgg tatgggacaa aaggactcat   3060

acgtaggaga tgaagcccaa agcaaaagag gtatcctcac cctgaaatac cccatcgaac   3120

acggtatcat caccaactgg gatgagttta aaccctctag ctgctttaca aagtactggt   3180

tccctttcca gcgggatgct ttatctaaac gcaatgagag aggtattcct caggccacat   3240

cgcttcctag ttccgctggg atccatcgtt ggcggccgaa gccgccattc catagtgagt   3300

tctggcgcgc ctcatcccag ttggtgatga taccgtgttc gatggggtat ttcagggtga   3360

ggatacctct tttgctttgg gcttcatctc ctacgtatga gtccttttgt cccataccga   3420

ccatgactcc ttgatgcctt gggcgaccga cgatcgaggg gaagacggca cggggtgcgt   3480

catctcctgc gaaaccggct ttgcacatac cggatccatt gtctacgaca agagccgcta   3540

catcgtcgtc acacatgttg tcttttgagg ttggacactg ctcactagac agaaaaacct   3600

cgtgccggac cgaatacccg gtctgaacga gggcggccgc acatgaggat cacccatgtc   3660

cgcgggctag ctaagatccg ctctaaccga aaaggaagga gttagacaac ctgaagtcta   3720

ggtccctatt tattttttta tagttatgtt agtattaaga acgttattta tatttcaaat   3780

ttttcttttt tttctgtaca gacgcgtgta cgcatgtaac attatactga aaaccttgct   3840

tgagaaggtt ttgggacgct cgaagatcca gctgcattaa tgaatcggcc aacgcgcggg   3900

gagaggcggt ttgcgtattg ggcgctcttc cgcttcctcg ctcactgact cgctgcgctc   3960

ggtcgttcgg ctgcggcgag cggtatcagc tcactcaaag gcggtaatac ggttatccac   4020

agaatcaggg gataacgcag gaaagaacat gtgagcaaaa ggccagcaaa aggccaggaa   4080

ccgtaaaaag gccgcgttgc tggcgttttt ccataggctc cgcccccctg acgagcatca   4140

caaaaatcga cgctcaagtc agaggtggcg aaacccgaca ggactataaa gataccaggc   4200

gtttccccct ggaagctccc tcgtgcgctc tcctgttccg accctgccgc ttaccggata   4260

cctgtccgcc tttctccctt cgggaagcgt ggcgctttct catagctcac gctgtaggta   4320

tctcagttcg gtgtaggtcg ttcgctccaa gctgggctgt gtgcacgaac cccccgttca   4380

gcccgaccgc tgcgccttat ccggtaacta tcgtcttgag tccaacccgg taagacacga   4440

cttatcgcca ctggcagcag ccactggtaa caggattagc agagcgaggt atgtaggcgg   4500

tgctacagag ttcttgaagt ggtggcctaa ctacggctac actagaagga cagtatttgg   4560

tatctgcgct ctgctgaagc cagttacctt cggaaaaaga gttggtagct cttgatccgg   4620

caaacaaacc accgctggta gcggtggttt ttttgtttgc aagcagcaga ttacgcgcag   4680

aaaaaaagga tctcaagaag atcctttgat cttttctacg gggtctgacg ctcagtggaa   4740

cgaaaactca cgttaaggga ttttggtcat gagattatca aaaaggatct tcacctagat   4800

ccttttaaat taaaaatgaa gttttaaatc aatctaaagt atatatgagt aaacttggtc   4860

tgacagttac caatgcttaa tcagtgaggc acctatctca gcgatctgtc tatttcgttc   4920
```

```
atccatagtt gcctgactcc ccgtcgtgta gataactacg atacgggagg gcttaccatc   4980
tggccccagt gctgcaatga taccgcgaga cccacgctca ccggctccag atttatcagc   5040
aataaaccag ccagccggaa gggccgagcg cagaagtggt cctgcaactt tatccgcctc   5100
catccagtct attaattgtt gccgggaagc tagagtaagt agttcgccag ttaatagttt   5160
gcgcaacgtt gttgccattg ctacaggcat cgtggtgtca cgctcgtcgt ttggtatggc   5220
ttcattcagc tccggttccc aacgatcaag gcgagttaca tgatccccca tgttgtgcaa   5280
aaaagcggtt agctccttcg gtcctccgat cgttgtcaga agtaagttgg ccgcagtgtt   5340
atcactcatg gttatggcag cactgcataa ttctcttact gtcatgccat ccgtaagatg   5400
cttttctgtg actggtgagt actcaaccaa gtcattctga gaatagtgta tgcggcgacc   5460
gagttgctct tgcccggcgt caatacggga taataccgcg ccacatagca gaactttaaa   5520
agtgctcatc attggaaaac gttcttcggg gcgaaaactc tcaaggatct taccgctgtt   5580
gagatccagt tcgatgtaac ccactcgtgc acccaactga tcttcagcat cttttacttt   5640
caccagcgtt tctgggtgag caaaaacagg aaggcaaaat gccgcaaaaa agggaataag   5700
ggcgacacgg aaatgttgaa tactcatact cttccttttt caatattatt gaagcattta   5760
tcagggttat tgtctcatga gcggatacat atttgaatgt atttagaaaa ataaacaaat   5820
aggggttccg cgcacatttc cccgaaaagt gccacctgaa cgaagcatct gtgcttcatt   5880
ttgtagaaca aaaatgcaac gcgagagcgc taatttttca aacaaagaat ctgagctgca   5940
tttttacaga acagaaatgc aacgcgaaag cgctatttta ccaacgaaga atctgtgctt   6000
catttttgta aaacaaaaat gcaacgcgag agcgctaatt tttcaaacaa agaatctgag   6060
ctgcattttt acagaacaga aatgcaacgc gagagcgcta ttttaccaac aaagaatcta   6120
tacttctttt ttgttctaca aaaatgcatc ccgagagcgc tatttttcta acaaagcatc   6180
ttagattact ttttttctcc tttgtgcgct ctataatgca gtctcttgat aactttttgc   6240
actgtaggtc cgttaaggtt agaagaaggc tactttggtg tctattttct cttccataaa   6300
aaaagcctga ctccacttcc cgcgtttact gattactagc gaagctgcgg gtgcattttt   6360
tcaagataaa ggcatccccg attatattct ataccgatgt ggattgcgca tactttgtga   6420
acagaaagtg atagcgttga tgattcttca ttggtcagaa aattatgaac ggtttcttct   6480
attttgtctc tatatactac gtataggaaa tgtttacatt ttcgtattgt tttcgattca   6540
ctctatgaat agttcttact acaatttttt tgtctaaaga gtaatactag agataaacat   6600
aaaaaatgta gaggtcgagt ttagatgcaa gttcaaggag cgaaaggtgg atgggtaggt   6660
tatataggga tatagcacag agatatatag caaagagata cttttgagca atgtttgtgg   6720
aagcggtatt cgcaatattt tagtagctcg ttacagtccg gtgcgttttt ggttttttga   6780
aagtgcgtct tcagagcgct tttggttttc aaaagcgctc tgaagttcct atactttcta   6840
gagaatagga acttcggaat aggaacttca aagcgtttcc gaaaacgagc gcttccgaaa   6900
atgcaacgcg agctgcgcac atacagctca ctgttcacgt cgcacctata tctgcgtgtt   6960
gcctgtatat atatatacat gagaagaacg gcatagtgcg tgtttatgct taaatgcgta   7020
cttatatgcg tctatttatg taggatgaaa ggtagtctag tacctcctgt gatattatcc   7080
cattccatgc ggggtatcgt atgcttcctt cagcactacc ctttagctgt tctatatgct   7140
gccactcctc aattggatta gtctcatcct tcaatgctat catttccttt gatattggat   7200
catattaaga aaccattatt atcatgacat taacctataa aaataggcgt atcacgaggc   7260
cctttcgtc                                                           7269
```

<210> SEQ ID NO 42
<211> LENGTH: 7601
<212> TYPE: DNA
<213> ORGANISM: Artificial Sequence
<220> FEATURE:
<223> OTHER INFORMATION: Recombinant plasmid pAPSE10442; beta actin hairpin + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3183)
<223> OTHER INFORMATION: restriction endonuclease AsiSI recognition sequence
<220> FEATURE:
<221> NAME/KEY: misc_feature
<222> LOCATION: (3185)..(3478)
<223> OTHER INFORMATION: beta actin sense gene fragment
<220> FEATURE:
<221> NAME/KEY: misc_feature
<222> LOCATION: (3478)..(3485)
<223> OTHER INFORMATION: restriction endonuclease PmeI recognition site
<220> FEATURE:
<221> NAME/KEY: misc_feature
<222> LOCATION: (3643)..(3937)
<223> OTHER INFORMATION: beta actin antisense strand gene fragment
<220> FEATURE:
<221> NAME/KEY: misc_feature
<222> LOCATION: (3973)..(3991)
<223> OTHER INFORMATION: bacteriophage MS2 pac sequence
<220> FEATURE:
<221> NAME/KEY: terminator
<222> LOCATION: (4008)..(4197)
<223> OTHER INFORMATION: yeast CYC1 terminator
<220> FEATURE:
<221> NAME/KEY: misc_feature
<222> LOCATION: (6191)..(7533)
<223> OTHER INFORMATION: yeast 2 micron ori

<400> SEQUENCE: 42
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240
atatgtgtac tttgcagtta tgacgccaga tggcagtagt ggaagatatt ctttattgaa 300
aaatagcttg tcaccttacg tacaatcttg atccggagct tttctttttt tgccgattaa 360
gaattaattc ggtcgaaaaa agaaaaggag agggccaaga gggagggcat tggtgactat 420

```
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctctta ttagtaaatg   2100
ccagagttag cagcgattgc agatgggatc ggattaccgt ctttcagcag gccctgcatt   2160
gccttaacaa tcagttcgca gtcggagttc gtcgcaaaaa tcggaatagt cagttccatg   2220
ttgaggtaag agcgccaggc cgcaactggg agttctacgc cgcctacggt ctgcgttgcg   2280
actttcggta cttcaacttt gatggtgtat ttgcgattct gcgcgctaga ctgacgaacg   2340
gagcacgtga ctttgtaggc ctgagagcgg ctgttagagc taatccattc cgcaacaccg   2400
ttggcgaagt tggacggagc tacggtaacg tcacccgtac cgccgttatc aaccagaacg   2460
aattgggtaa agttagacgc catgaattcg aattttcaaa aattcttact ttttttttgg   2520
atggacgcaa agaagtttaa taatcatatt acatggcatt accaccatat acatatccat   2580
atacatatcc atatctaatc ttacttatat gttgtggaaa tgtaaagagc cccattatct   2640
tagcctaaaa aaaccttctc tttggaactt tcagtaatac gcttaactgc tcattgctat   2700
attgaagtac ggattagaag ccgccgagcg ggtgacagcc ctccgaagga agactctcct   2760
ccgtgcgtcc tcgtcttcac cggtcgcgtt cctgaaacgc agatgtgcct cgcgccgcac   2820
```

```
tgctccgaac aataaagatt ctacaatact agcttttatg gttatgaaga ggaaaaattg   2880
gcagtaacct ggccccacaa accttcaaat gaacgaatca aattaacaac cataggatga   2940
taatgcgatt agtttttag ccttatttct ggggtaatta atcagcgaag cgatgatttt   3000
tgatctatta acagatatat aaatgcaaaa actgcataac cactttaact aatactttca   3060
acattttcgg tttgtattac ttcttattca aatgtaataa aagtatcaac aaaaaattgt   3120
taatatacct ctatacttta acgtcaagga gaaaaaaccc cggatccatt taaatgcgat   3180
cgcgcacgag gtttttctgt ctagtgagca gtgtccaacc tcaaaagaca acatgtgtga   3240
cgacgatgta gcggctcttg tcgtagacaa tggatccggt atgtgcaaag ccggtttcgc   3300
aggagatgac gcaccccgtg ccgtcttccc ctcgatcgtc ggtcgcccaa ggcatcaagg   3360
agtcatggtc ggtatgggac aaaaggactc atacgtagga gatgaagccc aaagcaaaag   3420
aggtatcctc accctgaaat accccatcga acacggtatc atcaccaact gggatgagtt   3480
taaaccctct agctgcttta caaagtactg gttccctttc cagcgggatg ctttatctaa   3540
acgcaatgag agaggtattc ctcaggccac atcgcttcct agttccgctg ggatccatcg   3600
ttggcggccg aagccgccat tccatagtga gttctggcgc gcctcatccc agttggtgat   3660
gataccgtgt tcgatggggt atttcagggt gaggatacct cttttgcttt gggcttcatc   3720
tcctacgtat gagtcctttt gtcccatacc gaccatgact ccttgatgcc ttgggcgacc   3780
gacgatcgag gggaagacgg cacggggtgc gtcatctcct gcgaaaccgg ctttgcacat   3840
accggatcca ttgtctacga caagagccgc tacatcgtcg tcacacatgt tgtcttttga   3900
ggttggacac tgctcactag acagaaaaac ctcgtgccgg accgaatacc cggtctgaac   3960
gagggcggcc gcacatgagg atcacccatg tccgcgggct agctaagatc cgctctaacc   4020
gaaaaggaag gagttagaca acctgaagtc taggtcccta tttatttttt tatagttatg   4080
ttagtattaa gaacgttatt tatatttcaa atttttcttt tttttctgta cagacgcgtg   4140
tacgcatgta acattatact gaaaaccttg cttgagaagg ttttgggacg ctcgaagatc   4200
cagctgcatt aatgaatcgg ccaacgcgcg gggagaggcg gtttgcgtat tgggcgctct   4260
tccgcttcct cgctcactga ctcgctgcgc tcggtcgttc ggctgcggcg agcggtatca   4320
gctcactcaa aggcggtaat acggttatcc acagaatcag gggataacgc aggaaagaac   4380
atgtgagcaa aaggccagca aaaggccagg aaccgtaaaa aggccgcgtt gctggcgttt   4440
ttccataggc tccgcccccc tgacgagcat cacaaaaatc gacgctcaag tcagaggtgg   4500
cgaaacccga caggactata aagataccag gcgtttcccc ctggaagctc cctcgtgcgc   4560
tctcctgttc cgaccctgcc gcttaccgga tacctgtccg cctttctccc ttcgggaagc   4620
gtggcgcttt ctcatagctc acgctgtagg tatctcagtt cggtgtaggt cgttcgctcc   4680
aagctgggct gtgtgcacga accccccgtt cagcccgacc gctgcgcctt atccggtaac   4740
tatcgtcttg agtccaaccc ggtaagacac gacttatcgc cactggcagc agccactggt   4800
aacaggatta gcagagcgag gtatgtaggc ggtgctacag agttcttgaa gtggtggcct   4860
aactacggct acactagaag gacagtattt ggtatctgcg ctctgctgaa gccagttacc   4920
ttcggaaaaa gagttggtag ctcttgatcc ggcaaacaaa ccaccgctgg tagcggtggt   4980
ttttttgttt gcaagcagca gattacgcgc agaaaaaaag gatctcaaga agatcctttg   5040
atcttttcta cggggtctga cgctcagtgg aacgaaaact cacgttaagg gattttggtc   5100
atgagattat caaaaaggat cttcacctag atccttttaa attaaaaatg aagttttaaa   5160
```

```
tcaatctaaa gtatatatga gtaaacttgg tctgacagtt accaatgctt aatcagtgag   5220
gcacctatct cagcgatctg tctatttcgt tcatccatag ttgcctgact ccccgtcgtg   5280
tagataacta cgatacggga gggcttacca tctggcccca gtgctgcaat gataccgcga   5340
gacccacgct caccggctcc agatttatca gcaataaacc agccagccgg aagggccgag   5400
cgcagaagtg gtcctgcaac tttatccgcc tccatccagt ctattaattg ttgccgggaa   5460
gctagagtaa gtagttcgcc agttaatagt ttgcgcaacg ttgttgccat tgctacaggc   5520
atcgtggtgt cacgctcgtc gtttggtatg gcttcattca gctccggttc ccaacgatca   5580
aggcgagtta catgatcccc catgttgtgc aaaaaagcgg ttagctcctt cggtcctccg   5640
atcgttgtca gaagtaagtt ggccgcagtg ttatcactca tggttatggc agcactgcat   5700
aattctctta ctgtcatgcc atccgtaaga tgcttttctg tgactggtga gtactcaacc   5760
aagtcattct gagaatagtg tatgcggcga ccgagttgct cttgcccggc gtcaatacgg   5820
gataataccg cgccacatag cagaacttta aaagtgctca tcattggaaa acgttcttcg   5880
gggcgaaaac tctcaaggat cttaccgctg ttgagatcca gttcgatgta acccactcgt   5940
gcacccaact gatcttcagc atcttttact ttcaccagcg tttctgggtg agcaaaaaca   6000
ggaaggcaaa atgccgcaaa aaagggaata agggcgacac ggaaatgttg aatactcata   6060
ctcttccttt ttcaatatta ttgaagcatt tatcagggtt attgtctcat gagcggatac   6120
atatttgaat gtatttagaa aaataaacaa ataggggttc cgcgcacatt tccccgaaaa   6180
gtgccacctg aacgaagcat ctgtgcttca ttttgtagaa caaaaatgca acgcgagagc   6240
gctaattttt caaacaaaga atctgagctg catttttaca gaacagaaat gcaacgcgaa   6300
agcgctattt taccaacgaa gaatctgtgc ttcatttttg taaaacaaaa atgcaacgcg   6360
agagcgctaa tttttcaaac aaagaatctg agctgcattt ttacagaaca gaaatgcaac   6420
gcgagagcgc tattttacca acaaagaatc tatacttctt ttttgttcta caaaaatgca   6480
tcccgagagc gctatttttc taacaaagca tcttagatta cttttttttct cctttgtgcg   6540
ctctataatg cagtctcttg ataacttttt gcactgtagg tccgttaagg ttagaagaag   6600
gctactttgg tgtctatttt ctcttccata aaaaaagcct gactccactt cccgcgttta   6660
ctgattacta gcgaagctgc gggtgcattt tttcaagata aaggcatccc cgattatatt   6720
ctataccgat gtggattgcg catactttgt gaacagaaag tgatagcgtt gatgattctt   6780
cattggtcag aaaattatga acggtttctt ctattttgtc tctatatact acgtatagga   6840
aatgtttaca ttttcgtatt gttttcgatt cactctatga atagttctta ctacaatttt   6900
tttgtctaaa gagtaatact agagataaac ataaaaaatg tagaggtcga gtttagatgc   6960
aagttcaagg agcgaaaggt ggatgggtag gttatatagg gatatagcac agagatatat   7020
agcaaagaga tacttttgag caatgtttgt ggaagcggta ttcgcaatat tttagtagct   7080
cgttacagtc cggtgcgttt ttggtttttt gaaagtgcgt cttcagagcg cttttggttt   7140
tcaaaagcgc tctgaagttc ctatactttc tagagaatag gaacttcgga ataggaactt   7200
caaagcgttt ccgaaaacga gcgcttccga aaatgcaacg cgagctgcgc acatacagct   7260
cactgttcac gtcgcaccta tatctgcgtg ttgcctgtat atatatatac atgagaagaa   7320
cggcatagtg cgtgtttatg cttaaatgcg tacttatatg cgtctattta tgtaggatga   7380
aaggtagtct agtacctcct gtgatattat cccattccat gcggggtatc gtatgcttcc   7440
ttcagcacta ccctttagct gttctatatg ctgccactcc tcaattggat tagtctcatc   7500
cttcaatgct atcatttcct ttgatattgg atcatattaa gaaaccatta ttatcatgac   7560
```

attaacctat aaaaataggc gtatcacgag gccctttcgt c 7601

<210> SEQ ID NO 43
<211> LENGTH: 7288
<212> TYPE: DNA
<213> ORGANISM: Artificial Sequence
<220> FEATURE:
<223> OTHER INFORMATION: Recombinant plasmid pAPSE10443; beta actin stem loop - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional promoter
<220> FEATURE:
<221> NAME/KEY: misc_feature
<222> LOCATION: (2844)..(2862)
<223> OTHER INFORMATION: bacteriophage MS2 pac sequence
<220> FEATURE:
<221> NAME/KEY: misc_feature
<222> LOCATION: (2863)..(2870)
<223> OTHER INFORMATION: restriction endonuclease AsiSI recognition sequence
<220> FEATURE:
<221> NAME/KEY: misc_feature
<222> LOCATION: (2872)..(3165)
<223> OTHER INFORMATION: beta actin sense gene fragment
<220> FEATURE:
<221> NAME/KEY: misc_feature
<222> LOCATION: (3165)..(3172)
<223> OTHER INFORMATION: restriction endonuclease PmeI recognition site
<220> FEATURE:
<221> NAME/KEY: misc_feature
<222> LOCATION: (3329)..(3624)
<223> OTHER INFORMATION: beta actin antisense strand gene fragment
<220> FEATURE:
<221> NAME/KEY: misc_feature
<222> LOCATION: (3660)..(3678)
<223> OTHER INFORMATION: bacteriophage MS2 pac sequence
<220> FEATURE:
<221> NAME/KEY: terminator
<222> LOCATION: (3695)..(3884)
<223> OTHER INFORMATION: yeast CYC1 terminator
<220> FEATURE:
<221> NAME/KEY: misc_feature
<222> LOCATION: (5878)..(7220)
<223> OTHER INFORMATION: yeast 2 micron ori

<400> SEQUENCE: 43
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240
atatgtgtac tttgcagtta tgacgccaga tggcagtagt ggaagatatt ctttattgaa 300
aaatagcttg tcaccttacg tacaatcttg atccggagct tttctttttt tgccgattaa 360

```
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctcaga tcttatcgtc   2100
gtcatccttg taatccatcg atactagtgc ggccgccctt tagtgagggt tgaattcgaa   2160
ttttcaaaaa ttcttacttt ttttttggat ggacgcaaag aagtttaata atcatattac   2220
atggcattac caccatatac atatccatat acatatccat atctaatctt acttatatgt   2280
tgtggaaatg taaagagccc cattatctta gcctaaaaaa accttctctt tggaactttc   2340
agtaatacgc ttaactgctc attgctatat tgaagtacgg attagaagcc gccgagcggg   2400
tgacagccct ccgaaggaag actctcctcc gtgcgtcctc gtcttcaccg gtcgcgttcc   2460
tgaaacgcag atgtgcctcg cgccgcactg ctccgaacaa taaagattct acaatactag   2520
cttttatggt tatgaagagg aaaaattggc agtaacctgg ccccacaaac cttcaaatga   2580
acgaatcaaa ttaacaacca taggatgata atgcgattag ttttttagcc ttatttctgg   2640
ggtaattaat cagcgaagcg atgatttttg atctattaac agatatataa atgcaaaaac   2700
tgcataacca ctttaactaa tactttcaac attttcggtt tgtattactt cttattcaaa   2760
```

```
tgtaataaaa gtatcaacaa aaaattgtta atatacctct atactttaac gtcaaggaga   2820
aaaaaccccg gatccattta aatacatgag gattacccat gtgcgatcgc gcacgaggtt   2880
tttctgtcta gtgagcagtg tccaacctca aaagacaaca tgtgtgacga cgatgtagcg   2940
gctcttgtcg tagacaatgg atccggtatg tgcaaagccg gtttcgcagg agatgacgca   3000
ccccgtgccg tcttcccctc gatcgtcggt cgcccaaggc atcaaggagt catggtcggt   3060
atgggacaaa aggactcata cgtaggagat gaagcccaaa gcaaaagagg tatcctcacc   3120
ctgaaatacc ccatcgaaca cggtatcatc accaactggg atgagtttaa accctctagc   3180
tgctttacaa agtactggtt ccctttccag cgggatgctt tatctaaacg caatgagaga   3240
ggtattcctc aggccacatc gcttcctagt tccgctggga tccatcgttg gcggccgaag   3300
ccgccattcc atagtgagtt ctggcgcgcc tcatcccagt tggtgatgat accgtgttcg   3360
atggggtatt tcagggtgag gatacctctt ttgctttggg cttcatctcc tacgtatgag   3420
tccttttgtc ccataccgac catgactcct tgatgccttg ggcgaccgac gatcgagggg   3480
aagacggcac ggggtgcgtc atctcctgcg aaaccggctt tgcacatacc ggatccattg   3540
tctacgacaa gagccgctac atcgtcgtca cacatgttgt cttttgaggt tggacactgc   3600
tcactagaca gaaaaacctc gtgccggacc gaatacccgg tctgaacgag ggcggccgca   3660
catgaggatc acccatgtcc gcgggctagc taagatccgc tctaaccgaa aaggaaggag   3720
ttagacaacc tgaagtctag gtccctattt attttttat agttatgtta gtattaagaa   3780
cgttatttat atttcaaatt tttcttttt ttctgtacag acgcgtgtac gcatgtaaca   3840
ttatactgaa aaccttgctt gagaaggttt tgggacgctc gaagatccag ctgcattaat   3900
gaatcggcca acgcgcgggg agaggcggtt tgcgtattgg gcgctcttcc gcttcctcgc   3960
tcactgactc gctgcgctcg gtcgttcggc tgcggcgagc ggtatcagct cactcaaagg   4020
cggtaatacg gttatccaca gaatcagggg ataacgcagg aaagaacatg tgagcaaaag   4080
gccagcaaaa ggccaggaac cgtaaaaagg ccgcgttgct ggcgtttttc cataggctcc   4140
gcccccctga cgagcatcac aaaaatcgac gctcaagtca gaggtggcga aacccgacag   4200
gactataaag ataccaggcg tttccccctg gaagctccct cgtgcgctct cctgttccga   4260
ccctgccgct taccggatac ctgtccgcct ttctcccttc gggaagcgtg gcgctttctc   4320
atagctcacg ctgtaggtat ctcagttcgg tgtaggtcgt tcgctccaag ctgggctgtg   4380
tgcacgaacc ccccgttcag cccgaccgct gcgccttatc cggtaactat cgtcttgagt   4440
ccaacccggt aagacacgac ttatcgccac tggcagcagc cactggtaac aggattagca   4500
gagcgaggta tgtaggcggt gctacagagt tcttgaagtg gtggcctaac tacggctaca   4560
ctagaaggac agtatttggt atctgcgctc tgctgaagcc agttaccttc ggaaaaagag   4620
ttggtagctc ttgatccggc aaacaaacca ccgctggtag cggtggtttt tttgtttgca   4680
agcagcagat tacgcgcaga aaaaaaggat ctcaagaaga tcctttgatc ttttctacgg   4740
ggtctgacgc tcagtggaac gaaaactcac gttaagggat tttggtcatg agattatcaa   4800
aaaggatctt cacctagatc cttttaaatt aaaaatgaag ttttaaatca atctaaagta   4860
tatatgagta aacttggtct gacagttacc aatgcttaat cagtgaggca cctatctcag   4920
cgatctgtct atttcgttca tccatagttg cctgactccc cgtcgtgtag ataactacga   4980
tacgggaggg cttaccatct ggccccagtg ctgcaatgat accgcgagac ccacgctcac   5040
cggctccaga tttatcagca ataaaccagc cagccggaag ggccgagcgc agaagtggtc   5100
```

```
ctgcaacttt atccgcctcc atccagtcta ttaattgttg ccgggaagct agagtaagta   5160
gttcgccagt taatagtttg cgcaacgttg ttgccattgc tacaggcatc gtggtgtcac   5220
gctcgtcgtt tggtatggct tcattcagct ccggttccca acgatcaagg cgagttacat   5280
gatcccccat gttgtgcaaa aaagcggtta gctccttcgg tcctccgatc gttgtcagaa   5340
gtaagttggc cgcagtgtta tcactcatgg ttatggcagc actgcataat tctcttactg   5400
tcatgccatc cgtaagatgc ttttctgtga ctggtgagta ctcaaccaag tcattctgag   5460
aatagtgtat gcggcgaccg agttgctctt gcccggcgtc aatacgggat aataccgcgc   5520
cacatagcag aactttaaaa gtgctcatca ttggaaaacg ttcttcgggg cgaaaactct   5580
caaggatctt accgctgttg agatccagtt cgatgtaacc cactcgtgca cccaactgat   5640
cttcagcatc ttttactttc accagcgttt ctgggtgagc aaaaacagga aggcaaaatg   5700
ccgcaaaaaa gggaataagg gcgacacgga aatgttgaat actcatactc ttcctttttc   5760
aatattattg aagcatttat cagggttatt gtctcatgag cggatacata tttgaatgta   5820
tttagaaaaa taaacaaata ggggttccgc gcacatttcc ccgaaaagtg ccacctgaac   5880
gaagcatctg tgcttcattt tgtagaacaa aaatgcaacg cgagagcgct aatttttcaa   5940
acaaagaatc tgagctgcat ttttacagaa cagaaatgca acgcgaaagc gctattttac   6000
caacgaagaa tctgtgcttc atttttgtaa aacaaaaatg caacgcgaga gcgctaattt   6060
ttcaaacaaa gaatctgagc tgcattttta cagaacagaa atgcaacgcg agagcgctat   6120
tttaccaaca aagaatctat acttcttttt tgttctacaa aaatgcatcc cgagagcgct   6180
atttttctaa caaagcatct tagattactt tttttctcct ttgtgcgctc tataatgcag   6240
tctcttgata actttttgca ctgtaggtcc gttaaggtta gaagaaggct actttggtgt   6300
ctattttctc ttccataaaa aaagcctgac tccacttccc gcgtttactg attactagcg   6360
aagctgcggg tgcatttttt caagataaag gcatccccga ttatattcta taccgatgtg   6420
gattgcgcat actttgtgaa cagaaagtga tagcgttgat gattcttcat tggtcagaaa   6480
attatgaacg gtttcttcta ttttgtctct atatactacg tataggaaat gtttacattt   6540
tcgtattgtt ttcgattcac tctatgaata gttcttacta caattttttt gtctaaagag   6600
taatactaga gataaacata aaaaatgtag aggtcgagtt tagatgcaag ttcaaggagc   6660
gaaaggtgga tgggtaggtt atatagggat atagcacaga gatatatagc aaagagatac   6720
ttttgagcaa tgtttgtgga agcggtattc gcaatatttt agtagctcgt tacagtccgg   6780
tgcgtttttg gtttttttgaa agtgcgtctt cagagcgctt ttggttttca aaagcgctct   6840
gaagttccta tactttctag agaataggaa cttcggaata ggaacttcaa agcgtttccg   6900
aaaacgagcg cttccgaaaa tgcaacgcga gctgcgcaca tacagctcac tgttcacgtc   6960
gcacctatat ctgcgtgttg cctgtatata tatatacatg agaagaacgg catagtgcgt   7020
gtttatgctt aaatgcgtac ttatatgcgt ctatttatgt aggatgaaag gtagtctagt   7080
acctcctgtg atattatccc attccatgcg gggtatcgta tgcttccttc agcactaccc   7140
tttagctgtt ctatatgctg ccactcctca attggattag tctcatcctt caatgctatc   7200
atttcctttg atattggatc atattaagaa accattatta tcatgacatt aacctataaa   7260
aataggcgta tcacgaggcc ctttcgtc                                      7288
```

<210> SEQ ID NO 44
<211> LENGTH: 7620
<212> TYPE: DNA
<213> ORGANISM: Artificial Sequence

```
<220> FEATURE:
<223> OTHER INFORMATION: Recombinant plasmid pAPSE10444; beta actin stem
      loop + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3194)
<223> OTHER INFORMATION: bacteriophage MS2 pac sequence
<220> FEATURE:
<221> NAME/KEY: misc_feature
<222> LOCATION: (3195)..(3202)
<223> OTHER INFORMATION: restriction endonuclease AsiSI recognition
      sequence
<220> FEATURE:
<221> NAME/KEY: misc_feature
<222> LOCATION: (3204)..(3497)
<223> OTHER INFORMATION: beta actin sense gene fragment
<220> FEATURE:
<221> NAME/KEY: misc_feature
<222> LOCATION: (3497)..(3504)
<223> OTHER INFORMATION: restriction endonuclease PmeI recognition site
<220> FEATURE:
<221> NAME/KEY: misc_feature
<222> LOCATION: (3661)..(3957)
<223> OTHER INFORMATION: beta actin antisense strand gene fragment
<220> FEATURE:
<221> NAME/KEY: misc_feature
<222> LOCATION: (3992)..(4010)
<223> OTHER INFORMATION: bacteriophage MS2 pac sequence
<220> FEATURE:
<221> NAME/KEY: terminator
<222> LOCATION: (4027)..(4216)
<223> OTHER INFORMATION: yeast CYC1 terminator
<220> FEATURE:
<221> NAME/KEY: misc_feature
<222> LOCATION: (6210)..(7552)
<223> OTHER INFORMATION: yeast 2 micron ori

<400> SEQUENCE: 44

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accataaacg acattactat atatataata taggaagcat ttaatagaca gcatcgtaat     240

atatgtgtac tttgcagtta tgacgccaga tggcagtagt ggaagatatt ctttattgaa     300

aaatagcttg tcaccttacg tacaatcttg atccggagct ttctttttt tgccgattaa      360

gaattaattc ggtcgaaaaa agaaaaggag agggccaaga gggagggcat tggtgactat     420

tgagcacgtg agtatacgtg attaagcaca caaaggcagc ttggagtatg tctgttatta     480
```

```
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tattttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctctta ttagtaaatg   2100
ccagagttag cagcgattgc agatgggatc ggattaccgt ctttcagcag gccctgcatt   2160
gccttaacaa tcagttcgca gtcggagttc gtcgcaaaaa tcggaatagt cagttccatg   2220
ttgaggtaag agcgccaggc cgcaactggg agttctacgc cgcctacggt ctgcgttgcg   2280
actttcggta cttcaacttt gatggtgtat ttgcgattct gcgcgctaga ctgacgaacg   2340
gagcacgtga ctttgtaggc ctgagagcgg ctgttagagc taatccattc cgcaacaccg   2400
ttggcgaagt tggacggagc tacggtaacg tcacccgtac cgccgttatc aaccagaacg   2460
aattgggtaa agttagacgc catgaattcg aattttcaaa aattcttact tttttttgg   2520
atggacgcaa agaagtttaa taatcatatt acatggcatt accaccatat acatatccat   2580
atacatatcc atatctaatc ttacttatat gttgtggaaa tgtaaagagc cccattatct   2640
tagcctaaaa aaaccttctc tttggaactt tcagtaatac gcttaactgc tcattgctat   2700
attgaagtac ggattagaag ccgccgagcg ggtgacagcc ctccgaagga agactctcct   2760
ccgtgcgtcc tcgtcttcac cggtcgcgtt cctgaaacgc agatgtgcct cgcgccgcac   2820
tgctccgaac aataaagatt ctacaatact agcttttatg gttatgaaga ggaaaaattg   2880
```

```
gcagtaacct ggccccacaa accttcaaat gaacgaatca aattaacaac cataggatga   2940
taatgcgatt agttttttag ccttatttct ggggtaatta atcagcgaag cgatgatttt   3000
tgatctatta acagatatat aaatgcaaaa actgcataac cactttaact aatactttca   3060
acattttcgg tttgtattac ttcttattca aatgtaataa aagtatcaac aaaaaattgt   3120
taatatacct ctatacttta acgtcaagga gaaaaaaccc cggatccatt taaatacatg   3180
aggattaccc atgtgcgatc gcgcacgagg tttttctgtc tagtgagcag tgtccaacct   3240
caaaagacaa catgtgtgac gacgatgtag cggctcttgt cgtagacaat ggatccggta   3300
tgtgcaaagc cggtttcgca ggagatgacg caccccgtgc cgtcttcccc tcgatcgtcg   3360
gtcgcccaag gcatcaagga gtcatggtcg gtatgggaca aaaggactca tacgtaggag   3420
atgaagccca aagcaaaaga ggtatcctca ccctgaaata ccccatcgaa cacggtatca   3480
tcaccaactg ggatgagttt aaaccctcta gctgctttac aaagtactgg ttccctttcc   3540
agcgggatgc tttatctaaa cgcaatgaga gaggtattcc tcaggccaca tcgcttccta   3600
gttccgctgg gatccatcgt tggcggccga agccgccatt ccatagtgag ttctggcgcg   3660
cctcatccca gttggtgatg ataccgtgtt cgatggggta tttcagggtg aggatacctc   3720
ttttgctttg ggcttcatct cctacgtatg agtccttttg tcccataccg accatgactc   3780
cttgatgcct tgggcgaccg acgatcgagg ggaagacggc acggggtgcg tcatctcctg   3840
cgaaaccggc tttgcacata ccggatccat tgtctacgac aagagccgct acatcgtcgt   3900
cacacatgtt gtcttttgag gttggacact gctcactaga cagaaaaacc tcgtgccgga   3960
ccgaataccc ggtctgaacg agggcggccg cacatgagga tcacccatgt ccgcgggcta   4020
gctaagatcc gctctaaccg aaaaggaagg agttagacaa cctgaagtct aggtccctat   4080
ttattttttt atagttatgt tagtattaag aacgttattt atatttcaaa tttttctttt   4140
ttttctgtac agacgcgtgt acgcatgtaa cattatactg aaaaccttgc ttgagaaggt   4200
tttgggacgc tcgaagatcc agctgcatta atgaatcggc caacgcgcgg ggagaggcgg   4260
tttgcgtatt gggcgctctt ccgcttcctc gctcactgac tcgctgcgct cggtcgttcg   4320
gctgcggcga gcggtatcag ctcactcaaa ggcggtaata cggttatcca cagaatcagg   4380
ggataacgca ggaaagaaca tgtgagcaaa aggccagcaa aaggccagga accgtaaaaa   4440
ggccgcgttg ctggcgtttt tccataggct ccgcccccct gacgagcatc acaaaaatcg   4500
acgctcaagt cagaggtggc gaaacccgac aggactataa agataccagg cgtttccccc   4560
tggaagctcc ctcgtgcgct ctcctgttcc gaccctgccg cttaccggat acctgtccgc   4620
ctttctccct tcgggaagcg tggcgctttc tcatagctca cgctgtaggt atctcagttc   4680
ggtgtaggtc gttcgctcca agctgggctg tgtgcacgaa ccccccgttc agcccgaccg   4740
ctgcgcctta tccggtaact atcgtcttga gtccaacccg gtaagacacg acttatcgcc   4800
actggcagca gccactggta acaggattag cagagcgagg tatgtaggcg gtgctacaga   4860
gttcttgaag tggtggccta actacggcta cactagaagg acagtatttg gtatctgcgc   4920
tctgctgaag ccagttacct tcggaaaaag agttggtagc tcttgatccg gcaaacaaac   4980
caccgctggt agcggtggtt tttttgtttg caagcagcag attacgcgca gaaaaaaagg   5040
atctcaagaa gatcctttga tcttttctac ggggtctgac gctcagtgga acgaaaactc   5100
acgttaaggg attttggtca tgagattatc aaaaaggatc ttcacctaga tccttttaaa   5160
ttaaaaatga agttttaaat caatctaaag tatatatgag taaacttggt ctgacagtta   5220
```

```
ccaatgctta atcagtgagg cacctatctc agcgatctgt ctatttcgtt catccatagt   5280
tgcctgactc cccgtcgtgt agataactac gatacgggag ggcttaccat ctggccccag   5340
tgctgcaatg ataccgcgag acccacgctc accggctcca gatttatcag caataaacca   5400
gccagccgga agggccgagc gcagaagtgg tcctgcaact ttatccgcct ccatccagtc   5460
tattaattgt tgccgggaag ctagagtaag tagttcgcca gttaatagtt tgcgcaacgt   5520
tgttgccatt gctacaggca tcgtggtgtc acgctcgtcg tttggtatgg cttcattcag   5580
ctccggttcc caacgatcaa ggcgagttac atgatccccc atgttgtgca aaaaagcggt   5640
tagctccttc ggtcctccga tcgttgtcag aagtaagttg gccgcagtgt tatcactcat   5700
ggttatggca gcactgcata attctcttac tgtcatgcca tccgtaagat gcttttctgt   5760
gactggtgag tactcaacca agtcattctg agaatagtgt atgcggcgac cgagttgctc   5820
ttgcccggcg tcaatacggg ataataccgc gccacatagc agaactttaa aagtgctcat   5880
cattggaaaa cgttcttcgg ggcgaaaact ctcaaggatc ttaccgctgt tgagatccag   5940
ttcgatgtaa cccactcgtg cacccaactg atcttcagca tcttttactt tcaccagcgt   6000
ttctgggtga gcaaaaacag gaaggcaaaa tgccgcaaaa aagggaataa gggcgacacg   6060
gaaatgttga atactcatac tcttcctttt tcaatattat tgaagcattt atcagggtta   6120
ttgtctcatg agcggataca tatttgaatg tatttagaaa aataaacaaa taggggttcc   6180
gcgcacattt ccccgaaaag tgccacctga acgaagcatc tgtgcttcat tttgtagaac   6240
aaaaatgcaa cgcgagagcg ctaatttttc aaacaaagaa tctgagctgc atttttacag   6300
aacagaaatg caacgcgaaa gcgctatttt accaacgaag aatctgtgct tcatttttgt   6360
aaaacaaaaa tgcaacgcga gagcgctaat ttttcaaaca aagaatctga gctgcatttt   6420
tacagaacag aaatgcaacg cgagagcgct attttaccaa caaagaatct atacttcttt   6480
tttgttctac aaaaatgcat cccgagagcg ctatttttct aacaaagcat cttagattac   6540
tttttttctc ctttgtgcgc tctataatgc agtctcttga taactttttg cactgtaggt   6600
ccgttaaggt tagaagaagg ctactttggt gtctattttc tcttccataa aaaaagcctg   6660
actccacttc ccgcgtttac tgattactag cgaagctgcg ggtgcatttt ttcaagataa   6720
aggcatcccc gattatattc tataccgatg tggattgcgc atactttgtg aacagaaagt   6780
gatagcgttg atgattcttc attggtcaga aaattatgaa cggtttcttc tattttgtct   6840
ctatatacta cgtataggaa atgtttacat tttcgtattg ttttcgattc actctatgaa   6900
tagttcttac tacaattttt ttgtctaaag agtaatacta gagataaaca taaaaaatgt   6960
agaggtcgag tttagatgca agttcaagga gcgaaaggtg gatgggtagg ttatataggg   7020
atatagcaca gagatatata gcaaagagat acttttgagc aatgtttgtg gaagcggtat   7080
tcgcaatatt ttagtagctc gttacagtcc ggtgcgtttt tggttttttg aaagtgcgtc   7140
ttcagagcgc ttttggtttt caaaagcgct ctgaagttcc tatactttct agagaatagg   7200
aacttcggaa taggaacttc aaagcgtttc cgaaaacgag cgcttccgaa aatgcaacgc   7260
gagctgcgca catacagctc actgttcacg tcgcacctat atctgcgtgt tgcctgtata   7320
tatatataca tgagaagaac ggcatagtgc gtgtttatgc ttaaatgcgt acttatatgc   7380
gtctatttat gtaggatgaa aggtagtcta gtacctcctg tgatattatc ccattccatg   7440
cggggtatcg tatgcttcct tcagcactac cctttagctg ttctatatgc tgccactcct   7500
caattggatt agtctcatcc ttcaatgcta tcatttcctt tgatattgga tcatattaag   7560
aaaccattat tatcatgaca ttaacctata aaaataggcg tatcacgagg ccctttcgtc   7620
```

<210> SEQ ID NO 45
<211> LENGTH: 7288
<212> TYPE: DNA
<213> ORGANISM: Artificial Sequence
<220> FEATURE:
<223> OTHER INFORMATION: Recpmbinant plasmid pAPSE10445; beta actin stem loop - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: misc_feature
<222> LOCATION: (2162)..(2826)
<223> OTHER INFORMATION: yeast GAL1, 10 bidirectional prmoter
<220> FEATURE:
<221> NAME/KEY: misc_feature
<222> LOCATION: (2844)..(2862)
<223> OTHER INFORMATION: bacteriophage MS2 pac sequence
<220> FEATURE:
<221> NAME/KEY: misc_feature
<222> LOCATION: (2863)..(2870)
<223> OTHER INFORMATION: restriction endonuclease AsiSI recognition sequence
<220> FEATURE:
<221> NAME/KEY: misc_feature
<222> LOCATION: (2872)..(3165)
<223> OTHER INFORMATION: beta actin sense gene fragment
<220> FEATURE:
<221> NAME/KEY: misc_feature
<222> LOCATION: (3165)..(3172)
<223> OTHER INFORMATION: restriction endonuclease PmeI recognition site
<220> FEATURE:
<221> NAME/KEY: misc_feature
<222> LOCATION: (3233)..(3251)
<223> OTHER INFORMATION: bacteriophage MS2 pac sequence
<220> FEATURE:
<221> NAME/KEY: misc_feature
<222> LOCATION: (3329)..(3624)
<223> OTHER INFORMATION: beta actin antisense strand gene fragment
<220> FEATURE:
<221> NAME/KEY: misc_feature
<222> LOCATION: (3660)..(3678)
<223> OTHER INFORMATION: bacteriophage MS2 pac sequence
<220> FEATURE:
<221> NAME/KEY: terminator
<222> LOCATION: (3695)..(3884)
<223> OTHER INFORMATION: yeast CYC1 terminator
<220> FEATURE:
<221> NAME/KEY: misc_feature
<222> LOCATION: (5878)..(7220)
<223> OTHER INFORMATION: yeast 2 micron ori

<400> SEQUENCE: 45
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240
atatgtgtac tttgcagtta tgacgccaga tggcagtagt ggaagatatt ctttattgaa 300

```
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctcaga tcttatcgtc   2100
gtcatccttg taatccatcg atactagtgc ggccgccctt tagtgagggt tgaattcgaa   2160
ttttcaaaaa ttcttacttt ttttttggat ggacgcaaag aagtttaata atcatattac   2220
atggcattac caccatatac atatccatat acatatccat atctaatctt acttatatgt   2280
tgtggaaatg taaagagccc cattatctta gcctaaaaaa accttctctt tggaactttc   2340
agtaatacgc ttaactgctc attgctatat tgaagtacgg attagaagcc gccgagcggg   2400
tgacagccct ccgaaggaag actctcctcc gtgcgtcctc gtcttcaccg gtcgcgttcc   2460
tgaaacgcag atgtgcctcg cgccgcactg ctccgaacaa taaagattct acaatactag   2520
cttttatggt tatgaagagg aaaaattggc agtaacctgg ccccacaaac cttcaaatga   2580
acgaatcaaa ttaacaacca taggatgata atgcgattag ttttttagcc ttatttctgg   2640
ggtaattaat cagcgaagcg atgatttttg atctattaac agatatataa atgcaaaaac   2700
```

```
tgcataacca ctttaactaa tactttcaac attttcggtt tgtattactt cttattcaaa   2760
tgtaataaaa gtatcaacaa aaaattgtta atatacctct atactttaac gtcaaggaga   2820
aaaaaccccg gatccattta aatacatgag gattacccat gtgcgatcgc gcacgaggtt   2880
tttctgtcta gtgagcagtg tccaacctca aaagacaaca tgtgtgacga cgatgtagcg   2940
gctcttgtcg tagacaatgg atccggtatg tgcaaagccg gtttcgcagg agatgacgca   3000
ccccgtgccg tcttcccctc gatcgtcggt cgcccaaggc atcaaggagt catggtcggt   3060
atgggacaaa aggactcata cgtaggagat gaagcccaaa gcaaaagagg tatcctcacc   3120
ctgaaatacc ccatcgaaca cggtatcatc accaactggg atgagtttaa accctctagc   3180
tgctttacaa agtactggtt ccctttccag cgggatgctt tatctaaacg caacatgagg   3240
atcacccatg tcgccacatc gcttcctagt tccgctggga tccatcgttg gcggccgaag   3300
ccgccattcc atagtgagtt ctggcgcgcc tcatcccagt tggtgatgat accgtgttcg   3360
atggggtatt tcagggtgag gatacctctt ttgctttggg cttcatctcc tacgtatgag   3420
tccttttgtc ccataccgac catgactcct tgatgccttg ggcgaccgac gatcgagggg   3480
aagacggcac ggggtgcgtc atctcctgcg aaaccggctt tgcacatacc ggatccattg   3540
tctacgacaa gagccgctac atcgtcgtca cacatgttgt cttttgaggt tggacactgc   3600
tcactagaca gaaaaacctc gtgccggacc gaatacccgg tctgaacgag ggcggccgca   3660
catgaggatc acccatgtcc gcgggctagc taagatccgc tctaaccgaa aaggaaggag   3720
ttagacaacc tgaagtctag gtccctattt atttttttat agttatgtta gtattaagaa   3780
cgttatttat atttcaaatt tttctttttt ttctgtacag acgcgtgtac gcatgtaaca   3840
ttatactgaa aaccttgctt gagaaggttt tgggacgctc gaagatccag ctgcattaat   3900
gaatcggcca acgcgcgggg agaggcggtt tgcgtattgg gcgctcttcc gcttcctcgc   3960
tcactgactc gctgcgctcg gtcgttcggc tgcggcgagc ggtatcagct cactcaaagg   4020
cggtaatacg gttatccaca gaatcagggg ataacgcagg aaagaacatg tgagcaaaag   4080
gccagcaaaa ggccaggaac cgtaaaaagg ccgcgttgct ggcgtttttc cataggctcc   4140
gcccccctga cgagcatcac aaaaatcgac gctcaagtca gaggtggcga aacccgacag   4200
gactataaag ataccaggcg tttccccctg gaagctccct cgtgcgctct cctgttccga   4260
ccctgccgct taccggatac ctgtccgcct ttctcccttc gggaagcgtg gcgctttctc   4320
atagctcacg ctgtaggtat ctcagttcgg tgtaggtcgt tcgctccaag ctgggctgtg   4380
tgcacgaacc ccccgttcag cccgaccgct gcgccttatc cggtaactat cgtcttgagt   4440
ccaacccggt aagacacgac ttatcgccac tggcagcagc cactggtaac aggattagca   4500
gagcgaggta tgtaggcggt gctacagagt tcttgaagtg gtggcctaac tacggctaca   4560
ctagaaggac agtatttggt atctgcgctc tgctgaagcc agttaccttc ggaaaaagag   4620
ttggtagctc ttgatccggc aaacaaacca ccgctggtag cggtggtttt tttgtttgca   4680
agcagcagat tacgcgcaga aaaaaaggat ctcaagaaga tcctttgatc ttttctacgg   4740
ggtctgacgc tcagtggaac gaaaactcac gttaagggat tttggtcatg agattatcaa   4800
aaaggatctt cacctagatc cttttaaatt aaaaatgaag ttttaaatca atctaaagta   4860
tatatgagta aacttggtct gacagttacc aatgcttaat cagtgaggca cctatctcag   4920
cgatctgtct atttcgttca tccatagttg cctgactccc cgtcgtgtag ataactacga   4980
tacgggaggg cttaccatct ggccccagtg ctgcaatgat accgcgagac ccacgctcac   5040
```

```
cggctccaga tttatcagca ataaaccagc cagccggaag ggccgagcgc agaagtggtc   5100
ctgcaacttt atccgcctcc atccagtcta ttaattgttg ccgggaagct agagtaagta   5160
gttcgccagt taatagtttg cgcaacgttg ttgccattgc tacaggcatc gtggtgtcac   5220
gctcgtcgtt tggtatggct tcattcagct ccggttccca acgatcaagg cgagttacat   5280
gatcccccat gttgtgcaaa aaagcggtta gctccttcgg tcctccgatc gttgtcagaa   5340
gtaagttggc cgcagtgtta tcactcatgg ttatggcagc actgcataat tctcttactg   5400
tcatgccatc cgtaagatgc ttttctgtga ctggtgagta ctcaaccaag tcattctgag   5460
aatagtgtat gcggcgaccg agttgctctt gcccggcgtc aatacgggat aataccgcgc   5520
cacatagcag aactttaaaa gtgctcatca ttggaaaacg ttcttcgggg cgaaaactct   5580
caaggatctt accgctgttg agatccagtt cgatgtaacc cactcgtgca cccaactgat   5640
cttcagcatc ttttactttc accagcgttt ctgggtgagc aaaaacagga aggcaaaatg   5700
ccgcaaaaaa gggaataagg gcgacacgga aatgttgaat actcatactc ttcctttttc   5760
aatattattg aagcatttat cagggttatt gtctcatgag cggatacata tttgaatgta   5820
tttagaaaaa taaacaaata ggggttccgc gcacatttcc ccgaaaagtg ccacctgaac   5880
gaagcatctg tgcttcattt tgtagaacaa aaatgcaacg cgagagcgct aatttttcaa   5940
acaaagaatc tgagctgcat ttttacagaa cagaaatgca acgcgaaagc gctattttac   6000
caacgaagaa tctgtgcttc atttttgtaa aacaaaaatg caacgcgaga gcgctaattt   6060
ttcaaacaaa gaatctgagc tgcattttta cagaacagaa atgcaacgcg agagcgctat   6120
tttaccaaca aagaatctat acttcttttt tgttctacaa aaatgcatcc cgagagcgct   6180
atttttctaa caaagcatct tagattactt tttttctcct ttgtgcgctc tataatgcag   6240
tctcttgata actttttgca ctgtaggtcc gttaaggtta gaagaaggct actttggtgt   6300
ctattttctc ttccataaaa aaagcctgac tccacttccc gcgtttactg attactagcg   6360
aagctgcggg tgcatttttt caagataaag gcatccccga ttatattcta taccgatgtg   6420
gattgcgcat actttgtgaa cagaaagtga tagcgttgat gattcttcat tggtcagaaa   6480
attatgaacg gtttcttcta ttttgtctct atatactacg tataggaaat gtttacattt   6540
tcgtattgtt ttcgattcac tctatgaata gttcttacta caattttttt gtctaaagag   6600
taatactaga gataaacata aaaaatgtag aggtcgagtt tagatgcaag ttcaaggagc   6660
gaaaggtgga tgggtaggtt atatagggat atagcacaga gatatatagc aaagagatac   6720
ttttgagcaa tgtttgtgga agcggtattc gcaatatttt agtagctcgt tacagtccgg   6780
tgcgtttttg gttttttgaa agtgcgtctt cagagcgctt ttggttttca aaagcgctct   6840
gaagttccta tactttctag agaataggaa cttcggaata ggaacttcaa agcgtttccg   6900
aaaacgagcg cttccgaaaa tgcaacgcga gctgcgcaca tacagctcac tgttcacgtc   6960
gcacctatat ctgcgtgttg cctgtatata tatatacatg agaagaacgg catagtgcgt   7020
gtttatgctt aaatgcgtac ttatatgcgt ctatttatgt aggatgaaag gtagtctagt   7080
acctcctgtg atattatccc attccatgcg gggtatcgta tgcttccttc agcactaccc   7140
tttagctgtt ctatatgctg ccactcctca attggattag tctcatcctt caatgctatc   7200
atttcctttg atattggatc atattaagaa accattatta tcatgacatt aacctataaa   7260
aataggcgta tcacgaggcc ctttcgtc                                      7288
```

<210> SEQ ID NO 46
<211> LENGTH: 7620

```
<212> TYPE: DNA
<213> ORGANISM: Artificial Sequence
<220> FEATURE:
<223> OTHER INFORMATION: Recombinant plasmid pAPSE10446; beta actin stem
      loop + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3194)
<223> OTHER INFORMATION: bacteriophage MS2 pac sequence
<220> FEATURE:
<221> NAME/KEY: misc_feature
<222> LOCATION: (3195)..(3202)
<223> OTHER INFORMATION: restriction endonuclease AsiSI recognition
      sequence
<220> FEATURE:
<221> NAME/KEY: misc_feature
<222> LOCATION: (3204)..(3497)
<223> OTHER INFORMATION: beta actin sense gene fragment
<220> FEATURE:
<221> NAME/KEY: misc_feature
<222> LOCATION: (3497)..(3504)
<223> OTHER INFORMATION: restriction endonuclease PmeI recognition site
<220> FEATURE:
<221> NAME/KEY: misc_feature
<222> LOCATION: (3565)..(3583)
<223> OTHER INFORMATION: bacteriophage MS2 pac sequence
<220> FEATURE:
<221> NAME/KEY: misc_feature
<222> LOCATION: (3662)..(3956)
<223> OTHER INFORMATION: beta actin antisense strand gene fragment
<220> FEATURE:
<221> NAME/KEY: misc_feature
<222> LOCATION: (3992)..(4010)
<223> OTHER INFORMATION: bacteriophage MS2 pac sequence
<220> FEATURE:
<221> NAME/KEY: terminator
<222> LOCATION: (4027)..(4216)
<223> OTHER INFORMATION: yeast CYC1 terminator
<220> FEATURE:
<221> NAME/KEY: misc_feature
<222> LOCATION: (6210)..(7552)
<223> OTHER INFORMATION: yeast 2 micron ori

<400> SEQUENCE: 46

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accataaacg acattactat atatataata taggaagcat ttaatagaca gcatcgtaat     240

atatgtgtac tttgcagtta tgacgccaga tggcagtagt ggaagatatt ctttattgaa     300
```

```
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctctta ttagtaaatg   2100
ccagagttag cagcgattgc agatgggatc ggattaccgt ctttcagcag gccctgcatt   2160
gccttaacaa tcagttcgca gtcggagttc gtcgcaaaaa tcggaatagt cagttccatg   2220
ttgaggtaag agcgccaggc cgcaactggg agttctacgc cgcctacggt ctgcgttgcg   2280
actttcggta cttcaacttt gatggtgtat ttgcgattct gcgcgctaga ctgacgaacg   2340
gagcacgtga ctttgtaggc ctgagagcgg ctgttagagc taatccattc cgcaacaccg   2400
ttggcgaagt tggacggagc tacggtaacg tcacccgtac cgccgttatc aaccagaacg   2460
aattgggtaa agttagacgc catgaattcg aattttcaaa aattcttact tttttttgg    2520
atggacgcaa agaagtttaa taatcatatt acatggcatt accaccatat acatatccat   2580
atacatatcc atatctaatc ttacttatat gttgtggaaa tgtaaagagc cccattatct   2640
tagcctaaaa aaaccttctc tttggaactt tcagtaatac gcttaactgc tcattgctat   2700
```

```
attgaagtac ggattagaag ccgccgagcg ggtgacagcc ctccgaagga agactctcct   2760
ccgtgcgtcc tcgtcttcac cggtcgcgtt cctgaaacgc agatgtgcct cgcgccgcac   2820
tgctccgaac aataaagatt ctacaatact agcttttatg gttatgaaga ggaaaaattg   2880
gcagtaacct ggccccacaa accttcaaat gaacgaatca aattaacaac cataggatga   2940
taatgcgatt agttttttag ccttatttct ggggtaatta atcagcgaag cgatgatttt   3000
tgatctatta acagatatat aaatgcaaaa actgcataac cactttaact aatactttca   3060
acattttcgg tttgtattac ttcttattca aatgtaataa aagtatcaac aaaaaattgt   3120
taatatacct ctatacttta acgtcaagga gaaaaaaccc cggatccatt taaatacatg   3180
aggattaccc atgtgcgatc gcgcacgagg tttttctgtc tagtgagcag tgtccaacct   3240
caaaagacaa catgtgtgac gacgatgtag cggctcttgt cgtagacaat ggatccggta   3300
tgtgcaaagc cggtttcgca ggagatgacg caccccgtgc cgtcttcccc tcgatcgtcg   3360
gtcgcccaag gcatcaagga gtcatggtcg gtatgggaca aaggactca tacgtaggag   3420
atgaagccca aagcaaaaga ggtatcctca ccctgaaata ccccatcgaa cacggtatca   3480
tcaccaactg ggatgagttt aaaccctcta gctgctttac aaagtactgg ttccctttcc   3540
agcgggatgc tttatctaaa cgcaacatga ggatcaccca tgtcgccaca tcgcttccta   3600
gttccgctgg gatccatcgt tggcggccga agccgccatt ccatagtgag ttctggcgcg   3660
cctcatccca gttggtgatg ataccgtgtt cgatggggta tttcagggtg aggatacctc   3720
ttttgctttg ggcttcatct cctacgtatg agtccttttg tcccataccg accatgactc   3780
cttgatgcct tgggcgaccg acgatcgagg ggaagacggc acggggtgcg tcatctcctg   3840
cgaaaccggc tttgcacata ccggatccat tgtctacgac aagagccgct acatcgtcgt   3900
cacacatgtt gtcttttgag gttggacact gctcactaga cagaaaaacc tcgtgccgga   3960
ccgaataccc ggtctgaacg agggcggccg cacatgagga tcacccatgt ccgcgggcta   4020
gctaagatcc gctctaaccg aaaaggaagg agttagacaa cctgaagtct aggtccctat   4080
ttattttttt atagttatgt tagtattaag aacgttattt atatttcaaa tttttctttt   4140
ttttctgtac agacgcgtgt acgcatgtaa cattatactg aaaaccttgc ttgagaaggt   4200
tttgggacgc tcgaagatcc agctgcatta atgaatcggc caacgcgcgg ggagaggcgg   4260
tttgcgtatt gggcgctctt ccgcttcctc gctcactgac tcgctgcgct cggtcgttcg   4320
gctgcggcga gcggtatcag ctcactcaaa ggcggtaata cggttatcca cagaatcagg   4380
ggataacgca ggaaagaaca tgtgagcaaa aggccagcaa aaggccagga accgtaaaaa   4440
ggccgcgttg ctggcgtttt tccataggct ccgcccccct gacgagcatc acaaaaatcg   4500
acgctcaagt cagaggtggc gaaacccgac aggactataa agataccagg cgtttccccc   4560
tggaagctcc ctcgtgcgct ctcctgttcc gaccctgccg cttaccggat acctgtccgc   4620
ctttctccct tcgggaagcg tggcgctttc tcatagctca cgctgtaggt atctcagttc   4680
ggtgtaggtc gttcgctcca agctgggctg tgtgcacgaa ccccccgttc agcccgaccg   4740
ctgcgcctta tccggtaact atcgtcttga gtccaacccg gtaagacacg acttatcgcc   4800
actggcagca gccactggta acaggattag cagagcgagg tatgtaggcg gtgctacaga   4860
gttcttgaag tggtggccta actacggcta cactagaagg acagtatttg gtatctgcgc   4920
tctgctgaag ccagttacct tcggaaaaag agttggtagc tcttgatccg gcaaacaaac   4980
caccgctggt agcggtggtt tttttgtttg caagcagcag attacgcgca gaaaaaaagg   5040
```

```
atctcaagaa gatcctttga tcttttctac ggggtctgac gctcagtgga acgaaaactc   5100

acgttaaggg attttggtca tgagattatc aaaaaggatc ttcacctaga tccttttaaa   5160

ttaaaaatga agttttaaat caatctaaag tatatatgag taaacttggt ctgacagtta   5220

ccaatgctta atcagtgagg cacctatctc agcgatctgt ctatttcgtt catccatagt   5280

tgcctgactc cccgtcgtgt agataactac gatacgggag ggcttaccat ctggccccag   5340

tgctgcaatg ataccgcgag acccacgctc accggctcca gatttatcag caataaacca   5400

gccagccgga agggccgagc gcagaagtgg tcctgcaact ttatccgcct ccatccagtc   5460

tattaattgt tgccgggaag ctagagtaag tagttcgcca gttaatagtt tgcgcaacgt   5520

tgttgccatt gctacaggca tcgtggtgtc acgctcgtcg tttggtatgg cttcattcag   5580

ctccggttcc caacgatcaa ggcgagttac atgatccccc atgttgtgca aaaaagcggt   5640

tagctccttc ggtcctccga tcgttgtcag aagtaagttg gccgcagtgt tatcactcat   5700

ggttatggca gcactgcata attctcttac tgtcatgcca tccgtaagat gcttttctgt   5760

gactggtgag tactcaacca agtcattctg agaatagtgt atgcggcgac cgagttgctc   5820

ttgcccggcg tcaatacggg ataataccgc gccacatagc agaactttaa aagtgctcat   5880

cattggaaaa cgttcttcgg ggcgaaaact ctcaaggatc ttaccgctgt tgagatccag   5940

ttcgatgtaa cccactcgtg cacccaactg atcttcagca tcttttactt tcaccagcgt   6000

ttctgggtga gcaaaaacag gaaggcaaaa tgccgcaaaa aagggaataa gggcgacacg   6060

gaaatgttga atactcatac tcttcctttt tcaatattat tgaagcattt atcagggtta   6120

ttgtctcatg agcggataca tatttgaatg tatttagaaa aataaacaaa taggggttcc   6180

gcgcacattt ccccgaaaag tgccacctga acgaagcatc tgtgcttcat tttgtagaac   6240

aaaaatgcaa cgcgagagcg ctaatttttc aaacaaagaa tctgagctgc atttttacag   6300

aacagaaatg caacgcgaaa gcgctatttt accaacgaag aatctgtgct tcatttttgt   6360

aaaacaaaaa tgcaacgcga gagcgctaat ttttcaaaca aagaatctga gctgcatttt   6420

tacagaacag aaatgcaacg cgagagcgct attttaccaa caaagaatct atacttcttt   6480

tttgttctac aaaaatgcat cccgagagcg ctatttttct aacaaagcat cttagattac   6540

tttttttctc ctttgtgcgc tctataatgc agtctcttga taactttttg cactgtaggt   6600

ccgttaaggt tagaagaagg ctactttggt gtctattttc tcttccataa aaaaagcctg   6660

actccacttc ccgcgtttac tgattactag cgaagctgcg ggtgcatttt ttcaagataa   6720

aggcatcccc gattatattc tataccgatg tggattgcgc atactttgtg aacagaaagt   6780

gatagcgttg atgattcttc attggtcaga aaattatgaa cggtttcttc tattttgtct   6840

ctatatacta cgtataggaa atgtttacat tttcgtattg ttttcgattc actctatgaa   6900

tagttcttac tacaattttt ttgtctaaag agtaatacta gagataaaca taaaaaatgt   6960

agaggtcgag tttagatgca agttcaagga gcgaaaggtg gatgggtagg ttatataggg   7020

atatagcaca gagatatata gcaaagagat acttttgagc aatgtttgtg gaagcggtat   7080

tcgcaatatt ttagtagctc gttacagtcc ggtgcgtttt tggttttttg aaagtgcgtc   7140

ttcagagcgc ttttggtttt caaaagcgct ctgaagttcc tatactttct agagaatagg   7200

aacttcggaa taggaacttc aaagcgtttc cgaaaacgag cgcttccgaa aatgcaacgc   7260
```

-continued

```
gagctgcgca catacagctc actgttcacg tcgcacctat atctgcgtgt tgcctgtata   7320

tatatataca tgagaagaac ggcatagtgc gtgtttatgc ttaaatgcgt acttatatgc   7380

gtctatttat gtaggatgaa aggtagtcta gtacctcctg tgatattatc ccattccatg   7440

cggggtatcg tatgcttcct tcagcactac cctttagctg ttctatatgc tgccactcct   7500

caattggatt agtctcatcc ttcaatgcta tcatttcctt tgatattgga tcatattaag   7560

aaaccattat tatcatgaca ttaacctata aaaataggcg tatcacgagg ccctttcgtc   7620
```